US009447189B2

(12) United States Patent
Deckert et al.

(10) Patent No.: US 9,447,189 B2
(45) Date of Patent: *Sep. 20, 2016

(54) CD37-BINDING MOLECULES AND IMMUNOCONJUGATES THEREOF

(75) Inventors: Jutta Deckert, Lexington, MA (US); Julianto Setiady, Waltham, MA (US); Peter U. Park, Somerville, MA (US)

(73) Assignee: ImmunoGen, Inc., Waltham, MA (US)

( * ) Notice: Subject to any disclaimer, the term of this patent is extended or adjusted under 35 U.S.C. 154(b) by 209 days.

This patent is subject to a terminal disclaimer.

(21) Appl. No.: 13/436,528

(22) Filed: Mar. 30, 2012

(65) Prior Publication Data

US 2012/0276119 A1 Nov. 1, 2012

Related U.S. Application Data

(60) Provisional application No. 61/470,863, filed on Apr. 1, 2011.

(51) Int. Cl.
*A61K 39/395* (2006.01)
*C07K 16/28* (2006.01)
*C12N 5/00* (2006.01)
*A61K 39/00* (2006.01)

(52) U.S. Cl.
CPC ..... *C07K 16/2896* (2013.01); *A61K 39/39541* (2013.01); *C12N 5/0087* (2013.01); *A61K 2039/505* (2013.01); *C07K 2317/24* (2013.01); *C07K 2317/73* (2013.01)

(58) Field of Classification Search
None
See application file for complete search history.

(56) References Cited

U.S. PATENT DOCUMENTS

| 5,122,368 | A  | 6/1992  | Greenfield et al. |
|-----------|----|---------|-------------------|
| 7,303,749 | B1 | 12/2007 | Chari             |
| 7,585,491 | B2 | 9/2009  | Govindan          |
| 7,601,354 | B2 | 10/2009 | Chari             |
| 7,989,598 | B2 | 8/2011  | Steeves et al.    |
| 8,088,387 | B2 | 1/2012  | Steeves et al.    |
| 8,765,917 | B2 | 7/2014  | Deckert et al.    |
| 2003/0114398 | A1 | 6/2003 | Chatterjee et al. |
| 2004/0166115 | A1 | 8/2004 | Griffiths et al.  |
| 2005/0136049 | A1 | 6/2005 | Ledbetter et al.  |
| 2006/0233822 | A1 | 10/2006 | Xia et al.       |
| 2006/0263349 | A1 | 11/2006 | McCutcheon et al. |
| 2007/0009519 | A1 | 1/2007 | Hariharan et al.  |
| 2007/0059306 | A1 | 3/2007 | Grosmaire et al.  |
| 2007/0237779 | A1 | 10/2007 | Ledbetter et al. |
| 2008/0075726 | A1 | 3/2008 | Smith et al.     |
| 2008/0226626 | A1 | 9/2008 | Hariharan et al.  |
| 2008/0227198 | A1 | 9/2008 | Hariharan et al.  |
| 2008/0279850 | A1 | 11/2008 | Brady et al.    |
| 2009/0136516 | A1 | 5/2009 | Tedder et al.    |
| 2009/0148447 | A1 | 6/2009 | Ledbetter et al. |
| 2009/0274692 | A1 | 11/2009 | Tan et al.      |
| 2009/0274713 | A1 | 11/2009 | Chari et al.    |
| 2010/0135900 | A1 | 6/2010 | Cerveny et al.   |
| 2010/0189722 | A1 | 7/2010 | Heider et al.    |
| 2011/0256056 | A1 | 10/2011 | Alper           |
| 2011/0256153 | A1 | 10/2011 | Deckert et al.  |
| 2012/0020963 | A1 | 1/2012 | Banchereau et al. |
| 2013/0295104 | A1 | 11/2013 | Deckert et al.  |
| 2015/0093397 | A1 | 4/2015 | Carrigan        |

FOREIGN PATENT DOCUMENTS

| EP | 0 328 147 B1 | 5/1994 |
|----|--------------|--------|
| WO | WO 01/24763 A2 | 4/2001 |
| WO | WO 02/060485 A2 | 8/2002 |
| WO | WO 02/102972 A2 | 12/2002 |
| WO | WO 03/083069 A2 | 10/2003 |
| WO | WO 2005/017148 A1 | 2/2005 |
| WO | WO 2005/037989 A2 | 4/2005 |
| WO | WO 2005/037992 A2 | 4/2005 |
| WO | WO 2006/074397 A2 | 7/2006 |
| WO | WO 2007/014278 A2 | 2/2007 |
| WO | WO 2007/140371 A2 | 6/2007 |
| WO | WO 2007/146968 A2 | 12/2007 |
| WO | WO 2008/052030 A2 | 5/2008 |
| WO | WO 2009/019312 A2 | 2/2009 |
| WO | WO 2009/065576 A1 | 5/2009 |
| WO | WO 2009/126858 A2 | 10/2009 |
| WO | WO 2009/126944 A1 | 10/2009 |
| WO | WO 2009/134977 A1 | 11/2009 |
| WO | WO 2010/008726 A1 | 1/2010 |
| WO | WO 2010/009124 A2 | 1/2010 |
| WO | WO 2010/126551 A1 | 11/2010 |
| WO | WO 2011/090754 A1 | 7/2011 |
| WO | WO 2011/090762 A1 | 7/2011 |
| WO | WO 2011/112978 A1 | 9/2011 |
| WO | WO 2012/135740 A2 | 10/2012 |
| WO | WO 2013/149171 A2 | 10/2013 |
| WO | WO 2014/143807 A2 | 9/2014 |

OTHER PUBLICATIONS

De Pascalis et al., "Grafting of "Abbreviated" Complementarity-Determining Regions Containing Specificity-Determining Residues Essential for Ligand Contact to Engineer a Less Immunogenic Humanized Monoclonal Antibody",The Journal of Immunology, 2002, 169: 3076-3084.*

MacCallum et al. "Antibody-antigen Interactions: Contact Analysis and Binding Site Topography", J. Mol. Biol. (1996) 262, 732-745.*

Angelisová, P., et al., "Association of four antigens of the tetraspans family (CD37, CD53, TAPA-1, and R2/C33) with MHC class II glycoproteins," *Immunogenetics* 39:249-256, Springer-Verlag, Germany (1994).

Barrena, S., et al., "Aberrant expression of tetraspanin molecules in B-cell chronic lymphoproliferative disorders and its correlation with normal B-cell maturation," *Leukemia* 19:1376-1383, Nature Publishing Group, England (2005).

(Continued)

*Primary Examiner* — Ron Schwadron
(74) *Attorney, Agent, or Firm* — Sterne, Kessler, Goldstein & Fox P.L.L.C.

(57) ABSTRACT

Methods of using CD37 agents, including, but not limited to, antibodies and immunoconjugates, that bind to CD37 to deplete B-cells (e.g., non-cancerous B-cells) and methods of treating autoimmune and inflammatory diseases are further provided.

27 Claims, 11 Drawing Sheets

(56) References Cited

OTHER PUBLICATIONS

Bernstein, I.D., et al., "High Dose Radiolabeled Antibody Therapy of Lymphoma," *Cancer Research (Suppl.)* 50:1017s-1021s, American Association for Cancer Research, United States (1990).
Blanc, V., et al., "SAR3419: An Anti-CD19-Maytansinoid Immunoconjugate for the Treatment of B-Cell Malignancies," *Clin. Cancer Res.* 17(20):6448-6458, American Association for Cancer Research, United States (2011).
Braslawsky, G.R., et al., "Antitumor Activity of Adriamycin (Hydrazone-linked) Immunoconjugates Compared with Free Adriamycin and Specificity of Tumor Cell Killing," *Cancer Research* 50:6608-6614, American Association for Cancer Research, United States (1990).
Dahle, J., et al., "Evaluating Antigen Targeting and Anti-tumor Activity of a New Anti-CD37 Radioimmunoconjugate Against Non-Hodgkin's Lymphoma," *Anticancer Research* 33:85-96, International Institute of Anticancer Research, Greece (2013).
Dijoseph, J.F., et al. "CD20-specific antibody-targeted chemotherapy of non-Hodgkin's B-cell lymphoma using calicheamicin-conjugated rituximab," *Cancer Immunol Immunother* 56:1107-1117, Springer-Verlag, Germany (2007).
Greenfield, R.S., et al., "Evaluation in Vitro of Adriamycin Immunoconjugates Synthesized Using an Acid-sensitive Hydrazone Linker," *Cancer Research* 50:6600-6607, American Association for Cancer Research, United States (1990).
Heider, K-H., et al., "A novel Fc-engineered monoclonal antibody to CD37 with enhanced ADCC and high proapoptotic activity for treatment of B-cell malignancies," *Blood* 118(15):4159-4168, The American Society of Hematology, United States (2011).
Kaminski, M.S., et al. "Imaging, Dosimetry, and Radioimmunotherapy With Iodine 131-Labeled Anti-CD37 Antibody in B-Cell Lymphoma," *Journal of Clinical Oncology* 10(11):1696-1711, American Society of Clinical Oncology, United States (1992).
Knobeloch, K-P., et al., "Targeted Inactivation of the Tetraspanin CD37 Impairs T-Cell-Dependent B-Cell Response under Suboptimal Costimulatory Conditions," *Molecular and Cellular Biology* 20(15):5369-5369, American Society for Microbiology, United States (2000).
Lambert, J.M., "Antibody-Maytansinoid Conjugates: A New Strategy for the Treatment of Cancer," *Drugs of the Future* 35(6):471-480, Prous Science, S.A.U., Spain (2010).
Lapalombella, R., et al., "Tetraspanin CD37 Directly Mediates Transduction of Survival and Apoptotic Signals," *Cancer Cell* 21:694-708, Elsevier Inc., United States (2012).
Link, M.P., et al., "A Unique Antigen on Mature B Cells Defined by a Monoclonal Antibody," *The Journal of Immunology* 137(9):3013-3018, The American Association of Immunologists, United States (1986).
Maecker, H.T., et al., "The tetraspanin superfamily: molecular facilitators," *FASEB J.* 11:428-442, The Federation, United States (1997).
Meyer-Wentrup, F., et al., "Dectin-1 Interaction with Tetraspanin CD37 Inhibits IL-6 Production," *The Journal of Immunology* 178:154-162, The American Association of Immunologist, Inc., United States (2007).
Moore, K., et al., "Use of the Monoclonal Antibody WR17, Identifying the CD37 gp40-45 Kd Antigen Complex, in the Diagnosis of B-Lymphoid Malignancy," *Journal of Pathology* 152:13-21, John Wiley & Sons, Ltd., England (1987).
Pagel, J.M, et al., "Phase 1 Study of TRU-016, An Anti-CD37 SMIP™ Protein in Relapsed and/or Refractory NHL Patients," *Blood (ASH Annual Meeting Abstracts)* 2011 118(21):Abstract 1636 (2011).
Polson, A.G., et al., "Antibody-Drag Conjugates for the Treatment of Non-Hodgkin's Lymphoma: Target and Linker-Drug Selection," *Cancer Res* 69(6):2358-2364, American Association for Cancer Research, United States (2009).

Press, O.W., et al., "Endocytosis and Degradation of Monoclonal Antibodies Targeting Human B-Cell Malignancies," *Cancer Research* 49:4906-4912, American Association for Cancer Research, United States (1989).
Press, O.W., et al., "Radiolabeled-Antibody Therapy of B-Cell Lymphoma with Autologous Bone Marrow Support," *N Engl J Med* 329(17):1219-1224, Massachusetts Medical Society, United States (1993).
Press, O.W., et al., "Retention of B-Cell-Specific Monoclonal Antibodies by Human Lymphoma Cells," *Blood* 83(5):1390-1397, The American Society of Hematology, United States (1994).
Press, O.W., et al., "Treatment of Refractory Non-Hodgkin's Lymphoma With Radiolabeled MB-1 (Anti-CD37) Antibody," *J. Clin. Oncol.* 7(8):1027-1038, American Society of Clinical Oncology, United States (1989).
Roguska, M.A., et al., "Humanization of murine monoclonal antibodies through variable domain resurfacing," *Proc. Natl. Acad. Sci. USA* 91:969-973, National Academy of Sciences, United States (1994).
Roguska, M.A., et al., "A comparison of two murine monoclonal antibodies humanized by CDR-grafting and variable domain resurfacing," *Protein Engineering* 9(10):895-904, Oxford University Press, England (1996).
Rops, A.L., et al., "The Tetraspanin CD37 Protects Against Glomerular IgA Deposition and Renal Pathology," *Am. J. Pathol.* 176:2188-2197, American Society for Investigative Pathology, United States (2010).
Schwartz-Albiez, R., et al., "The B Cell-Associated CD37 Antigen (gp40-52): Structure and Subcellular Expression of an Extensively Glycosylated Glycoprotein,"*The Journal of Immunology* 140(3):905-914, The American Association of Immunologists, United States (1988).
Sheng, K-C., et al., "Tetraspanins CD37 and CD151 differentially regulate Ag presentation and T-cell co-stimulation by DC," *Eur. J. Immunol.* 39:50-55, Wiley-VCH Verlag GmbH & Co. KGaA, Germany (2009).
Altshuler, E.P., et al., "Generation of Recombinant Antibodies and Means for Increasing Their Affinity," *Biochemistry(Moscow)* 75(13):1584-1605, Pleiades Publishing, Ltd., United States (2010).
Deckert, J., et al., "IMGN529: A therapeutic maytansinoid conjugate of an anti-CD37 antibody with multiple mechanisms of action for B-cell lymphoma and leukemia," AACR Poster Abstract #2, United States (Apr. 2011).
Deckert, J., et al., "Potent B-Cell Depletion by IMGN529, a CD37-Targeting Antibody-Maytansinoid Conjugate for the Treatment of B-Cell Malignancies," ASH 2011, Abstract #3726, United States (Nov. 2011).
Pinkas, J., "Antibody Maytansinoid Conjugates for the Treatment of Cancer," Protein Therapeutics Forum 2012:1-23, Jan. 30, 2012, United States (Jan. 2012).
Tedder, T.F., et al., "Structure of the Gene Encoding the Human B Lymphocyte Differentiation Antigen CD20 (B1)," *The Journal of Immunology* 142(7):2560-2568, The American Association of Immunologists, United States (1989).
Teicher, B.A. and Chari, R.V.J., "Antibody Conjugate Therapeutics: Challenges and Potential," *Clin. Cancer Res.* 17(20):6389-6397, American Association for Cancer Research, United States (2011).
Van Spriel, A.B., et al., "A Regulatory Role for CD37 in T Cell Proliferation," *The Journal of Immunology* 172:2953-2961, The American Association of Immunologists, United States (2004).
Van Spriel, A.B., et al., "The Tetraspanin Protein CD37 Regulates IgA Responses and Anti-Fungal Immunity," *PLoS Pathogens* 5(3) el000338:1-11, Public Library of Science, United States (2009).
Zhao, X., et al., "Targeting CD37-positive lymphoid malignancies with a novel engineered small modular immunopharmaceutical," *Blood* 110(7):2569-2577, The American Society of Hematology, United States (2007).
Kovtun, Y., et al. "Antibody-Maytansinoid Conjugates Designed to Bypass Multidrug Resistance," *Cancer Research* 70(6):2528-2537, American Association for Cancer Research, United States (2010).

(56) References Cited

OTHER PUBLICATIONS

Harris, C.L., et al. "Tumour Cell Killing Using Chemically Engineered Antibody Constructs Specific for Tumour Cells and the Complement Inhibitor CD59," *Clin. Exp. Immunol.* 107(2): 364-3701, Blackwell Publishing, England (1997).

Lai, K.C., et al., "The CD37-targeting ADS IMGN529 combines the potent anti-cancer activity of K7153A antibody with efficient maytansinoid delivery," *Oasis, The Online Abstract Submission System*, Abstract 11-A-226-AACR:pp. 1-2, Molecular Targets and Cancer Therapeutics, Nov. 12-16, 2011, San Francisco, United States (Nov. 2011), Accessed at http://www.abstractonline.com/plan/viewabstract.aspx48 mid=2889&skey=946d141d-1376-4bec-8e3f-a54580b89072&ckey=5af84375-1153-46e6-974c-e95ea6225aef&mkey=%7Ba57ff86d-d414-4079-bcbd-157746574f37%7D on Jul. 16, 2015.

Cragg, M.S., et al., "Complement-mediated lysis by anti-CD20 mAb correlates with segregation into lipd rafts," *Blood* 101(3):1045-1052, American Society of Hematology, United States (2003).

Awan, F.T, et al., "Phase 1 Study of Tru-016, An Anti-CD37 SMIP™ Protein in Naïve and Relapsed and/or Refractory CLL Patients," *Blood* (*ASH Annual Meeting Abstracts*) 118(21): Abstract 1792, pp. 1-3, United States (Nov. 2011). Accessed at http://www.bloodjournal.org/content/118/21/1792.full.pdf on Dec. 2, 2015.

Park, P.U., et al., "Antibody and linker selection for the anti-CD37 antibody-maytansinoid conjugate IMGN529 for the treatment of B-cell malignancies," *Experimental and Molecular Therapeutics Session*, AACR Annual Meeting 2011, Experimental and Molecular Therapeutics session, Abstract #2830, p. 1, United States (Apr. 2011). Accessed at: http://cancerres.aacrjournals.org/content/71/8_Supplement/2830.abstract on Jul. 20, 2015.

Zhao, X.B., et al., "Novel Anti-CD37 Small Modular Immunopharmaceutical (SMIP) Induces B-Cell-Specific, Caspase-Independent Apoptosis in Human CLL Cells," *Blood* 104(11), p. 689a, Abstract 2515, ASH Annual Meeting, American Society of Hematology, United States (2004). Accessed at: http://abstracts.hematologylibrary.org/cgi/content/short/104/11/2515 on Jul. 16, 2015.

International Search Report and Written Opinion for International Patent Appl. No. PCT/US12/31648, CD37-Binding Molecules and Immunoconjugates Thereof, inventors Deckert et al., filed Mar. 30, 2012, Commissioner for Patents, United States, pp. 1-17, mailed Sep. 20, 2012.

Preissuance Submission by Third Party under 37 C.F.R. § 1.290, filed in U.S. Appl. No. 13/045,693, CD37-Binding Molecules and Immunoconjugates Thereof, inventors Deckert et al., filed on Mar. 11, 2011, pp. 1-14, United States, dated May 30, 2013.

Preissuance Submission by Third Party under 37 C.F.R. § 1.290 in U.S. Appl. No. 13/436,528, CD37-Binding Molecules and Immunoconjugates Thereof, inventors Deckert et al., filed Mar. 30, 2012, pp. 1-15, United States, dated Aug. 26, 2013.

Preissuance Submission by Third Party under 37 C.F.R. § 1.290 in U.S. Appl. No. 13/796,768, CD37-Binding Molecules and Immunoconjugates Thereof, inventors Deckert et al., filed Mar. 12, 2013, pp. 1-18, United States, dated Apr. 1, 2014.

International Preliminary Report on Patentability for International Application No. PCT/US2012/031648, CD37-Binding Molecules and Immunoconjugates Thereof, inventors Deckert et al., filed Mar. 30, 2012, The International Bureau of WIPO, Switzerland, pp. 1-9, mailed Oct. 2, 2013.

International Search Report with Written Opinion for International Application No.PCT/US11/28172, CD37-Binding Molecules and Immunoconjugates Thereof, inventors Deckert et al., filed Mar. 11, 2011, International Searching Authority, United States, pp. 1-9, mailed Jul. 13, 2011.

International Search report for International Application No. PCT/US2013/034646, Methods for Increasing Efficacy of CD37-Based Therapy, inventor Carrigan, filed Oct. 3, 2013, United States Patent Office, Arlington, Virginia, pp. 1-3, mailed Sep. 16, 2013.

Zhao, X., "Targeting CD37 and folate receptor for cancer therapy: strategies based on engineered proteins and liposomes," OhioLink Electronic Theses & Dissertations Center, document No. osu1174678307, pp. 1-314, The Ohio State University, United States (2007). Accessed at https://etd.ohiolink.edu/ap/10?0::NO:10:P10_ACCESSION_NUM:osu1174678307 on Oct. 2, 2015.

Deckert, J., et al., "IMGN529: An Anti-CD37 Antibody-Maytansinoid Conjugate with Multiple Mechanisms of Actions for B-Cell Malignancies," *Keystone Symposia—B Cells: New Insights into Normal versus Dysregulated Function*, Apr. 2-6, 2011, Poster #306, pp. 1-11, United States (Apr. 2011).

Lai, K.C., et al., "The CD37-targeting ADC IMGN529 combines the potent anti-cancer activity of K7153A antibody with efficient maytansinoid delivery," *AACR-EORTC-NCI* 2011, Poster Abstract #B209, pp. 1-12, United States (Nov. 2011).

Robak, T., et al., "TRU-016, a humanized anti-CD37 IgG fusion protein for the potential treatment of B-cell malignancies," *Curr Opin Investig Drugs* 10(12): 1383-90, Thomson Reuters Ltd., United States (2009).

Zhao, X., et al., "CD37 Is a Potential Therapeutic Target for B-Cell Non-Hodgkin Lymphoma," *Blood: 2010 ASH Annual Meeting Abstracts* 116(21):1277-1278, Abstract No. 3098, American Society of Hematology, United States (Nov. 19, 2010).

\* cited by examiner

A

B

A

B

A

B

SEQUENCE LISTING

```
<160> NUMBER OF SEQ ID NOS: 194

<210> SEQ ID NO 1
<211> LENGTH: 280
<212> TYPE: PRT
<213> ORGANISM: Homo sapiens

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175
```

```
Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
        210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Tyr Arg
        275                 280

<210> SEQ ID NO 2
<211> LENGTH: 281
<212> TYPE: PRT
<213> ORGANISM: Mucaca mulatta

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Ile Leu Gly Ser Leu Ile Phe Cys
            20                  25                  30

Phe Gly Ile Trp Ile Leu Ile Asp Lys Thr Ser Phe Val Ser Phe Val
        35                  40                  45

Gly Leu Ala Phe Val Pro Leu Gln Ile Trp Ser Lys Val Leu Ala Ile
    50                  55                  60

Ser Gly Val Phe Thr Met Gly Leu Ala Leu Gly Cys Val Gly Ala
65                  70                  75                  80

Leu Lys Glu Leu Arg Cys Leu Leu Gly Leu Tyr Phe Gly Met Leu Leu
                85                  90                  95

Leu Leu Phe Ala Thr Gln Ile Thr Leu Gly Ile Leu Ile Ser Thr Gln
            100                 105                 110

Arg Ala Gln Leu Glu Arg Ser Leu Gln Asp Ile Val Glu Lys Thr Ile
        115                 120                 125

Gln Arg Tyr His Thr Asn Pro Glu Glu Thr Ala Ala Glu Glu Ser Trp
    130                 135                 140

Asp Tyr Val Gln Phe Gln Leu Arg Cys Cys Gly Trp His Ser Pro Gln
145                 150                 155                 160

Asp Trp Phe Gln Val Leu Thr Leu Arg Gly Asn Gly Ser Glu Ala His
                165                 170                 175

Arg Val Pro Cys Ser Cys Tyr Asn Leu Ser Ala Thr Asn Asp Ser Thr
            180                 185                 190

Ile Leu Asp Lys Val Ile Leu Pro Gln Leu Ser Arg Leu Gly Gln Leu
        195                 200                 205

Ala Arg Ser Arg His Ser Thr Asp Ile Cys Ala Val Pro Ala Asn Ser
    210                 215                 220

His Ile Tyr Arg Glu Gly Cys Ala Arg Ser Leu Gln Lys Trp Leu His
225                 230                 235                 240

Asn Asn Leu Ile Ser Ile Val Gly Ile Cys Leu Gly Val Gly Leu Leu
                245                 250                 255

Glu Leu Gly Phe Met Thr Leu Ser Ile Phe Leu Cys Arg Asn Leu Asp
            260                 265                 270
```

```
His Val Tyr Asn Arg Leu Arg Tyr Arg
        275                 280

<210> SEQ ID NO 3
<211> LENGTH: 281
<212> TYPE: PRT
<213> ORGANISM: Mus musculus

<400> SEQUENCE: 3

Met Ser Ala Gln Glu Ser Cys Leu Ser Leu Ile Lys Tyr Phe Leu Phe
1               5                   10                  15

Val Phe Asn Leu Phe Phe Phe Val Leu Gly Gly Leu Ile Phe Cys Phe
            20                  25                  30

Gly Thr Trp Ile Leu Ile Asp Lys Thr Ser Phe Val Ser Phe Val Gly
        35                  40                  45

Leu Ser Phe Val Pro Leu Gln Thr Trp Ser Lys Val Leu Ala Val Ser
    50                  55                  60

Gly Val Leu Thr Met Ala Leu Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Phe
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Leu Pro Ala Lys Ala His
210                 215                 220

Ile Tyr Arg Glu Gly Cys Ala Gln Ser Leu Gln Lys Trp Leu His Asn
225                 230                 235                 240

Asn Ile Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asp Arg Leu Ala Arg Tyr Arg
        275                 280

<210> SEQ ID NO 4
<211> LENGTH: 5
<212> TYPE: PRT
<213> ORGANISM: Artificial Sequence
<220> FEATURE:
<223> OTHER INFORMATION: CD37-3 VH-CDR1

<400> SEQUENCE: 4

Thr Ser Gly Val Ser
1               5
```

<210> SEQ ID NO 5
<211> LENGTH: 9
<212> TYPE: PRT
<213> ORGANISM: Artificial Sequence
<220> FEATURE:
<223> OTHER INFORMATION: CD37-3 VH-CDR2

<400> SEQUENCE: 5

Val Ile Trp Gly Asp Gly Ser Thr Asn
1               5

<210> SEQ ID NO 6
<211> LENGTH: 7
<212> TYPE: PRT
<213> ORGANISM: Artificial Sequence
<220> FEATURE:
<223> OTHER INFORMATION: CD37-3 VH-CDR3

<400> SEQUENCE: 6

Gly Gly Tyr Ser Leu Ala His
1               5

<210> SEQ ID NO 7
<211> LENGTH: 5
<212> TYPE: PRT
<213> ORGANISM: Artificial Sequence
<220> FEATURE:
<223> OTHER INFORMATION: CD37-12 VH-CDR1

<400> SEQUENCE: 7

Lys Tyr Gly Met Asn
1               5

<210> SEQ ID NO 8
<211> LENGTH: 10
<212> TYPE: PRT
<213> ORGANISM: Artificial Sequence
<220> FEATURE:
<223> OTHER INFORMATION: CD37-12 VH-CDR2

<400> SEQUENCE: 8

Trp Ile Asn Thr Asn Thr Gly Glu Ser Arg
1               5                   10

<210> SEQ ID NO 9
<211> LENGTH: 6
<212> TYPE: PRT
<213> ORGANISM: Artificial Sequence
<220> FEATURE:
<223> OTHER INFORMATION: CD37-12 VH-CDR3

<400> SEQUENCE: 9

Gly Thr Val Val Ala Asp
1               5

<210> SEQ ID NO 10
<211> LENGTH: 6
<212> TYPE: PRT
<213> ORGANISM: Artificial Sequence
<220> FEATURE:
<223> OTHER INFORMATION: CD37-38 VH-CDR1

<400> SEQUENCE: 10

Ser Gly Phe Gly Trp His
1               5

```
<210> SEQ ID NO 11
<211> LENGTH: 9
<212> TYPE: PRT
<213> ORGANISM: Artificial Sequence
<220> FEATURE:
<223> OTHER INFORMATION: CD37-38 VH-CDR2

<400> SEQUENCE: 11

Tyr Ile Leu Tyr Ser Gly Gly Thr Asp
1               5

<210> SEQ ID NO 12
<211> LENGTH: 11
<212> TYPE: PRT
<213> ORGANISM: Artificial Sequence
<220> FEATURE:
<223> OTHER INFORMATION: CD37-38 VH-CDR3

<400> SEQUENCE: 12

Gly Tyr Tyr Gly Tyr Gly Ala Trp Phe Val Tyr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: CD37-50 VH-CDR1

<400> SEQUENCE: 13

Ser Gly Phe Ala Trp His
1               5

<210> SEQ ID NO 14
<211> LENGTH: 9
<212> TYPE: PRT
<213> ORGANISM: Artificial Sequence
<220> FEATURE:
<223> OTHER INFORMATION: CD37-50  VH-CDR2

<400> SEQUENCE: 14

Tyr Ile Leu Tyr Ser Gly Ser Thr Val
1               5

<210> SEQ ID NO 15
<211> LENGTH: 11
<212> TYPE: PRT
<213> ORGANISM: Artificial Sequence
<220> FEATURE:
<223> OTHER INFORMATION: CD37-50 VH-CDR3

<400> SEQUENCE: 15

Gly Tyr Tyr Gly Tyr Gly Ala Trp Phe Ala Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: CD37-51 VH-CDR1

<400> SEQUENCE: 16

Ser Gly Phe Ala Trp His
1               5

<210> SEQ ID NO 17
```

```
<211> LENGTH: 9
<212> TYPE: PRT
<213> ORGANISM: Artificial Sequence
<220> FEATURE:
<223> OTHER INFORMATION: CD37-51 VH-CDR2

<400> SEQUENCE: 17

Tyr Ile His Tyr Ser Gly Ser Thr Asn
1               5

<210> SEQ ID NO 18
<211> LENGTH: 11
<212> TYPE: PRT
<213> ORGANISM: Artificial Sequence
<220> FEATURE:
<223> OTHER INFORMATION: CD37-51 VH-CDR3

<400> SEQUENCE: 18

Gly Tyr Tyr Gly Phe Gly Ala Trp Phe Val Tyr
1               5                   10

<210> SEQ ID NO 19
<211> LENGTH: 6
<212> TYPE: PRT
<213> ORGANISM: Artificial Sequence
<220> FEATURE:
<223> OTHER INFORMATION: CD37-56 VH-CDR1

<400> SEQUENCE: 19

Ser Gly Phe Ala Trp His
1               5

<210> SEQ ID NO 20
<211> LENGTH: 9
<212> TYPE: PRT
<213> ORGANISM: Artificial Sequence
<220> FEATURE:
<223> OTHER INFORMATION: CD37-56 VH-CDR2

<400> SEQUENCE: 20

Tyr Ile His Tyr Ser Gly Gly Thr Asn
1               5

<210> SEQ ID NO 21
<211> LENGTH: 11
<212> TYPE: PRT
<213> ORGANISM: Artificial Sequence
<220> FEATURE:
<223> OTHER INFORMATION: CD37-56 VH-CDR3

<400> SEQUENCE: 21

Gly Tyr Tyr Gly Phe Gly Ala Trp Phe Ala Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: CD37-57 VH-CDR1

<400> SEQUENCE: 22

Ser Gly Phe Ala Trp His
1               5

<210> SEQ ID NO 23
<211> LENGTH: 9
```

```
<212> TYPE: PRT
<213> ORGANISM: Artificial Sequence
<220> FEATURE:
<223> OTHER INFORMATION: CD37-57 VH-CDR2

<400> SEQUENCE: 23

Tyr Ile Leu Tyr Ser Gly Ser Thr Val
1               5

<210> SEQ ID NO 24
<211> LENGTH: 11
<212> TYPE: PRT
<213> ORGANISM: Artificial Sequence
<220> FEATURE:
<223> OTHER INFORMATION: CD37-57 VH-CDR3

<400> SEQUENCE: 24

Gly Tyr Tyr Gly Tyr Gly Ala Trp Phe Ala Tyr
1               5                   10

<210> SEQ ID NO 25
<211> LENGTH: 6
<212> TYPE: PRT
<213> ORGANISM: Artificial Sequence
<220> FEATURE:
<223> OTHER INFORMATION: CONSENSUS VH-CDR1
<220> FEATURE:
<221> NAME/KEY: MISC_FEATURE
<222> LOCATION: (4)..(4)
<223> OTHER INFORMATION: X is A or G

<400> SEQUENCE: 25

Ser Gly Phe Xaa Trp His
1               5

<210> SEQ ID NO 26
<211> LENGTH: 9
<212> TYPE: PRT
<213> ORGANISM: Artificial Sequence
<220> FEATURE:
<223> OTHER INFORMATION: CONSENSUS VH-CDR2
<220> FEATURE:
<221> NAME/KEY: MISC_FEATURE
<222> LOCATION: (3)..(3)
<223> OTHER INFORMATION: X is L or H
<220> FEATURE:
<221> NAME/KEY: MISC_FEATURE
<222> LOCATION: (7)..(7)
<223> OTHER INFORMATION: X is G or S
<220> FEATURE:
<221> NAME/KEY: MISC_FEATURE
<222> LOCATION: (9)..(9)
<223> OTHER INFORMATION: X is D, V or N

<400> SEQUENCE: 26

Tyr Ile Xaa Tyr Ser Gly Xaa Thr Xaa
1               5

<210> SEQ ID NO 27
<211> LENGTH: 11
<212> TYPE: PRT
<213> ORGANISM: Artificial Sequence
<220> FEATURE:
<223> OTHER INFORMATION: CONSENSUS VH-CDR3
<220> FEATURE:
<221> NAME/KEY: MISC_FEATURE
<222> LOCATION: (5)..(5)
<223> OTHER INFORMATION: X is Y or F
<220> FEATURE:
<221> NAME/KEY: MISC_FEATURE
<222> LOCATION: (10)..(10)
```

```
<223> OTHER INFORMATION: X is V or A

<400> SEQUENCE: 27

Gly Tyr Tyr Gly Xaa Gly Ala Trp Phe Xaa Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: CD37-3 VL-CDR1

<400> SEQUENCE: 28

Arg Ala Ser Glu Asn Ile Arg Ser Asn Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CD37-3 VL-CDR2

<400> SEQUENCE: 29

Val Ala Thr Asn Leu Ala Asp
1               5

<210> SEQ ID NO 30
<211> LENGTH: 9
<212> TYPE: PRT
<213> ORGANISM: Artificial Sequence
<220> FEATURE:
<223> OTHER INFORMATION: CD37-3 VL-CDR3

<400> SEQUENCE: 30

Gln His Tyr Trp Gly Thr Thr Trp Thr
1               5

<210> SEQ ID NO 31
<211> LENGTH: 15
<212> TYPE: PRT
<213> ORGANISM: Artificial Sequence
<220> FEATURE:
<223> OTHER INFORMATION: CD37-12 VL-CDR1

<400> SEQUENCE: 31

Arg Ala Ser Gln Ser Val Ser Thr Ser Ser Tyr Ser Tyr Leu Tyr
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: CD37-12 VL-CDR2

<400> SEQUENCE: 32

Tyr Ala Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: CD37-12 VL-CDR3
```

```
<400> SEQUENCE: 33

Gln His Ser Trp Glu Ile Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: CD37-38 VL-CDR1

<400> SEQUENCE: 34

Ser Ala Ser Ser Ser Val Thr Tyr Met His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: CD37-38 VL-CDR2

<400> SEQUENCE: 35

Asp Thr Ser Lys Leu Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: CD37-38 VL-CDR3

<400> SEQUENCE: 36

Gln Gln Trp Ile Ser Asn Pro Pro Thr
1               5

<210> SEQ ID NO 37
<211> LENGTH: 10
<212> TYPE: PRT
<213> ORGANISM: Artificial Sequence
<220> FEATURE:
<223> OTHER INFORMATION: CD37-50 VL-CDR1

<400> SEQUENCE: 37

Ser Ala Thr Ser Ser Val Thr Tyr Met His
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CD37-50 VL-CDR2

<400> SEQUENCE: 38

Asp Thr Ser Lys Leu Pro Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: CD37-50 VL-CDR3
```

```
<400> SEQUENCE: 39

Gln Gln Trp Ser Asp Asn Pro Pro Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Humanized CD37-50 VL-CDR2

<400> SEQUENCE: 40

Asp Thr Ser Asn Leu Pro Tyr
1               5

<210> SEQ ID NO 41
<211> LENGTH: 10
<212> TYPE: PRT
<213> ORGANISM: Artificial Sequence
<220> FEATURE:
<223> OTHER INFORMATION: CD37-51 VL-CDR1

<400> SEQUENCE: 41

Ser Ala Thr Ser Ser Val Thr Tyr Met His
1               5                   10

<210> SEQ ID NO 42
<211> LENGTH: 7
<212> TYPE: PRT
<213> ORGANISM: Artificial Sequence
<220> FEATURE:
<223> OTHER INFORMATION: CD37-51 VL-CDR2

<400> SEQUENCE: 42

Asp Thr Ser Lys Leu Ala Ser
1               5

<210> SEQ ID NO 43
<211> LENGTH: 9
<212> TYPE: PRT
<213> ORGANISM: Artificial Sequence
<220> FEATURE:
<223> OTHER INFORMATION: CD37-51 VL-CDR3

<400> SEQUENCE: 43

Gln Gln Trp Ser Ser Asn Pro Pro Thr
1               5

<210> SEQ ID NO 44
<211> LENGTH: 10
<212> TYPE: PRT
<213> ORGANISM: Artificial Sequence
<220> FEATURE:
<223> OTHER INFORMATION: CD37-56 VL-CDR1

<400> SEQUENCE: 44

Ser Ala Ser Ser Ser Val Thr Tyr Met His
1               5                   10

<210> SEQ ID NO 45
<211> LENGTH: 7
<212> TYPE: PRT
<213> ORGANISM: Artificial Sequence
<220> FEATURE:
<223> OTHER INFORMATION: CD37-56 VL-CDR2

<400> SEQUENCE: 45
```

```
Asp Thr Ser Lys Leu Ala Ser
1               5

<210> SEQ ID NO 46
<211> LENGTH: 9
<212> TYPE: PRT
<213> ORGANISM: Artificial Sequence
<220> FEATURE:
<223> OTHER INFORMATION: CD37-56 VL-CDR3

<400> SEQUENCE: 46

Gln Gln Trp Ile Ser Asp Pro Pro Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Humanized CD37-56 VL-CDR2

<400> SEQUENCE: 47

Asp Thr Ser Asn Leu Ala Ser
1               5

<210> SEQ ID NO 48
<211> LENGTH: 10
<212> TYPE: PRT
<213> ORGANISM: Artificial Sequence
<220> FEATURE:
<223> OTHER INFORMATION: CD37-57 VL-CDR1

<400> SEQUENCE: 48

Ser Ala Thr Ser Ser Val Thr Tyr Met His
1               5                   10

<210> SEQ ID NO 49
<211> LENGTH: 7
<212> TYPE: PRT
<213> ORGANISM: Artificial Sequence
<220> FEATURE:
<223> OTHER INFORMATION: CD37-57 VL-CDR2

<400> SEQUENCE: 49

Asp Thr Ser Lys Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: CD37-57 VL-CDR3

<400> SEQUENCE: 50

Gln Gln Trp Ser Asp Asn Pro Pro Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Humanized CD37-57 VL-CDR2

<400> SEQUENCE: 51
```

Asp Thr Ser Asn Leu Ala Ser
1               5

<210> SEQ ID NO 52
<211> LENGTH: 10
<212> TYPE: PRT
<213> ORGANISM: Artificial Sequence
<220> FEATURE:
<223> OTHER INFORMATION: CONSENSUS VL-CDR1
<220> FEATURE:
<221> NAME/KEY: MISC_FEATURE
<222> LOCATION: (3)..(3)
<223> OTHER INFORMATION: X is T or S

<400> SEQUENCE: 52

Ser Ala Xaa Ser Ser Val Thr Tyr Met His
1               5                   10

<210> SEQ ID NO 53
<211> LENGTH: 7
<212> TYPE: PRT
<213> ORGANISM: Artificial Sequence
<220> FEATURE:
<223> OTHER INFORMATION: CONSENSUS VL-CDR2
<220> FEATURE:
<221> NAME/KEY: MISC_FEATURE
<222> LOCATION: (4)..(4)
<223> OTHER INFORMATION: X is K or N
<220> FEATURE:
<221> NAME/KEY: MISC_FEATURE
<222> LOCATION: (6)..(6)
<223> OTHER INFORMATION: X is A or P
<220> FEATURE:
<221> NAME/KEY: MISC_FEATURE
<222> LOCATION: (7)..(7)
<223> OTHER INFORMATION: X is S or Y

<400> SEQUENCE: 53

Asp Thr Ser Xaa Leu Xaa Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: CONSENSUS VL-CDR3
<220> FEATURE:
<221> NAME/KEY: MISC_FEATURE
<222> LOCATION: (4)..(4)
<223> OTHER INFORMATION: X is I or S
<220> FEATURE:
<221> NAME/KEY: MISC_FEATURE
<222> LOCATION: (5)..(5)
<223> OTHER INFORMATION: X is S or D
<220> FEATURE:
<221> NAME/KEY: MISC_FEATURE
<222> LOCATION: (6)..(6)
<223> OTHER INFORMATION: X is N or D

<400> SEQUENCE: 54

Gln Gln Trp Xaa Xaa Xaa Pro Pro Thr
1               5

<210> SEQ ID NO 55
<211> LENGTH: 115
<212> TYPE: PRT
<213> ORGANISM: Artificial Sequence
<220> FEATURE:
<223> OTHER INFORMATION: muCD37-3

<400> SEQUENCE: 55

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ala Leu Lys
        50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 56
<211> LENGTH: 115
<212> TYPE: PRT
<213> ORGANISM: Artificial Sequence
<220> FEATURE:
<223> OTHER INFORMATION: chCD37-3

<400> SEQUENCE: 56

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ala Leu Lys
        50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 57
<211> LENGTH: 115
<212> TYPE: PRT
<213> ORGANISM: Artificial Sequence
<220> FEATURE:
<223> OTHER INFORMATION: huCD37-3v1.0

<400> SEQUENCE: 57

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Pro Ser Leu Lys

```
                50                  55                  60
Ser Arg Leu Ser Ile Lys Lys Asp His Ser Lys Ser Gln Val Phe Leu
 65                  70                  75                  80

Lys Leu Asn Ser Leu Thr Ala Ala Asp Thr Ala Thr Tyr Tyr Cys Ala
                 85                  90                  95

Lys Gly Gly Tyr Ser Leu Ala His Trp Gly Gln Gly Thr Leu Val Thr
                100                 105                 110

Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: huCD37-3v1.1

<400> SEQUENCE: 58

Gln Val Gln Val Gln Glu Ser Gly Pro Gly Leu Val Ala Pro Ser Gln
 1               5                  10                  15

Thr Leu Ser Ile Thr Cys Thr Val Ser Gly Phe Ser Leu Thr Thr Ser
                 20                  25                  30

Gly Val Ser Trp Val Arg Gln Pro Pro Gly Lys Gly Leu Glu Trp Leu
                 35                  40                  45

Gly Val Ile Trp Gly Asp Gly Ser Thr Asn Tyr His Ser Ser Leu Lys
                 50                  55                  60

Ser Arg Leu Ser Ile Lys Lys Asp His Ser Lys Ser Gln Val Phe Leu
 65                  70                  75                  80

Lys Leu Asn Ser Leu Thr Ala Ala Asp Thr Ala Thr Tyr Tyr Cys Ala
                 85                  90                  95

Lys Gly Gly Tyr Ser Leu Ala His Trp Gly Gln Gly Thr Leu Val Thr
                100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: muCD37-12

<400> SEQUENCE: 59

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Lys Tyr
                 20                  25                  30

Gly Met Asn Trp Val Lys Gln Ala Gln Gly Lys Gly Leu Lys Trp Met
                 35                  40                  45

Gly Trp Ile Asn Thr Asn Thr Gly Glu Ser Arg Asn Ala Glu Glu Phe
                 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Tyr Glu Asp Thr Ala Thr Tyr Phe Cys
                 85                  90                  95

Gly Arg Gly Thr Val Val Ala Asp Trp Gly Gln Gly Thr Thr Leu Thr
                100                 105                 110
```

Val Ser Ser
        115

<210> SEQ ID NO 60
<211> LENGTH: 115
<212> TYPE: PRT
<213> ORGANISM: Artificial Sequence
<220> FEATURE:
<223> OTHER INFORMATION: chCD37-12

<400> SEQUENCE: 60

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser
        115

<210> SEQ ID NO 61
<211> LENGTH: 120
<212> TYPE: PRT
<213> ORGANISM: Artificial Sequence
<220> FEATURE:
<223> OTHER INFORMATION: muCD37-38

<400> SEQUENCE: 61

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120

<210> SEQ ID NO 62
<211> LENGTH: 120
<212> TYPE: PRT
<213> ORGANISM: Artificial Sequence
<220> FEATURE:
<223> OTHER INFORMATION: chCD37-38

<400> SEQUENCE: 62

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120

<210> SEQ ID NO 63
<211> LENGTH: 120
<212> TYPE: PRT
<213> ORGANISM: Artificial Sequence
<220> FEATURE:
<223> OTHER INFORMATION: huCD37-38

<400> SEQUENCE: 63

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Gly Trp His Trp Ile Arg Gln Phe Pro Gly Lys Gly Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Ala Ala Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ser
        115                 120

<210> SEQ ID NO 64
<211> LENGTH: 120
<212> TYPE: PRT
<213> ORGANISM: Artificial Sequence
<220> FEATURE:
<223> OTHER INFORMATION: muCD37-50

<400> SEQUENCE: 64

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

```
Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
                100                 105                 110

Gly Thr Leu Val Thr Val Ser Ala
            115                 120

<210> SEQ ID NO 65
<211> LENGTH: 120
<212> TYPE: PRT
<213> ORGANISM: Artificial Sequence
<220> FEATURE:
<223> OTHER INFORMATION: huCD37-50

<400> SEQUENCE: 65

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
                20                  25                  30

Phe Ala Trp His Trp Ile Arg Gln His Pro Gly Asn Lys Leu Glu Trp
            35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
                100                 105                 110

Gly Thr Leu Val Thr Val Ser Ala
            115                 120

<210> SEQ ID NO 66
<211> LENGTH: 120
<212> TYPE: PRT
<213> ORGANISM: Artificial Sequence
<220> FEATURE:
<223> OTHER INFORMATION: muCD37-51

<400> SEQUENCE: 66

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Ser Ser Gly
                20                  25                  30

Phe Ala Trp His Trp Ile Arg Gln Phe Pro Gly Asn Lys Leu Glu Trp
            35                  40                  45

Met Gly Tyr Ile His Tyr Ser Gly Ser Thr Asn Tyr Ser Pro Ser Leu
    50                  55                  60

Lys Ser Arg Ile Ser Ile Thr Arg Asp Ser Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Val Tyr Trp Gly Gln
                100                 105                 110
```

```
Gly Thr Leu Val Thr Val Ser Ala
        115                 120
```

<210> SEQ ID NO 67
<211> LENGTH: 120
<212> TYPE: PRT
<213> ORGANISM: Artificial Sequence
<220> FEATURE:
<223> OTHER INFORMATION: huCD37-51

<400> SEQUENCE: 67

```
Glu Val Gln Leu Val Glu Ser Gly Pro Glu Val Lys Pro Gly Glu
1               5                   10                  15

Ser Leu Ser Leu Thr Cys Thr Val Ser Gly Tyr Ser Ile Ser Ser Gly
            20                  25                  30

Phe Ala Trp His Trp Ile Arg Gln Phe Pro Gly Lys Gly Leu Glu Trp
            35                  40                  45

Met Gly Tyr Ile His Tyr Ser Gly Ser Thr Asn Tyr Ser Pro Ser Leu
        50                  55                  60

Gln Gly Arg Ile Ser Ile Thr Arg Asp Ser Ser Ile Asn Gln Phe Phe
65                  70                  75                  80

Leu Gln Leu Asn Ser Val Thr Ala Ser Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala
        115                 120
```

<210> SEQ ID NO 68
<211> LENGTH: 120
<212> TYPE: PRT
<213> ORGANISM: Artificial Sequence
<220> FEATURE:
<223> OTHER INFORMATION: muCD37-56

<400> SEQUENCE: 68

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
            35                  40                  45

Met Gly Tyr Ile His Tyr Ser Gly Gly Thr Asn Tyr Asn Pro Ser Leu
        50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala
        115                 120
```

<210> SEQ ID NO 69
<211> LENGTH: 120
<212> TYPE: PRT
<213> ORGANISM: Artificial Sequence
<220> FEATURE:
<223> OTHER INFORMATION: huCD37-56

<400> SEQUENCE: 69

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala
        115                 120

<210> SEQ ID NO 70
<211> LENGTH: 120
<212> TYPE: PRT
<213> ORGANISM: Artificial Sequence
<220> FEATURE:
<223> OTHER INFORMATION: muCD37-57

<400> SEQUENCE: 70

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120

<210> SEQ ID NO 71
<211> LENGTH: 120
<212> TYPE: PRT
<213> ORGANISM: Artificial Sequence
<220> FEATURE:
<223> OTHER INFORMATION: huCD37-57

<400> SEQUENCE: 71

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

```
Met Gly Tyr Ile Leu Tyr Ser Gly Ser Thr Val Tyr Ser Pro Ser Leu
        50                  55                  60

Lys Ser Arg Ile Ser Ile Thr Arg Asp Thr Ser Lys Asn Gln Phe Phe
 65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
            115                 120

<210> SEQ ID NO 72
<211> LENGTH: 108
<212> TYPE: PRT
<213> ORGANISM: Artificial Sequence
<220> FEATURE:
<223> OTHER INFORMATION: muCD37-3

<400> SEQUENCE: 72

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Arg Ser Asn
                20                  25                  30

Leu Ala Trp Tyr Gln Lys Gln Gly Lys Ser Pro Gln Leu Leu Val
            35                  40                  45

Asn Val Ala Thr Asn Leu Ala Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105

<210> SEQ ID NO 73
<211> LENGTH: 108
<212> TYPE: PRT
<213> ORGANISM: Artificial Sequence
<220> FEATURE:
<223> OTHER INFORMATION: chCD37-3

<400> SEQUENCE: 73

Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Arg Ser Asn
                20                  25                  30

Leu Ala Trp Tyr Gln Gln Lys Gln Gly Lys Ser Pro Gln Leu Leu Val
            35                  40                  45

Asn Val Ala Thr Asn Leu Ala Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105
```

<210> SEQ ID NO 74
<211> LENGTH: 108
<212> TYPE: PRT
<213> ORGANISM: Artificial Sequence
<220> FEATURE:
<223> OTHER INFORMATION: huCD37-3 (1.0 and 1.1)

<400> SEQUENCE: 74

```
Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105
```

<210> SEQ ID NO 75
<211> LENGTH: 112
<212> TYPE: PRT
<213> ORGANISM: Artificial Sequence
<220> FEATURE:
<223> OTHER INFORMATION: muCD37-12

<400> SEQUENCE: 75

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110
```

<210> SEQ ID NO 76
<211> LENGTH: 112
<212> TYPE: PRT
<213> ORGANISM: Artificial Sequence
<220> FEATURE:
<223> OTHER INFORMATION: chCD37-12

<400> SEQUENCE: 76

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45
```

```
Lys Leu Leu Ile Lys Tyr Ala Ser Asn Leu Ala Ser Gly Val Pro Ala
        50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Tyr Thr Phe Gly Gly Gly Thr Lys Leu Glu Ile Lys Arg
                100                 105                 110

<210> SEQ ID NO 77
<211> LENGTH: 107
<212> TYPE: PRT
<213> ORGANISM: Artificial Sequence
<220> FEATURE:
<223> OTHER INFORMATION: muCD37-38

<400> SEQUENCE: 77

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Thr Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Gly
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ile Ser Asn Pro Pro Thr
                 85                  90                  95

Phe Gly Gly Gly Thr Lys Leu Glu Ile Lys Arg
                100                 105

<210> SEQ ID NO 78
<211> LENGTH: 107
<212> TYPE: PRT
<213> ORGANISM: Artificial Sequence
<220> FEATURE:
<223> OTHER INFORMATION: chCD37-38

<400> SEQUENCE: 78

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Thr Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Gly
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ile Ser Asn Pro Pro Thr
                 85                  90                  95

Phe Gly Gly Gly Thr Lys Leu Glu Ile Lys Arg
                100                 105

<210> SEQ ID NO 79
<211> LENGTH: 107
<212> TYPE: PRT
```

```
<213> ORGANISM: Artificial Sequence
<220> FEATURE:
<223> OTHER INFORMATION: huCD37-38

<400> SEQUENCE: 79

Asp Ile Val Leu Thr Gln Ser Pro Ala Ser Met Ser Ala Ser Pro Gly
1               5                   10                  15

Glu Arg Val Thr Met Thr Cys Ser Ala Ser Ser Ser Val Thr Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg
            100                 105

<210> SEQ ID NO 80
<211> LENGTH: 107
<212> TYPE: PRT
<213> ORGANISM: Artificial Sequence
<220> FEATURE:
<223> OTHER INFORMATION: muCD37-50

<400> SEQUENCE: 80

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Pro Tyr Gly Val Pro Gly Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg
            100                 105

<210> SEQ ID NO 81
<211> LENGTH: 107
<212> TYPE: PRT
<213> ORGANISM: Artificial Sequence
<220> FEATURE:
<223> OTHER INFORMATION: huCD37-50

<400> SEQUENCE: 81

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60
```

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg
            100                 105

<210> SEQ ID NO 82
<211> LENGTH: 107
<212> TYPE: PRT
<213> ORGANISM: Artificial Sequence
<220> FEATURE:
<223> OTHER INFORMATION: muCD37-51

<400> SEQUENCE: 82

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg
            100                 105

<210> SEQ ID NO 83
<211> LENGTH: 107
<212> TYPE: PRT
<213> ORGANISM: Artificial Sequence
<220> FEATURE:
<223> OTHER INFORMATION: huCD37-51

<400> SEQUENCE: 83

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
                20                  25                  30

His Trp Tyr Gln Gln Lys Pro Gly Gln Ser Pro Lys Arg Trp Ile Tyr
            35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg
            100                 105

<210> SEQ ID NO 84
<211> LENGTH: 107
<212> TYPE: PRT
<213> ORGANISM: Artificial Sequence
<220> FEATURE:
<223> OTHER INFORMATION: muCD37-56
```

<400> SEQUENCE: 84

Gln Ile Val Leu Thr Gln Ser Pro Ala Phe Met Ser Ala Ser Pro Gly
1               5                   10                  15

Asp Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg
            100                 105

<210> SEQ ID NO 85
<211> LENGTH: 107
<212> TYPE: PRT
<213> ORGANISM: Artificial Sequence
<220> FEATURE:
<223> OTHER INFORMATION: huCD37-56

<400> SEQUENCE: 85

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Pro Asp Gln Ser Pro Lys Arg Trp Ile Tyr
        35                  40                  45

Asp Thr Ser Asn Leu Ala Ser Gly Val Pro Ser Arg Phe Ser Gly Gly
    50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg
            100                 105

<210> SEQ ID NO 86
<211> LENGTH: 107
<212> TYPE: PRT
<213> ORGANISM: Artificial Sequence
<220> FEATURE:
<223> OTHER INFORMATION: muCD37-57

<400> SEQUENCE: 86

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

```
Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg
            100                 105

<210> SEQ ID NO 87
<211> LENGTH: 107
<212> TYPE: PRT
<213> ORGANISM: Artificial Sequence
<220> FEATURE:
<223> OTHER INFORMATION: huCD37-57

<400> SEQUENCE: 87

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
                20                  25                  30

His Trp Tyr Gln Gln Lys Pro Gly Gln Ser Pro Arg Arg Trp Ile Tyr
            35                  40                  45

Asp Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg
            100                 105

<210> SEQ ID NO 88
<211> LENGTH: 445
<212> TYPE: PRT
<213> ORGANISM: Artificial Sequence
<220> FEATURE:
<223> OTHER INFORMATION: muCD37-3

<400> SEQUENCE: 88

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
                20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ala Leu Lys
        50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
```

```
            165                 170                 175
Tyr Thr Leu Ser Ser Ser Val Thr Val Thr Ser Thr Trp Pro Ser
            180                 185                 190

Gln Ser Ile Thr Cys Asn Val Ala His Pro Ala Ser Ser Thr Lys Val
            195                 200                 205

Asp Lys Lys Ile Glu Pro Arg Gly Pro Thr Ile Lys Pro Cys Pro Pro
            210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
            245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
            275                 280                 285

Thr His Arg Glu Asp Tyr Asn Ser Thr Leu Arg Val Val Ser Ala Leu
            290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
            325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
            370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
            405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
            435                 440                 445

<210> SEQ ID NO 89
<211> LENGTH: 445
<212> TYPE: PRT
<213> ORGANISM: Artificial Sequence
<220> FEATURE:
<223> OTHER INFORMATION: chCD37-3

<400> SEQUENCE: 89

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
            35                  40                  45

Gly Val Ile Trp Gly Asp Gly Ser Thr Asn Tyr His Ser Ala Leu Lys
            50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
```

```
                    85                  90                  95
Lys Gly Gly Tyr Ser Leu Ala His Trp Gly Gln Gly Thr Leu Val Thr
                100                 105                 110
Val Ser Ala Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
            130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
                355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 90
<211> LENGTH: 444
<212> TYPE: PRT
<213> ORGANISM: Artificial Sequence
<220> FEATURE:
<223> OTHER INFORMATION: huCD37-3v1.0

<400> SEQUENCE: 90

Gln Val Gln Val Gln Glu Ser Gly Pro Gly Leu Val Ala Pro Ser Gln
```

-continued

```
1               5                   10                  15
Thr Leu Ser Ile Thr Cys Thr Val Ser Gly Phe Ser Leu Thr Thr Ser
                20                  25                  30
Gly Val Ser Trp Val Arg Gln Pro Gly Lys Gly Leu Glu Trp Leu
        35                  40                  45
Gly Val Ile Trp Gly Asp Gly Ser Thr Asn Tyr His Pro Ser Leu Lys
    50                  55                  60
Ser Arg Leu Ser Ile Lys Lys Asp His Ser Lys Ser Gln Val Phe Leu
65                  70                  75                  80
Lys Leu Asn Ser Leu Thr Ala Ala Asp Thr Ala Thr Tyr Tyr Cys Ala
                85                  90                  95
Lys Gly Gly Tyr Ser Leu Ala His Trp Gly Gln Gly Thr Leu Val Thr
                100                 105                 110
Val Ser Ser Ala Ser Thr Lys Gly Pro Ser Val Phe Pro Leu Ala Pro
                115                 120                 125
Ser Ser Lys Ser Thr Ser Gly Gly Thr Ala Ala Leu Gly Cys Leu Val
        130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
                180                 185                 190
Thr Gln Thr Tyr Ile Cys Asn Val Asn His Lys Pro Ser Asn Thr Lys
                195                 200                 205
Val Asp Lys Lys Val Glu Pro Lys Ser Cys Asp Lys Thr His Thr Cys
        210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
                260                 265                 270
Phe Asn Trp Tyr Val Asp Gly Val Glu Val His Asn Ala Lys Thr Lys
                275                 280                 285
Pro Arg Glu Glu Gln Tyr Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
                340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
        370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
```

His Tyr Thr Gln Lys Ser Leu Ser Leu Ser Pro Gly
            435                 440

<210> SEQ ID NO 91
<211> LENGTH: 444
<212> TYPE: PRT
<213> ORGANISM: Artificial Sequence
<220> FEATURE:
<223> OTHER INFORMATION: huCD37-3v1.1

<400> SEQUENCE: 91

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

```
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 92
<211> LENGTH: 445
<212> TYPE: PRT
<213> ORGANISM: Artificial Sequence
<220> FEATURE:
<223> OTHER INFORMATION: muCD37-12

<400> SEQUENCE: 92

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val
        195                 200                 205

Asp Lys Lys Ile Glu Pro Arg Gly Pro Thr Ile Lys Pro Cys Pro Pro
    210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270
```

Ile Ser Trp Phe Val Asn Asn Val Glu Val His Thr Ala Gln Thr Gln
            275                 280                 285

Thr His Arg Glu Asp Tyr Asn Ser Thr Leu Arg Val Val Ser Ala Leu
        290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
            355                 360                 365

Asp Phe Met Pro Glu Asp Ile Tyr Val Glu Trp Thr Asn Asn Gly Lys
370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 93
<211> LENGTH: 445
<212> TYPE: PRT
<213> ORGANISM: Artificial Sequence
<220> FEATURE:
<223> OTHER INFORMATION: chCD37-12

<400> SEQUENCE: 93

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
        35                  40                  45

Gly Trp Ile Asn Thr Asn Thr Gly Glu Ser Arg Asn Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

```
Thr Gln Thr Tyr Ile Cys Asn Val Asn His Lys Pro Ser Asn Thr Lys
            195                 200                 205
Val Asp Lys Lys Val Glu Pro Lys Ser Cys Asp Lys Thr His Thr Cys
210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
            245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
            275                 280                 285
Pro Arg Glu Glu Gln Tyr Asn Ser Thr Tyr Arg Val Val Ser Val Leu
            290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
            325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
            355                 360                 365
Gly Phe Tyr Pro Ser Asp Ile Ala Val Glu Trp Glu Ser Asn Gly Gln
            370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
            405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
            435                 440                 445

<210> SEQ ID NO 94
<211> LENGTH: 444
<212> TYPE: PRT
<213> ORGANISM: Artificial Sequence
<220> FEATURE:
<223> OTHER INFORMATION: muCD37-38

<400> SEQUENCE: 94

Asp Val Gln Leu Gln Glu Ser Gly Pro Asp Leu Val Lys Pro Ser Gln
1               5                   10                  15
Ser Leu Ser Leu Thr Cys Thr Val Thr Gly Tyr Ser Ile Thr Ser Gly
            20                  25                  30
Phe Gly Trp His Trp Ile Arg Gln Phe Pro Gly Asn Lys Leu Glu Trp
        35                  40                  45
Met Ala Tyr Ile Leu Tyr Ser Gly Gly Thr Asp Tyr Asn Pro Ser Leu
    50                  55                  60
Lys Ser Arg Ile Ser Ile Thr Arg Asp Thr Ser Lys Asn Gln Phe Phe
65                  70                  75                  80
Leu Arg Leu Ser Ser Val Thr Thr Glu Asp Thr Ala Thr Tyr Tyr Cys
                85                  90                  95
Ala Arg Gly Tyr Tyr Gly Tyr Gly Ala Trp Phe Val Tyr Trp Gly Gln
            100                 105                 110
```

Gly Thr Leu Val Thr Val Ser Ala Ala Lys Thr Thr Pro Pro Ser Val
            115                 120                 125

Tyr Pro Leu Ala Pro Gly Ser Ala Ala Gln Thr Asn Ser Met Val Thr
            130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
            165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
            210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
            290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
            325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asn Thr Asn Gly Ser
            385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
            435                 440

<210> SEQ ID NO 95
<211> LENGTH: 449
<212> TYPE: PRT
<213> ORGANISM: Artificial Sequence
<220> FEATURE:
<223> OTHER INFORMATION: chCD37-38

<400> SEQUENCE: 95

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

-continued

```
Phe Gly Trp His Trp Ile Arg Gln Phe Pro Gly Asn Lys Leu Glu Trp
             35                  40                  45

Met Ala Tyr Ile Leu Tyr Ser Gly Gly Thr Asp Tyr Asn Pro Ser Leu
 50                  55                  60

Lys Ser Arg Ile Ser Ile Thr Arg Asp Thr Ser Lys Asn Gln Phe Phe
 65                  70                  75                  80

Leu Arg Leu Ser Ser Val Thr Thr Glu Asp Thr Ala Thr Tyr Tyr Cys
                 85                  90                  95

Ala Arg Gly Tyr Tyr Gly Tyr Gly Ala Trp Phe Val Tyr Trp Gly Gln
                100                 105                 110

Gly Thr Leu Val Thr Val Ser Ala Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445
```

Gly

<210> SEQ ID NO 96
<211> LENGTH: 449
<212> TYPE: PRT
<213> ORGANISM: Artificial Sequence
<220> FEATURE:
<223> OTHER INFORMATION: huCD37-38

<400> SEQUENCE: 96

```
Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Gly Trp His Trp Ile Arg Gln Phe Pro Gly Lys Gly Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Ala Ala Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
```

```
                      355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 97
<211> LENGTH: 450
<212> TYPE: PRT
<213> ORGANISM: Artificial Sequence
<220> FEATURE:
<223> OTHER INFORMATION: muCD37-50

<400> SEQUENCE: 97

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270
```

```
Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
        290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Met Thr Lys Lys Gln Val Thr Leu
            355                 360                 365

Thr Cys Met Val Thr Asp Phe Met Pro Glu Asp Ile Tyr Val Glu Trp
        370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 98
<211> LENGTH: 449
<212> TYPE: PRT
<213> ORGANISM: Artificial Sequence
<220> FEATURE:
<223> OTHER INFORMATION: huCD37-50

<400> SEQUENCE: 98

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Val Thr Val Pro
            180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 99
<211> LENGTH: 450
<212> TYPE: PRT
<213> ORGANISM: Artificial Sequence
<220> FEATURE:
<223> OTHER INFORMATION: muCD37-51

<400> SEQUENCE: 99

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Ser Ser Gly
                20                  25                  30

Phe Ala Trp His Trp Ile Arg Gln Phe Pro Gly Asn Lys Leu Glu Trp
            35                  40                  45

Met Gly Tyr Ile His Tyr Ser Gly Ser Thr Asn Tyr Ser Pro Ser Leu
        50                  55                  60

Lys Ser Arg Ile Ser Ile Thr Arg Asp Ser Ser Lys Asn Gln Phe Phe
65                  70                  75                  80
```

-continued

```
Leu Gln Leu Asn Ser Val Thr Thr Glu Asp Thr Ala Thr Tyr Tyr Cys
                 85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450
```

<210> SEQ ID NO 100
<211> LENGTH: 449
<212> TYPE: PRT
<213> ORGANISM: Artificial Sequence
<220> FEATURE:
<223> OTHER INFORMATION: huCD37-51

<400> SEQUENCE: 100

```
Glu Val Gln Leu Val Glu Ser Gly Pro Glu Val Leu Lys Pro Gly Glu
1               5                   10                  15

Ser Leu Ser Leu Thr Cys Thr Val Ser Gly Tyr Ser Ile Ser Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Ser Thr Asn Tyr Ser Pro Ser Leu
    50                  55                  60

Gln Gly Arg Ile Ser Ile Thr Arg Asp Ser Ser Ile Asn Gln Phe Phe
65                  70                  75                  80

Leu Gln Leu Asn Ser Val Thr Ala Ser Asp Thr Ala Thr Tyr Tyr Cys
                85                  90                  95

Ala Arg Gly Tyr Tyr Gly Phe Gly Ala Trp Phe Val Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                405                 410                 415
Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 101
<211> LENGTH: 444
<212> TYPE: PRT
<213> ORGANISM: Artificial Sequence
<220> FEATURE:
<223> OTHER INFORMATION: muCD37-56

<400> SEQUENCE: 101

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320
```

```
Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 102
<211> LENGTH: 449
<212> TYPE: PRT
<213> ORGANISM: Artificial Sequence
<220> FEATURE:
<223> OTHER INFORMATION: huCD37-56

<400> SEQUENCE: 102

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240
```

```
Pro Ser Val Phe Leu Phe Pro Pro Lys Pro Lys Asp Thr Leu Met Ile
            245                 250                 255

Ser Arg Thr Pro Glu Val Thr Cys Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 103
<211> LENGTH: 450
<212> TYPE: PRT
<213> ORGANISM: Artificial Sequence
<220> FEATURE:
<223> OTHER INFORMATION: muCD37-57

<400> SEQUENCE: 103

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140
```

```
Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Val Thr Val Thr Ser
            180                 185                 190

Ser Thr Trp Pro Ser Gln Ser Ile Thr Cys Asn Val Ala His Pro Ala
                195                 200                 205

Ser Ser Thr Lys Val Asp Lys Lys Ile Glu Pro Arg Gly Pro Thr Ile
        210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Asp Val Ser Glu Asp
            260                 265                 270

Asp Pro Asp Val Gln Ile Ser Trp Phe Val Asn Asn Val Glu Val His
            275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
            355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
            435                 440                 445

Gly Lys
    450

<210> SEQ ID NO 104
<211> LENGTH: 449
<212> TYPE: PRT
<213> ORGANISM: Artificial Sequence
<220> FEATURE:
<223> OTHER INFORMATION: huCD37-57

<400> SEQUENCE: 104

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45
```

Met Gly Tyr Ile Leu Tyr Ser Gly Ser Thr Val Tyr Ser Pro Ser Leu
        50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
                100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 105

```
<211> LENGTH: 214
<212> TYPE: PRT
<213> ORGANISM: Artificial Sequence
<220> FEATURE:
<223> OTHER INFORMATION: muCD37-3

<400> SEQUENCE: 105

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 106
<211> LENGTH: 214
<212> TYPE: PRT
<213> ORGANISM: Artificial Sequence
<220> FEATURE:
<223> OTHER INFORMATION: chCD37-3

<400> SEQUENCE: 106

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Thr Val Ala Ala
```

```
                    100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 107
<211> LENGTH: 214
<212> TYPE: PRT
<213> ORGANISM: Artificial Sequence
<220> FEATURE:
<223> OTHER INFORMATION: huCD37-3 (1.0 and 1.1)

<400> SEQUENCE: 107

Asp Ile Gln Met Thr Gln Ser Pro Ser Ser Leu Ser Val Ser Val Gly
1               5                   10                  15
Glu Arg Val Thr Ile Thr Cys Arg Ala Ser Glu Asn Ile Arg Ser Asn
            20                  25                  30
Leu Ala Trp Tyr Gln Gln Lys Pro Gly Lys Ser Pro Lys Leu Leu Val
        35                  40                  45
Asn Val Ala Thr Asn Leu Ala Asp Gly Val Pro Ser Arg Phe Ser Gly
    50                  55                  60
Ser Gly Ser Gly Thr Asp Tyr Ser Leu Lys Ile Asn Ser Leu Gln Pro
65                  70                  75                  80
Glu Asp Phe Gly Thr Tyr Tyr Cys Gln His Tyr Trp Gly Thr Thr Trp
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 108
<211> LENGTH: 218
<212> TYPE: PRT
```

<213> ORGANISM: Artificial Sequence
<220> FEATURE:
<223> OTHER INFORMATION: muCD37-12

<400> SEQUENCE: 108

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 109
<211> LENGTH: 218
<212> TYPE: PRT
<213> ORGANISM: Artificial Sequence
<220> FEATURE:
<223> OTHER INFORMATION: chCD37-12

<400> SEQUENCE: 109

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

```
Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 110
<211> LENGTH: 213
<212> TYPE: PRT
<213> ORGANISM: Artificial Sequence
<220> FEATURE:
<223> OTHER INFORMATION: muCD37-38

<400> SEQUENCE: 110

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 111
<211> LENGTH: 213
<212> TYPE: PRT
<213> ORGANISM: Artificial Sequence
<220> FEATURE:
```

<223> OTHER INFORMATION: chCD37-38

<400> SEQUENCE: 111

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 112
<211> LENGTH: 213
<212> TYPE: PRT
<213> ORGANISM: Artificial Sequence
<220> FEATURE:
<223> OTHER INFORMATION: huCD37-38

<400> SEQUENCE: 112

Asp Ile Val Leu Thr Gln Ser Pro Ala Ser Met Ser Ala Ser Pro Gly
1               5                   10                  15

Glu Arg Val Thr Met Thr Cys Ser Ala Ser Ser Val Thr Tyr Met
            20                  25                  30

His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

```
Ala Ser Val Val Cys Leu Leu Asn Asn Phe Tyr Pro Arg Glu Ala Lys
            130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 113
<211> LENGTH: 213
<212> TYPE: PRT
<213> ORGANISM: Artificial Sequence
<220> FEATURE:
<223> OTHER INFORMATION: muCD37-50

<400> SEQUENCE: 113

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Pro Tyr Gly Val Pro Gly Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
        115                 120                 125

Ala Ser Val Val Cys Phe Leu Asn Asn Phe Tyr Pro Lys Asp Ile Asn
            130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 114
<211> LENGTH: 213
<212> TYPE: PRT
<213> ORGANISM: Artificial Sequence
<220> FEATURE:
<223> OTHER INFORMATION: huCD37-50
```

<400> SEQUENCE: 114

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 115
<211> LENGTH: 213
<212> TYPE: PRT
<213> ORGANISM: Artificial Sequence
<220> FEATURE:
<223> OTHER INFORMATION: muCD37-51

<400> SEQUENCE: 115

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn

```
                  130                 135                 140
Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
                195                 200                 205

Asn Arg Asn Glu Cys
        210
```

<210> SEQ ID NO 116
<211> LENGTH: 213
<212> TYPE: PRT
<213> ORGANISM: Artificial Sequence
<220> FEATURE:
<223> OTHER INFORMATION: huCD37-51

<400> SEQUENCE: 116

```
Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 117
<211> LENGTH: 213
<212> TYPE: PRT
<213> ORGANISM: Artificial Sequence
<220> FEATURE:
<223> OTHER INFORMATION: muCD37-56

<400> SEQUENCE: 117

```
Gln Ile Val Leu Thr Gln Ser Pro Ala Phe Met Ser Ala Ser Pro Gly
1               5                   10                  15

Asp Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Gly
        50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 118
<211> LENGTH: 213
<212> TYPE: PRT
<213> ORGANISM: Artificial Sequence
<220> FEATURE:
<223> OTHER INFORMATION: huCD37-56

<400> SEQUENCE: 118

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Val Thr Tyr Met
            20                  25                  30

His Trp Tyr Gln Gln Lys Pro Asp Gln Ser Pro Lys Arg Trp Ile Tyr
            35                  40                  45

Asp Thr Ser Asn Leu Ala Ser Gly Val Pro Ser Arg Phe Ser Gly Gly
        50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 119
<211> LENGTH: 213
<212> TYPE: PRT
<213> ORGANISM: Artificial Sequence
<220> FEATURE:
<223> OTHER INFORMATION: muCD37-57

<400> SEQUENCE: 119

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
            165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 120
<211> LENGTH: 213
<212> TYPE: PRT
<213> ORGANISM: Artificial Sequence
<220> FEATURE:
<223> OTHER INFORMATION: huCD37-57

<400> SEQUENCE: 120

Glu Ile Val Leu Thr Gln Ser Pro Ala Thr Met Ser Ala Ser Pro Gly
1               5                   10                  15

```
Glu Arg Val Thr Met Thr Cys Ser Ala Thr Ser Ser Val Thr Tyr Met
            20                  25                  30
His Trp Tyr Gln Gln Lys Pro Gly Gln Ser Pro Arg Trp Ile Tyr
        35                  40                  45
Asp Thr Ser Asn Leu Ala Ser Gly Val Pro Ala Arg Phe Ser Gly Ser
50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Asp Asn Pro Pro Thr
                85                  90                  95
Phe Gly Gln Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210
```

<210> SEQ ID NO 121
<211> LENGTH: 345
<212> TYPE: DNA
<213> ORGANISM: Artificial Sequence
<220> FEATURE:
<223> OTHER INFORMATION: muCD37-3

<400> SEQUENCE: 121

```
caggtgcagg tgaaggagtc aggacctggc ctggtggcgc cctcacagag cctgtccatt    60
acatgcactg tctcagggtt ctcattaacc acctctggtg taagctgggt tcgccagcct   120
ccaggaaagg gtctggagtg gctgggagta atatgggtg  acgggagcac aaactatcat   180
tcagctctca aatccagact gagcatcaag aaggatcact ccaagagcca gttttcttta   240
aaactgaaca gtctgcaaac tgatgacaca gccacgtact actgtgccaa aggaggctac   300
tcgttggctc actggggcca aggactctg  gtcacagtct ctgca                    345
```

<210> SEQ ID NO 122
<211> LENGTH: 431
<212> TYPE: DNA
<213> ORGANISM: Artificial Sequence
<220> FEATURE:
<223> OTHER INFORMATION: chCD37-3

<400> SEQUENCE: 122

```
aagcttgcca ccatggctgt cctggcactg ctcctctgcc tggtgacata cccaagctgt    60
gtcctatcac aggtgcaggt gaaggagtca ggacctggcc tggtggcgcc ctcacagagc   120
ctgtccatta catgcactgt ctcagggttc tcattaacca cctctggtgt aagctgggtt   180
cgccagcctc aggaaaggg  tctggagtgg ctgggagtaa tatgggtga  cgggagcaca   240
```

| | | |
|---|---|---|
| aactatcatt cagctctcaa atccagactg agcatcaaga aggatcactc caagagccaa | 300 | |
| gttttcttaa aactgaacag tctgcaaact gatgacacag ccacgtacta ctgtgccaaa | 360 | |
| ggaggctact cgttggctca ctggggccaa gggactctgg tcacagtctc tgcagcctct | 420 | |
| acgaagggcc c | 431 | |

<210> SEQ ID NO 123
<211> LENGTH: 431
<212> TYPE: DNA
<213> ORGANISM: Artificial Sequence
<220> FEATURE:
<223> OTHER INFORMATION: huCD37-3v1.0

<400> SEQUENCE: 123

| | | |
|---|---|---|
| aagcttgcca ccatgggttg gagctgcatt attctgtttc tggtggccac cgccaccggt | 60 | |
| gtgcactcac aagtccaagt ccaagaatct ggtccaggtc tggtggcccc ttcccaaact | 120 | |
| ctgagcatca cctgtaccgt ttctggtttt agccttacca cctctggtgt gagttgggta | 180 | |
| cgccaaccac ccggtaaggg tctcgaatgg ctgggtgtaa tctggggtga tggttccaca | 240 | |
| aattaccatc cttccctcaa gtcccgcctt agcatcaaaa aggatcacag caaaagtcaa | 300 | |
| gttttcctga aactgaatag tctgacagca gccgatacag ccacctacta ttgcgccaag | 360 | |
| ggtggttata gtcttgcaca ctggggtcaa ggtaccctcg ttaccgtctc ctcagctagt | 420 | |
| accaagggcc c | 431 | |

<210> SEQ ID NO 124
<211> LENGTH: 431
<212> TYPE: DNA
<213> ORGANISM: Artificial Sequence
<220> FEATURE:
<223> OTHER INFORMATION: huCD37-3v1.1

<400> SEQUENCE: 124

| | | |
|---|---|---|
| aagcttgcca ccatgggctg gagctgtatc attctgtttc tggtggcgac agctactggg | 60 | |
| gtccactccc aagtgcaggt acaagagtcc gggcctggat tggtcgcacc aagccagacc | 120 | |
| ctctctatca cttgtaccgt tagcgggttc tctctgacaa ccagtggagt gagttgggtg | 180 | |
| aggcagccac caggaaaggg actgagtgg ctggggtga tttggggcga cggcagcaca | 240 | |
| aactatcatt ccagtcttaa atctcggttg tccattaaaa aagaccatag taatctcaa | 300 | |
| gttttcctga aactcaatag cctgacagcc gcagacactg ctacgtatta ctgcgccaaa | 360 | |
| ggaggataca gtctggctca ctggggacag gggaccctgg tgaccgtgtc atccgcatca | 420 | |
| acaaagggcc c | 431 | |

<210> SEQ ID NO 125
<211> LENGTH: 345
<212> TYPE: DNA
<213> ORGANISM: Artificial Sequence
<220> FEATURE:
<223> OTHER INFORMATION: muCD37-12

<400> SEQUENCE: 125

| | | |
|---|---|---|
| cagatccagt tggtgcagtc tggacctgag ctgaagaagc ctggagagac agtcaagatc | 60 | |
| tcctgcaagg cttctgggta taccttcaca aagtatggaa tgaactgggt gaagcaggct | 120 | |
| caaggaaagg gtttaaagtg gatgggctgg ataaacacca acactggaga gtcaagaaat | 180 | |
| gctgaagaat tcaagggacg gtttgccttc tctttggaaa cctctgccag cactgcctat | 240 | |

```
ttgcagatca acaacctcaa atatgaggac acggctacat atttctgtgg aaggggcacg      300
gtagtagcgg actggggcca aggcaccact ctcacagtct cctca                     345
```

<210> SEQ ID NO 126
<211> LENGTH: 431
<212> TYPE: DNA
<213> ORGANISM: Artificial Sequence
<220> FEATURE:
<223> OTHER INFORMATION: chCD37-12

<400> SEQUENCE: 126

```
aagcttgcca ccatggggtg gtcatgcata atcctctttc tggtcgctac tgctaccggt       60
gtgcactcac agattcagct ggttcaaagt ggcccagagc tgaaaaagcc aggggaaaca      120
gtgaaaataa gttgcaaggc atccggttac actttcacaa agtacggcat gaactgggtc      180
aagcaggccc agggcaaggg gctcaaatgg atgggttgga tcaataccaa cactggcgag      240
tctaggaatg ctgaggagtt taagggccgg tttgccttca gcctggagac aagtgccagc      300
acagcttacc tgcaaatcaa caatctgaag tatgaggata cagcaaccta tttctgcggc      360
cgcggcactg tcgttgcaga ctggggacaa ggtaccacct tgactgtatc cagtgccagc      420
actaagggcc c                                                          431
```

<210> SEQ ID NO 127
<211> LENGTH: 360
<212> TYPE: DNA
<213> ORGANISM: Artificial Sequence
<220> FEATURE:
<223> OTHER INFORMATION: muCD37-38

<400> SEQUENCE: 127

```
gatgtgcagc ttcaggagtc aggacctgac ctggtgaaac cttctcagtc actttcactc       60
acctgcactg tcactggcta ctccatcacc agtggttttg gctggcactg gatccggcag      120
tttccaggaa acaagctgga atggatggcc tacatactct acagtggtgg cactgactac      180
aacccatctc tcaaaagtcg aatctctatc actcgagaca cttccaagaa ccagttcttc      240
ctgcggttga gttctgtgac tactgaggac acagccacat attactgtgc aagaggctac      300
tatggttacg gggcctggtt tgtttactgg ggccaaggga ctctggtcac tgtctctgca      360
```

<210> SEQ ID NO 128
<211> LENGTH: 446
<212> TYPE: DNA
<213> ORGANISM: Artificial Sequence
<220> FEATURE:
<223> OTHER INFORMATION: chCD37-38

<400> SEQUENCE: 128

```
aagcttgcca ccatgggctg gagttgtatc attctgtttt tggtggccac cgccactgga       60
gtccattccc aagtgcaact ccaggaatct ggccctgacc tggttaagcc atctcagagc      120
ctctccctga cctgcactgt tacaggatac tcaatcacat caggctttgg ctggcactgg      180
atcagacaat ttcccgggaa caagttggaa tggatggctt acattctgta tagcgggggt      240
accgattaca atccttccct caagagccga atctctatca ccagggatac aagcaagaac      300
caattttttc tccgcctcag ctctgtgact accgaagata ccgctactta ctattgtgcc      360 agggctact atggatatgg tgcatggttc gtctattggg gccagggaac cctggtgact      420
gtgagcgctg cctctaccaa gggccc                                          446
```

<210> SEQ ID NO 129
<211> LENGTH: 446
<212> TYPE: DNA
<213> ORGANISM: Artificial Sequence
<220> FEATURE:
<223> OTHER INFORMATION: huCD37-38

<400> SEQUENCE: 129

```
aagcttgcca ccatgggttg gagctgcatc attcttttcc tggtcgctac tgcaactgga       60
gtccactcac aggtccagct gcaagagtcc ggtcctgggc ttgtgaaacc cagccagtcc      120
ctcagtctca cctgtactgt ctctggctac tctattacca gtgggttcgg ctggcattgg      180
attaggcagt ttcccggtaa ggggctggag tggatggcat atatcctgta cagcggagga      240
accgattaca acccaagtct gaagagcagg atcagcatta cccgggacac aagcaaaaac      300 cagttttttcc ttcggctgtc tagtgttaca gctgcagaca ccgctactta ctattgtgct      360
cggggttact atggctatgg ggcttggttt gtgtattggg acaaggcac tcttgtgacc       420 gtgagcagcg cctcaacaaa gggccc                                           446
```

<210> SEQ ID NO 130
<211> LENGTH: 360
<212> TYPE: DNA
<213> ORGANISM: Artificial Sequence
<220> FEATURE:
<223> OTHER INFORMATION: muCD37-50

<400> SEQUENCE: 130

```
gatgtgcagc ttcaggagtc aggacctgac ctgttgaaac cttctcagtc actttcactc       60
acctgcactg tcactggcta ctccatcacc agtggttttg cctggcactg gatccggcag      120
tttccaggaa acaaactgga atggatgggc tacatactct acagtggtag cactgtctac      180
agcccatctc tcaaaagtcg aatctctatc actcgagaca catccaagaa ccacttcttc      240
ctgcagttga attctgtgac tactgaggac acagccacat attactgtgc aagagggtac      300
tatggttacg gcgcctggtt tgcttactgg ggccaaggga ctctggtcac tgtctctgca      360
```

<210> SEQ ID NO 131
<211> LENGTH: 360
<212> TYPE: DNA
<213> ORGANISM: Artificial Sequence
<220> FEATURE:
<223> OTHER INFORMATION: muCD37-51

<400> SEQUENCE: 131

```
gatgtgcagc ttcaggagtc aggacctgac ctgttgaaac cttctcagtc actttcactc       60
acctgcactg tcactggcta ctccatctcc agtggttttg cctggcactg gatccggcag      120
tttccaggaa acaaactgga atggatgggc tacatacact acagtggtag cactaactac      180
agcccatctc tcaaaagtcg aatctctatc actcgagact catccaagaa ccagttcttc      240
ctgcagttga attctgtgac tactgaggac acagccacat attactgtgc aagaggatac      300
tatggtttcg gcgcctggtt tgtttactgg ggccaaggga ctctggtcac tgtctctgca      360
```

<210> SEQ ID NO 132
<211> LENGTH: 360
<212> TYPE: DNA
<213> ORGANISM: Artificial Sequence
<220> FEATURE:
<223> OTHER INFORMATION: muCD37-56

<400> SEQUENCE: 132

```
gatgtgcagc ttcaggagtc aggacctgac ctggtgaaac cttctcagtc actttcactc    60
acctgcactg tcactggcta ctccatcacc agtggttttg cctggcactg gatccggcag   120
tttccaggaa acaaactgga atggatgggc tacatacact acagtggtgg cactaactac   180
aacccatctc tcaaaagtcg agtctctatc actcgagaca catccaagaa ccagttcttc   240
ctgcagttga attctgtgac tactgaggac acagccacat attactgtgc aagaggctac   300
tatggtttcg gggcctggtt tgcttactgg ggccaaggga ctctggtccc tgtctctgca   360
```

<210> SEQ ID NO 133
<211> LENGTH: 446
<212> TYPE: DNA
<213> ORGANISM: Artificial Sequence
<220> FEATURE:
<223> OTHER INFORMATION: huCD37-56

<400> SEQUENCE: 133

```
aagcttgcca ccatggggtg gagctgcatt atcctgttcc tcgtcgccac cgcaaccggc    60
gtccactccc aggtgcagct gcaagaaagc gggccaggat tggtaaaacc ttcccagtct   120
ctgagtctta cttgtaccgt atctggatac agtatcacat ctggcttcgc ctggcattgg   180
attcgccagt ttcccggcaa ggggcttgag tggatggggt atattcatta ttctggaggt   240
accaactaca accctccct gaagagtcga gtctcaatta ccagggacac ttccaagaac   300
caattctttt tgcagcttaa ttcagtgacc gctgccgaca ccgctactta ctactgcgcc   360
cggggctact atgggtttgg tgcctggttc gcctactggg gccagggac cctggtgccc   420 gtgtctgctg cctccacaaa gggccc                                        446
```

<210> SEQ ID NO 134
<211> LENGTH: 360
<212> TYPE: DNA
<213> ORGANISM: Artificial Sequence
<220> FEATURE:
<223> OTHER INFORMATION: muCD37-57

<400> SEQUENCE: 134

```
gatgtgcagc ttcaggagtc aggacctgac ctgttgaaac cttctcagtc actttcactc    60
acctgcactg tcactggcta ctccatcacc agtggttttg cctggcactg gatccggcag   120
tttccaggaa acaaactgga atggatgggc tacatactct acagtggtag cactgtctac   180
agcccatctc tcaaaagtcg aatctctatc actcgagaca catccaagaa ccagttcttc   240
ctgcagttga attctgtgac tactgaggac acagccacat attactgtgc aagagggtac   300
tatggttacg gcgcctggtt tgcttactgg ggccaaggga ctctggtcac tgtctctgca   360
```

<210> SEQ ID NO 135
<211> LENGTH: 446
<212> TYPE: DNA
<213> ORGANISM: Artificial Sequence
<220> FEATURE:
<223> OTHER INFORMATION: huCD37-57

<400> SEQUENCE: 135

```
aagcttgcca ccatgggctg gagctgcatc attctgtttc tggtggccac agcaactggc    60
gttcacagtc aagtccaact gcaggagagc ggccccggac tcctgaaacc atctcagtca   120
ctcagtctga catgtactgt gagcggctac agcattacct caggcttcgc ttggcattgg   180
atcaggcagt tccccggaaa aggtctggag tggatggggt acattctgta cagcggcagt   240
acagtgtatt caccctcctt gaaatctagg atatcaatca cacgtgatac aagcaaaaat   300
```

```
cagttcttcc tccagctgaa ctccgtcacc gccgcagaca cagcaaccta ttattgtgct    360
cgcggatact acggatatgg cgcatggttc gcctattggg gccaggggac actcgtgacc    420
gtttccgccg cctccacaaa gggccc                                         446
```

<210> SEQ ID NO 136
<211> LENGTH: 324
<212> TYPE: DNA
<213> ORGANISM: Artificial Sequence
<220> FEATURE:
<223> OTHER INFORMATION: muCD37-3

<400> SEQUENCE: 136

```
gacatccaga tgactcagtc tccagcctcc ctttctgtat ctgtgggaga aactgtcacc     60
atcacatgtc gagcaagtga gaatattcgc agtaatttag catggtatca gcagaaacag    120
ggaaaatctc ctcagctcct ggtcaatgtt gcaacaaact tagcagatgg tgtgccatca    180
aggttcagtg gcagtggatc aggcacacag tattccctca agatcaacag cctgcagtct    240
gaagattttg ggacttatta ctgtcaacat tattgggta ctacgtggac gttcggtgga    300
ggcaccaagc tggaaatcaa acgt                                           324
```

<210> SEQ ID NO 137
<211> LENGTH: 399
<212> TYPE: DNA
<213> ORGANISM: Artificial Sequence
<220> FEATURE:
<223> OTHER INFORMATION: chCD37-3

<400> SEQUENCE: 137

```
gaattcgcca ccatgagtgt gcccactcag gtcctggggt tgctgctgct gtggcttaca     60
gatgccagat gtgacatcca gatgactcag tctccagcct cccttctgt atctgtggga   120 gaaactgtca ccatcacatg tcgagcaagt gagaatattc gcagtaattt agcatggtat   180
cagcagaaac agggaaaatc tcctcagctc ctggtcaatg ttgcaacaaa cttagcagat   240
ggtgtgccat caaggttcag tggcagtgga tcaggcacac agtattccct caagatcaac   300
agcctgcagt ctgaagattt tgggacttat tactgtcaac attattgggg tactacgtgg   360
acgttcggtg gaggcaccaa gctggaaatc aaacgtacg                          399
```

<210> SEQ ID NO 138
<211> LENGTH: 396
<212> TYPE: DNA
<213> ORGANISM: Artificial Sequence
<220> FEATURE:
<223> OTHER INFORMATION: huCD37-3 (1.0 and 1.1)

<400> SEQUENCE: 138

```
gaattcgcca ccatgggttg gtcctgcatc atcttgtttc tcgtggccac agccaccggt     60
gttcactctg atatacaaat gactcaaagc ccttccagtt tgagcgtaag tgtgggtgaa   120
cgcgtaacaa tcacctgtag agctagtgaa aacatccgca gtaatctcgc atggtaccaa   180
caaaagccag gtaagtcacc taagctcctc gtgaatgttg ctaccaacct cgctgatggt   240
gtgccttcac gattctctgg ttcaggttcc ggtaccgatt attcacttaa gatcaactca   300
ctccaaccag aagatttcgg tacatattac tgtcaacact actggggtac gacctggaca   360
ttcggtcaag gtactaagct ggaaatcaag cgtacg                              396
```

<210> SEQ ID NO 139

```
<211> LENGTH: 336
<212> TYPE: DNA
<213> ORGANISM: Artificial Sequence
<220> FEATURE:
<223> OTHER INFORMATION: muCD37-12

<400> SEQUENCE: 139
gacattgtgc taacacagtc tcctgcttcc ttagctgtat ctctgggca gagggccacc      60
atctcatgca gggccagcca aagtgtcagt acatctagct atagttattt gtactggttc     120
cagcagaaac caggacagcc acccaaactc ctcatcaagt atgcatccaa cctagcatct    180
ggggtccctg ccaggttcag tggcagtggg tctgggacag acttcaccct caacatccat    240
cctgtggagg aggaggatac tgcaacatat tactgtcaac acagttggga gattccgtac    300
acgttcggag ggggaccaa actggaaata aaacgg                               336

<210> SEQ ID NO 140
<211> LENGTH: 408
<212> TYPE: DNA
<213> ORGANISM: Artificial Sequence
<220> FEATURE:
<223> OTHER INFORMATION: chCD37-12

<400> SEQUENCE: 140
gaattcgcca ccatgggttg gtcctgtata atcctgttct tggtggccac cgctactggc     60
gttcatagtg atattgtact cactcagtca ccagccagtc tggcagtgtc cctgggccag    120
cgtgccacca tctcctgccg ggcctcacag tccgtgagca ctagctctta ttcctatctc    180
tactggtttc aacagaagcc aggacagccc ctaagctgc tgatcaagta cgcctccaac     240
ctcgccagcg gcgttcccgc tagattctct ggttccggta gcggaactga tttcactttg    300
aacatccacc ccgttgagga gaggatacc gccacttact attgtcaaca ctcttgggag    360
attccttaca cctttggagg aggaacaaag ctcgaaatta agcgtacg                 408

<210> SEQ ID NO 141
<211> LENGTH: 321
<212> TYPE: DNA
<213> ORGANISM: Artificial Sequence
<220> FEATURE:
<223> OTHER INFORMATION: muCD37-38

<400> SEQUENCE: 141
caaattgttc tcacccagtc tccagcaatc atgtctgcat ctccagggga gaaggtcacc     60
atgacctgca gtgccagctc aagtgtaact tacatgcact ggtaccagca gaagtcaggc    120
acctccccca aaagatggat ttatgacaca tccaaactgg cttctggagt ccctgctcgc    180
ttcagtggcg gtgggtctgg gacctcttac tctctcacaa tcagcagcat ggaggctgaa    240
gatgctgcca cttattactg ccagcagtgg attagtaacc cacccacgtt cggagggggg    300
accaagctgg aaattaaacg g                                              321

<210> SEQ ID NO 142
<211> LENGTH: 393
<212> TYPE: DNA
<213> ORGANISM: Artificial Sequence
<220> FEATURE:
<223> OTHER INFORMATION: chCD37-38

<400> SEQUENCE: 142
gaattcgcca ccatgggctg gtcctgtatc atcctgtttc tcgtggccac agctacaggt     60
gttcattctc agattgtgct gacccaatca ccagctatta tgtccgctag ccccggcgag   120
```

```
aaagtgacaa tgacatgtag cgctagctct tctgtgactt acatgcattg gtatcaacag    180
aagtcaggta ccagtcccaa gcgttggatc tacgacacat ccaaactggc ctccggagtc    240
cctgccaggt tcagcggagg tgggtccggc accagttatt cactgaccat atcctctatg    300
gaagctgaag atgctgctac ttattattgt caacaatgga tttctaaccc cccaccttt     360 ggtggcggaa caaagctgga gatcaagcgt acg                                  393
```

<210> SEQ ID NO 143
<211> LENGTH: 393
<212> TYPE: DNA
<213> ORGANISM: Artificial Sequence
<220> FEATURE:
<223> OTHER INFORMATION: huCD37-38

<400> SEQUENCE: 143

```
gaattcgcca ccatgggatg gtcctgcatt attctgttct tggtcgccac tgctactggc    60
gttcactctg acattgtgct cacacagtct ccagcctcaa tgtctgcttc ccccggtgag    120
cgggtgacca tgacatgctc tgccagttcc tccgtgacat atatgcattg gtatcagcaa    180
aaacccggta cctctccaaa agatggatc tacgacactt caaagcttgc atcaggcgtt     240
cctgccagat tttccgggtc tgggtctggc acttcataca gtctgaccat agttccatg     300 gaagctgaag atgcagccac ctattactgt cagcagtgga tttcaaatcc tctaccttc    360 ggcggcggaa ccaaactgga gataaagcgt acg                                  393
```

<210> SEQ ID NO 144
<211> LENGTH: 321
<212> TYPE: DNA
<213> ORGANISM: Artificial Sequence
<220> FEATURE:
<223> OTHER INFORMATION: muCD37-50

<400> SEQUENCE: 144

```
caaattgttc tcacccagtc tccagcaatc atgtctgcat ctccagggga aaggtcacc    60 atgacctgca gtgccacctc aagtgtgact tacatgcact ggtaccagca gaagtcaggc    120
acctccccca aagatggat ttatgacaca tccaaactgc cttatggagt ccctggtcgt     180
ttcagtggta gtgggtctgg gacctcttac tctctcacaa tcagcagcat ggaggctgaa    240
gatgctgcca cttattactg ccagcagtgg agtgataacc cacccacgtt cggctcgggg    300
acaaagttgg aaataaagcg g                                               321
```

<210> SEQ ID NO 145
<211> LENGTH: 393
<212> TYPE: DNA
<213> ORGANISM: Artificial Sequence
<220> FEATURE:
<223> OTHER INFORMATION: huCD37-50

<400> SEQUENCE: 145

```
gaattcgcca ccatgggttg gtcatgcatt attctgttcc tggttgctac cgcaacagga    60
gtacatagtg agatagtcct cacccaaagt cctgctacta tgtctgccag cccaggagag    120
cgtgtgacca tgacttgctc tgcaacctca agtgtgacat acatgcattg gtatcagcaa    180
aagcctggcc aatcccctaa aggtggatc tacgatactt ctaatctgcc atacggtgtg     240
cccgcaaggt tctccgggag tggcagtggc accagtata gtctgaccat cagttcaatg    300
gaagcagagg atgcagcaac ctattattgt cagcagtggt ccgataatcc ccctactttt    360
```

```
ggtcaggta caaagctgga gattaagcgt acg                              393
```

```
<210> SEQ ID NO 146
<211> LENGTH: 321
<212> TYPE: DNA
<213> ORGANISM: Artificial Sequence
<220> FEATURE:
<223> OTHER INFORMATION: muCD37-51

<400> SEQUENCE: 146
caaattgttc tcacccagtc tccagcaatc atgtctgcat ctccagggga gaaggtcacc    60
atgacctgca gtgccacctc aagtgtgact tacatgcact ggtaccagca gaagtcaggc   120
acctccccca aaagatggat ttatgacaca tccaaactgg cttctggagt ccctgctcgc   180
ttcagtggca gtgggtctgg gacctcttac tctctcacaa tcagcaacat ggaggctgaa   240
gatgctgcca cttattactg ccagcagtgg agtagtaacc cacccacgtt cggctcgggg   300
acaaagttgg aaataaagcg g                                              321
```

```
<210> SEQ ID NO 147
<211> LENGTH: 393
<212> TYPE: DNA
<213> ORGANISM: Artificial Sequence
<220> FEATURE:
<223> OTHER INFORMATION: huCD37-51

<400> SEQUENCE: 147
gaattcgcca ccatgggatg gagctgtatt attctgttcc tggttgctac tgctactggc    60
gtccattccg agatagtcct cacccagagc cccgcaacca tgagtgcctc ccctggggag   120
cgagtgacta tgacttgttc cgccacttct tcagttacct atatgcattg gtatcagcag   180
aaacctggac agtctccaaa gcgttggatt tacgacacct ccaacctggc ttcaggagtt   240
cctgctaggt tcagcggatc tgggtctggc acaagttatt cactcaccat tagttccatg   300
gaggccgaag atgccgctac ttactactgt cagcagtgga gcagcaaccc ccctacattc   360
gggcagggaa ctaagctgga gatcaaacgt acg                                 393
```

```
<210> SEQ ID NO 148
<211> LENGTH: 321
<212> TYPE: DNA
<213> ORGANISM: Artificial Sequence
<220> FEATURE:
<223> OTHER INFORMATION: muCD37-56

<400> SEQUENCE: 148
caaattgttc tcacccagtc tccagcattc atgtctgcat ctccagggga taaggtcacc    60
atgacctgca gtgccagttc aagtgttact tacatgcact ggtatcagca gaagtcaggc   120
acctccccca aaagatggat ttatgacaca tccaaactgg cttctggagt ccctgctcgc   180
ttcagtggcg gtgggtctgg gacctcttac tctctcacaa tcagcaccat ggaggctgaa   240
gatgctgcca cttattactg ccagcagtgg attagtgacc cacccacgtt cggaggggggg   300
accaagctgg aaataaaacg g                                              321
```

```
<210> SEQ ID NO 149
<211> LENGTH: 393
<212> TYPE: DNA
<213> ORGANISM: Artificial Sequence
<220> FEATURE:
<223> OTHER INFORMATION: huCD37-56

<400> SEQUENCE: 149
```

```
gaattcgcca ccatgggctg gtcctgtatc atcctgtttc tggtggcaac cgctactggg      60
gttcactctg atattgtcct gacacagagt ccagccttca tgagtgcttc tcccggagaa     120
aaggtcacaa tgacttgttc agcttcctcc tccgtcacat acatgcattg gtaccagcag     180
aagcctgacc agagtcctaa gaggtggatc tatgatacaa gcaatctggc ttccggtgtc     240
ccctcccgct tttcaggcgg cggaagcgga actgactata gccttaccat ctcctcaatg     300
gaagccgagg acgctgctac atattactgc cagcaatgga tcagcgaccc tcctactttc     360
ggacagggaa caaaattgga aattaagcgt acg                                  393

<210> SEQ ID NO 150
<211> LENGTH: 321
<212> TYPE: DNA
<213> ORGANISM: Artificial Sequence
<220> FEATURE:
<223> OTHER INFORMATION: muCD37-57

<400> SEQUENCE: 150
caaattgttc tcacccagtc tccagcaatc atgtctgcat ctccagggga gaaggtcacc      60
atgacctgca gtgccacctc aagtgtgact tacatgcact ggtaccagca gaagtcaggc     120
acctccccca aagatggat ttatgacaca tccaaactgg cttctggagt ccctgctcgc      180
ttcagtggca gtgggtctgg gacctcttac tctctcacaa tcagcagcat ggaggctgaa     240
gatgctgcca cttattactg ccagcagtgg agtgataacc cacccacgtt cggctcgggg     300
acaaagttgg aaataaagcg g                                               321

<210> SEQ ID NO 151
<211> LENGTH: 393
<212> TYPE: DNA
<213> ORGANISM: Artificial Sequence
<220> FEATURE:
<223> OTHER INFORMATION: huCD37-57

<400> SEQUENCE: 151
gaattcgcca ccatggggtg gtcctgtatt atcctgttcc tggtcgcaac cgccacaggc      60
gttcactccg agatcgtgtt gactcagagc ccagccacca tgtccgcttc ccccggggag     120
agagtgacaa tgacttgttc cgccacaagt tctgtaacct acatgcattg gtaccagcaa     180
aaaccaggac agagtccccg tcgttggatt tatgatacct ctaacctggc ttcaggcgtt     240
cctgcccgct tttctggtag tggatctggg acttcctata gccttaccat aagctctatg     300
gaagccgagg acgccgctac atactactgc cagcagtgga gtgataaccc ccccaccttc     360
gggcagggaa ccaaattgga gatcaaacgt acg                                  393

<210> SEQ ID NO 152
<211> LENGTH: 1410
<212> TYPE: DNA
<213> ORGANISM: Artificial Sequence
<220> FEATURE:
<223> OTHER INFORMATION: chCD37-3

<400> SEQUENCE: 152
aagcttgcca ccatggctgt cctggcactg ctcctctgcc tggtgacata cccaagctgt      60
gtcctatcac aggtgcaggt gaaggagtca ggacctggcc tggtggcgcc ctcacagagc     120
ctgtccatta catgcactgt ctcagggttc tcattaacca cctctggtgt aagctgggtt     180
cgccagcctc caggaaaggg tctggagtgg ctggagtaa tatggggtga cgggagcaca     240
```

```
aactatcatt cagctctcaa atccagactg agcatcaaga aggatcactc caagagccaa    300 gtttcttaa aactgaacag tctgcaaact gatgacacag ccacgtacta ctgtgccaaa    360
ggaggctact cgttggctca ctggggccaa gggactctgg tcacagtctc tgcagcctct    420
acgaagggcc catcagtttt ccccttggct ccaagttcta aatccacaag cggtggaaca    480
gctgcactgg gatgcctcgt taaagattat ttccctgagc ctgtgacagt gagctggaat    540
agcggagcat tgacttcagg tgtgcacact tttcccgctg tgttgcagtc ctccggtctg    600
tactcactgt ccagtgtcgt aaccgtccct tctagcagct gggaaccca gacctacatc    660 tgtaacgtca accataaacc atccaacaca aaggtggata agaaggttga accaaagagc    720
tgtgataaga cacatacatg ccctccttgt cctgcaccag agctcctcgg aggtccatct    780
gtgttcctgt tccccccaa acccaaggac actcttatga tctctcgtac tccagaggtc    840
acctgtgttg ttgtcgacgt gagccatgaa gatcccgagg ttaaattcaa ctggtacgtg    900
gatggagtcg aggttcacaa tgccaagacc aagcccaggg aggagcaata taattctaca    960
tatcgggtag tgagcgttct gaccgtgctc caccaagatt ggctcaatgg aaaagagtac    1020
aagtgcaagg tgtccaacaa ggctcttccc gctcccattg agaaaactat ctccaaagcc    1080
aaggggcagc cacgggaacc ccaggtgtat acattgcccc catctagaga cgagctgacc    1140
aagaaccagg tgagtctcac ttgtctggtc aaggggtttt acccttctga cattgctgta    1200
gagtgggagt ctaacggaca gccagaaaac aactacaaga caactccccc agtgctggac    1260
agcgacggga gcttcttcct ctactccaag ttgactgtag acaagtctag atggcagcaa    1320
ggaaacgttt ctcctgctc agtaatgcat gaggctctgc acaatcacta cccagaaaa    1380 tcactgtccc ttagcccagg gtgactcgag                                    1410

<210> SEQ ID NO 153
<211> LENGTH: 1410
<212> TYPE: DNA
<213> ORGANISM: Artificial Sequence
<220> FEATURE:
<223> OTHER INFORMATION: huCD37-3v1.0

<400> SEQUENCE: 153
aagcttgcca ccatggggttg gagctgcatt attctgtttc tggtggccac cgccaccggt    60
gtgcactcac aagtccaagt ccaagaatct ggtccaggtc tggtggcccc ttcccaaact    120
ctgagcatca cctgtaccgt ttctggtttt agccttacca cctctggtgt gagttgggta    180
cgccaaccac ccggtaaggg tctcgaatgg ctgggtgtaa tctggggtga tggttccaca    240
aattaccatc cttccctcaa gtcccgcctt agcatcaaaa aggatcacag caaaagtcaa    300 gtttcctga aactgaatag tctgacagca gccgatacag ccacctacta ttgcgccaag    360
ggtggttata gtcttgcaca ctggggtcaa ggtaccctcg ttaccgtctc ctcagctagt    420
accaagggcc catcagtttt ccccttggct ccaagttcta aatccacaag cggtggaaca    480
gctgcactgg gatgcctcgt taaagattat ttccctgagc ctgtgacagt gagctggaat    540
agcggagcat tgacttcagg tgtgcacact tttcccgctg tgttgcagtc ctccggtctg    600
tactcactgt ccagtgtcgt aaccgtccct tctagcagct gggaaccca gacctacatc    660 tgtaacgtca accataaacc atccaacaca aaggtggata agaaggttga accaaagagc    720
tgtgataaga cacatacatg ccctccttgt cctgcaccag agctcctcgg aggtccatct    780
gtgttcctgt tccccccaa acccaaggac actcttatga tctctcgtac tccagaggtc    840
acctgtgttg ttgtcgacgt gagccatgaa gatcccgagg ttaaattcaa ctggtacgtg    900
```

```
gatggagtcg aggttcacaa tgccaagacc aagcccaggg aggagcaata taattctaca    960
tatcgggtag tgagcgttct gaccgtgctc caccaagatt ggctcaatgg aaaagagtac   1020
aagtgcaagg tgtccaacaa ggctcttccc gctcccattg agaaaactat ctccaaagcc   1080
aaggggcagc cacgggaacc ccaggtgtat acattgcccc catctagaga cgagctgacc   1140
aagaaccagg tgagtctcac ttgtctggtc aaggggtttt accttctga cattgctgta    1200 gagtgggagt ctaacggaca gccagaaaac aactacaaga caactccccc agtgctggac   1260
agcgacggga gcttcttcct ctactccaag ttgactgtag acaagtctag atggcagcaa   1320
ggaaacgttt tctcctgctc agtaatgcat gaggctctgc acaatcacta tacccagaaa   1380
tcactgtccc ttagcccagg gtgactcgag                                    1410
```

<210> SEQ ID NO 154
<211> LENGTH: 1410
<212> TYPE: DNA
<213> ORGANISM: Artificial Sequence
<220> FEATURE:
<223> OTHER INFORMATION: huCD37-3v1.1

<400> SEQUENCE: 154

```
aagcttgcca ccatgggctg agctgtatc attctgtttc tggtggcgac agctactggg     60
gtccactccc aagtgcaggt acaagagtcc gggcctggat tggtcgcacc aagccagacc   120
ctctctatca cttgtaccgt tagcgggttc tctctgacaa ccagtggagt gagttgggtg   180
aggcagccac caggaaaggg actggagtgg ctggggggtga tttggggcga cggcagcaca   240
aactatcatt ccagtcttaa atctcggttg tccattaaaa aagaccatag taaatctcaa   300
gttttcctga aactcaatag cctgacagcc gcagacactg ctacgtatta ctgcgccaaa   360
ggaggataca gtctggctca ctggggacag gggaccctgg tgaccgtgtc atccgcatca   420
acaaagggcc catcagtttt ccccttggct ccaagttcta atccacaag cggtggaaca    480 gctgcactgg gatgcctcgt taaagattat ttccctgagc ctgtgacagt gagctggaat   540
agcggagcat tgacttcagg tgtgcacact tttcccgctg tgttcagtc ctccggtctg    600 tactcactgt ccagtgtcgt aaccgtccct tctagcagct ggggaaccca gacctacatc   660
tgtaacgtca accataaacc atccaacaca aaggtggata agaaggttga accaaagagc   720
tgtgataaga cacatacatg ccctccttgt cctgcaccag agctcctcgg aggtccatct   780
gtgttcctgt ttcccccaa acccaaggac actcttatga tctctcgtac tccagaggtc    840
acctgtgttg ttgtcgacgt gagccatgaa gatcccgagg ttaaattcaa ctggtacgtg    900
gatggagtcg aggttcacaa tgccaagacc aagcccaggg aggagcaata taattctaca    960
tatcgggtag tgagcgttct gaccgtgctc caccaagatt ggctcaatgg aaaagagtac   1020
aagtgcaagg tgtccaacaa ggctcttccc gctcccattg agaaaactat ctccaaagcc   1080
aaggggcagc cacgggaacc ccaggtgtat acattgcccc catctagaga cgagctgacc   1140
aagaaccagg tgagtctcac ttgtctggtc aaggggtttt accttctga cattgctgta    1200 gagtgggagt ctaacggaca gccagaaaac aactacaaga caactccccc agtgctggac   1260
agcgacggga gcttcttcct ctactccaag ttgactgtag acaagtctag atggcagcaa   1320
ggaaacgttt tctcctgctc agtaatgcat gaggctctgc acaatcacta tacccagaaa   1380
tcactgtccc ttagcccagg gtgactcgag                                    1410
```

<210> SEQ ID NO 155

<211> LENGTH: 1410
<212> TYPE: DNA
<213> ORGANISM: Artificial Sequence
<220> FEATURE:
<223> OTHER INFORMATION: chCD37-12

<400> SEQUENCE: 155

| | | | | | |
|---|---|---|---|---|---|
| aagcttgcca | ccatggggtg | gtcatgcata | atcctctttc | tggtcgctac | tgctaccggt | 60 |
| gtgcactcac | agattcagct | ggttcaaagt | ggcccagagc | tgaaaaagcc | aggggaaaca | 120 |
| gtgaaaataa | gttgcaaggc | atccggttac | actttcacaa | agtacggcat | gaactgggtc | 180 |
| aagcaggccc | agggcaaggg | gctcaaatgg | atgggttgga | tcaataccaa | cactggcgag | 240 |
| tctaggaatg | ctgaggagtt | taagggccgg | tttgccttca | gcctggagac | aagtgccagc | 300 |
| acagcttacc | tgcaaatcaa | caatctgaag | tatgaggata | cagcaaccta | tttctgcggc | 360 |
| cgcggcactg | tcgttgcaga | ctggggacaa | ggtaccacct | tgactgtatc | cagtgccagc | 420 |
| actaagggcc | catcagtttt | cccccttggct | ccaagttcta | aatccacaag | cggtggaaca | 480 |
| gctgcactgg | gatgcctcgt | taagattat | ttccctgagc | ctgtgacagt | gagctggaat | 540 |
| agcggagcat | tgacttcagg | tgtgcacact | tttcccgctg | tgttgcagtc | ctccggtctg | 600 |
| tactcactgt | ccagtgtcgt | aaccgtccct | tctagcagct | gggaaccca | gacctacatc | 660 |
| tgtaacgtca | accataaacc | atccaacaca | aaggtggata | gaaggttga | accaaagagc | 720 |
| tgtgataaga | cacatacatg | ccctccttgt | cctgcaccag | agctcctcgg | aggtccatct | 780 |
| gtgttcctgt | tccccccaa | acccaaggac | actcttatga | tctctcgtac | tccagaggtc | 840 |
| acctgtgttg | ttgtcgacgt | gagccatgaa | gatcccgagg | ttaaattcaa | ctggtacgtg | 900 |
| gatggagtcg | aggttcacaa | tgccaagacc | aagcccaggg | aggagcaata | taattctaca | 960 |
| tatcgggtag | tgagcgttct | gaccgtgctc | caccaagatt | ggctcaatgg | aaaagagtac | 1020 |
| aagtgcaagg | tgtccaacaa | ggctcttccc | gctcccattg | agaaaactat | ctccaaagcc | 1080 |
| aaggggcagc | cacgggaacc | ccaggtgtat | acattgcccc | catctagaga | cgagctgacc | 1140 |
| aagaaccagg | tgagtctcac | ttgtctggtc | aaggggtttt | acccttctga | cattgctgta | 1200 |
| gagtgggagt | ctaacggaca | gccagaaaac | aactacaaga | caactccccc | agtgctggac | 1260 |
| agcgacggga | gcttcttcct | ctactccaag | ttgactgtag | acaagtctag | atggcagcaa | 1320 |
| ggaaacgttt | tctcctgctc | agtaatgcat | gaggctctgc | acaatcacta | tcccagaaa | 1380 |
| tcactgtccc | ttagcccagg | gtgactcgag | | | | 1410 |

<210> SEQ ID NO 156
<211> LENGTH: 1425
<212> TYPE: DNA
<213> ORGANISM: Artificial Sequence
<220> FEATURE:
<223> OTHER INFORMATION: chCD37-38

<400> SEQUENCE: 156

| | | | | | |
|---|---|---|---|---|---|
| aagcttgcca | ccatgggctg | gagttgtatc | attctgtttt | tggtggccac | cgccactgga | 60 |
| gtccattccc | aagtgcaact | ccaggaatct | ggccctgacc | tggttaagcc | atctcagagc | 120 |
| ctctccctga | cctgcactgt | tacaggatac | tcaatcacat | caggctttgg | ctggcactgg | 180 |
| atcagacaat | ttcccgggaa | caagttggaa | tggatggctt | acattctgta | tagcggggt | 240 |
| accgattaca | atccttccct | caagagccga | atctctatca | ccagggatac | aagcaagaac | 300 |
| caatttttc | tccgcctcag | ctctgtgact | accgaagata | ccgctactta | ctattgtgcc | 360 |
| agggggctact | atggatatgg | tgcatggttc | gtctattggg | gccagggaac | cctggtgact | 420 |

```
gtgagcgctg cctctaccaa gggcccatca gttttcccct tggctccaag ttctaaatcc      480
acaagcggtg aacagctgc actgggatgc ctcgttaaag attatttccc tgagcctgtg      540
acagtgagct ggaatagcgg agcattgact tcaggtgtgc acacttttcc cgctgtgttg      600
cagtcctccg gtctgtactc actgtccagt gtcgtaaccg tcccttctag cagcttggga      660
acccagacct acatctgtaa cgtcaaccat aaaccatcca acacaaaggt ggataagaag      720
gttgaaccaa agagctgtga taagacacat acatgccctc cttgtcctgc accagagctc      780
ctcggaggtc catctgtgtt cctgtttccc ccaaaccca aggacactct tatgatctct       840
cgtactccag aggtcacctg tgttgttgtc gacgtgagcc atgaagatcc cgaggttaaa      900
ttcaactggt acgtggatgg agtcgaggtt cacaatgcca agaccaagcc cagggaggag     960
caatataatt ctacatatcg ggtagtgagc gttctgaccg tgctccacca agattggctc    1020
aatggaaaag agtacaagtg caaggtgtcc aacaaggctc ttcccgctcc cattgagaaa    1080
actatctcca aagccaaggg gcagccacgg gaacccagg tgtatacatt gcccccatct     1140
agagacgagc tgaccaagaa ccaggtgagt ctcacttgtc tggtcaaggg gttttaccct   1200
tctgacattg ctgtagagtg ggagtctaac ggacagccag aaaacaacta caagacaact    1260
cccccagtgc tggacagcga cgggagcttc ttcctctact ccaagttgac tgtagacaag    1320
tctagatggc agcaaggaaa cgttttctcc tgctcagtaa tgcatgaggc tctgcacaat    1380
cactataccc agaaatcact gtcccttagc ccagggtgac tcgag                    1425

<210> SEQ ID NO 157
<211> LENGTH: 1425
<212> TYPE: DNA
<213> ORGANISM: Artificial Sequence
<220> FEATURE:
<223> OTHER INFORMATION: huCD37-38

<400> SEQUENCE: 157
aagcttgcca ccatgggttg agctgcatc attcttttcc tggtcgctac tgcaactgga       60
gtccactcac aggtccagct gcaagagtcc ggtcctgggc ttgtgaaacc cagccagtcc     120
ctcagtctca cctgtactgt ctctggctac tctattacca gtgggttcgg ctggcattgg    180
attaggcagt ttcccggtaa ggggctggag tggatggcat atatcctgta cagcggagga    240
accgattaca acccaagtct gaagagcagg atcagcatta cccgggacac aagcaaaaac    300 cagttttttcc ttcggctgtc tagtgttaca gctgcagaca ccgctactta ctattgtgct    360
cggggttact atggctatgg ggcttggttt gtgtattggg acaaggcac tcttgtgacc      420 gtgagcagcg cctcaacaaa gggcccatca gttttcccct tggctccaag ttctaaatcc    480
acaagcggtg aacagctgc actgggatgc ctcgttaaag attatttccc tgagcctgtg     540
acagtgagct ggaatagcgg agcattgact tcaggtgtgc acacttttcc cgctgtgttg    600
cagtcctccg gtctgtactc actgtccagt gtcgtaaccg tcccttctag cagcttggga    660
acccagacct acatctgtaa cgtcaaccat aaaccatcca acacaaaggt ggataagaag    720
gttgaaccaa agagctgtga taagacacat acatgccctc cttgtcctgc accagagctc    780
ctcggaggtc catctgtgtt cctgtttccc ccaaaccca aggacactct tatgatctct      840
cgtactccag aggtcacctg tgttgttgtc gacgtgagcc atgaagatcc cgaggttaaa    900
ttcaactggt acgtggatgg agtcgaggtt cacaatgcca agaccaagcc cagggaggag    960
caatataatt ctacatatcg ggtagtgagc gttctgaccg tgctccacca agattggctc   1020
```

| aatggaaaag agtacaagtg caaggtgtcc aacaaggctc ttcccgctcc cattgagaaa | 1080 |
| actatctcca aagccaaggg gcagccacgg gaacccagg tgtatacatt gcccccatct | 1140 |
| agagacgagc tgaccaagaa ccaggtgagt ctcacttgtc tggtcaaggg gttttaccct | 1200 |
| tctgacattg ctgtagagtg ggagtctaac ggacagccag aaaacaacta caagacaact | 1260 |
| cccccagtgc tggacagcga cgggagcttc ttcctctact ccaagttgac tgtagacaag | 1320 |
| tctagatggc agcaaggaaa cgttttctcc tgctcagtaa tgcatgaggc tctgcacaat | 1380 |
| cactataccc agaaatcact gtcccttagc ccagggtgac tcgag | 1425 |

<210> SEQ ID NO 158
<211> LENGTH: 1425
<212> TYPE: DNA
<213> ORGANISM: Artificial Sequence
<220> FEATURE:
<223> OTHER INFORMATION: huCD37-50

<400> SEQUENCE: 158

| aagcttgcca ccatggggtg gtcctgcata atccttttcc tggttgctac tgctaccgga | 60 |
| gtccattcac aggtgcagct gcaggagtcc ggccccggcc tgctcaagcc ttctcagagt | 120 |
| ctgagtctga cttgtactgt ttctggctac agcataacca gcggtttcgc ttggcactgg | 180 |
| atcagacagc atcccggcaa caaactggag tggatgggat acatactgta ctcaggctca | 240 |
| actgtctatt cccctccct gaaatccgg atcagtatta cccgtgacac ttctaagaac | 300 |
| catttttttc tgcagctgaa cagcgttacc gcagctgaca ctgcaaccta ctactgtgcc | 360 |
| cggggatatt atggatacgg agcttggttc gcttactggg gccaaggcac cctcgtaact | 420 |
| gtgagtgctg cttccaccaa gggcccatca gttttcccct ggctccaag ttctaaatcc | 480 |
| acaagcggtg aacagctgc actgggatgc ctcgttaaag attatttccc tgagcctgtg | 540 |
| acagtgagct ggaatagcgg agcattgact tcaggtgtgc acactttttcc cgctgtgttg | 600 |
| cagtcctccg gtctgtactc actgtccagt gtcgtaaccg tcccttctag cagcttggga | 660 |
| acccagacct acatctgtaa cgtcaaccat aaaccatcca acacaaaggt ggataagaag | 720 |
| gttgaaccaa agagctgtga taagacacat acatgccctc cttgtcctgc accagagctc | 780 |
| ctcggaggtc catctgtgtt cctgtttccc cccaaaccca aggacactct tatgatctct | 840 |
| cgtactccag aggtcacctg tgttgttgtc gacgtgagcc atgaagatcc cgaggttaaa | 900 |
| ttcaactggt acgtggatgg agtcgaggtt cacaatgcca agaccaagcc cagggaggag | 960 |
| caatataatt ctacatatcg ggtagtgagc gttctgaccg tgctccacca agattggctc | 1020 |
| aatggaaaag agtacaagtg caaggtgtcc aacaaggctc ttcccgctcc cattgagaaa | 1080 |
| actatctcca aagccaaggg gcagccacgg gaacccagg tgtatacatt gcccccatct | 1140 |
| agagacgagc tgaccaagaa ccaggtgagt ctcacttgtc tggtcaaggg gttttaccct | 1200 |
| tctgacattg ctgtagagtg ggagtctaac ggacagccag aaaacaacta caagacaact | 1260 |
| cccccagtgc tggacagcga cgggagcttc ttcctctact ccaagttgac tgtagacaag | 1320 |
| tctagatggc agcaaggaaa cgttttctcc tgctcagtaa tgcatgaggc tctgcacaat | 1380 |
| cactataccc agaaatcact gtcccttagc ccagggtgac tcgag | 1425 |

<210> SEQ ID NO 159
<211> LENGTH: 1425
<212> TYPE: DNA
<213> ORGANISM: Artificial Sequence
<220> FEATURE:
<223> OTHER INFORMATION: huCD37-51

<400> SEQUENCE: 159

```
aagcttgcca ccatgggttg gtcttgcatc atcctgttcc tggtggccac tgccactggc      60
gtgcattcag aagttcagtt ggtggagtcc ggcccagaag tgctgaaacc cggcgaatca     120
ctgtccctga cttgtaccgt gtcaggttat agcatcagca gcggctttgc ttggcactgg     180
attcggcagt tccaggcaa gggactggaa tggatgggct acatccatta cagtggctca     240
accaattaca gccctagcct gcagggccga atctctatta ccagggatag ttctattaac     300
cagttttttcc tgcagcttaa ttccgtgact gcctctgaca cagcaactta ctattgcgcc    360
cgtggctact acgggttcgg agcctggttt gtatactggg gtcagggcac cctggtcact    420
gtctcagccg cctctaccaa gggcccatca gttttcccct ggctccaag ttctaaatcc    480
acaagcggtg aacagctgc actgggatgc ctcgttaaag attatttccc tgagcctgtg    540
acagtgagct ggaatagcgg agcattgact tcaggtgtgc acacttttcc cgctgtgttg    600
cagtcctccg gtctgtactc actgtccagt gtcgtaaccg tcccttctag cagcttggga    660
acccagacct acatctgtaa cgtcaaccat aaaccatcca acacaaaggt ggataagaag    720
gttgaaccaa agagctgtga taagacacat acatgccctc cttgtcctgc accagagctc    780
ctcggaggtc catctgtgtt cctgtttccc cccaaaccca aggacactct tatgatctct    840
cgtactccag aggtcacctg tgttgttgtc gacgtgagcc atgaagatcc cgaggttaaa    900
ttcaactggt acgtggatgg agtcgaggtt cacaatgcca agaccaagcc cagggaggag    960
caatataatt ctacatatcg ggtagtgagc gttctgaccg tgctccacca agattggctc   1020
aatggaaaag agtacaagtg caaggtgtcc aacaaggctc ttcccgctcc cattgagaaa   1080
actatctcca aagccaaggg gcagccacgg gaaccccagg tgtatacatt gcccccatct   1140
agagacgagc tgaccaagaa ccaggtgagt ctcacttgtc tggtcaaggg gttttaccct   1200
tctgacattg ctgtagagtg ggagtctaac ggacagccag aaaacaacta caagacaact   1260
cccccagtgc tggacagcga cgggagcttc ttcctctact ccaagttgac tgtagacaag   1320
tctagatggc agcaaggaaa cgttttctct tgctcagtaa tgcatgaggc tctgcacaat   1380
cactataccc agaaatcact gtcccttagc ccagggtgac tcgag                   1425
```

<210> SEQ ID NO 160
<211> LENGTH: 1425
<212> TYPE: DNA
<213> ORGANISM: Artificial Sequence
<220> FEATURE:
<223> OTHER INFORMATION: huCD37-56

<400> SEQUENCE: 160

```
aagcttgcca ccatggggtg gagctgcatt atcctgttcc tcgtcgccac cgcaaccggc      60
gtccactccc aggtgcagct gcaagaaagc gggccaggat tggtaaaacc ttcccagtct     120
ctgagtctta cttgtaccgt atctggatac agtatcacat ctggcttcgc ctggcattgg     180
attcgccagt tccccggcaa ggggcttgag tggatggggt atattcatta ttctggaggt     240
accaactaca acccttccct gaagagtcga gtctcaatta ccaggacac ttccaagaac     300
caattctttt tgcagcttaa ttcagtgacc gctgccgaca ccgctactta ctactgcgcc    360
cggggctact atgggttggg tgcctggttc gcctactggg gccagggac cctggtgccc    420
gtgtctgctg cctccacaaa gggcccatca gttttcccct ggctccaag ttctaaatcc    480
acaagcggtg aacagctgc actgggatgc ctcgttaaag attatttccc tgagcctgtg    540
```

```
acagtgagct ggaatagcgg agcattgact tcaggtgtgc acactttcc cgctgtgttg        600 cagtcctccg gtctgtactc actgtccagt gtcgtaaccg tcccttctag cagcttggga        660
acccagacct acatctgtaa cgtcaaccat aaaccatcca acacaaaggt ggataagaag        720
gttgaaccaa agagctgtga taagacacat acatgccctc cttgtcctgc accagagctc        780
ctcggaggtc catctgtgtt cctgtttccc cccaaaccca aggacactct tatgatctct        840
cgtactccag aggtcacctg tgttgttgtc gacgtgagcc atgaagatcc cgaggttaaa        900
ttcaactggt acgtggatgg agtcgaggtt cacaatgcca agaccaagcc cagggaggag        960
caatataatt ctacatatcg ggtagtgagc gttctgaccg tgctccacca agattggctc       1020
aatggaaaag agtacaagtg caaggtgtcc aacaaggctc ttcccgctcc cattgagaaa       1080
actatctcca aagccaaggg gcagccacgg gaaccccagg tgtatacatt gcccccatct       1140
agagacgagc tgaccaagaa ccaggtgagt ctcacttgtc tggtcaaggg gttttaccct       1200
tctgacattg ctgtagagtg ggagtctaac ggacagccag aaaacaacta caagacaact       1260
cccccagtgc tggacagcga cgggagcttc ttcctctact ccaagttgac tgtagacaag       1320
tctagatggc agcaaggaaa cgttttctcc tgctcagtaa tgcatgaggc tctgcacaat       1380
cactataccc agaaatcact gtcccttagc ccagggtgac tcgag                       1425

<210> SEQ ID NO 161
<211> LENGTH: 1425
<212> TYPE: DNA
<213> ORGANISM: Artificial Sequence
<220> FEATURE:
<223> OTHER INFORMATION: huCD37-57

<400> SEQUENCE: 161
aagcttgcca ccatgggctg gagctgcatc attctgtttc tggtggccac agcaactggc         60
gttcacagtc aagtccaact gcaggagagc ggccccggac tcctgaaacc atctcagtca        120
ctcagtctga catgtactgt gagcggctac agcattacct caggcttcgc ttggcattgg        180
atcaggcagt tccccggaaa aggtctggag tggatggggt acattctgta cagcggcagt        240
acagtgtatt cacctccctt gaaatctagg atatcaatca cacgtgatac aagcaaaaat        300
cagttcttcc tccagctgaa ctccgtcacc gccgcagaca cagcaaccta ttattgtgct        360
cgcggatact acggatatgg cgcatggttc gcctattggg gccagggac actcgtgacc        420 gtttccgccg cctccacaaa gggcccatca gttttccct tggctccaag ttctaaatcc         480
acaagcggtg aacagctgc actgggatgc ctcgttaaag attatttccc tgagcctgtg        540
acagtgagct ggaatagcgg agcattgact tcaggtgtgc acactttcc cgctgtgttg        600 cagtcctccg gtctgtactc actgtccagt gtcgtaaccg tcccttctag cagcttggga        660
acccagacct acatctgtaa cgtcaaccat aaaccatcca acacaaaggt ggataagaag        720
gttgaaccaa agagctgtga taagacacat acatgccctc cttgtcctgc accagagctc        780
ctcggaggtc catctgtgtt cctgtttccc cccaaaccca aggacactct tatgatctct        840
cgtactccag aggtcacctg tgttgttgtc gacgtgagcc atgaagatcc cgaggttaaa        900
ttcaactggt acgtggatgg agtcgaggtt cacaatgcca agaccaagcc cagggaggag        960
caatataatt ctacatatcg ggtagtgagc gttctgaccg tgctccacca agattggctc       1020
aatggaaaag agtacaagtg caaggtgtcc aacaaggctc ttcccgctcc cattgagaaa       1080
actatctcca aagccaaggg gcagccacgg gaaccccagg tgtatacatt gcccccatct       1140
agagacgagc tgaccaagaa ccaggtgagt ctcacttgtc tggtcaaggg gttttaccct       1200
```

| | |
|---|---|
| tctgacattg ctgtagagtg ggagtctaac ggacagccag aaaacaacta caagacaact | 1260 |
| cccccagtgc tggacagcga cgggagcttc ttcctctact ccaagttgac tgtagacaag | 1320 |
| tctagatggc agcaaggaaa cgttttctcc tgctcagtaa tgcatgaggc tctgcacaat | 1380 |
| cactataccc agaaatcact gtcccttagc ccagggtgac tcgag | 1425 |

<210> SEQ ID NO 162
<211> LENGTH: 717
<212> TYPE: DNA
<213> ORGANISM: Artificial Sequence
<220> FEATURE:
<223> OTHER INFORMATION: chCD37-3

<400> SEQUENCE: 162

| | |
|---|---|
| gaattcgcca ccatgagtgt gcccactcag gtcctggggt tgctgctgct gtggcttaca | 60 |
| gatgccagat gtgacatcca gatgactcag tctccagcct cccttctgt atctgtggga | 120 |
| gaaactgtca ccatcacatg tcgagcaagt gagaatattc gcagtaattt agcatggtat | 180 |
| cagcagaaac agggaaaatc tcctcagctc ctggtcaatg ttgcaacaaa cttagcagat | 240 |
| ggtgtgccat caaggttcag tgcagtgga tcaggcacac agtattccct caagatcaac | 300 |
| agcctgcagt ctgaagattt tgggacttat tactgtcaac attattgggg tactacgtgg | 360 |
| acgttcggtg gaggcaccaa gctggaaatc aaacgtacgg tggctgcacc atctgtcttc | 420 |
| atcttcccgc catctgatga gcagttgaaa tctggaactg cctctgttgt gtgcctgctg | 480 |
| aataacttct atcccagaga ggccaaagta cagtggaagg tggataacgc ctccaatcg | 540 |
| ggtaactccc aggagagtgt cacagagcag gacagcaagg acagcaccta cagcctcagc | 600 |
| agcaccctga cgctgagcaa agcagactac gagaaacaca agtctacgc ctgcgaagtc | 660 |
| acccatcagg gcctgagctc gcccgtcaca aagagcttca caggggaga gtgttag | 717 |

<210> SEQ ID NO 163
<211> LENGTH: 714
<212> TYPE: DNA
<213> ORGANISM: Artificial Sequence
<220> FEATURE:
<223> OTHER INFORMATION: huCD37-3 (1.0 and 1.1)

<400> SEQUENCE: 163

| | |
|---|---|
| gaattcgcca ccatgggttg gtcctgcatc atcttgtttc tcgtggccac agccaccggt | 60 |
| gttcactctg atatacaaat gactcaaagc ccttccagtt tgagcgtaag tgtgggtgaa | 120 |
| cgcgtaacaa tcacctgtag agctagtgaa aacatccgca gtaatctcgc atggtaccaa | 180 |
| caaaagccag gtaagtcacc taagctcctc gtgaatgttg ctaccaacct cgctgatggt | 240 |
| gtgccttcac gattctctgg ttcaggttcc ggtaccgatt attcacttaa gatcaactca | 300 |
| ctccaaccag aagatttcgg tacatattac tgtcaacact actggggtac gacctggaca | 360 |
| ttcggtcaag gtactaagct ggaaatcaag cgtacggtgg ctgcaccatc tgtcttcatc | 420 |
| ttcccgccat ctgatgagca gttgaaatct ggaactgcct ctgttgtgtg cctgctgaat | 480 |
| aacttctatc ccagagaggc caaagtacag tggaaggtgg ataacgccct ccaatcgggt | 540 |
| aactcccagg agagtgtcac agagcaggac agcaaggaca gcacctacag cctcagcagc | 600 |
| accctgacgc tgagcaaagc agactacgag aaacacaaag tctacgcctg cgaagtcacc | 660 |
| catcagggcc tgagctcgcc cgtcacaaag agcttcaaca ggggagagtg ttag | 714 |

<210> SEQ ID NO 164

<211> LENGTH: 726
<212> TYPE: DNA
<213> ORGANISM: Artificial Sequence
<220> FEATURE:
<223> OTHER INFORMATION: chCD37-12

<400> SEQUENCE: 164

```
gaattcgcca ccatgggttg gtcctgtata atcctgttct tggtggccac cgctactggc      60
gttcatagtg atattgtact cactcagtca ccagccagtc tggcagtgtc cctgggccag     120
cgtgccacca tctcctgccg ggcctcacag tccgtgagca ctagctctta ttcctatctc     180
tactggtttc aacagaagcc aggacagccc cctaagctgc tgatcaagta cgcctccaac     240
ctcgccagcg gcgttcccgc tagattctct ggttccggta gcggaactga tttcactttg     300
aacatccacc ccgttgagga gaggatacc gccacttact attgtcaaca ctcttgggag      360
attccttaca cctttggagg aggaacaaag ctcgaaatta gcgtacggt ggctgcacca      420
tctgtcttca tcttcccgcc atctgatgag cagttgaaat ctggaactgc ctctgttgtg     480
tgcctgctga ataacttcta tcccagagag gccaaagtac agtggaaggt ggataacgcc     540
ctccaatcgg gtaactccca ggagagtgtc acagagcagg acagcaagga cagcacctac     600
agcctcagca gcaccctgac gctgagcaaa gcagactacg agaaacacaa agtctacgcc     660
tgcgaagtca cccatcaggg cctgagctcg cccgtcacaa gagcttcaa caggggagag      720
tgttag                                                                726
```

<210> SEQ ID NO 165
<211> LENGTH: 711
<212> TYPE: DNA
<213> ORGANISM: Artificial Sequence
<220> FEATURE:
<223> OTHER INFORMATION: chCD37-38

<400> SEQUENCE: 165

```
gaattcgcca ccatgggctg gtcctgtatc atcctgtttc tcgtggccac agctacaggt      60
gttcattctc agattgtgct gacccaatca ccagctatta tgtccgctag ccccggcgag     120
aaagtgacaa tgacatgtag cgctagctct tctgtgactt acatgcattg gtatcaacag     180
aagtcaggta ccagtcccaa gcgttggatc tacgacacat ccaaactggc ctccggagtc     240
cctgccaggt tcagcggagg tgggtccggc accagttatt cactgaccat atcctctatg     300
gaagctgaag atgctgctac ttattattgt caacaatgga tttctaaccc cccaccttt      360
ggtggcggaa caaagctgga gatcaagcgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata cgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g               711
```

<210> SEQ ID NO 166
<211> LENGTH: 711
<212> TYPE: DNA
<213> ORGANISM: Artificial Sequence
<220> FEATURE:
<223> OTHER INFORMATION: huCD37-38

<400> SEQUENCE: 166

```
gaattcgcca ccatgggatg gtcctgcatt attctgttct tggtcgccac tgctactggc      60
```

```
gttcactctg acattgtgct cacacagtct ccagcctcaa tgtctgcttc ccccggtgag    120
cgggtgacca tgacatgctc tgccagttcc tccgtgacat atatgcattg gtatcagcaa    180
aaacccggta cctctccaaa aagatggatc tacgacactt caaagcttgc atcaggcgtt    240
cctgccagat tttccgggtc tgggtctggc acttcataca gtctgaccat tagttccatg    300
gaagctgaag atgcagccac ctattactgt cagcagtgga tttcaaatcc tcctaccttc    360
ggcggcggaa ccaaactgga gataaagcgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac    540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g             711
```

<210> SEQ ID NO 167
<211> LENGTH: 711
<212> TYPE: DNA
<213> ORGANISM: Artificial Sequence
<220> FEATURE:
<223> OTHER INFORMATION: huCD37-50

<400> SEQUENCE: 167

```
gaattcgcca ccatgggttg gtcatgcatt attctgttcc tggttgctac cgcaacagga    60
gtacatagtg atatagtcct cacccaaagt cctgctacta tgtctgccag cccaggagag    120
cgtgtgacca tgacttgctc tgcaacctca agtgtgacat acatgcattg gtatcagcaa    180
aagcctggcc aatcccctaa aaggtggatc tacgatactt ctaatctgcc ataccggtgtg   240 cccgcaaggt tctccgggag tgggtcagtggc accagttata gtctgaccat cagttcaatg    300
gaagcagagg atgcagcaac ctattattgt cagcagtggt ccgataatcc ccctactttt    360
ggtcagggta caaagctgga gattaagcgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata cgccctcca atcgggtaac    540 tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g             711
```

<210> SEQ ID NO 168
<211> LENGTH: 711
<212> TYPE: DNA
<213> ORGANISM: Artificial Sequence
<220> FEATURE:
<223> OTHER INFORMATION: huCD37-51

<400> SEQUENCE: 168

```
gaattcgcca ccatgggatg gagctgtatt attctgttcc tggttgctac tgctactggc    60
gtccattccg atatagtcct cacccagagc cccgcaacca tgagtgcctc ccctggggag    120
cgagtgacta tgacttgttc cgccacttct tcagttacct atatgcattg gtatcagcag    180
aaacctggac agtctccaaa gcgttggatt tacgacacct ccaacctggc ttcaggagtt    240
cctgctaggt tcagcggatc tgggtctggc acaagttatt cactcaccat tagttccatg    300
gaggccgaag atgccgctac ttactactgt cagcagtgga gcagcaaccc ccctacattc    360
```

```
gggcagggaa ctaagctgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g              711
```

<210> SEQ ID NO 169
<211> LENGTH: 711
<212> TYPE: DNA
<213> ORGANISM: Artificial Sequence
<220> FEATURE:
<223> OTHER INFORMATION: huCD37-56

<400> SEQUENCE: 169

```
gaattcgcca ccatgggctg gtcctgtatc atcctgtttc tggtggcaac cgctactggg     60
gttcactctg atattgtcct gacacagagt ccagccttca tgagtgcttc tcccggagaa    120
aaggtcacaa tgacttgttc agcttcctcc tccgtcacat acatgcattg gtaccagcag    180
aagcctgacc agagtcctaa gaggtggatc tatgatacaa gcaatctggc ttccggtgtc    240
ccctcccgct tttcaggcgg cggaagcgga actgactata gccttaccat ctcctcaatg    300
gaagccgagg acgctgctac atattactgc cagcaatgga tcagcgaccc tcctactttc    360
ggacagggaa caaaattgga aattaagcgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g              711
```

<210> SEQ ID NO 170
<211> LENGTH: 711
<212> TYPE: DNA
<213> ORGANISM: Artificial Sequence
<220> FEATURE:
<223> OTHER INFORMATION: huCD37-57

<400> SEQUENCE: 170

```
gaattcgcca ccatggggtg gtcctgtatt atcctgttcc tggtcgcaac cgccacaggc     60
gttcactccg agatcgtgtt gactcagagc ccagccacca tgtccgcttc ccccggggag    120
agagtgacaa tgacttgttc cgccacaagt tctgtaacct acatgcattg gtaccagcaa    180
aaaccaggac agagtccccg tcgttggatt tatgatacct ctaacctggc ttcaggcgtt    240
cctgcccgct tttctggtag tggatctggg acttcctata gccttaccat aagctctatg    300
gaagccgagg acgccgctac atactactgc cagcagtgga gtgataaccc ccccacctcc    360 ggcagggaa ccaaattgga gatcaaacgt acggtggctg caccatctgt cttcatcttc    420
ccgccatctg atgagcagtt gaaatctgga actgcctctg ttgtgtgcct gctgaataac    480
ttctatccca gagaggccaa agtacagtgg aaggtggata acgccctcca atcgggtaac    540
tcccaggaga gtgtcacaga gcaggacagc aaggacagca cctacagcct cagcagcacc    600
ctgacgctga gcaaagcaga ctacgagaaa cacaaagtct acgcctgcga agtcacccat    660
cagggcctga gctcgcccgt cacaaagagc ttcaacaggg gagagtgtta g              711
```

<210> SEQ ID NO 171
<211> LENGTH: 5
<212> TYPE: PRT
<213> ORGANISM: Artificial Sequence
<220> FEATURE:
<223> OTHER INFORMATION: 252-3 VH-CDR1

<400> SEQUENCE: 171

Ser Tyr Gly Met Ser
1               5

<210> SEQ ID NO 172
<211> LENGTH: 17
<212> TYPE: PRT
<213> ORGANISM: Artificial Sequence
<220> FEATURE:
<223> OTHER INFORMATION: 252-3 VH-CDR2

<400> SEQUENCE: 172

Thr Ile Ser Ser Gly Gly Ser Tyr Thr Tyr Ser Pro Asp Ser Val Lys
1               5                   10                  15

Gly

<210> SEQ ID NO 173
<211> LENGTH: 10
<212> TYPE: PRT
<213> ORGANISM: Artificial Sequence
<220> FEATURE:
<223> OTHER INFORMATION: 252-3 VH-CDR3

<400> SEQUENCE: 173

His Ser Tyr Tyr Asp Thr Ser Val Asp Tyr
1               5                   10

<210> SEQ ID NO 174
<211> LENGTH: 11
<212> TYPE: PRT
<213> ORGANISM: Artificial Sequence
<220> FEATURE:
<223> OTHER INFORMATION: 252-3 VL-CDR1

<400> SEQUENCE: 174

Arg Ala Ser Gln Asp Ile Ser Asn Tyr Leu Asn
1               5                   10

<210> SEQ ID NO 175
<211> LENGTH: 7
<212> TYPE: PRT
<213> ORGANISM: Artificial Sequence
<220> FEATURE:
<223> OTHER INFORMATION: 252-3 VL-CDR2

<400> SEQUENCE: 175

Tyr Thr Ser Lys Leu His Ser
1               5

<210> SEQ ID NO 176
<211> LENGTH: 9
<212> TYPE: PRT
<213> ORGANISM: Artificial Sequence
<220> FEATURE:
<223> OTHER INFORMATION: 252-3 VL-CDR3

<400> SEQUENCE: 176

Gln Gln Gly Asn Ala Leu Pro Trp Thr

<210> SEQ ID NO 177
<211> LENGTH: 119
<212> TYPE: PRT
<213> ORGANISM: Artificial Sequence
<220> FEATURE:
<223> OTHER INFORMATION: 252-3 VH

<400> SEQUENCE: 177

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Thr Tyr Ser Pro Asp Ser Val
    50                  55                  60

Lys Gly Arg Phe Thr Ile Ser Arg Asp Asn Ala Lys Lys Thr Leu Tyr
65                  70                  75                  80

Leu Gln Met Ser Ser Leu Lys Ser Glu Asp Thr Ala Met Tyr Tyr Cys
                85                  90                  95

Ala Arg His Ser Tyr Tyr Asp Thr Ser Val Asp Tyr Trp Gly Gln Gly
            100                 105                 110

Thr Ser Val Thr Val Ser Ser
        115

<210> SEQ ID NO 178
<211> LENGTH: 108
<212> TYPE: PRT
<213> ORGANISM: Artificial Sequence
<220> FEATURE:
<223> OTHER INFORMATION: 252-3 VL

<400> SEQUENCE: 178

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Ala Leu Pro Trp
                85                  90                  95

Thr Phe Gly Gly Gly Thr Lys Leu Glu Leu Lys Arg
            100                 105

<210> SEQ ID NO 179
<211> LENGTH: 449
<212> TYPE: PRT
<213> ORGANISM: Artificial Sequence
<220> FEATURE:
<223> OTHER INFORMATION: 252-3 Full-Length Heavy Chain

<400> SEQUENCE: 179

Glu Val Gln Leu Val Glu Ser Gly Gly Asp Leu Val Lys Pro Gly Gly
1               5                   10                  15

```
Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
            35                  40                  45

Ala Thr Ile Ser Ser Gly Gly Ser Tyr Thr Tyr Ser Pro Asp Ser Val
 50                  55                  60

Lys Gly Arg Phe Thr Ile Ser Arg Asp Asn Ala Lys Lys Thr Leu Tyr
 65                  70                  75                  80

Leu Gln Met Ser Ser Leu Lys Ser Glu Asp Thr Ala Met Tyr Tyr Cys
                85                  90                  95

Ala Arg His Ser Tyr Tyr Asp Thr Ser Val Asp Tyr Trp Gly Gln Gly
            100                 105                 110

Thr Ser Val Thr Val Ser Ser Ala Lys Thr Thr Ala Pro Ser Val Tyr
            115                 120                 125

Pro Leu Ala Pro Val Cys Gly Asp Thr Thr Gly Ser Ser Val Thr Leu
130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
            275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430
```

```
Gly Leu His Asn His His Thr Thr Lys Ser Phe Ser Arg Thr Pro Gly
            435                 440                 445

Lys

<210> SEQ ID NO 180
<211> LENGTH: 214
<212> TYPE: PRT
<213> ORGANISM: Artificial Sequence
<220> FEATURE:
<223> OTHER INFORMATION: 252-3 Full-length Light Chain

<400> SEQUENCE: 180

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Lys Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Ala Leu Pro Trp
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Pro Ile Val Lys Ser
        195                 200                 205

Phe Asn Arg Asn Glu Cys
    210

<210> SEQ ID NO 181
<211> LENGTH: 10
<212> TYPE: PRT
<213> ORGANISM: Artificial Sequence
<220> FEATURE:
<223> OTHER INFORMATION: 252-3 VH-CDR2

<400> SEQUENCE: 181

Thr Ile Ser Ser Gly Gly Ser Tyr Thr Tyr
1               5                   10

<210> SEQ ID NO 182
<211> LENGTH: 357
<212> TYPE: DNA
<213> ORGANISM: Artificial Sequence
<220> FEATURE:
<223> OTHER INFORMATION: VH 252-3

<400> SEQUENCE: 182
```

```
gaggtgcagg tggtggagtc tgggggagac ttagtgaagc ctggagggtc cctgaaactc      60
tcctgtgcag cctctggatt cactttcagt agctatggca tgtcttgggt tcgccagact     120
ccagacaaga ggctggagtg ggtcgcaacc attagtagtg gtggtagtta cacctactct     180
ccagacagtg tgaaggggcg attcaccatc tccagagaca atgccaagaa aaccctgtac     240
ctgcaaatga gcagtctgaa gtctgaggac acagccatgt attactgtgc aagacatagt     300
tactacgata ctagcgtcga ctactggggt caaggaacct cagtcaccgt ctcctca       357
```

<210> SEQ ID NO 183
<211> LENGTH: 324
<212> TYPE: DNA
<213> ORGANISM: Artificial Sequence
<220> FEATURE:
<223> OTHER INFORMATION: VL 252-3

<400> SEQUENCE: 183

```
gatatccaga tgacacagac tacatcctcc ctgtctgcct ctctgggaga cagagtcacc      60
atcagttgca gggcaagtca ggacattagc aattatttaa actggtatca gcagaaaccc     120
gatggaactg ttaaactcct gatctactac acatcaaaat tacactcagg agtcccatca     180
aggttcagtg gcagtgggtc tggaacagat tattctctca ccattagcaa cctggagcaa     240
gaagatattg ccacttactt ttgccaacag ggtaatgcgc ttccgtggac gttcggtgga     300
ggcaccaagc tggaactcaa acgg                                            324
```

<210> SEQ ID NO 184
<211> LENGTH: 281
<212> TYPE: PRT
<213> ORGANISM: Artificial Sequence
<220> FEATURE:
<223> OTHER INFORMATION: hCD37-M1

<400> SEQUENCE: 184

```
Met Ser Ala Gln Glu Ser Cys Leu Ser Leu Ile Lys Tyr Phe Leu Phe
  1               5                  10                  15

Val Phe Asn Leu Phe Phe Phe Val Leu Gly Ser Leu Ile Phe Cys Phe
                 20                  25                  30

Gly Ile Trp Ile Leu Ile Asp Lys Thr Ser Phe Val Ser Phe Val Gly
             35                  40                  45

Leu Ala Phe Val Pro Leu Gln Ile Trp Ser Lys Val Leu Ala Ile Ser
         50                  55                  60

Gly Ile Phe Thr Met Gly Ile Ala Leu Leu Gly Cys Val Gly Ala Leu
 65                  70                  75                  80

Lys Glu Leu Arg Cys Leu Leu Gly Leu Tyr Phe Gly Met Leu Leu Leu
                 85                  90                  95

Leu Phe Ala Thr Gln Ile Thr Leu Gly Ile Leu Ile Ser Thr Gln Arg
                100                 105                 110

Val Arg Leu Glu Arg Arg Val Gln Glu Leu Val Leu Arg Thr Ile Gln
            115                 120                 125

Ser Tyr Arg Thr Asn Pro Asp Glu Thr Ala Ala Glu Glu Ser Trp Asp
        130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
```

```
            180             185             190
Leu Asp Lys Val Ile Leu Pro Gln Leu Ser Arg Leu Gly His Leu Ala
                195                 200                 205
Arg Ser Arg His Ser Ala Asp Ile Cys Ala Val Pro Ala Glu Ser His
        210                 215                 220
Ile Tyr Arg Glu Gly Cys Ala Gln Gly Leu Gln Lys Trp Leu His Asn
225                 230                 235                 240
Asn Leu Ile Ser Ile Val Gly Ile Cys Leu Gly Val Gly Leu Leu Glu
                245                 250                 255
Leu Gly Phe Met Thr Leu Ser Ile Phe Leu Cys Arg Asn Leu Asp His
                260                 265                 270
Val Tyr Asn Arg Leu Ala Arg Tyr Arg
                275                 280

<210> SEQ ID NO 185
<211> LENGTH: 128
<212> TYPE: PRT
<213> ORGANISM: Artificial Sequence
<220> FEATURE:
<223> OTHER INFORMATION: muCD37-R176

<400> SEQUENCE: 185

Ile Ser Thr Gln Arg Val Arg Leu Glu Arg Arg Val Gln Glu Leu Val
1               5                   10                  15
Leu Arg Thr Ile Gln Ser Tyr Arg Thr Asn Pro Asp Glu Thr Ala Ala
                20                  25                  30
Glu Glu Ser Trp Asp Tyr Ala Gln Phe Gln Leu Arg Cys Cys Gly Trp
            35                  40                  45
Gln Ser Pro Arg Asp Trp Asn Lys Ala Gln Met Leu Lys Ala Asn Glu
    50                  55                  60
Ser Glu Glu Pro Arg Val Pro Cys Ser Cys Tyr Asn Ser Thr Ala Thr
65                  70                  75                  80
Asn Asp Ser Thr Val Phe Asp Lys Leu Phe Phe Ser Gln Leu Ser Arg
                85                  90                  95
Leu Gly Pro Arg Ala Lys Leu Arg Gln Thr Ala Asp Ile Cys Ala Leu
                100                 105                 110
Pro Ala Lys Ala His Ile Tyr Arg Glu Gly Cys Ala Gln Ser Leu Gln
            115                 120                 125

<210> SEQ ID NO 186
<211> LENGTH: 281
<212> TYPE: PRT
<213> ORGANISM: Artificial Sequence
<220> FEATURE:
<223> OTHER INFORMATION: hCD37-M45

<400> SEQUENCE: 186

Met Ser Ala Gln Glu Ser Cys Leu Ser Leu Ile Lys Tyr Phe Leu Phe
1               5                   10                  15
Val Phe Asn Leu Phe Phe Phe Val Leu Gly Ser Leu Ile Phe Cys Phe
                20                  25                  30
Gly Ile Trp Ile Leu Ile Asp Lys Thr Ser Phe Val Ser Phe Val Gly
            35                  40                  45
Leu Ala Phe Val Pro Leu Gln Ile Trp Ser Lys Val Leu Ala Ile Ser
    50                  55                  60
Gly Ile Phe Thr Met Gly Ile Ala Leu Leu Gly Cys Val Gly Ala Leu
65                  70                  75                  80
```

```
Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Pro Arg Ala
        195                 200                 205

Lys Leu Arg Gln Thr Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 187
<211> LENGTH: 281
<212> TYPE: PRT
<213> ORGANISM: Artificial Sequence
<220> FEATURE:
<223> OTHER INFORMATION: hCD37m ECD-H45

<400> SEQUENCE: 187

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160
```

Trp Asn Lys Ala Gln Met Leu Lys Ala Asn Glu Ser Glu Pro Arg
            165                 170                 175

Val Pro Cys Ser Cys Tyr Asn Ser Thr Ala Thr Asn Asp Ser Thr Val
        180                 185                 190

Phe Asp Lys Leu Phe Phe Ser Gln Leu Ser Arg Leu Gly His Leu Ala
        195                 200                 205

Arg Ser Arg His Ser Ala Asp Ile Cys Ala Val Pro Ala Glu Ser His
        210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
                260                 265                 270

Val Tyr Asn Arg Leu Ala Arg Tyr Arg
                275                 280

<210> SEQ ID NO 188
<211> LENGTH: 281
<212> TYPE: PRT
<213> ORGANISM: Artificial Sequence
<220> FEATURE:
<223> OTHER INFORMATION: hCD37m ECD-H5

<400> SEQUENCE: 188

Met Ser Ala Gln Glu Ser Cys Leu Ser Leu Ile Lys Tyr Phe Leu Phe
1               5                   10                  15

Val Phe Asn Leu Phe Phe Val Leu Gly Ser Leu Ile Phe Cys Phe Phe
                20                  25                  30

Gly Ile Trp Ile Leu Ile Asp Lys Thr Ser Phe Val Ser Phe Val Gly
            35                  40                  45

Leu Ala Phe Val Pro Leu Gln Ile Trp Ser Lys Val Leu Ala Ile Ser
50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
        130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
            165                 170                 175

Val Pro Cys Ser Cys Tyr Asn Ser Thr Ala Thr Asn Asp Ser Thr Val
        180                 185                 190

Phe Asp Lys Leu Phe Phe Ser Gln Leu Ser Arg Leu Gly Pro Arg Ala
        195                 200                 205

Lys Leu Arg Gln Thr Ala Asp Ile Cys Ala Val Pro Ala Glu Ser His
        210                 215                 220

Ile Tyr Arg Glu Gly Cys Ala Gln Gly Leu Gln Lys Trp Leu His Asn
225                 230                 235                 240

```
Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 189
<211> LENGTH: 281
<212> TYPE: PRT
<213> ORGANISM: Artificial Sequence
<220> FEATURE:
<223> OTHER INFORMATION: hCD37m ECD-H4

<400> SEQUENCE: 189

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Val Arg Leu Glu Arg Arg Val Gln Glu Leu Val Leu Arg Thr Ile Gln
        115                 120                 125

Ser Tyr Arg Thr Asn Pro Asp Glu Thr Ala Ala Glu Glu Ser Trp Asp
    130                 135                 140

Tyr Ala Gln Phe Gln Leu Arg Cys Cys Gly Trp Gln Ser Pro Arg Asp
145                 150                 155                 160

Trp Asn Lys Ala Gln Met Leu Lys Ala Asn Glu Ser Glu Glu Pro Arg
                165                 170                 175

Val Pro Cys Ser Cys Tyr Asn Ser Thr Ala Thr Asn Asp Ser Thr Val
            180                 185                 190

Phe Asp Lys Leu Phe Phe Ser Gln Leu Ser Arg Leu Gly His Leu Ala
        195                 200                 205

Arg Ser Arg His Ser Ala Asp Ile Cys Ala Leu Pro Ala Lys Ala His
    210                 215                 220

Ile Tyr Arg Glu Gly Cys Ala Gln Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 190
<211> LENGTH: 281
<212> TYPE: PRT
<213> ORGANISM: Artificial Sequence
<220> FEATURE:
```

<223> OTHER INFORMATION: hCD37-Mac4

<400> SEQUENCE: 190

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Ser Trp Asp
130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Gln Leu Ala
        195                 200                 205

Arg Ser Arg His Ser Thr Asp Ile Cys Ala Val Pro Ala Glu Ser His
210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 191
<211> LENGTH: 280
<212> TYPE: PRT
<213> ORGANISM: Artificial Sequence
<220> FEATURE:
<223> OTHER INFORMATION: hCD37-Mac45

<400> SEQUENCE: 191

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Gln Leu Ala
        195                 200                 205

Arg Ser Arg His Ser Thr Asp Ile Cys Ala Val Pro Ala Asn Ser His
210                 215                 220

Ile Tyr Arg Glu Gly Cys Ala Arg Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr
        275                 280

<210> SEQ ID NO 192
<211> LENGTH: 281
<212> TYPE: PRT
<213> ORGANISM: Artificial Sequence
<220> FEATURE:
<223> OTHER INFORMATION: hCD37-Mac5

<400> SEQUENCE: 192

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
130                 135                 140

```
Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Asn Ser His
    210                 215                 220

Ile Tyr Arg Glu Gly Cys Ala Arg Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280
```

```
<210> SEQ ID NO 193
<211> LENGTH: 446
<212> TYPE: DNA
<213> ORGANISM: Artificial Sequence
<220> FEATURE:
<223> OTHER INFORMATION: VH huCD37-50

<400> SEQUENCE: 193
aagcttgcca ccatggggtg gtcctgcata atccttttcc tggttgctac tgctaccgga      60
gtccattcac aggtgcagct gcaggagtcc ggccccggcc tgctcaagcc ttctcagagt     120
ctgagtctga cttgtactgt ttctggctac agcataacca gcggtttcgc ttggcactgg     180
atcagacagc atcccggcaa caaactggag tggatgggat acatactgta ctcaggctca     240
actgtctatt ccccctccct gaaatcccgg atcagtatta cccgtgacac ttctaagaac     300
cattttttc tgcagctgaa cagcgttacc gcagctgaca ctgcaaccta ctactgtgcc     360
cggggatatt atggatacgg agcttggttc gcttactggg ccaaggcac cctcgtaact     420
gtgagtgctg cttccaccaa gggccc                                         446
```

```
<210> SEQ ID NO 194
<211> LENGTH: 446
<212> TYPE: DNA
<213> ORGANISM: Artificial Sequence
<220> FEATURE:
<223> OTHER INFORMATION: VH huCD37-51

<400> SEQUENCE: 194
aagcttgcca ccatgggttg gtcttgcatc atcctgttcc tggtggccac tgccactggc      60
gtgcattcag aagttcagtt ggtggagtcc ggcccagaag tgctgaaacc cggcgaatca     120
ctgtccctga cttgtaccgt gtcaggttat agcatcagca gcggctttgc ttggcactgg     180
attcggcagt tccaggcaa gggactggaa tggatgggct acatccatta cagtggctca     240
accaattaca gcctagcct gcagggccga atctctatta ccaggatag ttctattaac     300
cagttttttcc tgcagcttaa ttccgtgact gcctctgaca cagcaactta ctattgcgcc     360
cgtggctact acgggttcgg agcctggttt gtatactggg gtcagggcac cctggtcact     420
gtctcagccg cctctaccaa gggccc                                         446
```

CD37-BINDING MOLECULES AND IMMUNOCONJUGATES THEREOF

CROSS REFERENCE TO RELATED APPLICATIONS

This application claims the priority benefit of U.S. Provisional Application No. 61/470,863, filed Apr. 1, 2011, which is herein incorporated by reference in its entirety.

REFERENCE TO A SEQUENCE LISTING SUBMITTED ELECTRONICALLY VIA EFS-WEB

The content of the electronically submitted sequence listing (Name: 2921_0170001_SEQIDListing.ascii.txt, Size: 233,101 bytes, and Date of Creation: Jun. 12, 2012) is herein incorporated by reference in its entirety.

FIELD OF THE INVENTION

The field of the invention generally relates to antibodies, antigen-binding fragments thereof, polypeptides, and immunoconjugates that bind to CD37, as well as to methods of using such CD37-binding molecules for the treatment of diseases, such as autoimmune diseases and inflammatory diseases.

BACKGROUND OF THE INVENTION

Leukocyte antigen CD37 ("CD37"), also known as GP52-40, tetraspanin-26, or TSPAN26, is a transmembrane protein of the tetraspanin superfamily (Maecker et al., 1997 FASEB J. 11:428-442). It is a heavily glycosylated protein with four transmembrane domains that is expressed on B cells during the pre-B to peripheral mature B-cell stages, but is reportedly absent on terminal differentiation to plasma cells. (Link et al., 1987, J Pathol. 152:12-21). The CD37 antigen is only weakly expressed on T-cells, myeloid cells, and granulocytes (Schwartz-Albiez et al. 1988, J. Immunol., 140(3)905-914). However, CD37 is also expressed on malignant B-cells such as those founding, non-Hodgkin's lymphoma (NHL) and chronic lymphoid leukemia (CLL) (Moore et al. 1986, J Immunol. 137(9):3013-8).

While the exact physiological role of CD37 is unclear, studies in CD37-deficient mice suggest an immunoregulatory function. Although mice deficient in CD37 expression have normal development (Knobeloch et al. 2000, Mol Cell Biol., 20(15):5363-9), in the C57/Bl6 background, CD37−/− T cells are hyper-proliferative (van Spriel et al., J Immunol. 172, 2953 (2004)), CD37−/− dendritic cells (DC) exhibit an increased antigen presentation (Sheng et al., Eur J Immunol. 39, 50 (2009)), and CD37−/− macrophages show increased dectin-1-induced IL-6 production (Meyer-Wentrup et al., J Immunol. 178, 154 (2007)). CD37-deficient C57/Bl6 mice also contain significantly higher level of IgA than the wild-type mice (van Spriel et al., PLoS Pathol. 5, e1000338 (2009) and Rops et al., Am J Pathol. 176, 2188 (2010)). All of these results suggest a general regulatory role of CD37 in the immune system. Interestingly, crosslinking of CD37 antigen by antibody on human T cells inhibits T cell proliferation induced by CD3 stimulation (van Spriel et al., J Immunol. 172, 2953 (2004)).

Antibodies are emerging as a promising method to treat human diseases including autoimmune diseases. Currently, an anti-CD20 antibody called rituximab has been approved for rheumatoid arthritis (RA) treatment (Edwards J C et al. 2006, Nat Rev Immunol. 6: 119). Rituximab is used in the United States in combination with methotrexate (MTX) to reduce signs and symptoms in adult patients with moderately- to severely-active RA who have had an inadequate response to at least one TNF antagonist. Many studies address the use of rituximab in a variety of non-malignant autoimmune or inflammatory disorders, including RA, in which B-cells and autoantibodies appear to play a role in disease pathophysiology. Edwards et al., Biochem Soc. Trans. 30:824-828 (2002). Targeting of CD20 using anti-CD20 antibody has been reported to potentially relieve signs and symptoms of a number of autoimmune or inflammatory diseases including, for example, RA (Leandro et al., Ann. Rheum. Dis. 61:883-888 (2002); Edwards et al., Arthritis Rheum., 46 (Suppl. 9): S46 (2002); Stahl et al., Ann. Rheum. Dis., 62 (Suppl. 1): OP004 (2003); Emery et al., Arthritis Rheum. 48(9): S439 (2003)), lupus (Eisenberg, Arthritis. Res. Ther. 5:157-159 (2003); Leandro et al. Arthritis Rheum. 46: 2673-2677 (2002); Gorman et al., Lupus, 13: 312-316 (2004)), immune thrombocytopenic purpura (D'Arena et al., Leuk. Lymphoma 44:561-562 (2003); Stasi et al., Blood, 98: 952-957 (2001); Saleh et al., Semin. Oncol., 27 (Supp 12):99-103 (2000); Zaja et al., Haematologica, 87:189-195 (2002); Ratanatharathorn et al., Ann. Int. Med., 133:275-279 (2000)), pure red cell aplasia (Auner et al., Br. J. Haematol., 116:725-728 (2002)); autoimmune anemia (Zaja et al., supra (erratum appears in Hacmatologica 87:336 (2002)), cold agglutinin disease (Layios et al., Leukemia, 15:187-8 (2001); Berentsen et al., Blood, 103: 2925-2928 (2004); Berentsen et al., Br. J. Haematol., 115:79-83 (2001); Bauduer, Br. J. Haematol., 112:1083-1090 (2001); Zaja et al., Br. J. Haematol., 115:232-233 (2001)), type B syndrome of severe insulin resistance (Coll et al., N. Engl. J. Med., 350:310-311 (2004), mixed cryoglobulinermia (DeVita et al., Arthritis Rheum. 46 Suppl. 9:S206/S469 (2002)), myasthenia gravis (Zaja et al., Neurology, 55:1062-1063 (2000); Wylam et al., J. Pediatr., 143:674-677 (2003)), Wegener's granulomatosis (Specks et al., Arthritis & Rheumatism 44:2836-2840 (2001)), microscopic polyangiitis (MPA), refractory pemphigus vulgaris (Dupuy et al., Arch Dermatol., 140:91-96 (2004)), dermatomyositis (Levine, Arthritis Rheum., 46 (Suppl. 9):S1299 (2002)), Sjogren's syndrome (Somer et al., Arthritis & Rheumatism, 49:394-398 (2003)), active type-II mixed cryoglobulinemia (Zaja et al., Blood, 101:3827-3834 (2003)), pemphigus vulgaris (Dupay et al., Arch. Dermatol., 140:91-95 (2004)), autoimmune neuropathy (Pestronk et al., J. Neurol. Neurosurg. Psychiatry 74:485-489 (2003)), paraneoplastic opsoclonus-myoclonus syndrome (Pranzatelli et al. Neurology 60 (Suppl. 1) PO5.128:A395 (2003)), and relapsing-remitting multiple sclerosis (RRMS). Cross et al. (abstract) "Preliminary Results from a Phase II Trial of Rituximab in MS" Eighth Annual Meeting of the Americas Committees for Research and Treatment in Multiple Sclerosis, 20-21 (2003).

In animal models, B-cell depletion using antibodies against B-cell antigens such as CD20 has been shown to inhibit or ameliorate several autoimmune diseases including systemic lupus erythematosus (SLE), experimental autoimmune encephalomyclitis (EAE; mouse model of multiple sclerosis), type-1 diabetes (T1D) and rheumatoid arthritis (RA). Rituximab has been shown to deplete both malignant and normal B cells in vivo in animal models as well as patients (Maloney D G et al, Blood. 1994; 84(8):2457-66; Reff M E, et al. Blood. 1994; 83(2):435-45; Schröder C, et al. Transpl Immunol. 2003; 12(1):19-28). It can also deplete normal B-cells from human peripheral blood mononuclear cells (PBMCs) in in vitro experiments (Vugmeyster Y, et al, Cytometry A. 2003; 52(2):101-9; Vugmeystecr Y and Howell K. Int Immunopharmacol. 2004; 4(8):1117-24).

Campath-1H (alumtuzumab), an anti-CD52 chimeric IgG1, binds to the CD52 antigen, which is highly expressed on all lymphocytes (Ginaldi L. et al, Leuk Res. 1998 February; 22(2):185-91; Hale G, et al, Tissue Antigens. 1990 March; 35(3):118-27). It is used in patients to deplete malignant lymphocytes and is approved for treating chronic lymphocytic leukemia. It has also shown efficacy in treating multiple sclerosis and is currently in Phase III clinical testing (N Engl J Med 2008; 359:1786-1801; ClinicalTrials.gov NCT00530348 & NCT00548405). It has been shown to deplete normal lymphocytes in vitro as well (Hale G, et al. Blood. 1983 October; 62(4):873-82; Waldmann H and Hale G Philos Trans R Soc Lond B Biol Sci. 2005 Sep. 29; 360(1461):1707-11).

CD37-binding agents are also being tested as potential therapeutics for B-cell malignancies. Emergent Biosolutions (formerly Trubion Pharmaceuticals) developed the CD37-binding agents SMIP-016 and TRU-016 (Zhao et al., 2007, Blood, 110.2569-2577). SMIP-016 is a single chain polypeptide that includes variable regions from a hybridoma and engineered human constant regions. TRU-016 is a humanized version of the anti-CD37 SMIP protein. See e.g. U.S. Published Application No. 2007/0059306. TRU-016 is being tested clinically for the treatment of chronic lymphocytic leukemia (CLL). Boehringer Ingelheim has also disclosed a CD37 binding agent in International Published Application No. WO 2009/019312. However, no CDC activity has been described for any of these binding agents and no in vitro pro-apoptotic activity has been described in the absence of cross-linking agents.

Radio-immunotherapy (RIT) has been attempted using a radio-labeled anti-CD37 antibody MB-1 in two separate trials. Therapeutic doses of $^{131}$I-MB-1 were administered to six relapsed NHL patients (Press et al. 1989 J Clin Oncol. 7(8):1027-38; Press at el. 1993, N Engl J Med. 329(17): 1219-24). All six patients achieved a complete remission (CR) with a duration of four to thirty-one months. In another trial, $^{131}$I-MB-1 was administered to ten relapsed NHL patients (Kaminski et al. 1992 J Clin Oncol. 10(11):1696-711). A total of four patients had a response ranging in duration from two to six months, although only one CR was reported. However, not all patients could be treated due to an unfavorable biodistribution of the radio-label which raised concern for radiation exposure of vital non-target organs. Indeed, RIT related toxicities were observed in these trials including severe myclosupression and cardiopulmonary toxicity. While these clinical data suggest that anti-CD37 radio-immunoconjugates may be effective, these therapies are cumbersome to administer, and at relapse post-RIT patients cannot be retreated with RIT due to the risks associated with high doses of radiation.

To overcome the limitations of RIT, antibody-cytotoxic agent conjugates (ACC), also called antibody-drug conjugates (ADC), have been developed. These are immunoconjugates that include a cytotoxic agent covalently linked to an antibody through a chemical linker which can allow for specific delivery of cytotoxic drugs to cells expressing a protein recognized by the antibody. However, proteins that are poorly internalized are not considered to be favorable targets for such therapeutics. CD37 is structurally similar to CD20 as both antigens contain four transmembrane domains, although CD20 is not part of the tetraspanin family (Tedder et al. 1989, J. Immun. 142: 2560-2568). Antibodies against several B-cell antigens including CD37 and CD20 have been studied for their ability to undergo endocytosis and degradation (Press et al. 1989, Cancer Res. 49(17): 4906-12, and Press et al. 1994, Blood. 83(5):1390-7). The anti-CD37 antibody MB-1 was retained on the cell surface and internalized slowly in Daudi lymphoma cells in vitro. The MB-1 antibody also had a low rate of endocytosis and intracellular metabolism in NHL patient cells in vitro. Similar results were obtained with the anti-CD20 antibody IF5, which was also retained mainly on the lymphoma cell surface and internalized poorly. ADCs of CD20 antibodies have been studied previously but have not demonstrated significantly strong potency, especially when non-disulfide or acid stable linkers are used (see for example Poison et al., 2009, Cancer Res., 69(6):2358-2364). In light of these observations, CD37 has not been considered a favorable target for antibody-drug conjugates.

While their role in cancer treatment has been studied, the potential effect of CD37-directed therapies such as antibodies, antibody derivatives or radio-immunoconjugates on cells involved in autoimmune diseases, inflammatory diseases or other disorders of the immune system is not well understood. Furthermore, none of the compounds described above have been demonstrated to induce depletion of target cells involved ii manifestation or progression of these types of diseases.

Therefore, there exists a need for CD37 binding agents including antibodies, antigen-binding fragments thereof, and antibody-drug conjugates (immunoconjugates) as a means to treat autoimmune diseases, inflammatory diseases, or other disorders of the immune system. The present invention addresses that need.

BRIEF SUMMARY OF THE INVENTION

In one aspect, the present disclosure provides a method for depleting B-cells or treating a disease associated with aberrant B-cell activity, comprising administering to a patient an effective amount of a humanized CD37 targeting antibody or immunoconjugate provided herein. In some embodiments, the B-cells are non-cancerous B-cells. In some embodiments, the B-cells do not overexpress CD37.

In certain embodiments, the disease associated with aberrant B-cell activity is a disease associated with B-cell autoantibody production, and/or a disease associated with inappropriate T-cell stimulation in connection with a B-cell pathway.

In certain embodiments, the disease characterized by autoantibody production is rheumatoid arthritis, multiple sclerosis, type I diabetes mellitus, idiopathic inflammatory myopathy, systemic lupus crythematosus (SLE), myasthenia gravis, Grave's disease, dermatomyositis, polymyositis, or other autoimmune diseases.

In certain embodiments, the present disclosure provides a method for depleting a B-cell comprising contacting a B-cell (e.g., in a population of cells comprising a non-cancerous B-cell) with an antibody or antigen binding fragment thereof that specifically binds to CD37, wherein the antibody or fragment thereof is capable of inducing apoptosis in vitro in the absence of a cross-linking agent. In certain embodiments, the present disclosure provides a method for treating a patient having an autoimmune or inflammatory disease comprising administering to the patient a therapeutically effective amount of an antibody or antigen-binding fragment thereof that specifically binds to CD37, wherein the antibody or fragment thereof is capable of inducing apoptosis in vitro in the absence of a cross-linking agent. In some embodiments, the antibody or antigen-binding fragment thereof is also capable of inducing complement dependent cytotoxicity (CDC). In some embodiments, the antibody or antigen-binding fragment thereof is also capable of inducing antibody dependent cell mediated cytotoxicity (ADCC). In some embodiments, the antibody or antigen-binding fragment thereof has a long serum half-life.

In certain embodiments, the present disclosure provides a method for depleting a B-cell comprising contacting a B-cell (e.g., in a population of cells comprising a non-cancerous B-cell) with an antibody or antigen binding fragment thereof that specifically binds to the same CD37 epitope as an antibody selected from the group consisting of: (a) an antibody comprising the polypeptide of SEQ ID NO:55 and the polypeptide of SEQ ID NO:72; (b) an antibody comprising the polypeptide of SEQ ID NO:56 and the polypeptide of SEQ ID NO:73; (c) an antibody comprising the polypeptide of SEQ ID NO:57 and the polypeptide of SEQ ID NO:74; (d) an antibody comprising the polypeptide of SEQ ID NO:58 and the polypeptide of SEQ ID NO:74; (e) an antibody comprising the polypeptide of SEQ ID NO:59 and the polypeptide of SEQ ID NO:75; (f) an antibody comprising the polypeptide of SEQ ID NO:60 and the polypeptide of SEQ ID NO:76; (g) an antibody comprising the polypeptide of SEQ ID NO:61 and the polypeptide of SEQ ID NO:77; (h) an antibody comprising the polypeptide of SEQ ID NO:62 and the polypeptide of SEQ ID NO:78; (i) an antibody comprising the polypeptide of SEQ ID NO:63 and the polypeptide of SEQ ID NO:79; (j) an antibody comprising the polypeptide of SEQ ID NO:64 and the polypeptide of SEQ ID NO:80; (k) an antibody comprising the polypeptide of SEQ ID NO:65 and the polypeptide of SEQ ID NO:8; (l) an antibody comprising the polypeptide of SEQ ID NO:66 and the polypeptide of SEQ ID NO:82; (m) an antibody comprising the polypeptide of SEQ ID NO:67 and the polypeptide of SEQ ID NO:83; (n) an antibody comprising the polypeptide of SEQ ID NO:68 and the polypeptide of SEQ ID NO:84; (o) an antibody comprising the polypeptide of SEQ ID NO:69 and the polypeptide of SEQ ID NO:85; (p) an antibody comprising the polypeptide of SEQ ID NO:70 and the polypeptide of SEQ ID NO:86; (q) an antibody comprising the polypeptide of SEQ ID NO:71 and the polypeptide of SEQ ID NO:87; and (r) an antibody comprising the polypeptide of SEQ ID NO:177 and the polypeptide of SEQ ID NO:178.

In certain embodiments, the present disclosure provides a method for treating a patient having an autoimmune or inflammatory disease comprising administering to the patient a therapeutically effective amount of an antibody or antigen-binding fragment thereof that specifically binds to the same CD37 epitope as an antibody selected from the group described above. In some embodiments, the antibody or antigen-binding fragment thereof competitively inhibits an antibody selected from the group described above.

In certain embodiments, the present disclosure provides a method for depleting a B-cell comprising contacting a B-cell (e.g., in a population of cells comprising a non-cancerous B-cell) with an antibody or antigen-binding fragment thereof that specifically binds to CD37 and specifically binds to the polypeptide of SEQ ID NO: 184. In certain embodiments, the present disclosure provides a method for treating a patient having an autoimmune or inflammatory disease comprising administering to the patient a therapeutically effective amount of an antibody or antigen-binding fragment thereof that specifically binds to CD37 and specifically binds to the polypeptide of SEQ ID NO: 184. In some embodiments, the antibody or antigen-binding fragment thereof does not bind to the polypeptide of SEQ ID NO: 185.

In certain embodiments, the present disclosure provides a method for depleting a B-cell comprising contacting a B-cell (e.g., in a population of cells comprising a non-cancerous B-cell) with an antibody or antigen-binding fragment thereof that specifically binds to CD37 and does not specifically bind to the polypeptide of SEQ ID NO: 185. In certain embodiments, the present disclosure provides a method for treating a patient having an autoimmune or inflammatory disease comprising administering to the patient a therapeutically effective amount of an antibody or antigen-binding fragment thereof that specifically binds to CD37 and does not specifically bind to the polypeptide of SEQ ID NO: 185.

In certain embodiments, the present disclosure provides a method for depleting a B-cell comprising contacting a B-cell (e.g., in a population of cells comprising a non-cancerous B-cell) with an antibody or antigen-binding fragment thereof produced by a hybridoma selected from the group consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Designation PTA-10666, deposited with the ATCC on Feb. 18, 2010, ATCC Deposit Designation PTA-10667, deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010. In certain embodiments, the present disclosure provides a method for treating a patient having an autoimmune or inflammatory disease comprising administering to the patient a therapeutically effective amount of an antibody or antigen-binding fragment thereof produced by a hybridoma described above.

In certain embodiments, the present disclosure provides a method for depleting a B-cell comprising contacting a B-cell (e.g., in a population of cells comprising a non-cancerous B-cell) with an antibody or antigen-binding fragment thereof that specifically binds to CD37, wherein the antibody comprises polypeptide sequences selected from the group consisting of: (a) SEQ ID NOs: 4, 5, and 6 and SEQ ID NOs: 28, 29, and 30; (b) SEQ ID NOs: 7, 8, and 9 and SEQ ID NOs: 31, 32, and 33; (c) SEQ ID NOs: 10, 11, and 12 and SEQ ID NOs: 34, 35, and 36; (d) SEQ ID NOs: 13, 14, and 15 and SEQ ID NOs: 37, 38, and 39; (e) SEQ ID NOs: 13, 14, and 15 and SEQ ID NOs: 37, 40, and 39; (f) SEQ ID NOs: 16, 17, and 18 and SEQ ID NOs: 41, 42, and 43; (g) SEQ ID NOs: 19, 20, and 21 and SEQ ID NOs: 44, 45, and 46; (h) SEQ ID NOs: 19, 20, and 21 and SEQ ID NOs: 44, 47, and 46; (i) SEQ ID NOs: 22, 23, and 24 and SEQ ID NOs: 48, 49, and 50; (j) SEQ ID NOs: 22, 23, and 24 and SEQ ID NOs: 48, 51, and 50; (k) SEQ ID NOs: 25, 26, and 27 and SEQ ID NOs: 52, 53, and 54; (l) SEQ ID NOs: 171, 172 or 181, and 173 and SEQ ID NOs: 174, 175, and 176; (m) variants of (a) to (l) comprising 1, 2, 3, or 4 conservative amino acid substitutions. In certain embodiments, the present disclosure provides a method for treating a patient having an autoimmune or inflammatory disease comprising administering to the patient a therapeutically effective amount of an antibody or antigen-binding fragment thereof with an antibody or antigen-binding fragment thereof that specifically binds to CD37, wherein the antibody comprises polypeptide sequences selected from the group described above. In some embodiments, the antibody or antigen-binding fragment thereof comprises polypeptide sequences that are at least 90% identical to polypeptide sequences described above. In some embodiments, the polypeptide sequences are at least 95% identical to the polypeptide sequences. In some embodiments, the polypeptide sequences are at least 99% identical to the polypeptide sequences. In some embodiments, the antibody or antigen-binding fragment thereof comprises polypeptide sequences that are at least 90% identical, at least 95% identical, at least 99% identical, or identical to the polypeptide sequences of SEQ ID NO: 57 and SEQ ID NO:74. In some embodiments, the antibody or antigen-binding fragment thereof comprises polypeptide sequences that are at least 90% identical, at least 95% identical, at least 99% identical, or identical to the polypeptide sequences of SEQ ID NO: 58 and SEQ ID NO:74. In some embodiments, the antibody or antigen-binding fragment thereof comprises polypeptide sequences that are at least 90% identical, at least 95% identical, at least 99% identical, or identical to the polypeptide sequences of SEQ ID NO: 63 and SEQ ID NO:79. In some embodiments, the antibody or antigen-binding fragment thereof comprises polypeptide sequences that are at least 90% identical, at least 95% identical, at least 99% identical, or identical to the polypeptide sequences of SEQ ID NO: 65 and SEQ ID NO:81.

In some embodiments, the antibody or antigen binding fragment thereof is murine, non-human, humanized, chimeric, resurfaced, or human.

In some embodiments, the antibody or antibody fragment is capable of inducing apoptosis of a cell expressing CD37 in vitro in the absence of cross-linking agents. In some embodiments, the antibody or antigen binding fragment is capable of inducing complement dependent cytotoxicity (CDC). In some embodiments, the antibody is capable of inducing antibody dependent cell mediated cytotoxicity (ADCC).

In certain embodiments, the present disclosure provides a method for depleting a B-cell comprising contacting a B-cell (e.g., in a population of cells comprising a non-cancerous B-cell) with a human or humanized antibody or antigen binding fragment thereof that specifically binds to CD37, wherein the antibody or fragment thereof is capable of inducing apoptosis of a cell expressing CD37 in vitro in the absence of cross-linking agents. In certain embodiments, the present disclosure provides a method for treating a patient having an autoimmune or inflammatory disease comprising administering to the patient a therapeutically effective amount of a human or humanized antibody or antigen binding fragment thereof that specifically binds to CD37, wherein the antibody or fragment thereof is capable of inducing apoptosis of a cell expressing CD37 in vitro in the absence of cross-linking agents. In some embodiments, the human or humanized antibody or antigen binding fragment thereof is also capable of inducing complement dependent cytotoxicity (CDC). In some embodiments, the human or humanized antibody or antigen binding fragment thereof is also capable of inducing antibody dependent cell mediated cytotoxicity (ADCC).

In some embodiments, the antibody or antigen-binding fragment binds to human CD37 and macaque CD37.

In some embodiments, the antibody is a full length antibody. In some embodiments, an antigen-binding fragment is used. In some embodiments, the antibody or antigen-binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv)2, or scFv-Fc.

In some embodiments, the antibody or antigen-binding fragment thereof is linked via a linker (L) to a cytotoxic agent (C) to form an immunoconjugate.

In certain embodiments, the present disclosure provides a method for depleting a B-cell comprising contacting a B-cell (e.g., in a population of cells comprising a non-cancerous B-cell) with a composition comprising an immunoconjugate having the formula (A)-(L)-(C), wherein: (A) is an antibody or antigen binding fragment that specifically binds to CD37; (L) is a non-cleavable linker: and (C) is a cytotoxic agent; and wherein the linker (L) links (A) to (C). In certain embodiments, the present disclosure provides a method for treating a patient having an autoimmune or inflammatory disease comprising administering to the patient a therapeutically effective amount of a composition comprising an immunoconjugate having the formula (A)-(L)-(C), wherein: (A) is an antibody or antigen binding fragment that specifically binds to CD37; (L) is a non-cleavable linker: and (C) is a cytotoxic agent; and wherein the linker (L) links (A) to (C). In some embodiments, the immunoconjugate has a serum half-life that is comparable to that of the naked antibody.

In certain embodiments, the present disclosure provides a method for depleting a B-cell comprising contacting a B-cell (e.g., in a population of cells comprising a non-cancerous B-cell) with a composition comprising an immunoconjugate having the formula (A)-(L)-(C), wherein: (A) is an antibody or antigen binding fragment that specifically binds to CD37; (L) is a linker: and (C) is a maytansinoid; and wherein the linker (L) links (A) to (C). In certain embodiments, the present disclosure provides a method for treating a patient having an autoimmune or inflammatory disease comprising administering to the patient a therapeutically effective amount of a composition comprising an immunoconjugate having the formula (A)-(L)-(C), wherein: (A) is an antibody or antigen binding fragment that specifically binds to CD37; (L) is a linker; and (C) is a maytansinoid; and wherein the linker (L) links (A) to (C).

In some embodiments, the linker is a non-cleavable linker. In some embodiments, the immunoconjugate further comprises a second (C). In some embodiments, the immunoconjugate further comprises a third (C). In some embodiments, the immunoconjugate further comprises a fourth (C). In some embodiments, the immunoconjugate comprises 2-6 (C). In some embodiments, the immunoconjugate comprises 3-4 (C).

In some embodiments, the linker is selected from the group consisting of a cleavable linker, a non-cleavable linker, a hydrophilic linker, and a dicarboxylic acid based linker. In some embodiments, the linker is selected from the group consisting of: N-succinimidyl 4-(2-pyridyldithio)pentanoate (SPP): N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). In some embodiments, the linker is N-succinimidyl-[(N-maleimidopropionamido)-tetraethyleneglycol]ester (NHS-PEG4-maleimide).

In some embodiments, the cytotoxic agent is selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. In some embodiments, the cytotoxic agent is a maytansinoid. In some embodiments, the cytotoxic agent is N(2')-deacetyl-N(2')-(3-mercapto-1-oxopropyl)-maytansine (DM1) or N(2')-deacetyl-N2-(4-mercapto-4-methyl-1-oxopentyl)-maytansine (DM4).

In some embodiments, the composition comprising an immunoconjugate comprises multiple cytotoxic agents (C) with an average of about 3 to about 4 (C) per (A). In some embodiments, the immunoconjugates have an average of about 3.5 (C) per (A). In some embodiments, the immunoconjugates have an average of about 3.5±0.5 (C) per (A).

In some embodiments, the composition comprising an immunoconjugate comprises an antibody comprising SEQ ID NO:57 and SEQ ID NO:74 or SEQ ID NO:58 and SEQ ID NO:74, an SMCC linker, and DM1. In some embodiments, the composition comprising an immunoconjugate comprises an antibody comprising SEQ ID NO:63 and SEQ ID NO:79, an SMCC linker, and DM1. In some embodiments, the composition comprising an immunoconjugate comprises an antibody comprising SEQ ID NO:65 and SEQ ID NO:81, an SMCC linker, and DM1.

In some embodiments, the antibody or antigen-binding fragment is capable of depleting B-cells. In some embodiments, the antibody or antigen-binding fragment is capable of inhibiting T-cell responses.

In some embodiments, the B-cell is in a composition further comprising a T-cell. In some embodiments, the B-cell is in a composition comprising peripheral blood mononuclear cells. In some embodiments, the peripheral blood mononuclear cells were obtained from a human. In some embodiments, the B-cell is in whole blood. In some embodiments, the whole blood was obtained from a human. In some embodiments, the B-cell is in an organism. In some embodiments, the B-cell is in a patient having an autoimmune or inflammatory disease.

In some embodiments, the B-cell is an autoreactive B-cell.

In some embodiments, at least about 30% of B-cells are depleted. In some embodiments, less than about 5% of T-cells are depleted.

In some embodiments, a second therapeutic agent is administered. In some embodiments, the second therapeutic is selected from the group consisting of methotrexate, an anti-CD20 therapeutic, an anti-IL-6 receptor therapeutic, an anti-IL-12/23p40 therapeutic, a chemotherapeutic, an immunosuppressant, an anti-Interferon beta-1a therapeutic, glatiramer acetate, an anti-α4-integrin therapeutic, fingolimod, an anti-BLys therapeutic, CTLA-Fc, or an anti-TNF therapeutic. In some embodiments, the second therapeutic is an antibody directed against an antigen selected from a group consisting of CD3, CD14, CD19, CD20, CD22, CD25, CD28, CD30, CD33, CD36, CD38, CD40, CD44, CD52, CD55, CD59, CD56, CD70, CD79, CD80, CD103, CD134, CD137, CD138, and CD152. In some embodiments, the second therapeutic is an antibody directed against an antigen selected from the group consisting of IL-2, IL-6, IL-12, IL-23, IL-12/23 p40, IL-17, IFNγ, TNFα, IFNα, IL-15. IL-21, IL-1a, IL-1b, IL-18, IL-8, IL-4, GM-CSF, IL-3, and IL-5.

In some embodiments, the autoimmune or inflammatory disease is selected from the group consisting of rheumatoid arthritis, multiple sclerosis, type I diabetes mellitus, idiopathic inflammatory myopathy, systemic lupus erythematosus (SLE), myasthenia gravis, Grave's disease, dermatomyositis, polymyositis, Crohn's disease, ulcerative colitis, gastritis, Hashimoto's thyroiditis, asthma, psoriasis, psoriatic arthritis, dertmatitis, systemic sclerodema and sclerosis, inflammatory bowel disease (IBD), respiratory distress syndrome, meningitis, encephalitis, uveitis, glmerulonephritis, eczema, atherosclerosis, leukocyte adhesion deficiency, Raynaud's syndrome, Sjögen's syndrome, Reiter's disease, Beheet's diasease, immune complex nephritis, IgA enphropathy, IgM polyneuropathies, immune-mediated thrombocytopenias, acute idiopathic thrombocytopenic purpura, chronic idiopathic thembocytopenic purpura, hemolytic anemia, myasthenia gravis, lupus nephritis, atopic dermatitis, pemphigus vulgaris, opsoclonus-myoclonus syndrome, pure red cell aplasia, mixed cryoglobulinermia, ankylosing spondylitis, hepatitis C-associated cryoglobulinemic vasculitis, chronic focal encephalitis, bullous pemphigoid, hemophilia A, membranoproliferative glomerulonephritis, adult and juvenile dermatomyositis, adult polymyositis, chronic urticaria, primary biliary cirrhosis, neuromyelitis optica, Graves' dysthyroid disease, bullous pemphigoid, membranoproliferative glomerulonephritis, Churg-Strauss syndrome, juvenile onset diabetes, homolytic anemia, atopic dermatitis, systemic sclerosis, Sjögen's syndrome and glomerulonephritis, dermatomyositis, ANCA, aplastic anemia, autoimmune hemolytic anemia (AIHA), factor VIII deficiency, hemophilia A, autoimmune neutropenia, Castleman's syndrome, Goodpasture's syndrome, solid organ transplant rejection, graft versus host disease (GVHD), autoimmune hepatitis, lymphoid interstitial pneumonitis, HIV, bronchiolitis obliterans (non-transplant), Guillain-Barre Syndrome, large vessel vasculitis, giant cell (Takayasu's) arteritis, medium vessel vasculitis, Kawasaki's Disease, polyarteritis nodosa. Wegener's granulomatosis, microscopic polyangiitis (MPA). Omenn's syndrome, chronic renal failure, acute infectious mononucleosis, HIV and herpes virus associated diseases.

BRIEF DESCRIPTION OF THE DRAWINGS/FIGURES

Figure 3:
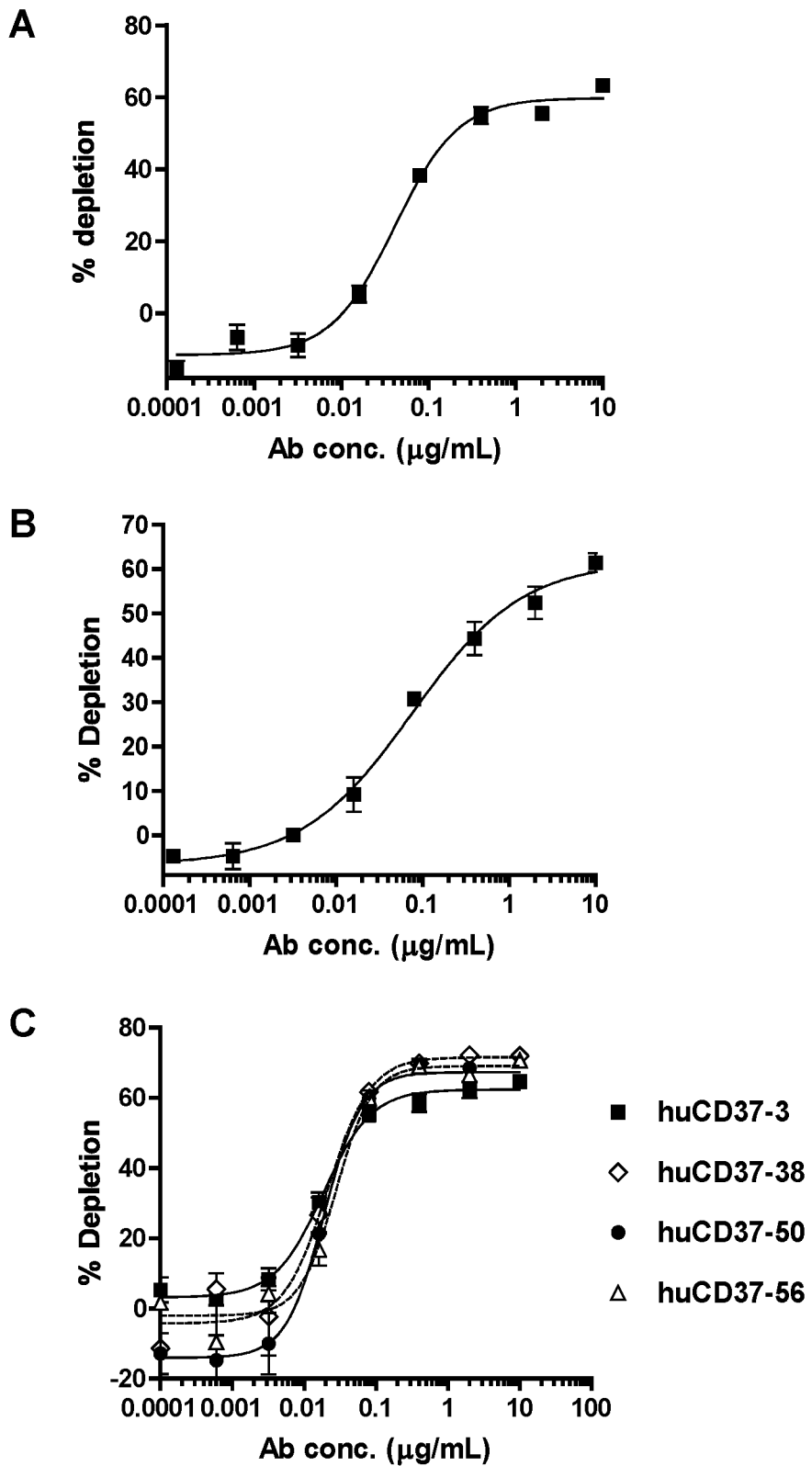

FIG. 3 depicts the results of in vitro depletion experiments using purified human PBMC samples treated with varying concentrations of huCD37-3-SMCC-DM1. Results from two different donors are shown in panels A and B. FIG. 3 (C) shows the results using huCD37-3, huCD37-38, huCD37-50 and huCD37-56.

Figure 4:
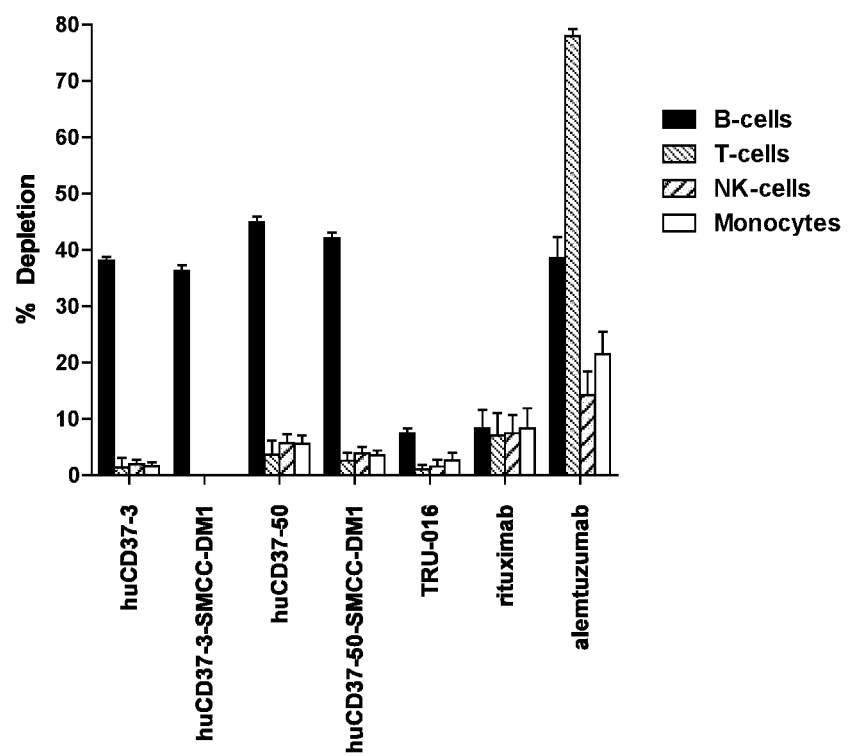

FIG. 4 depicts the results of in vitro depletion experiments using unpurified whole human blood samples treated with 10 μg/mL of huCD37-3, huCD37-3-SMCC-DM1, huCD37-50, huCD37-50-SMCC-DM1, rituximab, TRU-016, or alemtuzumab.

Figure 5:
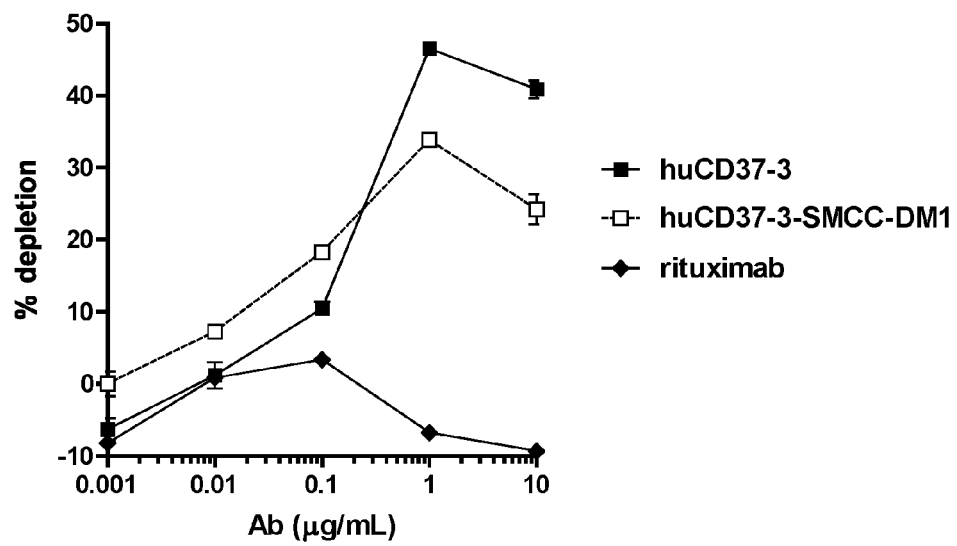
Figure 5:
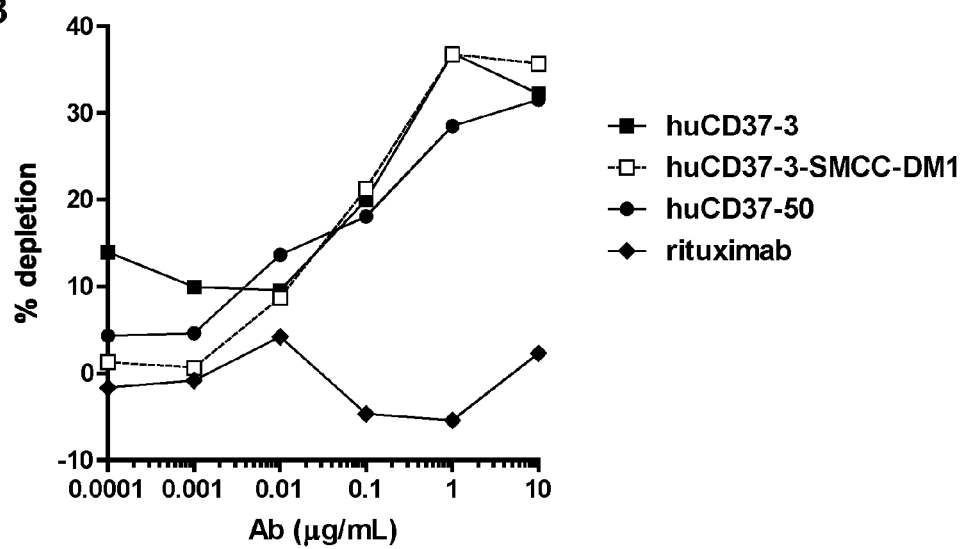

FIG. 5 depicts the results of in vitro depletion experiments using unpurified whole human blood samples treated with varying concentrations of (A) huCD37-3, huCD37-3-SMCC-DM1, and rituximab and (B) huCD37-3, huCD37-3-SMCC-DM1, huCD37-50, and rituximab.

Figure 6:
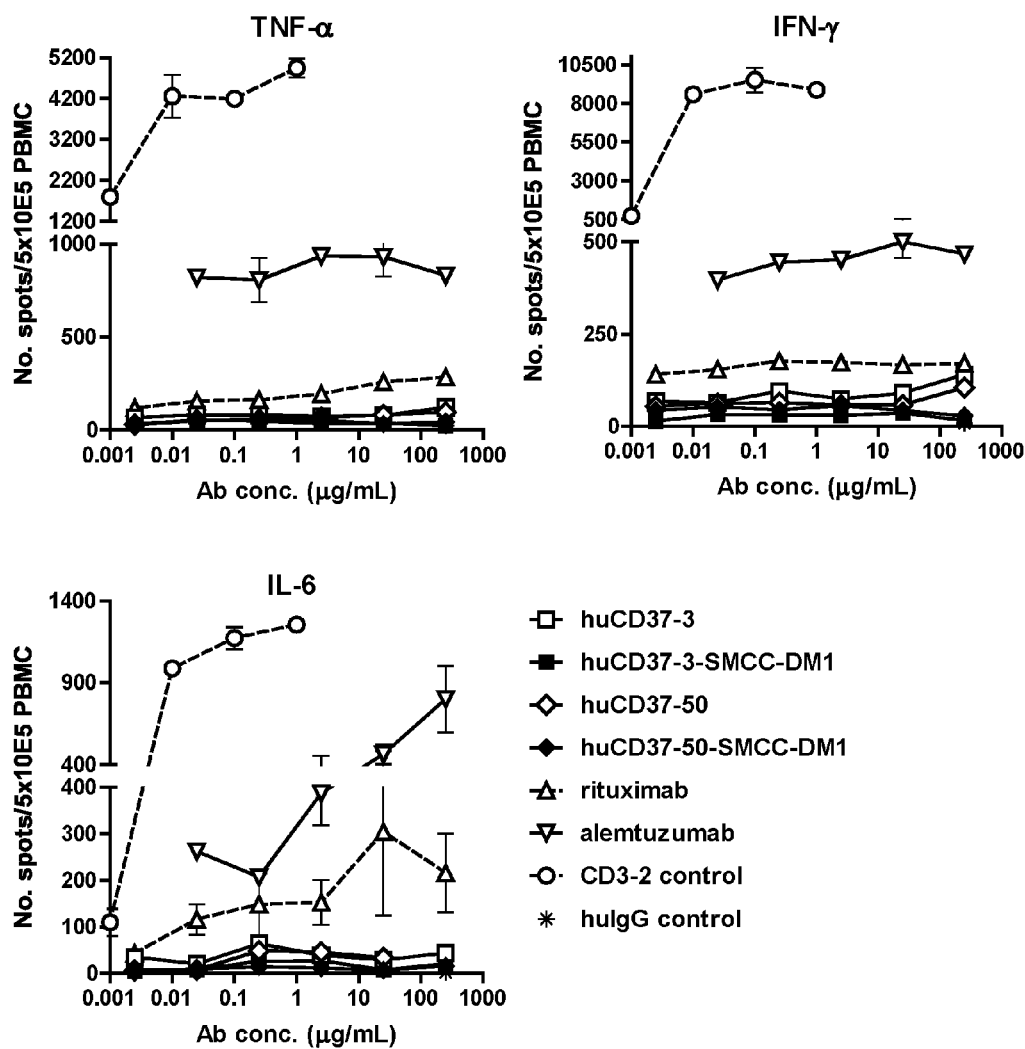

FIG. 6 depicts release of IFN-γ (Interferon), TNF-α (Tumor Necrosis Factor) and IL-6 (Interleukin-6) measured by ELISpot as number of spots per $5 \times 10^5$ peripheral blood mononuclear cells (PBMCs) from one healthy human donor incubated for 18-20 hours with compounds at a concentration of 2.5 ng/mL to 250 µg/mL.

Figure 7:
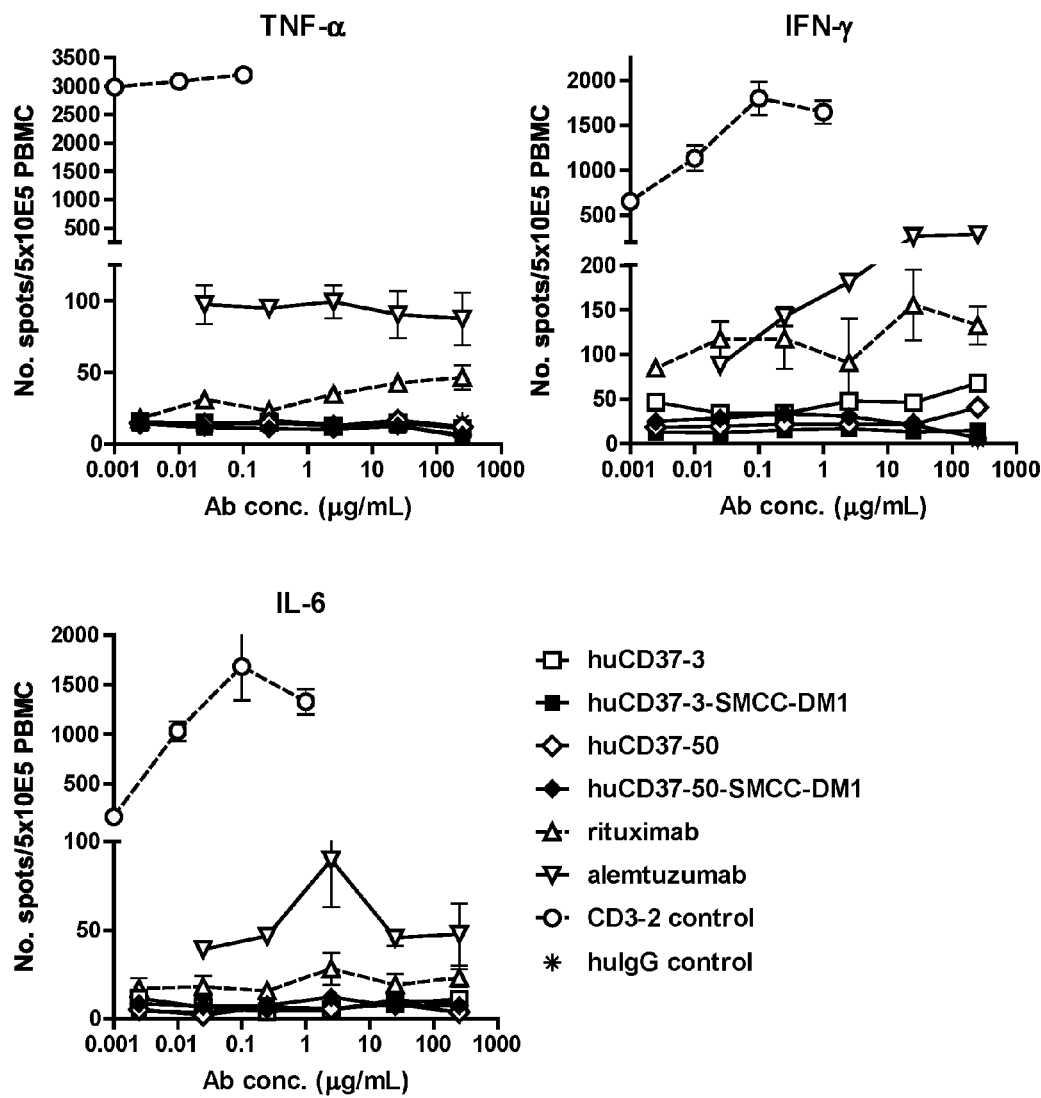

FIG. 7 depicts release of IFN-γ (Interferon), TNF-α (Tumor Necrosis Factor) and IL-6 (Interleukin-6) measured by ELISpot as number of spots per $5 \times 10^5$ peripheral blood mononuclear cells (PBMCs) from a second healthy human donor incubated for 18-20 hours with compounds at a concentration of 2.5 ng/mL to 250 µg/mL.

Figure 8:
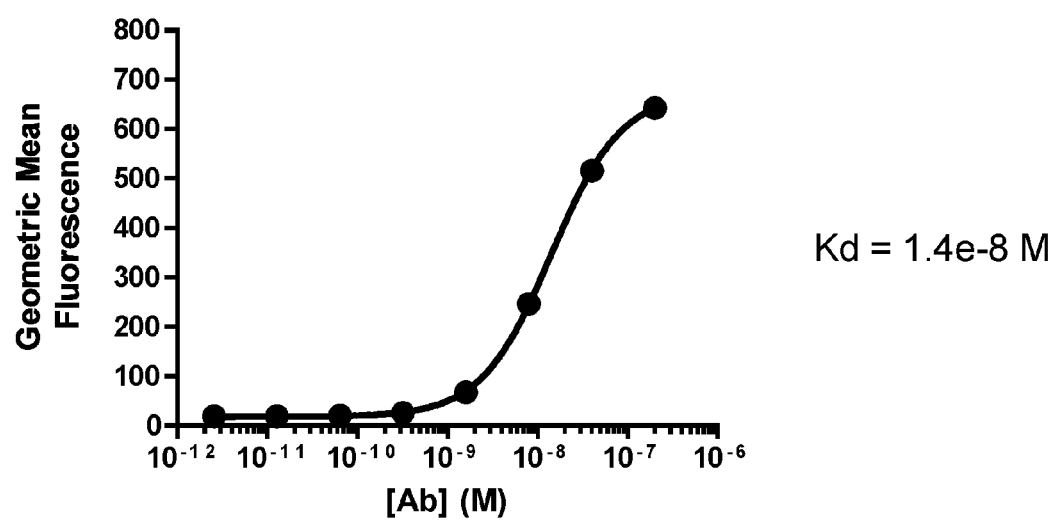

FIG. 8 depicts the binding curve of anti-muCD37 monoclonal antibody clone 252-3.

Figure 9:
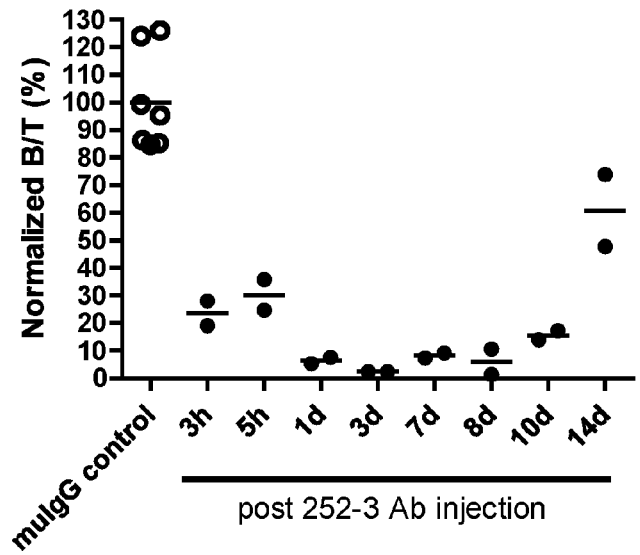
Figure 9:
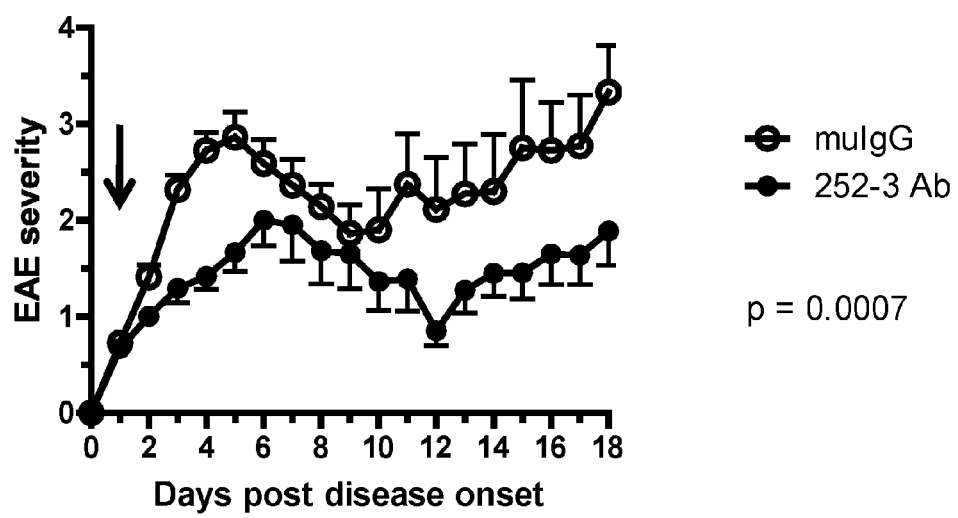

FIG. 9 shows the activity of the 252-3 antibody in depleting peripheral blood B cells (A) and in inhibiting EAE (B) in C57Bl/6 mice. In (A), each symbol represent one mouse; to compare the B cell level in control vs. experimental mice, B cell level was normalized with T cell level and ratio of B/T cell in control mice was considered 100%. In (B), open and closed symbols represent mean of EAE score in control group (n=10) and 252-3 antibody treated group (n=10), respectively; arrow indicates day of antibody injection.

Figure 10:
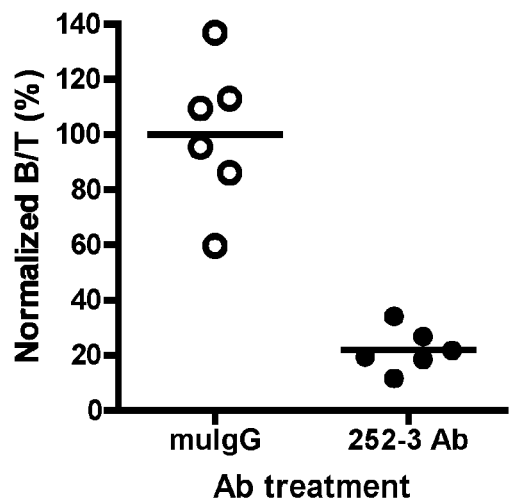
Figure 10:
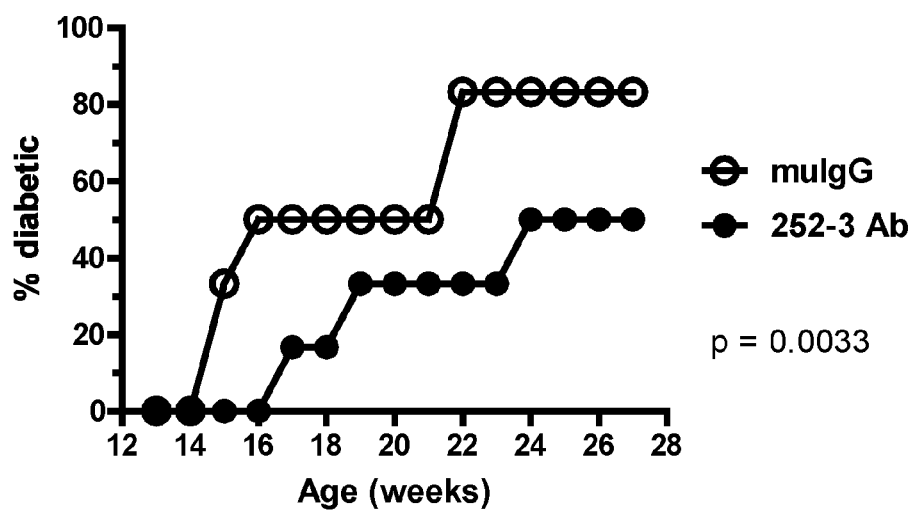

FIG. 10 shows the activity of the 252-3 antibody in depleting peripheral blood B cells (A) and in inhibiting T1D (B) in NOD mice. In (A), each symbol represent one mouse: to compare the B cell level in control vs. experimental mice, B cell level was normalized with T cell level and ratio of B/T cell in control mice was considered 100%. In (B), open and closed symbols represent the diabetes incidence in control group (n=6) and 252-3 antibody treated group (n=6), respectively.

Figure 11:
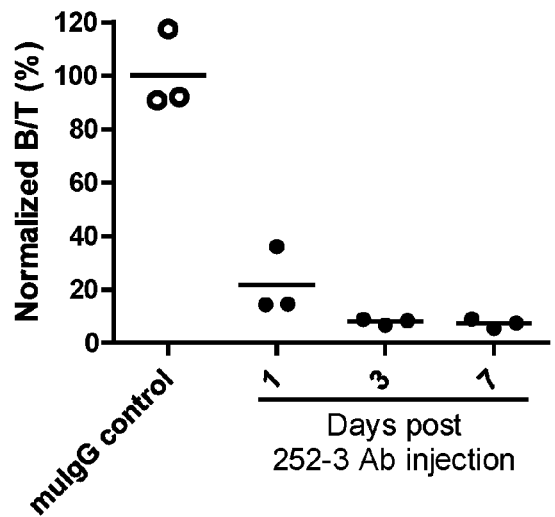
Figure 11:
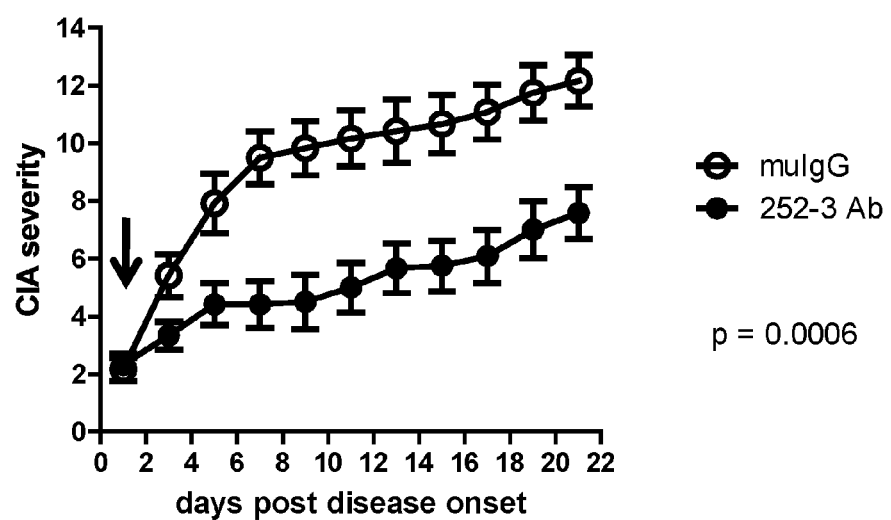

FIG. 11 shows the activity of the 252-3 antibody in depleting peripheral blood B cells (A) and in inhibiting CIA (B) in DBA/1 mice. In (A), each symbol represent one mouse; to compare the B cell level in control vs. experimental mice, B cell level was normalized with T cell level and ratio of B/T cell in control mice was considered 100%. In (B), open and closed symbols represents mean of CIA score in control group (n=12) and 252-3 antibody treated group (n=12), respectively; arrow indicates day of antibody injection.

DETAILED DESCRIPTION OF THE INVENTION

The present invention provides methods of depleting B-cells and of treating diseases associated with aberrant B-cell activity and/or aberrant T-cell stimulation in connection with a B-cell pathway using CD37 binding molecules.

I. DEFINITIONS

To facilitate an understanding of the present invention, a number of terms and phrases are defined below.

The term CD37 as used herein, refers to any native CD37, unless otherwise indicated. CD37 is also referred to as GP52-40, leukocyte antigen CD37, and Tetraspanin-26. The term "CD37" encompasses "full-length," unprocessed CD37 as well as any form of CD37 that results from processing in the cell. The term also encompasses naturally occurring variants of CD37, e.g., splice variants, allelic variants, and isoforms. The CD37 polypeptides described herein can be isolated from a variety of sources, such as from human tissue types or from another source, or prepared by recombinant or synthetic methods.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as CD37. In some embodiments, blocking antibodies or antagonist antibodies substantially or completely inhibit the biological activity of the antigen. The biological activity can be reduced by 10%, 20%, 30%, 50%, 70%, 80%. 90%, 95%, or even 100%.

The term "anti-CD37 antibody" or "an antibody that binds to CD37" refers to an antibody that is capable of binding CD37 with sufficient affinity such that the antibody is useful as a diagnostic and/or therapeutic agent in targeting CD37. The extent of binding of an anti-CD37 antibody to an unrelated, non-CD37 protein can be less than about 10% of the binding of the antibody to CD37 as measured, e.g., by a radioimmunoassay (RIA). In certain embodiments, an antibody that binds to CD37 has a dissociation constant (Kd) of ≤1 µM, ≤100 nM, ≤10 nM, ≤1 nM, or ≤0.1 nM.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113' of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-CD37 antibody or fragment thereof) and is defined by a generic formula: C-L-A, wherein C=cytotoxin, L=linker, and A=cell binding agent or anti-CD37 antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti CD37 antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include B-cell lymphomas including NHL, precursor B-cell lymphoblastic leukemia/lymphoma and mature B-cell neoplasms, such as B-cell chronic lymphocytic leukemia (CLL)/small lymphocytic lymphoma (SLL), B-cell prolymphocytic leukemia, lymphoplasmacytic lymphoma, mantic cell lymphoma (MCL), follicular lymphoma (FL), including low-grade, intermediate-grade and high-grade FL, cutaneous follicle center lymphoma, marginal zone B-cell lymphoma (MALT type, nodal and splenic type), hairy cell leukemia, diffuse large B-cell lymphoma, Burkitt's lymphoma, plasmacytoma, plasma cell myeloma, post-transplant lymphoproliferative disorder, and anaplastic large-cell lymphoma (ALCL). Non-cancerous cells are cells that do not result in the formation of tumors or neoplasms or the development of cancer. However, non-cancerous cells can contribute to disease, e.g., autoimmune diseases, and include, for example auto-reactive B-cells.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "autoreactive" refers to a cell, tissue, protein, antibody or other substance that produces an immune response directed against an organism's own cells, tissues, proteins, antibodies, or other substances.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In some embodiments, the therapeutically effective amount of the drug can reduce the number of B-cells; reduce the number of autoreactive B-cells; decrease the symptoms of disease; or slow the progression of disease. See the definition herein of "treating". A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g., radioisotope labels or fluorescent labels) or, in the case of an enzymatic label, can catalyze chemical alteration of a substrate compound or composition which is detectable.

Terms such as "treating" or "treatment" or "to treat" or "alleviating" or "to alleviate" refer to therapeutic measures that cure, slow down, lessen symptoms of, and/or halt progression of a diagnosed pathologic condition or disorder. Thus, those in need of treatment include those already diagnosed with or suspected of having the disorder. Prophylactic or preventative measures refer to therapeutic measures that prevent and/or slow the development of a targeted pathologic condition or disorder. Thus, those in need of prophylactic or preventative measures include those prone to have the disorder and those in whom the disorder is to be prevented. In certain embodiments, a subject is successfully "treated" if the patient shows one or more of the following: decreased B-cells; decreased autoreactive B-cells; decreased B-cell activity; decreased aberrant B-cell activity; decreased non-malignant B-cells, decreased non-cancerous B-cells, reduced immunoglobulin level; reduced morbidity and mortality; improvement in quality of life; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgap-dna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48):444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%. 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine; methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the CD37 to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. CD37 BINDING AGENTS

The present invention provides agents that specifically bind CD37. These agents are referred to herein as "CD37 binding agents." Exemplary CD37-binding agents have been described in U.S. Published Application No. 2011/0256153, which is herein incorporated by reference in its entirety.

The full-length amino acid sequences for human, macaca, and murine CD37 are known in the art and also provided herein as represented by SEQ ID NOs: 1-3, respectively.

Human CD37:
(SEQ ID NO: 1)
MSAQESCLSLIKYFLFVFNLFFFVLGSLIFCFGIWILIDKTSFVSFVGLAFVPLQIWSKVL

AISGIFINGIALLGCVGALKELRCLLGLYFGMLLLLFATQITLGILISTQRAQLERSLRDVVEKTIQ

KYGTNPEETAAEESWDYVQFQLRCCGWHYPQDWFQVLILRGNGSEAHRVPCSCYNLSATNDSTI

LDKVILPQLSRLGHLARSRHSADICAVPAESHIYREGCAQGLQKWLHNNLISIVGICLGVGLLELG

FMTLSIFLCRNLDHVYNRLAYR

Macaca mulatta CD37:
(SEQ ID NO: 2)
MSAQESCLSLIKYFLFVFNLFFFVILGSLIFCFGIWILIDKTSFVSFVGLAFVPLQIWSKV

LAISGVFTMGLALLGCVGALKELRCLLGLYFGMLLLLFATQITLGILISTQRAQLERSLQDIVEKTI

QRYHTNPEETAAEESWDYVQFQLRCCGWHSPQDWFQVLTLRGNGSEAHRVPCSCYNLSATNDS

TILDKVILPQLSRLGQLARSRHSTDICAVPANSHIYREGCARSLQKWLHNNLISIVGICLGVGLLEL

GFMTLSIFLCRNLDHVYNRLRYR

Murine CD37 (NP_031671):
(SEQ ID NO: 3)
MSAQESCLSLIKYFLFVFNLFFFVLGGLIFCFGTWILIDKTSFVSFVGLSFVPLQTWSKV

LAVSGVLTMALALLGCVGALKELRCLLGLYFGMLLLLFATQITLGILISTQRVRLERRVQELVLR

TIQSYRTNPDETAAEESWDYAQFQLRCCGWQSPRDWNKAQMLKANESEEPFVPCSCYNSTATN

DSTVFDKLFFSQLSRLGPRAKLRQTADICALPAKAFITYREGCAQSLQKWLHNNIISIVGICLGVGL

LELGFMTLSIFLCRNLDHVYDRLARYR

In certain embodiments, the CD37 binding agents are antibodies, immunoconjugates or polypeptides. In some embodiments, the CD37 binding agents are humanized antibodies.

In certain embodiments, the CD37-binding agents are capable of inducing complement dependent cytotoxicity. Examples of CD37-binding agents that are capable of inducing complement dependent cytotoxicy are disclosed, for example, in U.S. Published Application No. 2011/0256153, which is herein incorporated by reference in its entirety. For example, treatment of cells with the CD37-binding agents can result in CDC activity that reduces cell viability to less than about 80%, less than about 70%, less than about 60%, less than about 50%, less than about 40% or less than about 35% of the cell viability of untreated cells. Treatment of cells with the CD37-binding agents can also result in CDC activity that reduces cell viability to about 70-80%, about 60-70%, about 50-60%, about 40-50%, or about 30-40% of the cell viability of untreated cells. In some particular embodiments, the CD37-binding agents are capable of inducing complement dependent cytotoxicity in Ramos cells.

In certain embodiments, the CD37-binding agents are capable of inducing antibody dependent cell mediated cytotoxicity (ADCC). Examples of CD-37 binding agents that are capable of inducing antibody dependent cell mediated cytotoxicity (ADCC) are disclosed, for example, in U.S. Published Application No. 2011/0256153, which is herein incorporated by reference in its entirety. For example, treatment of cells with the CD37-binding agents can result in ADCC activity that produces at least about 15%, at least about 20%, at least about 25%, at least about 30%, at least about 35%, at least about 40%, at least about 45%, at least about 50%, or at least about 60% cell lysis. Treatment of cells with the CD37-binding agents can result in ADCC activity that produces about 10-20%, about 20-30%, about 30-40%, or about 40-50% cell lysis. Treatment of cells with the CD37-binding agents can also result in ADCC activity that produces about 10-50%, about 20-50%, about 30-50%, or about 40-50% cell lysis. In some particular embodiments, the CD37-binding agents are capable of inducing ADCC in Daudi, Ramos, and/or Granata-519 cells.

In some embodiments, the CD37-binding agents are capable of inducing apoptosis. In some embodiment, the CD37-binding agents are capable of inducing apoptosis in the absence of cross-linking agents. Examples of CD37-binding agents that are capable of inducing apoptosis in vitro in the absence of a cross-linking agent are disclosed, for example, in U.S. Published Application No. 2011/0256153, which is herein incorporated by reference in its entirety. For example, treatment of cells with the CD37-binding agents can induce apoptosis in at least about 15%, at least about 20%, at least about 25%, at least about 30%, at least about 35%, at least about 40%, at least about 45%, at least about 50%, or at least about 55% of cells. In some particular embodiments, the CD37-binding agents are capable of inducing apoptosis in Ramos cells and/or Raji cells.

In some embodiments, the CD37-binding agents are capable of depleting B-cells. In some embodiments, the B-cells are autoreactive B-cells. In some embodiments, the B-cells are not cancer cells. In some embodiments, the B-cells are not tumor cells. In some embodiments, the B-cells are not cancerous cells. In some embodiments, the B-cells overexpress CD37. In some embodiments, the B-cells do not overexpress CD37.

Treatment of cells, with CD37-binding agents can result in depletion of at least about 25%, at least about 30%, at least about 35%, at least about 40%, at least about 45%, at least about 50%, at least about 55%, at least about 60%, at least about 65%, at least about 70%, or least about 75% of B-cells.

In some embodiments, the CD37-binding agents do not deplete T-cells under the same conditions in which B-cells are depleted. For example, treatment of cells with CD37-binding agents can result in depletion of less than about 20%, less than about 15%, less than about 10%, or less than about 5% of T-cells. In certain embodiments, the CD37-binding agents deplete at least about 25% of B-cells and deplete less than about 10% of T-cells. In certain embodiments, the CD37-binding agents deplete at least about 30% of B-cells and deplete less than about 5% of T-cells.

In some embodiments, the CD37-binding agents do not deplete monocytes under the same conditions in which B-cells are depleted. For example, treatment of cells with CD37-binding agents can result in depletion of less than about 20%, less than about 15%, less than about 10%, or less than about 5% of monocytes. In certain embodiments, the CD37-binding agents deplete at least about 25% of B-cells and deplete less than about 10% of monocytes. In certain embodiments, the CD37-binding agents deplete at least about 30% of B-cells and deplete less than about 5% of monocytes.

In certain embodiments, immunoconjugates or other agents that specifically bind human CD37 trigger cell death via a cytotoxic agent. For example, in certain embodiments, an antibody to human CD37 is conjugated to a maytansinoid that is activated in cells expressing the CD37 by protein internalization. In certain alternative embodiments, the agent or antibody is not conjugated to a maytansinoid or other cytotoxic molecule.

The CD37-binding agents include CD37 antibodies such as CD37-3, CD37-12, CD37-38, CD37-50, CD37-51, CD37-56 and CD37-57 and fragments, variants and derivatives thereof. The CD37-binding agents also include CD37-binding agents that specifically bind to the same CD37 epitope as an antibody selected from the group consisting of CD37-3, CD37-12, CD37-38, CD37-50, CD37-51, CD37-56 and CD37-57. The CD37-binding agents also include CD37-binding agents that competitively inhibit an antibody selected from the group consisting of CD37-3, CD37-12, CD37-38, CD37-50, CD37-51, CD37-56 and CD37-57.

In some particular embodiments, CD37-binding agents can be characterized by their ability to bind chimeric CD37 polypeptides, including murine/human and macaca/human chimeric polypeptides described in U.S. Published Application No. 2011/0256153, which is herein incorporated by reference in its entirety, and provided in the table below.

| Chimeric Polypeptide | Sequence |
|---|---|
| hCD37-MI | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRVRLERRV QELVLRTIQSYRTNPDETAAEESWDYVQFQLRCCGWHYPQDWFQVLILRGNGSEAH RVPCSCYNLSATNDSTILDKVILPQLSRLGHLARSRHSADICAVPAESHIYREGCAQGL QKWLHNNLISIVGICLGVGLLELGFMTLSIFLCRNLDHVYNRLARYR (SEQ ID NO: 184) |
| muCD37-R176 | ISTQRVRLERRVQELVLRTIQSYRTNPDETAAEESWDYAQFQLRCCGWQSPRDWNK AQMLKANESEEPRVPCSCYNSTATNDSTVFDKLFFSQLSRLGPRAKLRQTADICALPA KAHIYREGCAQSLQ (SEQ ID NO:185) |
| hCD37-M45 | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRAQLERSLR DVVEKTIQKYGINPEETAAEESWDYVQFQLRCCGWHYPQDWFQVLILRGNGSEAH RVPCSCYNLSATNDSTILDKVILPQLSRLGPRAKLRQTADICALPAKAHIYREGCAQS LQKWLHNNLISIVGICLGVGLLELGFMTLSIFLCRNLDHVYNRLARYR (SEQ ID NO: 186) |
| hCD37m ECD-H45 | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRVRLERRV QELVLRTIQSYRTNPDETAAEESWDYAQFQLRCCGWQSPRDWNKAQMLKANESEEP RVPCSCYNSTATNDSTVFDKLFFSQLSRLGHLARSRHSADICAVPAESHIYREGCAQG LQKWLHNNLISIVGICLGVGLLELGFMTLSIFLCRNLDHVYNRLARYR (SEQ ID NO: 187) |
| hCD37m ECD-H5 | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRVRLERRV QELVLRTIQSYRTNPDETAAEESWDYAQFQLRCCGWQSPRDWNKAQMLKANESEEP RVPCSCYNSTATNDSTVFDKLFFSQLSRLGPRAKLRQTADICAVPAESHIYREGCAQG LQKWLHNNLISIVGICLGVGLLELGFMTLSIFLCRNLDHVYNRLARYR (SEQ ID NO: 188) |
| hCD37m ECD-H4 | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRVRLERRV QELVLRTIQSYRTNPDETAAEESWDYAQFQLRCCGWQSPRDWNKAQMLKANESEEP RVPCSCYNSTATNDSTVFDKLFFSQLSRLGHLARSRHSADlCALPAKAHIYREGCAQS LQKWLHNNLISIVGICLGVGLLELGFMTLSIFLCRNLDHVYNRLARYR (SEQ ID NO: 189) |
| hCD37-Mac4 | MSAQESCLSLIKYFLFVFNLFFFVLGSLIFCFGIWILIDKTSFVSFVGLAFVPLQIWSKV LAISGIFTMGIALLGCVGALKELRCLLGLYFGMLLLLFATQITLGILISTQRAQLERSLR DVVEKTIQKYGTNPEETAAEESWDYVQFQLRCCGWHYPQDWFQVLILRGNGSEAH RVPCSCYNLSATNDSTILDKVILPQLSRLGQLARSRHSTDICAVPAESHIYREGCAQGL QKWLHNNLISIVGICLGVGLLELGFMTLSIFLCRNLDHVYNRLARYR (SEQ ID NO: 190) |

```
hCD37-    MSAQESCLSLIKYFLFVFNLFFFVLGSLIFCFGIWILIDKTSFVSFVGLAFVPLQIWSKV
Mac45     LAISGIFTMGIALLGCVGALKELRCLLGLYFGMLLLLFATQITLGILISTQRAQLERSLR
          DVVEKTIQKYGTNPEETAAEESWDYVQFQLRCCGWHYPQDWFQVL1LRGNGSEAH
          RVPCSCYNLSATNDSTILDKVILPQLSRLGQLARSRHSTDICAVPANSHIYREGCARSL
          QKWLHNNLISIVGICLGVGLLELGFMTLSIFLCRNLDHVYNRLARY (SEQ ID NO: 191)

hCD37-    MSAQESCLSLIKYFLFVFNLFFFVLGSLIFCFGIWILIDKTSFVSFVGLAFVPLQIWSKV
Mac5      LAISGIFTMGIALLGCVGALKELRCLLGLYFGMLLLLFATQITLGILISTQRAQLERSLR
          DVVEKTIQKYGTNPEETAAEESWDYVQFQLRCCGWHYPQDWFQVLILRGNGSEAH
          RVPCSCYNLSATNDSTILDKVILPQLSRLGHLARSRHSADICAVPANSHIYREGCARSL
          QKWLHNNLISIVGICLGVGLLELGFMTLSIFLCRNLDHVYNRLARYR (SEQ ID NO:
          192)
```

In some particular embodiments, the binding of the CD37-binding agents to CD37 does not require human CD37 amino acids 109-138. Thus, some CD37-binding agents bind to a polypeptide comprising the amino acid sequence of SEQ ID NO: 184. In other embodiments, the binding of the CD37-binding agents to CD37 is disrupted by mutation of human CD37 amino acids 202-243. Thus, some CD37-binding agents do not bind to a polypeptide comprising the amino acid sequence of SEQ ID NO:185.

In some embodiments, the CD37-binding agents bind to a polypeptide of SEQ ID NO:184 and to a polypeptide of SEQ ID NO:186, but do not bind to a polypeptide of SEQ ID NO:185.

In some embodiments, the CD37-binding agents bind to a polypeptide of SEQ ID NO: 187. In some embodiments, the CD37-binding agents bind to a polypeptide of SEQ ID NO:187 and a polypeptide of SEQ ID NO:188. In some embodiments, the CD37-binding agents bind to a polypeptide of SEQ ID NO: 187 and a polypeptide of SEQ ID NO: 189.

In some embodiments, the CD37-binding agent binds to a polypeptide of SEQ ID NO:190, but does not bind to a polypeptide of SEQ ID NO:191. In some embodiments, the CD37-binding agent binds to a polypeptide of SEQ ID NO: 192, but does not bind to a polypeptide of SEQ ID NO: 191.

CD37 peptide fragments to which certain CD37-binding agents bind to include, but are not limited to, CD37 fragments comprising, consisting essentially of, or consisting of amino acids 200-243 of SEQ ID NO: 1, amino acids 202-220 or SEQ ID NO:1, or amino acids 221-243 of SEQ ID NO:1. In some embodiments, the CD37-binding agent is specifically binds to a human CD37 epitope comprising amino acids 202-243 of SEQ ID NO:1. In some embodiments, the binding of the CD37-binding agent to CD37 requires amino acids 202-243 of SEQ ID NO:1. In some embodiments, the binding of the CD37-binding agent to CD37 requires amino acids 200-220 of SEQ ID NO:1. In some embodiments, the binding of the CD37-binding agent to CD37 requires amino acids 221-243 of SEQ ID NO:1.

Examples of CD37-binding agents with the aforementioned binding properties are described in U.S. Published Application No. 2011/0256153, which is herein incorporated by reference in its entirety.

The CD37-binding agents also include CD37-binding agents that comprise the heavy and light chain CDR sequences of CD37-3, CD37-12, CD37-38, CD37-50, CD37-51, CD37-56 or CD37-57. The heavy and light chain CDRs of CD37-38, CD37-50, CD37-51, CD37-56 and CD37-57 contain related sequences. Therefore, the CD37-binding agents can also comprise heavy and light chain CDR sequences that comprise a consensus sequence obtained by the alignment of CD37-38, CD37-50, CD37-51, CD37-56 and CD37-57. The CDR sequences of CD37-3, CD37-12, CD37-38, CD37-50, CD37-51, CD37-56 and CD37-57, as well as the consensus sequence of CD37-38, CD37-50, CD37-51, CD37-56 and CD37-57 are described in Tables 1 and 2 below.

TABLE 1

Variable heavy chain CDR amino acid sequences

| Antibody | VH-CDR1 | VH-CDR2 | VH-CDR3 |
| --- | --- | --- | --- |
| CD37-3 | TSGVS (SEQ ID NO: 4) | VIWGDGSTN (SEQ ID NO: 5) | GGYSLAH (SEQ ID NO: 6) |
| CD37-12 | KYGMN (SEQ ID NO: 7) | WINTNTGESR (SEQ ID NO: 8) | GTVVAD (SEQ ID NO: 9) |
| CD37-38 | SGFGWH (SEQ ID NO: 10) | YILYSGGTD (SEQ ID NO: 11) | GYYGYGAWFVY (SEQ ID NO: 12) |
| CD37-50 | SGFAWH (SEQ ID NO: 13) | YILYSGSTV (SEQ ID NO: 14) | GYYGYGAWFAY (SEQ ID NO: 15) |
| CD37-51 | SGFAWH (SEQ ID NO: 16) | Y1HYSGSTN (SEQ ID NO: 17) | GYYGFGAWFVY (SEQ ID NO: 18) |

TABLE 1-continued

Variable heavy chain CDR amino acid sequences

| Antibody | VH-CDR1 | VH-CDR2 | VH-CDR3 |
|---|---|---|---|
| CD37-56 | SGFAWH (SEQ ID NO: 19) | YIHYSGGTN (SEQ ID NO: 20) | GYYGFGAWFAY (SEQ ID NO: 21) |
| CD37-57 | SGFAWH (SEQ ID NO: 22) | YILYSGSTV (SEQ ID NO: 23) | GYYGYGAWFAY (SEQ ID NO: 24) |
| CONSENSUS | SGF[A or G]WH (SEQ ID NO: 25) | YI[L or H]YSG[G or S]T[D, V, or N] (SEQ ID NO: 26) | GYYG[Y or F]GAWF[V or A]Y (SEQ ID NO: 27) |
| 252-3 | SYGMS (SEQ ID NO: 171) | TISSGGSYTYSPDSVKG (SEQ ID NO: 172) | HSYYDTSVDY (SEQ ID NO: 173) |
| 252-3 | SYGMS (SEQ ID NO: 171) | TISSGGSYTY (SEQ ID NO: 181) | HSYYDTSVDY (SEQ ID NO: 173) |

TABLE 2

Variable light chain CDR amino acid sequences

| Antibody | VL-CDR1 | VL-CDR2 | VL-CDR3 |
|---|---|---|---|
| CD37-3 | RASENIRSNLA (SEQ ID NO: 28) | VATNLAD (SEQ ID NO: 29) | QHYWGTTWT (SEQ ID NO: 30) |
| CD37-12 | RASQSVSTSSYSYLY (SEQ ID NO: 31) | YASNLAS (SEQ ID NO: 32) | QHSWEIPYT (SEQ ID NO: 33) |
| CD37-38 | SASSSVTYMH (SEQ ID NO: 34) | DTSKLAS (SEQ ID NO: 35) | QQWISNPPT (SEQ ID NO: 36) |
| CD37-50 | SATSSVTYMH (SEQ ID NO: 37) | DTSKLPY (SEQ ID NO: 38) Humantzed DTSNLPY (SEQ ID NO: 40) | QQWSDNPPT (SEQ ID NO: 39) |
| CD37-51 | SATSSVTYMH (SEQ IDNO: 41) | DTSKLAS (SEQ ID NO: 42) | QQWSSNPPT (SEQ ID NO: 43) |
| CD37-56 | SASSSVTYMH (SEQ ID NO: 44) | DTSKLAS (SEQ ID NO: 45) Humantzed DTSNLAS (SEQ ID NO: 47) | QQWISDPPT (SEQ ID NO: 46) |
| CD37-57 | SATSSVTYMH (SEQ ID NO: 48) | DTSKLAS (SEQ ID NO: 49) Humantzed DTSNLAS (SEQ ID NO: 51) | QQWSDNPPT (SEQ ID NO: 50) |
| CONSENSUS | SA[T or S]SSVTYMH (SEQ ID NO: 52) | DTS[K or N]L[A or P][S or Y] (SEQ ID NO: 53) | QQW[I or S][S or D][N or D]PPT (SEQ ID NO: 54) |
| 252-3 | RASQDISNYLN (SEQ ID NO: 174) | YTSKLHS (SEQ ID NO: 175) | QQGNALPWT (SEQ ID NO: 176) |

The CD37 binding molecules can be antibodies or antigen binding fragments that specifically bind to CD37 that comprise the CDRs of CD37-3, CD37-12, CD37-50, CD37-51, CD37-56, or CD37-57 with up to four (i.e., 0, 1, 2, 3, or 4) conservative amino acid substitutions per CDR.

The CD37 binding molecules can comprise one of the individual variable light chains or variable heavy chains described herein. Antibodies and polypeptides can also comprise both a variable light chain and a variable heavy chain. The variable light chain and variable heavy chain sequences of murine, chimeric, and humanized CD37-3, CD37-12, CD37-50, CD37-51. CD37-56, and CD37-57 antibodies are provided in Tables 3 and 4 below.

TABLE 3

Variable heavy chain amino acid sequences

| Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 55) |
| chCD37-3 | QVQVKESGPGLVAPSQSLS1TCTVSGFSLITSGVSWVRQPPGKGLEWLGVIW GDGSTNYHSALKSRLS1KKDHSKSQVFLKLNSLQTDDTATYYCAKGGYSLA HWGQGTLVTVSA (SEQ ID NO: 56) |
| huCD37-3v1.0 | QVQVQESGPG LVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSS (SEQ ID NO: 57) |
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSS (SEQ ID NO: 58) |
| muCD37-I2 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 59) |
| chCD37-I2 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 60) |
| muCD37-38 | DVQLQESGPDLVKPSQSLSLTCTVTGYSITSGFGWHWIRQFPGNKLEWMAY ILYSGGTDYNPSLKSRISITRDTSKNQFFLFtLSSVTTEDTATYYCARGYYGYG AWFVYWGQGTLVTVSA (SEQ ID NO: 61) |
| chCD37-38 | QVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSA (SEQ ID NO: 62) |
| huCD37-38 | QVQLQESGPGLVKPSQSLSLTCTVSGYSITSGFGWHWIRQFPGKGLEWMAYI LYSGGTDYNPSLKSRISITRDTSKNQFFLRLSSVTAADTATYYCARGYYGYG AWFVYWGQGTLVTVSS (SEQ ID NO: 63) |
| muCD37-50 | DVQLQESGPDLLKPSQSLSLTCTVTGYSITSGFAWHWIRQFPGNKLEWMGYI LYSGSTVYSPSLKSRISITRDTSKNHFFLQLNSVTTEDTATYYCARGYYGYG AWFAYWGQGTLVTVSA (SEQ ID NO: 64) |
| huCD37-50 | QVQLQESGPGLLKPSQSLSLTCTVSGYSITSGFAWHWIRQHPGNKLEWMGY ILYSGSTVYSPSLKSRISITRDTSKNHFFLQLNSVTAADTATYYCARGYYGYG AWFAYWGQGTLVTVSA (SEQ ID NO: 65) |
| muCD37-51 | DVQLQESGPDLLKPSQSLSLTCTVTGYSISSGFAWHWIRQFPGNKLEWMGYI HYSGSTNYSPSLKSRISITRDSSKNQFFLQLNSVTTEDTATYYCARGYYGFGA WFVYWGQGTLVTVSA (SEQ ID NO: 66) |
| huCD37-51 | EVQLVESGPEVLKPGESLSLTCTVSGYS1SSGFAWHWIRQFPGKGLEWMGYI HYSGSTNYSPSLQGRISITRDSSINQFFLQLNSVTASDTATYYCARGYYGFGA WFVYWGQGTLVTVSA (SEQ ID NO: 67) |
| muCD37-56 | DVQLQESGPDLVKPSQSLSLTCTVTGYSITSGFAWHWIRQFPGNKLEWMGY IHYSGGTNYNPSLKSRVSITRDTSKNQFFLQLNSVTTEDTATYYCARGYYGF GAWFAYWGQGTLVPVSA (SEQ ID NO: 68) |
| huCD37-56 | QVQLQESGPGLVKPSQSLSLTCTVSGYSITSGFAWHWIRQFPGKGLEWMGYI HYSGGTNYNPSLKSRVSITRDTSKNQFFLQLNSVTAADTATYYCARGYYGF GAWFAYWGQGTLVPVSA (SEQ ID NO: 69) |
| muCD37-57 | DVQLQESGPDLLKPSQSLSLICTVTGYSITSGFAWHWIRQFPGNKLEWMGYI LYSGSTVYSPSLKSRISITRDTSKNQFFLQLNSVTTEDTATYYCARGYYGYG AWFAYWGQGTLVTVSA (SEQ ID NO: 70) |
| huCD37-57 | QVQLQESGPGLLKPSQSLSLTCTVSGYSITSGFAWHWIRQFPGKGLEWMGYI LYSGSTVYSPSLKSRISITRDTSKNQFFLQLNSVTAADTATYYCARGYYGYG AWFAYWGQGTLVTVSA (SEQ ID NO: 71) |
| 252-3 | EVQVVESGGDLVKPGGSLKLSCAASGFTFSSYGMSWVRQTPDKRLEWVATI SSGGSYTYSPDSVKGRFTISRDNAKKTLYLQMSSLKSEDTAMYYCARHSYY DTSVDYWGQGTSVTVSS (SEQ ID NO: 177) |

TABLE 4

Variable light chain amino acid sequences

| Antibody | VL Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 72) |
| chCD37-3 | DIQMTQSPASLSVSVGETVTITCRASENIRSNLAWYQQKQGKSPQLLVNVAT NLADGVPSRFSGSGSGTQYSLKINSLQSEDEGTYYCQHYWGTTWTFGGGTK LEIKR (SEQ ID NO: 73) |
| huCD37-3 (1.0 and 1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK LEIKR (SEQ ID NO: 74) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 75) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 76) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKR (SEQ ID NO: 77) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQW1SNPPTFGGGTKL EIKR (SEQ ID NO: 78) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKR (SEQ ID NO: 79) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKR (SEQ ID NO: 80) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKR (SEQ ID NO: 81) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKR (SEQ ID NO: 82) |
| huCD37-51 | EIVLTQSPATMSASPGERVTMTCSATSSVTYMHWYQQKPGQSPKRWIYDTS KLASGVPARFSGSGSGTSYSLTISSMEAEDAATYYCQQWSSNPPTFGQGTKL EIKR (SEQ ID NO: 83) |
| muCD37-56 | QIVLTQSPAFMSASPGDKVTMTCSASSSVTYMHWYQQKSGTSPKRWIYDTS KLASGVPARFSGGGSGTSYSLTISTMEAEDAATYYCQQWISDPPTFGGGTKL EIKR (SEQ ID NO: 84) |
| huCD37-56 | DIVLTQSPAFMSASPGEKVTMTCSASSSVTYMHWYQQKPDQSPKRWIYDTS NLASGVPSRFSGGGSGTDYSLTISSMEAEDAATYYCQQWISDPPTFGQGTKL EIKR (SEQ ID NO: 85) |
| muCD37-57 | QIVLTQSPAIMSASPGEKVTMTCSATSSVTYMHWYQQKSGTSPKRWIYDTS KLASGVPARFSGSGSGTSYSLTISSMEAEDAATYYCQQWSDNPPTFGSGTKL EIKR (SEQ ID NO: 86) |
| huCD37-57 | EIVLTQSPATMSASPGERVTMTCSATSSVTYMHWYQQKPGQSPRRWIYDTS NLASGVPARFSGSGSGTSYSLTISSMEAEDAATYYCQQWSDNPPTFGQGTKL EIKR (SEQ ID NO: 87) |
| 252-3 | DIQMTQTTSSLSASLGDRVTISCRASQDISNYLNWYQQKPDGTVKLLIYYTS KLHSGVPSRFSGSGSGTDYSLTISNLEQEDIATYFCQQGNALPWTFGGGTKL ELKR (SEQ ID NO: 178) |

Also provided are polypeptides that comprise: (a) a polypeptide having at least about 90% sequence identity to SEQ ID NOs:55-71 or 177; and/or (b) a polypeptide having at least about 90% sequence identity to SEQ ID NOs:72-87 or 178. In certain embodiments, the polypeptide comprises a polypeptide having at least about 95%, at least about 96%, at least about 97%, at least about 98%, or at least about 99% sequence identity to SEQ ID NOs:55-87, 177, or 178. Thus, in certain embodiments, the polypeptide comprises (a) a polypeptide having at least about 95% sequence identity to SEQ ID NOs:55-71 or 177, and/or (b) a polypeptide having at least about 95% sequence identity to SEQ ID NOs:72-87 or 178. In certain embodiments, the polypeptide comprises (a) a polypeptide having the amino acid sequence of SEQ ID NOs:55-71 or 177; and/or (b) a polypeptide having the amino acid sequence of SEQ ID NOs:72-87 or 178. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:55-87, 177, or 178 differs from SEQ ID NOs:55-87 by conservative amino acid substitutions only.

Polypeptides can comprise one of the individual light chains or heavy chains described herein. Antibodies and polypeptides can also comprise both a light chain and a heavy chain. The light chain and variable chain sequences of murine, chimeric, and humanized CD37-3, CD37-12, CD37-50, CD37-51, CD37-56, and CD37-57 antibodies are provided in Tables 5 and 6 below.

TABLE 5

| | Full-length heavy chain amino acid sequences |
|---|---|
| Antibody | Full-Length Heavy Chain Amino Acid Sequence (SEQ ID NO) |
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAAKTTAPSVYPLAPVCGDTTGSSVTLGCLVKGYFPEPVTL TWNSGSLSSGVHTFPAVLQSDLYTLSSSVTVTSSTWPSQSITCNVAHPASSTK VDKKIEPRGPTIKPCPPCKCPAPNLLGGPSVFIFPPKIKDVLMISLSPIVTCVVV DVSEDDPDVQISWFVNNVEVHTAQTQTHREDYNSTLRVVSALPIQHQDWM SGKEFKCKVNNKDLPAPIERTISKPKGSVRAPQVYVLPPPEEEMTKKQVTLT CMVTDFMPEDIYVEWTNNGKTELNYKNTEPVLDSDGSYFMYSKLRVEKKN WVERNSYSCSVVHEGLHNHHTTKSFSRTPGK (SEQ ID NO: 88) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSAASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNICALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPGK (SEQ ID NO: 89) |
| huCD37-3v1.0 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDILMISRTPEVTCV VVDVSHEDPEVKFNWYVDGVEVHNAKTKPREEQYNSTYRVVSVLTVLHQ DWLNGKEYKCKVSNICALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 90) |
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 91) |
| muCD37-12 | QIQLVQSGPELKKPGETVKISCICASGYTFTKYGMNWVKQAQGKGLKWMG WINTNTGESRNAEEFKGRFAFSLETSASTAYLQINNLKYEDTATYFCGRGTV VADWGQGTTLTVSSAKTTAPSVYPLAPVCGDTTGSSVTLGCLVKGYFPEPV TLTWNSGSLSSGVHTFPAVLQSDLYTLSSSVTVTSSTWPSQSITCNVAHPASS TKVDKKIEPRGPTIKPCPPCKCPAPNLLGGPSVFIFPPKIKDVLMISLSPIVTCV VVDVSEDDPDVQISWFVNNVEVHTAQTQTHREDYNSTLRVVSALPIQHQD WMSGKEFKCKVNNKDLPAPIERTISKPKGSVRAPQVYVLPPPEEEMIKKQV TLTCMVTDFMPEDIYVEWTNNGKTELNYKNTEPVLDSDGSYFMYSKLRVE KKNWVERNSYSCSVVHEGLHNHHTTKSFSRTPGK (SEQ ID NO: 92) |
| chCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVL HQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPGK (SEQ ID NO: 93) |

TABLE 5-continued

Full-length heavy chain amino acid sequences

| Antibody | Full-Length Heavy Chain Amino Acid Sequence (SEQ ID NO) |
|---|---|
| muCD37-38 | DVQLQESGPDLVKPSQSLSLTCTVTGYSITSGFGWHWIRQFPGNKLEWMAY<br>ILYSGGTDYNPSLKSRISITRDTSKNQFFLRLSSVTTEDTATYYCARGYYGYG<br>AWFVYWGQGTLVTVSAAKTTPPSVYPLAPGSAAQTNSMVTLGCLVKGYFP<br>EPVTVTWNSGSLSSGVHTFPAVLESDLYTLSSSVTVPSSMRPSETVTCNVAH<br>PASSTKVDKKIVPRDCGCKPCICTVPEVSSVFIFPPKPKDVLTITLTPKVICVV<br>VDISKDDPEVQFSWFVDDVEVHTAQTQPREEQFNSTFRSVSELPIMHQDWL<br>NGKEFKCRVNSAAFPAPIEKTISKTKGRPICAPQVYTIPPPKEQMAKDKVSLT<br>CMITDFFPEDITVEWQWNGQPAENYKNTQPIMNTINGSYFVYSKLNVQKSN<br>WEAGNTFTCSVLHEGLHNHHTEKSLSHSPGK (SEQ ID NO: 94) |
| chCD37-38 | QVQLQESGPDLVKPSQSLSLTCTVTGYSITSGFGWHWIRQFPGNKLEWMAY<br>ILYSGGTDYNPSLKSRISITRDTSKNQFFLRLSSVTTEDTATYYCARGYYGYG<br>AWFVYWGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDILMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 95) |
| huCD37-38 | QVQLQESGPGLVKPSQSLSLTCTVSGYSITSGFGWHWIRQFPGKGLEWMAYI<br>LYSGGTDYNPSLKSRISITRDTSKNQFFLRLSSVTAADTATYYCARGYYGYG<br>AWFVYWGQGTLVTVSSASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNICALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 96) |
| muCD37-50 | DVQLQESGPDLLKPSQSLSLICTVTGYSITSGFAWHWIRQFPGNKLEWMGYI<br>LYSGSTVYSPSLKSRISITRDTSKNHFFLQLNSVTTEDTATYYCARGYYGYG<br>AWFAYWGQGTLVTVSAAKTTAPSVYPLAPVCGDTTGSSVTLGCLVKGYFP<br>EPVTLTWNSGSLSSGVHTFPAVLQSDLYTLSSSVTVTSSTWPSQSITCNVAHP<br>ASSTKVDICKEEPRGPTIKPCPPCKCPAPNLLGGPSVFIFPPKIKDVLMISLSPIV<br>TCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKK<br>QVTLTCMVTDFMPEDIYVEWTNNGKTELNYKNTEPVLDSDGSYFMYSKLR<br>VEKKNWVERNSYSCSVVHEGLHNHHTTKSFSRTPGK (SEQ ID NO: 97) |
| huCD37-50 | QVQLQESGPGLLKPSQSLSLTCTVSGYSITSGFAWHWIRQHPGNKLEWMGY<br>ILYSGSTVYSPSLKSRISITRDTSKNHFFLQLNSVTAADTATYYCARGYYGYG<br>AWFAYWGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 98) |
| muCD37-5 | IDVQLQESGPDLLKPSQSLSLTCTVTGYSISSGFAWHWIRQFPGNKLEWMGYI<br>HYSGSTNYSPSLKSRISITRDSSKNQFFLQLNSVTTEDTATYYCARGYYGFGA<br>WFVYWGQGTLVTVSAAKTTAPSVYPLAPVCGDTTGSSVTLGCLVKGYFPEP<br>VTLTWNSGSLSSGVHTFPAVLQSDLYTLSSSVTVTSSTWPSQSITCNVAHPAS<br>STKVDKK1EPRGPTIKPCPPCKCPAPNLLGGPSVFIFPPKIKDVLMISLSPIVTC<br>VVVDVSEDDPDVQISWFVNNVEVHTAQTQTHREDYNSTLRVVSALPIQHQD<br>WMSGKEFKCKVNNKDLPAPIERTISKPKGSVRAPQVYVLPPPEEEMTKKQV<br>TLTCMVTDFMPEDIYVEWTNNGKTELNYKNTEPVLDSDGSYFMYSKLRVE<br>KKNWVERNSYSCSVVHEGLHNHHTTKSFSRTPGK (SEQ ID NO: 99) |
| huCD37-51 | EVQLVESGPEVLKPGESLSLICTVSGYSISSGFAWHWIRQFPGKGLEWMGYI<br>HYSGSTNYSPSLQGRISITRDSSINQFFLQLNSVTASDTATYYCARGYYGFGA<br>WFVYWGQGTLVTVSAASTKGPSVFPLAPSSKSTSGGTAALGCLVKDYFPEP<br>VTVSWNSGALTSGVHTFPAVLQSSGLYSLSSVVTVPSSSLGTQTYICNVNHK<br>PSNTKVDKKVEPKSCDKTHTCPPCPAPELLGGPSVFLFPPKPKDILMISRTPE<br>VTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 100) |
| muCD37-56 | DVQLQESGPDLVKPSQSLSLICTVTGYSITSGFAWHWIRQFPGNKLEWMGY<br>IHYSGGINYNPSLKSRVSITRDTSKNQFFLQLNSVTTEDTATYYCARGYYGF<br>GAWFAYWGQGTLVPVSAAKTTPPSVYPLAPGSAAQTNSMVTLGCLVKGYF<br>PEPVTVTWNSGSLSSGVHTFPAVLESDLYTLSSSVTVPSSMRPSETVTCNVA<br>HPASSTKVDKKIVPRDCGCKPCICTVPEVSSVFIFPPKPKDVLTITLTPKVICV<br>VVDISKDDPEVQFSWFVDDVEVHTAQTQPREEQFNSTFRSVSELPIMHQDW |

TABLE 5-continued

Full-length heavy chain amino acid sequences

| Antibody | Full-Length Heavy Chain Amino Acid Sequence (SEQ ID NO) |
|---|---|
|  | LNGKEFKCRVNSAAFPAPIEKTISKTKGRPKAPQVYTIPPPKEQMAKDKVSL<br>TCMITDFFPEDITVEWQWNGQPAENYKNTQPIMNTNGSYFVYSKLNVQKSN<br>WEAGNTFTCSVLHEGLHNHHTEKSLSHSPGK (SEQ ID NO: 101) |
| huCD37-56 | QVQLQESGPGLVKPSQSLSLTCTVSGYSITSGFAWHWIRQFPGKGLEWMGYI<br>HYSGGTNYNPSLKSRVSITRDTSKNQFFLQLNSVTAADTATYYCARGYYGF<br>GAWFAYWGQGTLVPVSAASTKGPSVFPLAPSSKSTSGGTAALGCLVKDYFP<br>EPVTVSWNSGALTSGVHTFPAVLQSSGLYSLSSVVTVPSSSLGTQTYICNVN<br>HKPSNTKVDKKVEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVL<br>TVLHQDWLNGKEYKCKVSNKALPAPIEKTISICAKGQPREPQVYTLPPSRDEL<br>TKNQVSLICLVKGFYPSDIAVEWESNGQPENNYKTTPPVLDSDGSFFLYSKL<br>TVDKSRWQQGNVFSCSVMHEALHNHYTQKSLSLSPG (SEQ ID NO: 102) |
| muCD37-57 | DVQLQESGPDLLKPSQSLSLTCTVTGYSITSGFAWHWIRQFPGNKLEWMGYI<br>LYSGSTVYSPSLKSRISITRDTSKNQFFLQLNSVTTEDTATYYCARGYYGYG<br>AWFAYWGQGTLVTVSAAKTTAPSVYPLAPVCGDTTGSSVTLGCLVKGYFP<br>EPVTLTWNSGSLSSGVHTFPAVLQSDLYTLSSSVTVTSSTWPSQSITCNVAHP<br>ASSTKVDKKIEPRGPTIKPCPPCKCPAPNLLGGPSVFIPPPKIKDVLMISLSPIV<br>TCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKK<br>QVTLTCMVTDFMPEDIYVEWTNNGKTELNYKNTEPVLDSDGSYFMYSKLR<br>VEKKNWVERNSYSCSVVHEGLHNHHTTKSFSRTPGK (SEQ ID NO:103) |
| huCD37-57 | QVQLQESGPGLLKPSQSLSLTCTVSGYSITSGFAWHWIRQFPGKGLEWMGYI<br>LYSGSTVYSPSLKSRISITRDTSKNQFFLQLNSVTAADTATYYCARGYYGYG<br>AWFAYWGQGTLVTVSSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 104) |
| 252-3 | EVQVVESGGDLVKPGGSLKLSCAASGFTFSSYGMSWVRQTPDKRLEWVATI<br>SSGGSYTYSPDSVKGRFTISRDNAKKTLYLQMSSLKSEDTAMYYCARHSYY<br>DTSVDYWGQGTSVTVSSAKTTAPSVYPLAPVCGDTTGSSVTLGCLVKGYFP<br>EPVTLTWNSGSLSSGVHTFPAVLQSDLYTLSSSVTVISSTWPSQSITCNVAHP<br>ASSTKVDKKIEPRGPTIKPCPPCKCPAPNLLGGPSVFIPPPKIKDVLMISLSPIV<br>TCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKK<br>QVTLTCMVTDFMPED1YVEWTNNGKTELNYKNTEPVLDSDGSYFMYSKLR<br>VEKKNWVERNSYSCSVVHEGLHNHHTTKSFSRTPGK (SEQ ID NO:179) |

TABLE 6

Full-length light chain amino acid sequences

| Antibody | Full-length Light Chain Amino Acid Sequence (SEQ ID NO) |
|---|---|
| muCD37-3 | DIQMTQSPASLSVSVGETVTITCRASENIRSNLAWYQQKQGKSPQLLVNVAT<br>NLADGVPSRFSGSGSGTQYSLKINSLQSEDFGTYYCQHYWGTTVVTFGGGTK<br>LEIKRADAAPTVSIFPPSSEQLTSGGASVVCFLNNFYPKDINVKWKIDGSERQ<br>NGVLNSWTDQDSKDSTYSMSSILTLTKDEVERHNSYTCEATHKTSTSPIVKS<br>FNRNEC (SEQ ID NO: 105) |
| chCD37-3 | DIQMTQSPASLSVSVGETVTITCRASENIRSNLAWYQQKQGKSPQLLVNVAT<br>NLADGVPSRFSGSGSGTQYSLKINSLQSEDFGTYYCQHYWGTTWTFGGGTK<br>LEIKRTVAAPSVF1FPPSDEQLKSGTASVVCLLNNFYPREAKVQWKVDNALQ<br>SGNSQESVTEQDSKDSTYSLSSILTLSKADYEKHKVYACEVTHQLSSPVTK<br>SFNRGEC (SEQ ID NO: 106) |
| huCD37-3<br>(1.0 and 1.1) | DIQMTQSPSSLSVSVGERVTITCRASENIRSNLAWYQQKPGKSPKLLVNVAT<br>NLADGVPSRFSGSGSGTDYSLKINSLQPEDFGTYYCQHYWGTTWTFGQGTK<br>LEIKRTVAAPSVFIFPPSDEQLKSGTASVVCLLNNFYPREAKVQWKVDNALQ<br>SGNSQESVTEQDSKDSTYSLSSTLTLSKADYEKHKVYACEVTHQGLSSPVTK<br>SFNRGEC (SEQ ID NO: 107) |
| muCD37-12 | DIVLTQSPASLAVSLGQRATISCRASQSVSTSSYSYLYWFQQKPGQPPKLLIK<br>YASNLASGVPARFSGSGSGTDFTLNIHPVEEEDTATYYCQHSWEIPYTFGGG<br>TKLEIKRADAAPTVSIFPPSSEQLTSGGASVVCFLNNFYPKDINVKWKIDGSE<br>RQNGVLNSWTDQDSKDSTYSMSSTLTLTKDEYERHNSYTCEATHKTSTSPI<br>VKSFNRNEC (SEQ ID NO: 108) |

TABLE 6-continued

Full-length light chain amino acid sequences

| Antibody | Full-length Light Chain Amino Acid Sequence (SEQ ID NO) |
| --- | --- |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPV TKSFNRGEC (SEQ ID NO: 109) |
| muCD37-38 | QIVLTQSPAIMSASPGEKVTMTCSASSSVTYMHWYQQKSGTSPKRWIYDTS KLASGVPARFSGGGSGTSYSLT1SSMEAEDAATYYCQQWISNPPTFGGGTKL EIKRADAAPTVSIFPPSSEQLTSGGASVVCFLNNFYPKDINVKWKIDGSERQN GVLNSWIDQDSKDSTYSMSSTLTLTKDEVERHNSYTCEATHKTSTSPIVKSF NRNEC (SEQ ID NO: 110) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTY$LSSTLTLSKADYEKHKVYACEVTHQGLSSPVTKS FNRGEC (SEQ ID NO: 111) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 112) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTICDEVERHNSYTCEATHKTSTSPIVKSF NRNEC (SEQ ID NO: 113) |
| huCD37-50 | EIVLTQSPATMSASPGERVTMTCSATSSVTYMHWYQQKPGQSPICRWIVDTS NLPYGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 114) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 115) |
| huCD37-5 | IEIVLTQSPATMSASPGERVIMTCSATSSVTYMHWYQQKPGQSPKRWIYDTS KLASGVPARFSGSGSGTSYSLTISSMEAEDAATYYCQQWSSNPPTFGQGTKL EIKRTVAAPSVFIFPPSDEQLKSGTASVVCLLNNEYPREAKVQWKVDNALQS GNSQESVTEQDSKDSTYSLSSTLTLSKADYEKHKVYACEVTIIQGLSSPVTKS FNRGEC (SEQ ID NO: 116) |
| muCD37-56 | QIVLTQSPAFMSASPGDKVTMTCSASSSVTYMHWYQQKSGTSPKRWIYDTS KLASGVPARFSGGGSGTSYSLTISTMEAEDAATYYCQQWISDPPTEGGGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 117) |
| huCD37-56 | DIVLTQSPAFMSASPGEKVTMTCSASSSVTYMHWYQQKPDQSPKRWIYDTS NLASGVPSRFSGGGSGTDYSLTISSMEAEDAATYYCQQWISDPPTFGQGTKL EIKRTVAAPSVFIFPPSDEQLKSGTASVVCLLNNEYPREAKVQWKVDNALQS GNSQESVTEQDSKDSTYSLSSTLTLSKADYEKHKVYACEVTHQGLSSPVTKS FNRGEC (SEQ ID NO: 118) |
| muCD37-57 | QIVLTQSPAIMSASPGEKVTMTCSATSSVTYMHWYQQKSGTSPKRWIYDTS KLASGVPARFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 119) |
| huCD37-57 | EIVLTQSPATMSASPGERVTMTCSATSSVTYMHWYQQKPGQSPRRWIYDTS NLASGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 120) |

TABLE 6-continued

Full-length light chain amino acid sequences

| Antibody | Full-length Light Chain Amino Acid Sequence (SEQ ID NO) |
|---|---|
| 252-3 | DIQMTQTTSSLSASLGDRVTISCRASQDISNYLNWYQQKPDGTVKLLIYYTS<br>KLHSGVPSRFSGSGSGTDYSLTISNLEQEDIATYFCQQGNALPWTFGGGTKL<br>ELKRADAAPTVSIFPPSSEQLTSGGASVVCFLNNFYPKDINVKWKIDGSERQ<br>NGVLNSWTDQDSKDSTYSMSSTLTLTKDEYERHNSYTCEATHKTSTSPIVKS<br>FNRNEC (SEQ ID NO: 180) |

Also provided are polypeptides that comprise: (a) a polypeptide having at least about 90% sequence identity to SEQ ID NOs:88-104 or 179; and/or (b) a polypeptide having at least about 90% sequence identity to SEQ ID NOs: 105-120 or 180. In certain embodiments, the polypeptide comprises a polypeptide having at least about 95%, at least about 96%, at least about 97%, at least about 98%, or at least about 99% sequence identity to SEQ ID NOs:88-120, 179, or 180. Thus, in certain embodiments, the polypeptide comprises (a) a polypeptide having at least about 95% sequence identity to SEQ ID NOs:88-104 or 179, and/or (b) a polypeptide having at least about 95% sequence identity to SEQ ID NOs:105-120 or 180. In certain embodiments, the polypeptide comprises (a) a polypeptide having the amino acid sequence of SEQ ID NOs:88-104 or 179; and/or (b) a polypeptide having the amino acid sequence of SEQ ID NOs:105-120 or 180. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:88-120, 179, or 180 differs from SEQ ID NOs:88-120, 179, or 180 by conservative amino acid substitutions only.

In certain embodiments, the CD37 antibody can be the antibody produced from a hybridoma selected from the group consisting of consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Designation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010 (American Type Culture Collection (ATCC) at 10801 University Boulevard, Manassas, Va. 20110). In certain embodiments, the antibody comprises the VH-CDRs and the VL-CDRS of the antibody produced from a hydridoma selected from the group consisting of PTA-10665, PTA-10666, PTA-10667, PTA-10668, PTA-10669, and PTA-10670.

In certain embodiments, the CD37 antibody can comprise a light chain encoded by the recombinant plasmid DNA phuCD37-3LC (ATCC Deposit Designation PTA-10722, deposited with the ATCC on Mar. 18, 2010). In certain embodiments, the CD37 antibody can comprise a heavy chain encoded by the recombinant plasmid DNA phuCD37-3HCv.1.0 (ATCC Deposit Designation PTA-10723, deposited with the ATCC on Mar. 18, 2010). In certain embodiments, the CD37 antibody can comprise a light chain encoded by the recombinant plasmid DNA phuCD37-3LC (PTA-10722) and a heavy chain encoded by the recombinant plasmid DNA phuCD37-3HCv.1.0 (PTA-10723). In certain embodiments, the CD37 antibody can comprise the VL-CDRs encoded by the recombinant plasmid DNA phuCD37-3LC (PTA-10722) and the VH-CDRs encoded by the recombinant plasmid DNA phuCD37-3HCv.1.0 (PTA-10723).

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable mycloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human CD37 is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to CD37 is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., 376:1182 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a CD37. Bispecific antibodies are antibodies that are capable of specifically recognizing and binding at least two different epitopes. The different epitopes can either be within the same molecule (e.g. the same CD37) or on different molecules such that both, for example, the antibodies can specifically recognize and bind a CD37 as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to CD37 are multispecific.

In certain embodiments are provided an antibody fragment to, for example, increase tissue penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from E. coli or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to CD37 (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for CD37, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody, fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human CD37. In this regard, the variable region can comprise or be derived from any type of mammal that can be induced to mount a humoral response and generate immunoglobulins against the desired antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not always necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the CD37-binding antibodies provide for altered effector functions that, in turn, affect the biological profile of the administered antibody. For example, the deletion or inactivation (through point mutations or other means) of a constant region domain can reduce Fc receptor binding of the circulating modified antibody. In other cases, it can be that constant region modifications, consistent with this invention, moderate complement binding and thus reduce the serum half life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, a CD37-binding agent that is an antibody does not have one or more effector functions. For instance in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain can be enough to substantially reduce Fc binding. Similarly, it can be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human CD37. It will be recognized in the art that some amino acid sequences of the invention can be varied without significant effect of the structure or function of the protein. Thus, the invention further includes variations of the polypeptides which show substantial activity or which include regions of an antibody, or fragment thereof, against CD37 protein. Such mutants include deletions, insertions, inversions, repeats, and type substitutions.

The polypeptides and analogs can be further modified to contain additional chemical moieties not normally part of the protein. Those derivatized moieties can improve the solubility, the biological half life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human CD37. Recombinant expression vectors are replicable DNA constructs which have synthetic or cDNA-derived DNA fragments encoding a polypeptide chain of an anti-CD37 antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

Suitable host cells for expression of a CD37-binding polypeptide or antibody (or a CD37 protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413, 746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a CD37-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the CD37-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275: 2677-83 (2008), each of which is incorporated by reference herein in its entirety. In certain embodiments, phage display technology has been used to identify/produce the CD37-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein CD37-binding agents are known to those skilled in the art. See, e.g., Kennedy et al., J. Comb. Chem, 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. No. 5,270,163, U.S. Pat. No. 5,683,867, U.S. Pat. No. 5,763,595, U.S. Pat. No. 6,344,321, U.S. Pat. No. 7,368,236, U.S. Pat. No. 5,582,981, U.S. Pat. No. 5,756,291, U.S. Pat. No. 5,840,867, U.S. Pat. No. 7,312,325, U.S. Pat. No. 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. IMMUNOCONJUGATES

The present invention is also directed to conjugates (also referred to herein as immunoconjugates), comprising the anti-CD37 antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivatives, methotrexate, cisplatin, carboplatin, daunorubicin, doxorubicin, vincristine, vinblastine, melphalan, mitomycin C, chlorambucil and morpholino doxorubicin.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-CD37 antibody or fragment thereof through a disulfide bond. The linker molecule or crosslinking agent comprises a reactive chemical group that can react with the anti-CD37 antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem. J.*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio)pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-CD37 antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cells and have the desired biochemical properties of high conjugation yield and high monomer ratio with minimal protein aggregation.

Specifically contemplated in this aspect is an anti-CD37 antibody drug conjugate of formula (I) or a conjugate of formula (I'):

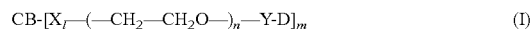

$$\text{CB-}[X_l\text{—}(\text{—}CH_2\text{—}CH_2O\text{—})_n\text{—}Y\text{-}D]_m \qquad (I)$$

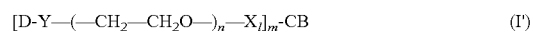

$$[D\text{-}Y\text{—}(\text{—}CH_2\text{—}CH_2O\text{—})_n\text{—}X_l]_m\text{-CB} \qquad (I')$$

wherein:
CB represents an anti-CD37 antibody or fragment;
D represents a drug;
X represents an aliphatic, an aromatic or a heterocyclic unit attached to the cell-binding agent via a thioether bond, an amide bond, a carbamate bond, or an ether bond;
Y represents an aliphatic, an aromatic or a heterocyclic unit attached to the drug via a disulfide bond;
l is 0 or 1;
m is an integer from 2 to 8; and
n is an integer from 1 to 24.

In some embodiments, m is an integer from 2 to 6.
In some embodiments, m is an integer from 3 to 5.
In some embodiments, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-CD37 antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see US Publication No. 20050169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the CD37 antibody is linked to the drug via a non-cleavable bond through the intermediacy of a PEG spacer. Suitable crosslinking reagents comprising hydrophilic PEG chains that form linkers between a drug and the anti-CD37 antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z-X_l-(-CH_2-CH_2-O-)_n-Y_p-D$, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-CD37 antibody drug conjugate of formula (II) or of formula (II'):

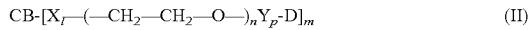  (II)

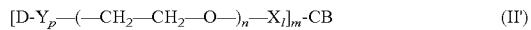  (II')

wherein, CB represents an anti-CD37 antibody or fragment;
D represents a drug;
X represents an aliphatic, an aromatic or a heterocyclic unit bonded to the cell-binding agent via a thioether bond, an amide bond, a carbamate bond, or an ether bond;
Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;
l is 0 or 1;
p is 0 or 1;
m is an integer from 2 to 15; and
n is an integer from 1 to 2000.
In some embodiments, m is an integer from 2 to 8; and
In some embodiments, n is an integer from 1 to 24.
In some embodiments, m is an integer from 2 to 6.
In some embodiments, m is an integer from 3 to 5.
In some embodiments, n is an integer from 2 to 8.
Examples of suitable PEG-containing linkers include linkers having an N-succinimidyl ester or N-sulfosuccinimidyl ester moiety for reaction with the anti-CD37 antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in WO2009/0134976; the contents of which are entirely incorporated herein by reference.

The present invention includes aspects wherein about 2 to about 8 drug molecules ("drug load"), for example, maytansinoid, are linked to an anti-CD37 antibody or fragment thereof. "Drug load", as used herein, refers to the number of drug molecules (e.g., a maytansinoid) that can be attached to a cell binding agent (e.g., an anti-CD37 antibody or fragment thereof). In one aspect, the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 9.0, 8.1). $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl)maytansine (DM4) can be used.

Thus, in one aspect, an immunoconjugate comprises 1 maytansinoid per antibody. In another aspect, an immunoconjugate comprises 2 maytansinoids per antibody. In another aspect, an immunoconjugate comprises 3 maytansinoids per antibody. In another aspect, an immunoconjugate comprises 4 maytansinoids per antibody. In another aspect, an immunoconjugate comprises 5 maytansinoids per antibody. In another aspect, an immunoconjugate comprises 6 maytansinoids per antibody. In another aspect, an immunoconjugate comprises 7 maytansinoids per antibody. In another aspect, an immunoconjugate comprises 8 maytansinoids per antibody.

In one aspect, an immunoconjugate comprises about 1 to about 8 maytansinoids per antibody. In another aspect, an immunoconjugate comprises about 2 to about 7 maytansinoids per antibody. In another aspect, an immunoconjugate comprises about 2 to about 6 maytansinoids per antibody. In another aspect, an immunoconjugate comprises about 2 to about 5 maytansinoids per antibody. In another aspect, an immunoconjugate comprises about 3 to about 5 maytansinoids per antibody. In another aspect, an immunoconjugate comprises about 3 to about 4 maytansinoids per antibody.

In one aspect, a composition comprising immunoconjugates has an average of about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1) drug molecules (e.g., maytansinoids) attached per antibody. In one aspect, a composition comprising immunoconjugates has an average of about 1 to about 8 drug molecules (e.g., maytansinoids) per antibody. In one aspect, a composition comprising immunoconjugates has an average of about 2 to about 7 drug molecules (e.g., maytansinoids) per antibody. In one aspect, a composition comprising immunoconjugates has an average of about 2 to about 6 drug molecules (e.g., maytansinoids) per antibody. In one aspect, a composition comprising immunoconjugates has an average of about 2 to about 5 drug molecules (e.g., maytansinoids) per antibody. In one aspect, a composition comprising immunoconjugates has an average of about 3 to about 5 drug molecules (e.g., maytansinoids) per antibody. In one aspect, a composition comprising immunoconjugates has an average of about 3 to about 4 drug molecules (e.g.; maytansinoids) per antibody.

In one aspect, a composition comprising immunoconjugates has an average of about 2±0.5, about 3±0.5, about 4±0.5, about 5±0.5, about 6±0.5, about 7±0.5, or about 8±0.5 drug molecules (e.g., maytansinoids) attached per antibody. In one aspect, a composition comprising immunoconjugates has an average of about 3.5-0.5 drug molecules (e.g., maytansinoids) per antibody.

The anti-CD37 antibody or fragment thereof can be modified by reacting a bifunctional crosslinking reagent with the anti-CD37 antibody or fragment thereof, thereby resulting in the covalent attachment of a linker molecule to the anti-CD37 antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-CD37 antibody or fragment" refers to the conjugate molecule comprising at least one drug derivative bound to a cell-binding agent anti-CD37 antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

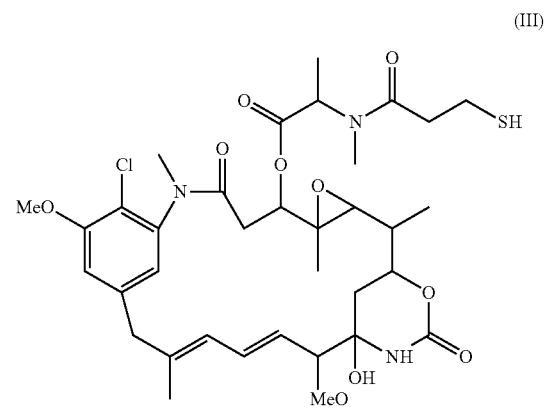 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

(III)

In another embodiment, the conjugates of the present invention utilize the thiol-containing maytansinoid $N^{2'}$-deacetyl-$N^{2'}$-(4-methyl-4-mercapto-1-oxopentyl)-maytansine (e.g., DM4) as the cytotoxic agent. DM4 is represented by the following structural formula (IV):

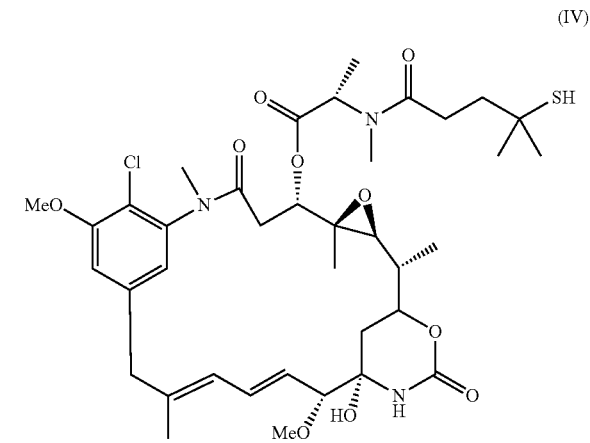 [SMILES: COc1cc2cc(c1Cl)N(C)C(=O)C[C@H](OC(=O)[C@H](C)N(C)C(=O)CCC(C)(C)S)[C@]1(C)O[C@H]1[C@H](C)C1C[C@@](O)(NC(=O)O1)[C@H](OC)/C=C/C=C(\C)C2]

(IV)

Another maytansinoid comprising a side chain that contains a sterically hindered thiol bond is $N^{2'}$-deacetyl-$N^{2'}$(4- mercapto-1-oxopentyl)-maytansine (termed DM3), represented by the following structural formula (V):

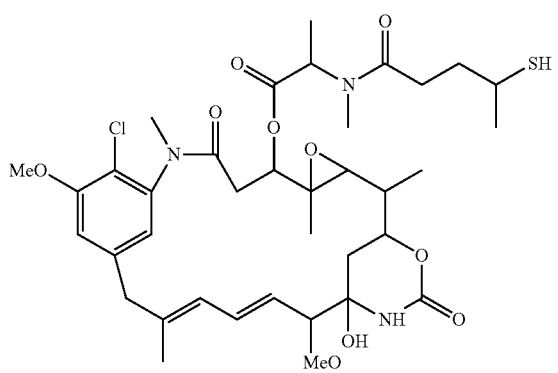

Each of the maytansinoids taught in U.S. Pat. Nos. 5,208,020 and 7,276,497, can also be used in the conjugate of the present invention. In this regard, the entire disclosure of U.S. Pat. Nos. 5,208,020 and 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

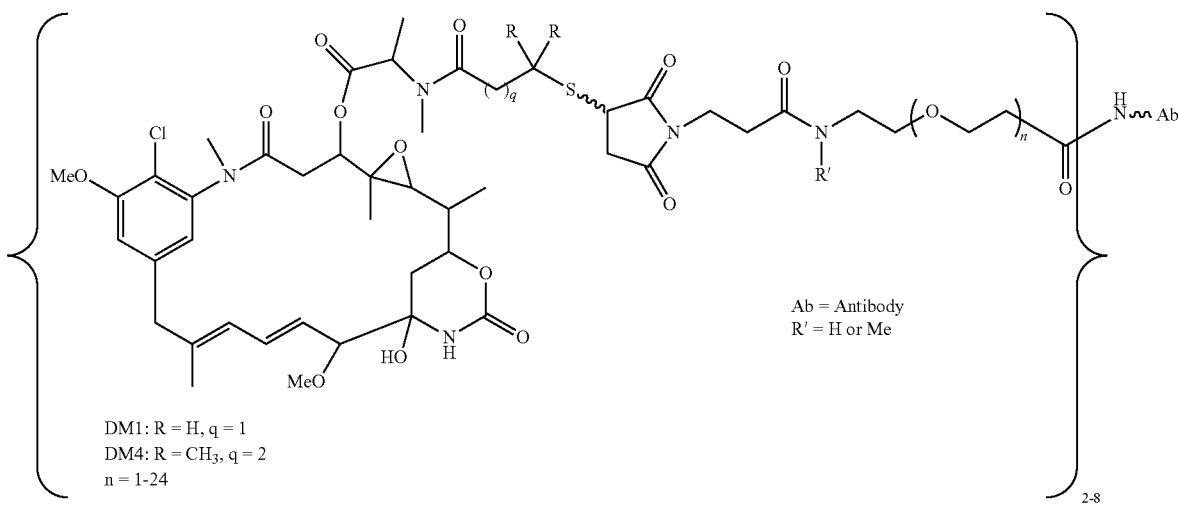

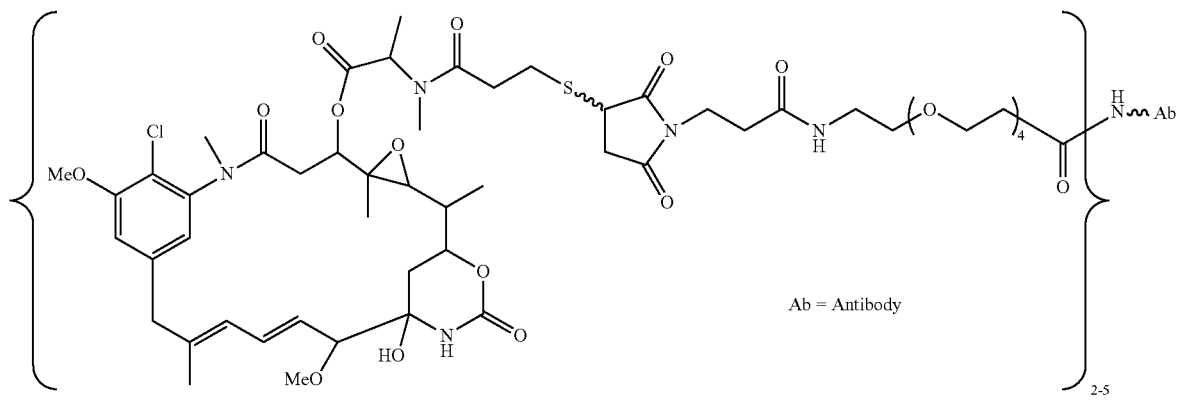

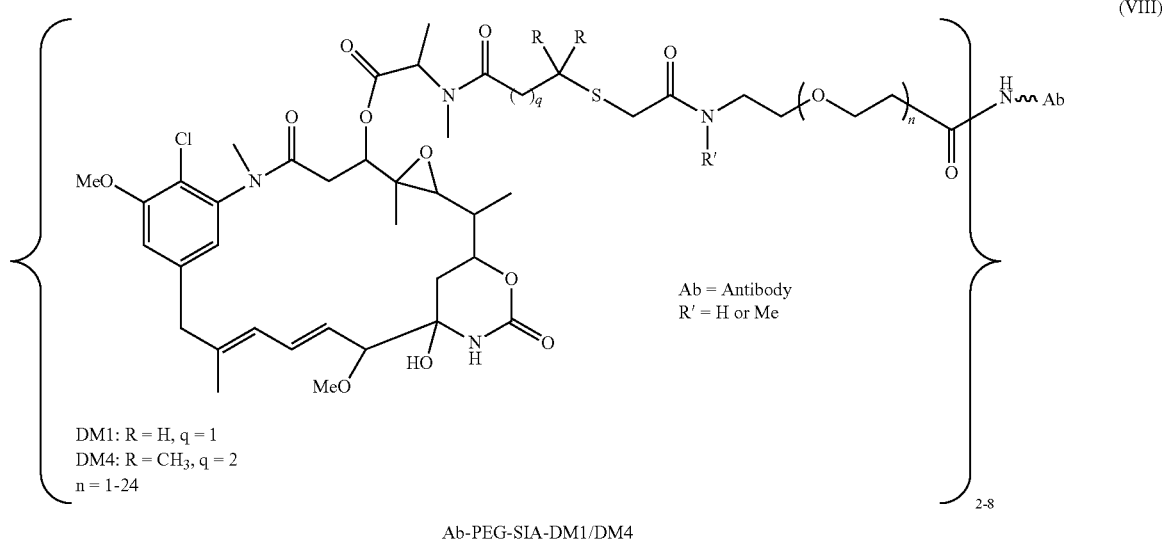
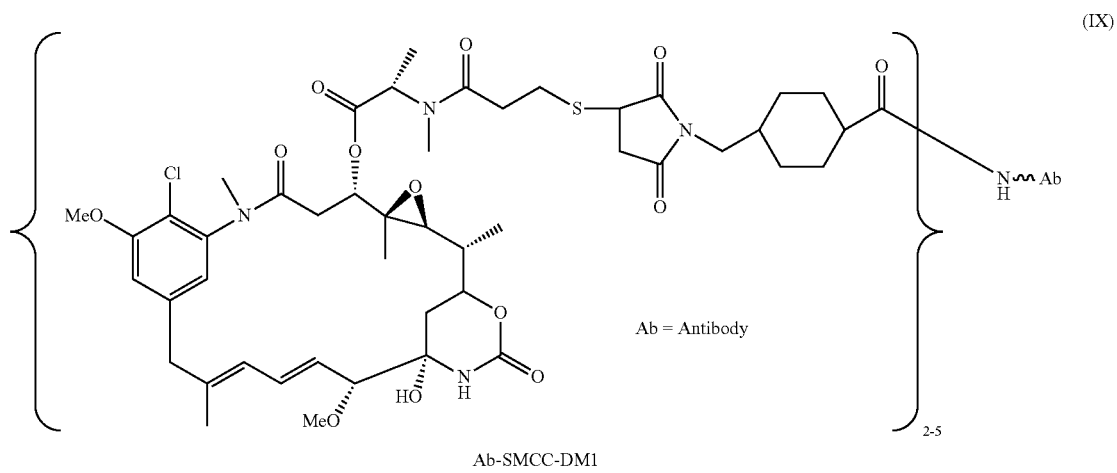
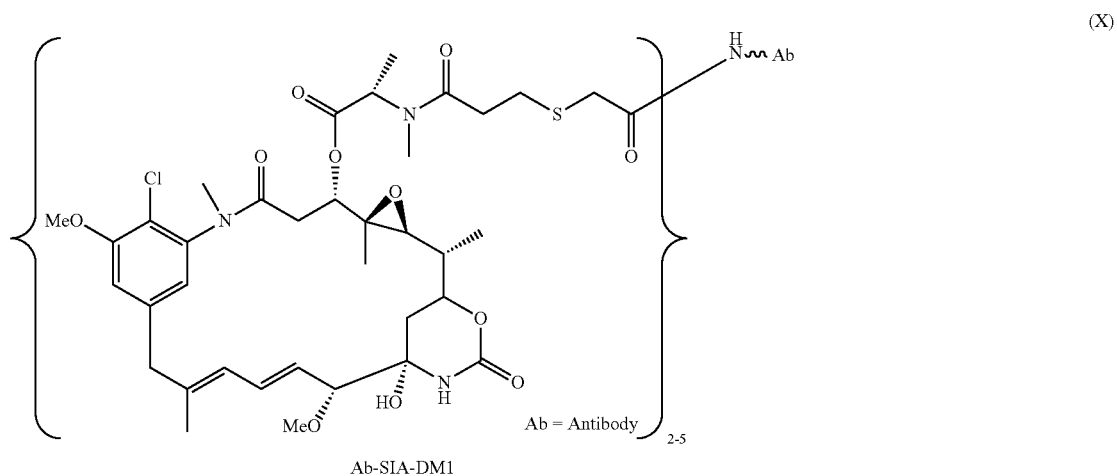

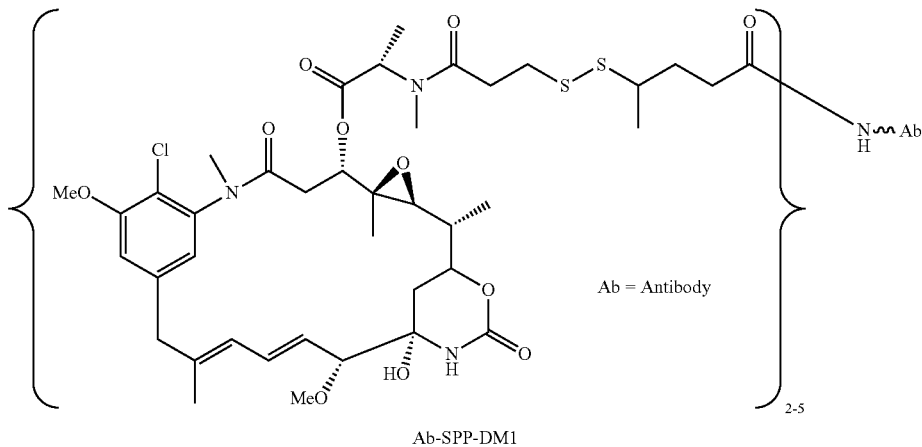
Ab-SPP-DM1 (XI)

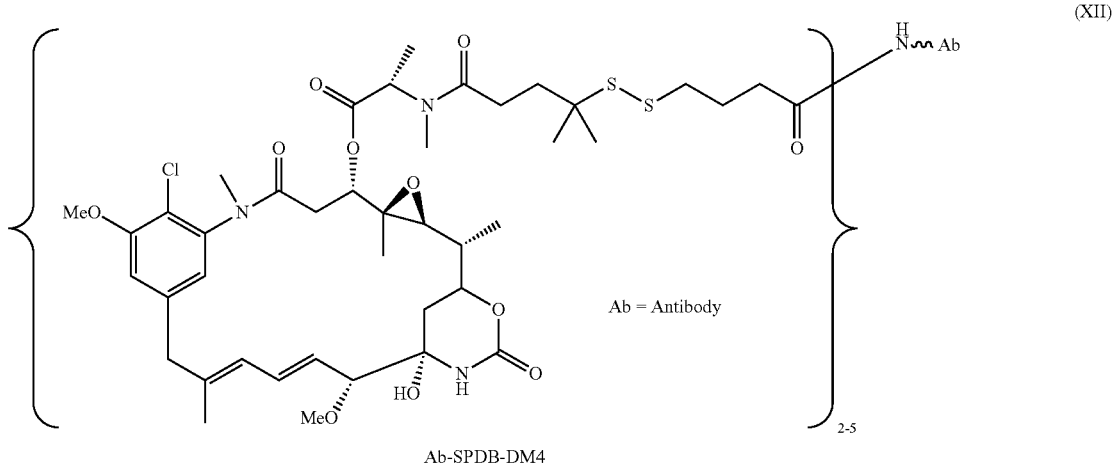
Ab-SPDB-DM4 (XII)

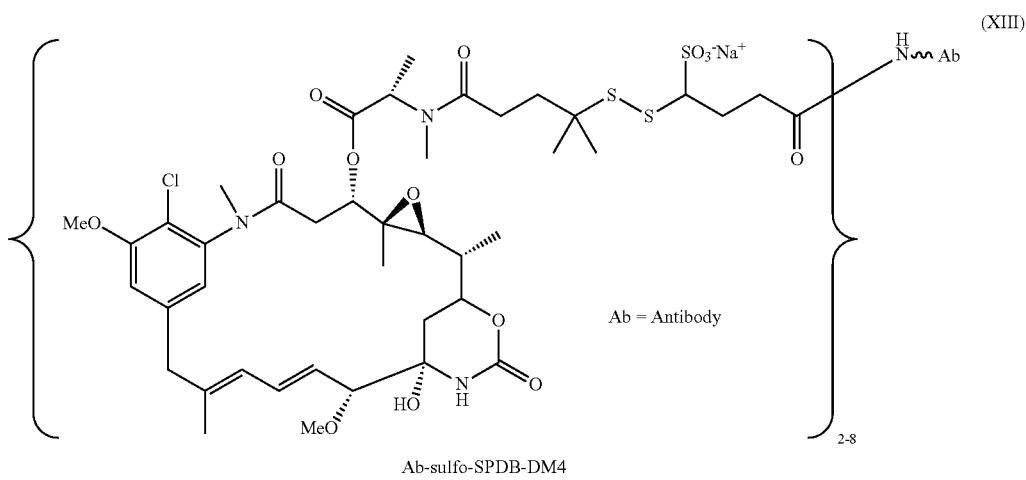
Ab-sulfo-SPDB-DM4 (XIII)

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, about 1-10, 2-5, 3-4, or about 3.5. In one aspect, the average number of maytansinoid molecules/antibody is about 3.5±0.5.

Anthracycline compounds, as well as derivatives, intermediates and modified versions thereof, can also be used to prepare anti-CD37 immunoconjugates. For example, doxorubicin, doxorubicin derivatives, doxorubicin intermediates, and modified doxorubicins can be used in anti-CD37 conjugates. Exemplary compounds are described in WO 2010/009124, which is herein incorporated by reference in its entirety. Such compounds include, for example, compounds of the following formula:

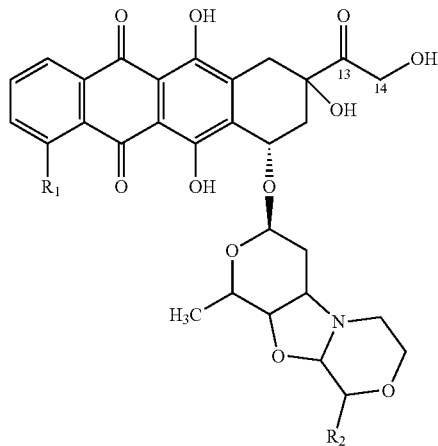

wherein $R_1$ is a hydrogen atom, hydroxy or methoxy group and $R_2$ is a $C_1$-$C_5$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such as the human lymphoma cell line Daudi and the human lymphoma cell line Ramos, can easily be used for the assessment of cytotoxicity of these compounds. Cells to be evaluated can be exposed to the compounds for 4 to 5 days and the surviving fractions of cells measured in direct assays by known methods. $IC_{50}$ values can then be calculated from the results of the assays.

The immunoconjugates can, according to some embodiments described herein, be internalized into cells. The immunocongugate, therefore, can exert a therapeutic effect when it is taken up by, or internalized, by a CD37-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a CD37-expressing cell.

In some embodiments, the immunoconjugates are capable of depleting B-cells, e.g. autoreactive B-cells. For example, in some embodiments, treatment with an immunoconjugate results in a depletion of at least about 25%, at least about 30%, at least about 35%, at least about 40%, at least about 45%, at least about 50%, at least about 55%, at least about 60%, at least about 65%, at least about 70%, or at least about 75% of B-cells.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody, that has been modified to introduce an active disulfide or maleimide moiety, to produce a cleavable or non cleavable conjugate. Between 1-20 siRNA molecules can be linked to an antibody by this method.

III. POLYNUCLEOTIDES

In certain embodiments, the invention encompasses polynucleotides comprising polynucleotides that encode a polypeptide that specifically binds CD37 or a fragment of such a polypeptide. For example, the invention provides a polynucleotide comprising a nucleic acid sequence that encodes an antibody to a human CD37 or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs:4-120.

The invention further provides a polynucleotide comprising a sequence selected from those shown in Tables 7-10 below.

TABLE 7

| Variable heavy chain polynucleotide sequences | |
| --- | --- |
| Antibody | VH Polynucleotide Sequence (SEQ ID NO) |
| muCD37-3 | caggtgcaggtgaaggagtcaggacetggcctggtggcgccctcacagagcctgtccattacatgcactg tctcaggguctcattaaccacctctggtgtaagctgggttcgcgagcctccaggaaagggtctggagtg gctgggagtaatatggggtgacgmagcacaaactatcattcagctctcaaatccagactgagcatcaag aaggatcactccaagagccaagttcuaaaactgaacagtctgcaaactgatgacacagccacgtact actgtgccaaaggaggetactcguggctcactggggccaagggactctggtcacagtctctgca (SEQ ID NO: 121) |
| chCD37-3 | aagcttgccaccatggctgtcctggcactgctcctctgcctggtgacataccaagctgtgtcctatcacaggtgcaggtg aaggagtcaggacctggcctutggcgccctcacagagcctgtccattacatgcactgtctcagggttctcattaaccac ctctggtgtaagctgggucgccagcctccaggaaagggtctggagtggctgggagtaatatggggtgacgggagcac aaactatcattcagctctcaaatccagactgagcatcaagaaggatcactccaagagccaagtttctaaanctgaacagt ctgcaaactgatgacacagccacgtactactgtgccaaaggaggctactcgttggctcactggggccaagggactctgg tcacagtctctgcagcctetacgaaggaccc (SEQ ID NO: 122) |

TABLE 7-continued

Variable heavy chain polynucleotide sequences

| Antibody | VH Polynucleotide Sequence (SEQ ID NO) |
| --- | --- |
| huCD373v1.0 | aagcttgccaccatgggttggagctgattattctgtttctggtggccaccgccaccggtgtgcactcacaagtccaagtc caagaatctggtccaggtctggtggcccttcccaaactctgagcatcacctgtaccgttctggguttagccttaccacctc tggtgtgagttgggtacgccaaccaccggtaagggtctcgaatggctgggtgtaatctggggtgatggttccacaaatt accatccttccctcaagtcccgccttagcatcaaaaaggatcacagcaaaagtcaagttttcctsaaactgaatagtctgac agcagccgatacagccacctactattgcgccaagggtggttatagtctgcacactgggtcaaggtaccctcgttaccgt ctcctcaactagtaccaaaaaccc (SEQ ID NO: 123) |
| huCD373v1.1 | aagcttgccaccatgggctggagctgtatcattctgtttctggtggcgacagctactggtccactcccaagtgcaggta caagagtccgggcctggattggtcgcaccaagccagaccctctctatcacugtaccgttagcggguctttctgacaacc agtggagtgagttgggtgaggcagccaccaggaaacggactggagtggctcgggggtgatttgggcgacggcagca caaactatcattccagtcttaaatctcggttgtccattaaaaaagaccatagtaaatctcaagttcctgaaactcaatagcct gacagccgcagacactgctacgtattactgcgccaaaggaggatacagtctggctcactggggacaggggaccctggt gaccgtgtcatccgcatcaacaaagggccc (SEQ ID NO: 124) |
| muCD37-12 | cagatccagttggtgcagtctggacctgagctgaagaagcctggagagacagtcaagatctcctgcaagg cttctgggtataccttcacaaagtatggaatgaactgggtgaagcaggctcaaggaaagggtttaaagtg gatgggctggttttaaacaccaacactggttgttgtcaagaaatgctgttagaattcttagggacggtttgccttc tctttggaaacctctgccagcactgcctatttgcagatcaacaacctcaaatatgaggacacggctacat atttctgtggaagggcacggtagtagcggactggggccaaggcaccactctcacagtctcctca (SEQ ID NO: 125) |
| chC037-12 | aagcttgccaccatgggtggtcatgcataatcctctttctggtcgctactgctaccggtgtgcactcacagattcagctgg ttcaaagtggcccagagctgaaaaagctaggggaaacagtgaaataagttgcaaggcatccggttacactttcacaaa gtacggcatgaactgggtcaagcaggcccaggcaaggggctcaaatggatgggttgttatcaataccaacactggcg agtctaggaatgctgaggagtttaagggccggtttgccttcagcctggagacaagtgccagcacagcttacctgcaaatc aacaatctgaagtatgaggatacagcacctatttctgcggccgcggcactgtcgttgcagactggggacaaggtacca ccttgactgtatccactccaccactaagggccc (SEQ ID NO: 126) |
| muCD37-38 | gatgtgcagcttcaggagtcaggacctgacctggtgaaaccttctcagtcactttcactcacctgcactg tcactggctactccatcaccagtggttttggctggcactggatccggcagtttccaggaaacaagctgga atggatggctacatactctacagtggtggcactgactacaacccatctctcaaaagtcgaatctctatc actcgagacacttccaagaaccagttcttcctgcggttgagttctgtgactactgaggacacagccacat attactgtcaagaggctactatggttacggggcctggtttgtttactggggccaagggactctggtcac tgtctcgca (SEQ ID NO: 127) |
| chCD37-38 | aagcttgccaccatgggctggagttgtatcattctgttttggtggccaccgccactggagtccattcccaagtgcaactcc aggaatctggccctgacctggttaagccatctcagagcctctccctgacctgcactgttacaggatactcaatcacatcag gctttggctggcactggatcagacaattttcccgggaacaagttggaatggatggcttacattctgtatagcgggggtaccg attacaatccttccctcaagagccgaatctctatcaccaggagtacaagcaagaaccaattttttctccgcctcagctctgtg actaccgaagataccgctacttactattgtgccaggggtactatggatatggtcatggttcgtctattggggccaggga accctggtgactgtgagcgctgcctctaccaagggccc (SEQ ID NO: 128) |
| muCD37-38 | aagcttgccaccatgggttggagctgcatcattctttcctggtcgctactgcaactggagtccactcattaggtccagctgc aagagtccggtcctgggcttgtgaaacccagccagtccctcagtctcacctgtactgtctctggctactctattaccagtgg gttcggctggcattggattaggcagtttacggtaaggggctggagtggatggcatatatcctgtacagcggaggaacc gattacaacccaagtctgaagagcaggatcagcattaccccgggacacaagcaaaaaccagtttttccttcggctgtcagt gttacagctgcagacaccgctacttactattgtgctcggggttactatggctatggggcttggttttgtgtattggggacaag gccactcttgtgaccgtgagcagcgcctcaacaaagggccc (SEQ ID NO: 129) |
| muCD37-50 | gatgtgcagcttcaggagtcaggacctgacctgttgaaaccttctcagtcactttcactcacctgcactg tcactggctactccatcaccagtggttttggctggcactggatccggcagtttccaggaaacaactgga atggatgggctacatactctacagtggtagcactgtctacagccatctctcaaaagtcgaatctctatc actcgagacacatccaagaaccacttcttcctgcagttgaattctgtgactactgaggacacagccacat attactgtcaagaggggtactatggttacggcgcctggtttgcttactggggccaagggactctggtcac tgtctctgca (SEQ ID NO: 130) |
| huCD37-50 | aagcttgccaccatggggtggtcctgcataatcctttcctggttgctactgctaccggagtccattcacaggtgcagctgc aggagtccggccccgcctgctcaagccttctcagagtctgagtctgacttgtactgtgtttctggctacagcataaccagcg gttcgcttggcactggatcagacagcatcccggcaacaaactggagtggatgggatacatactgtactcaggctcaact gtctattccccctccctgaaatcccggatcagtattacccgtgacacttctaagaaccattttttttctgcagctgaacagcgtt accgcagctgacactgcaacctactactgtgcccggggatatggatacggagcttggttcgcttactggggccaagg caccctcgtaactctaattcctccttccaccaagggccc (SEQ ID NO: 193) |
| muCD37-5t | gatgtgcagcttcaggagtcaggacctgacctgttgaaaccttctcagtcactttcactcacctgcactg tcactggctactccatctccagtggttttgcctggcactggatccggcagtttccaggaaacaaactgga atggatgggctacatacactacagtggttttgcactaactacagccccatctctcaaaagtcgaatctctatc actcgagactcatccaagaaccagttcttcctgcagttgaattctgtgactactgaggacacagccacat attactgtcaagaggatactatggtttcggcgcctggtttgtttactggggccaagggactctggtcac tgtctctgca (SEQ ID NO: 131) |
| huCD37-5t | Aagcttgccaccatgggttggtcttgcatcatcctgttcctggtggccactgccactggcgtgcattcagaagttcagttgg tggagtccgcccccagaagtgctgaaaccccggcgaatcactgtccctgacttgtaccgtgtcaggttatagcatcagcagc ggctttgcttggcactggattcggcagtttccaggcaagggactggaatggatgggctacatccattacagtggctcaac caattacagcccctagcctgcagggccgtatctctattaccagggatagttctattaaccagttttttcctgcagcttaattccgt gactgcctctgacacagcaacttactattgcgcccgtggctactacgggncggagcctggttttgtatactgggtcggg caccctgtgtcactgtctcacccucctctaccaaceecccc (SEQ ID NO: 194) |

TABLE 7-continued

Variable heavy chain polynucleotide sequences

| Antibody | VH Polynucleotide Sequence (SEQ ID NO) |
|---|---|
| muCD37-56 | gatgtgcagcttcaggagtcaggacctgacctggtgaaaccttctcagtcactucactcacctgcactg<br>tcactggctactccatcaccagtggttttgcctggcuctggatccggcagtccaggaaacaaactgga<br>atggatgggctacatacactacagtggtggcactaactacaacccatctctcaaaagtcgagtctctatc<br>actcgagacacatccaagaaccagttcttcctgcagtgaattctgtgactactgaggacacagccacatattactgtgcaa<br>gaggctactatggtttcggggcctggtttgcttactggggccaagggactctggtccctctctctgtca (SEQ ID NO: 132) |
| huCD37-56 | aagcttgccaccatggggtggagctgctttatcctgttcctcgtcgccaccgcaaccggcgtccactcccaggtgcagct<br>gcaagaaagcggggccaggaugglaaaaccttcccagtctctgagtcttacugtaccgtatctggatacagtatcacatct<br>ggctcgcctggcanggattcgccagutcccggcaaggggctgagtggatggggtataucattattctggaggtacca<br>actacaacccuccctgaagagtcgagtttcaattaccagggacacttccaagaaccaa(tctttgcagcttaattcagtg<br>accgctgccgacaccgctacuactactgcgcccggggctactatgggtuggtgcctggttcgcctactggggccaggg<br>gaccctggtgcccgtgtctgctgcctccacaaagggccc (SEQ ID NO: 133) |
| muCD37-57 | gatgtgcagcttcaggagtcaggacctgacctgttgaaaccttctcagtcacttctcactcacctgcactg<br>tcactggctactccatcaccagtggtutgcctggcactggatccggcagtttccaggaaacaaactgga<br>atggatgggctacatactctacagtggtagcactgtctacagccatctctcaaaagtcgaatctctatc<br>actcgagacacatccaagaaccagttcttcctgcagttgaattctgtgactactgaggacacagccacatattactgtgcaa<br>gagggtactatggttacggcgcctggtttgcuactggggccaagggactctggtcactgtctctgca (SEQ ID NO: 134) |
| huCD37-57 | aagcttgccaccatgggctggagctgcatcattctgtuctggtggccacagcaactggcgttcacagtcaagtccaactg<br>caggagagcggccccggactcctgaaaccatctcagtcactcagtctgacatgtactgtgagcggctacagcauacctc<br>aggcttcgcttggcattggatcaggcagHccccggaaaaggtctggagtggatggggtacattctgtacagcggcagta<br>cagtgtattcaccctccugaaatctaggatatcaatcacacgtgatacaagcaaaaatcagttcucctccagctgaactcc<br>gtcaccgccgcagacacagcaacctauattgtgctcgcggatactacggatatggcgcatggucgcctattggggcca<br>tcccacactCRmacccmccRCCRCctccacaaoccccc (SEQ ID NO: 135) |
| 252-3 | gaggtgcaggtggtggagtctggggggagacuagtgaagcctggagggtccctgaaactctcctgtgcagcctctggat<br>tcactttcagtagctatggcatgtcttgggttcgccagactccagacaagaggctggagtgggtcgcaaccattagtagtg<br>gtggtagttacacctactctccagacagtgtgaaggggcgattcaccatctccagagacaatgccaagaaaaccctgtac<br>ctgcaaotgagcagtctgaagtctgagsacacagccatgtattactgtgcaagacataguactacgatactagcgtcgac<br>tactggggtcaaggaacctcagtcaccgtctcctca (SEQ ID NO: 182) |

TABLE 8

Variable light chain polynucleotide sequences

| Antibody | VL Potynucleotide Sequence (SEQ ID NO) |
|---|---|
| muCD37-3 | gacatccagatgactcagtctccagcctccctttctgtatctgtgggagaaactgtcaccatcacatgtc<br>gagcaagtgagaatattcgcagtaatttagcatggtatcagcagaaacaggaaaatctcctcagctcct<br>ggtaatttgttgcaacaaacuagaagatggtgtgccatcttaggttcagtggcagtggatcaggcacacag<br>tauccctcaagatcaacagcctgcagtctgaagattttgggacttattactgtcaacattattgggta<br>ctacgtggacgttcggtggaggcaccaagctggaaatcaaacgt (SEO ID NO: 136) |
| chCD37-3 | gaattcgccaccatgagtgtgcccactcaggtcctggggttgctgctgctgtggcttacagatgccagatgtgacatccag<br>atgactcagtctccagcctcccttctgtatctgtgggagaaactgtcaccatcacatgtcgagcaagtgagaatattcgca<br>gtaatttagcatggtatcagcagaaacaggaaaatctcctcagctcctggtcaatttgttgcaacaaacttagcagatggt<br>gccatcaaggttcagtggcagtggatcaggcacacagtattcctcaagatcaacagcctgcagtctgaagattttggga<br>cttattactgtcaacattauggggtactacgtggacgttcggtggaggcaccaagctggaaatcaaacgtacg (SEQ ID NO: 137) |
| huCD37-3<br>(1.0 and 1.1) | gaattcgccaccatgggttggtcctgcaxatcngutctcgtggccacagccaccggtgncactctgatatacaaatgac<br>tcaaagcccuccagutgagcgtaagtgtgggtgaacgcgtaacaatcacctgtagagctagtgaaaacatccgcagta<br>atctcgcatggtaccaacaaaagccaggtaagtcacctaagctcctcgtgaatgttgctaccaacctcgctgatggtgtgc<br>cttcacgattctctggttcaggttccggtaccgattattcacttaagatcaactcactccaaccagaagatttcggtacatatta<br>ctgtcaacactactggggtacgacctggacattcggtcaaggtactaagctggaaatcaagcgtacg (SEQ ID NO: 138) |
| muCD37-12 | gacattgtgctaacacagtctcctgcttcttagctgtatctctggggcagagggccaccatctcatgca<br>gggccagccaaagtgtcagtacatctagctatagttatttgtactggttccagcagaaaccaggacagcc<br>acccaaactcctcatcaagtatgcatccaacctagcatctggggtccctgccaggttcagtggcagtggg<br>tctgggacagacttcaccctcaacatccatcctgtggaggagggagtactgcaacatattactgtcaac<br>acagttgggagattccgtacacgttcggaggggggaccaaactggaaataaaacgg (SEQ ID NO: 139) |
| chCD37-12 | gaattcgccaccatgggttggtcctgtataatcctgttcttggtggccaccgctactggcgttcatagtgatattgtactcact<br>cagtcaccagccagtctgtcagtgtcctgggcagcgtgccaccatctcctgccgggcctcaacgtccgtgagcacta<br>gctcttattcctatctctactggttcaacagaagccaggacagcccccttaagctgctgatcaagtacgcctccaacctcgc<br>cagcggcgttccgctagattctctggttccggtagcggaactgatttcactttgaacatccaccccgttgaggaagagga<br>taccgccacttactattgtcaacacttgggagattccttacacctttggaggaggaacaaagctcgaaattaagcgtacg<br>(SEQ ID NO: 140) |

TABLE 8-continued

Variable light chain polynucleotide sequences

| Antibody | VL Polynucleotide Sequence (SEQ ID NO) |
|---|---|
| muCD37-38 | caaaattgttctcacccagtctccagcaatcatgtctgcatctccaggggagaaggtcaccatgacctgca<br>gtgccagctcaagtgtaacttacatgcactggtaccagcagaagtcaggcacctcccccaaaagatggat<br>ttatgacacatccaaactggcttctggagtccctgctcgcttcagtggcggtgggtctgggacctcttac<br>tctctcacaatcagcagcatggaggctgaagatgctgccacttattactgccagcagtggattagtaacc<br>cacccacgttcggagggggggaccaagctggaaattaaacgg (SEQ ID NO: 141) |
| chCD37-38 | gaattcgccaccatgggctggtcctgtatcatcctgtttctcgtggccacagctacaggtgttcattctcagattgtgctgac<br>ccaatcaccagctattatgtccgctagccccggcgagaaagtgacaatgacatgtagcgctagctcttctgtgacttacat<br>gcattggtatcaacagaagtcaggtaccagtcccaagcgttggatctacgacacatccaaactggcctccggagtccctg<br>ccaggttcagcggaggtgggtccggcaccagttattcactgaccatatcctctatggaagctgaagatgctgctacttatta<br>ttgtcaacaatggatttctaaccccccacctttggtggcggaacaaagctggagatcaagcgtacg (SEQ ID NO: 142) |
| huCD37-38 | gaattcgccaccatgggatggtcctgcattattctgttcttggtcgccactgctactggcgttcactctgacattgtgctcaca<br>cagtctccagcctcaatgtctgcttccccggtgagcggtgaccatgacatgctctgccagttcctccgtgacatatatgc<br>attggtatcagcaaaaaccggtacctctccaaaaagatggatctacgacacttcaaagcttgcatcaggcgttcctgcca<br>gattttccgggtctgggtctggcacttcatacagtctgaccattagttccatggaggctgaagatgcagccacctattactgt<br>cagcagtggatttcaaatcctcctaccttcggcggcggaaccaaactggagataaagcgtacg (SEQ ID NO: 143) |
| muCD37-50 | caaattgttctcacccagtctccagcaatcatgtctgcatctccaggggagaaggtcaccatgacctgca<br>gtgccacctcaagtgtgacttactggtaccagcagaagtcaggcacctcccccaaaagatggatttatgacaca<br>tccaaactgccttatggagtccctggtcgtttcagtggtagtgggtctgggacctcttactctctcacaatcagcagcatgg<br>aggctgaagatgctgccacttattactgccagcagtggagtgataacccacccacgttcggctcggggacaaagttgga<br>aataaagcgg (SEQ ID NO: 144) |
| huCD37-50 | gaattcgccaccatgggttggtcatgcattattctgtcctggttgctaccgcaacaggagtacatagtgagatagtcctcac<br>ccaaagtcctgctactatgtctgccagccaggagagcgtgtgaccatgacatgctctgccagttcaagtgtgacatacat<br>gcattggtatcagcaaaaagcctggccaatcccctaaaaggtggatctacgatacttctaatctgccatacgtgtgcccgc<br>aaggttctccgggagtggcagtggcaccagttatagtctgaccatcagttcaatggaagcagaggatgcagcaacctatt<br>attgtcagcagtggtccgataatccccctactttggtcagggtacaaagctggagattaagcgtacg (SEQ ID NO: 145) |
| muCD37-51 | caaattgttctcacccagtctccagcaatcatgtctgcatctccaggggagaaggtcaccatgacctgca<br>gtgccacctcaagtgtgacttacatggtaccagcagaagtcaggcacctcccccaaaagatggatttatgacaca<br>tccaaactggcttctggagtccctgctcgcttcagtggcagtgggtctgggacctcttactctctcacaatcagcaacatgg<br>aggctgaagatgctgccacttattactgccagcagtggagtagtaacccacgttcggctcggggacaaagttgga<br>aataaagcgg (SEQ ID NO: 146) |
| huCD37-51 | gaattcgccaccatgggatggagctgtattattctgttcctggttgctactgctactggcgtccattccgagatagtcctcac<br>ccagagccccgcaaccatgagtgcctcccctggggagcgagtgactatgacttgttccgccacttcttcagttacctatat<br>gcattggtatcagcagaaacctggacagtctccaaagcgttggatttacgacacctccaacctggcttcaggagttcctgc<br>taggttcagcggatctgggtctggcacaagttattcactcaccattagttccatggaggccgaagatgccgctacttactac<br>tgtcagcagtggagcagcaaccccctacattcgggcaggggaactaagctggagatcaaacgtacg (SEQ ID NO: 147) |
| muCD37-56 | caaattgttctcacccagtctccagcattcatgtctgcatctccaggggataaggtcaccatgacctgca<br>gtgccagttcaagtgttacttacatgcactggtatcagcagaagtcaggcacctcccccaaaagatggatttatgacacat<br>ccaaactggcttctggagtccctgctcgcttacatgcactggtatcagcagaagtcaggcacctcccccaaaagatggattt<br>atgacacatccaaactggcttctggagtccctgctcgcttcagtggcggtgggtctgggacctcttac<br>tctctcacaatcagcaccatggaggctgaagatgctgccacttattactgccagcagtggattagtgacc<br>cacccacgttcggaggggggaccaagctggaaattaaacgg (SEQ ID NO: 148) |
| huCD37-56 | gaattcgccaccatgggctggtcctgtatcatcctgtttctggtggcaaccgctactggggttcactctgatattgtcctgac<br>acagagtccagccttcatgagtgcttctcccggagaaaaggtcacaatgacttgttcagcttcctcctcgtcacatacatg<br>cattggtaccagcaaaagcctgaccagagtcctaagaggtgatctatgataccaagaaccttctggctgtgtccctc<br>ccgcttttcaggcggcggaagcggaactgactatgccttaccatctcctcaatggaagccgaggacgctgctacatatt<br>actgccagcaatggatcagcgaccctcctactttcggacagggaacaaaattggaaattaagcgtacg (SEQ ID NO: 149) |
| muCD37-57 | caaattgttctcacccagtctccagcaatcatgtctgcatctccaggggagaaggtcaccatgacctgca<br>gtgccacctcaagtgtgacttacatgcactggtaaccagcagaagtcaggcacctcccccaaaagatggatttatgacaca<br>tccaaactggcttctggagtccctgctcgcttcagtggcagtgggtctgggacctcttactctctcacaatcagcagcatgg<br>aggctgaagatgctgccacttattactgccagcagtggagtgataacccacccacgttcggctcggggacaaagttgga<br>aataaagcgg (SEQ ID NO: 150) |
| huCD37-57 | gaattcgccaccatgggggtggtcctgtattatcctgttcctggtcgcaaccgccacaggcgttcactccgagatcgtgttga<br>ctcagagcccagccaccatgtccgcttccccggggagagagtgacaatgacttgttccgccacacaagttctgtaacctac<br>atgcattggtaccagcaaaaaccaggacagagtcccctgcgttggatttatgataccctaaacctggcttcaggcgttcctg<br>cccgcttttctggtagtggatctgggacttcctatagccttaccataagcctgaagccgaggacgccgctacatacta<br>ctgccagcagtggagtgataaccccccacctttcgggcagggaaccaaattggagatcaaacgtacg (SEQ ID NO: 151) |
| 252-3 | gatatccagatgacacagactacatcctccctgtctgcctctctgggagacagagtcaccatcagttgcagggc<br>aagtcaggacattagcaattatttaaactggtatcagcagaaaacccgatggaactgttaaactcctgatctactac<br>acatcaaaattacactcaggagtcccatcaaggttcagtggcagtgggtctggaacagattattctctcaccatt<br>agcaacctggagcaagaagatattgccacttacttttgccaacagggtaatgcgcttccgtggacgttcggtgg<br>aggcaccaagctggaactcaaacgg (SEQ ID NO: 183) |

TABLE 9

Full-length heavy chain polynucleotide sequences

| Antibody | Full-Length Heavy Chain Polynucleotide Sequence (SEQ ID NO) |
|---|---|
| chCD37-3 | aagcttgccaccatggctgtcctggcactgctcctctgcctggtgacatacccaagctgtgcctatcacaggtgcaggtg aaggagtcaggacctggcctggtggcgccctcacagagcctgtcattacatgcactgtctcagggttctcattaaccac ctctggtgtaagctgggttcgccagcctccaggaaagggtctggagtggctgggagtaatatgggtgacgggagcac aaactatcattcagctctcaaatccagactgagcatcaagaaggatcactccaagagccaagttttcttaaaactgaacagt ctgcaaactgatgacacagccacgtactactgtgccaaaggaggctactcgttggctcactgggggccaagggactctgg tcacagtctctgcagcctctacgaagggcccatcagttttccccttggctccaagttctaaatccacaagcggtggaacag ctgcactgggatgcctcgttaaagattatttccctgagcctgtgacagtgagctggaatagcggagcattgacttcaggtgt gcacacttttcccgctgtgttgcagtcctccggtctgtactcactgtccagtgtcgtaaccgtcccttctagcagcttgggaa cccagacctacatctgtaacgtcaaccataaaccatccaacacaaaggtggataagaaggttgaaccaaagagctgtga taagacacatacatgcccctccttgtcctgcaccagagctcctcggaggtccatctgtgttcctgtttccccccaaacccaag gacactcttatgatctctcgtactccagaggtcacctgtgttgttgtcgacgtgagccatgaagatcccgaggttaaattcaa ctggtacgtggatggagtcgaggttcacaatgccaagaccaagcccagggaggagcaatataattctacatatcgggta gtgagcgttctgaccgtgctccaccaagattggctcaatggaaaagagtacaagtgcaaggtgtccaacaaggctcttcc cgctcccattgagaaaactatctccaaagccaagggcagccacgggaaccccagtgtatacattgcccccatctaga gacgagctgaccaagaaccaggtgagtctcacttgtctggtcaaggggttttaccttctgacattgctgtagagtgggag tctaacggacagccagaaaacaactacaagacaactcccccagtgctggacagcgacgggagcttcttcctctactcca agttgactgtagacaagtctagatggcagcaaggaaacgttttctcctgctcagtaatgcatgaggctctgcacaatcacta tacccagaaatcactgtcccttagcccagggtgactcgag (SEQ ID NO: 152) |
| huCD37-3v1.0 | aagcttgccaccatggggttggagctgcattattctgtttctggtggccaccgccaccggtgtgcactcacaagtccaagtc caagaatctggtctccaggtctggtggcccccttcccaaactctgagcatcacctgtaccgtttctggttttagccttaccacctc tggtgtgagttgggtacgccaaccaccccggtaagggtctcgaatggctgggtgtaatctgggtgatggttccacaaatt accatcctttccctcaagtcccgccttagcatcaaaaaggatcacagcaaaagtcaagttttcctgaaactgaatagtctgac agcagccgatacagccacctactattgcgccaaggggtggttatagtcttgcacactggggtcaaggtaccctcgttaccgt ctcctcagctagtaccaagggcccatcagttttccccttggctccaagttctaaatccacaagcggtggaacagctgcact gggatgcctcgttaaagattatttccctgagcctgtgacagtgagctggaatagcggagcattgacttcaggtgtgcacac tttccccgctgtgttgcagtcctccggtctgtactcactgtccagtgtcgtaaccgtcccttctagcagcttgggaaccccaga cctacatctgtaacgtcaaccataaaccatccaacacaaaggtggataagaaggttgaaccaaagagctgtgataagac acatacatgcccctccttgtcctgcaccagagctcctcggaggtccatctgtgttcctgtttccccccaaacccaaggacact cttatgatctctcgtactccagaggtcacctgtgttgttgtcgacgtgagccatgaagatcccgaggttaaattcaactggta cgtggatggagtcgaggttcacaatgccaagaccaagcccagggaggagcaatataattctacatatcgggtagtgagc gttctgaccgtgctccaccaagattggctcaatggaaaagagtacaagtgcaaggtgtccaacaaggctcttcccgctcc cattgagaaaactatctccaaagccaagggcagccacgggaaccccagtgtatacattgcccccatctagagacga gctgaccaagaaccaggtgagtctcacttgtctggtcaaggggttttaccttctgacattgctgtagagtgggagtctaac ggacagccagaaaacaactacaagacaactcccccagtgctggacagcgacgggagcttcttcctctactccaagttga ctgtagacaagtctagatggcagcaaggaaacgttttctcctgctcagtaatgcatgaggctctgcacaatcactataccc agaaatcactgtcccttagcccagggtgactcgag (SEQ ID NO: 153) |
| huCD37-3v1.1 | aagcttgccaccatgggctggagctgtatcattctgtttctggtggcgacagctactggggtccactccaagtgcaggta caagagtccgggcctggattggtcgcaccaagccagaccctctctatcacttgtaccgttagcgggttctctctgacaacc agtggagtgagttgggtgaggcagccaccaggaaagggactggagtggctgggggtgatttgggcgacggcagca caaactcattccagtctaaatctcggttgtccattaaaaaagaccatagtaaatctcaagttttcctgaaactcaatagcct gacagccgcagacactgctacgtattactgcgccaaaggaggatacagtctggctcactggggacaggggaccctggt gaccgtgtcatccgcatcaacaaagggcccatcagttttccccttggctccaagttctaaatccacaagcggtggaacag ctgcactgggatgcctcgttaaagattatttccctgagcctgtgacagtgagctggaatagcggagcattgacttcaggtgt gcacacttttcccgctgtgttgcagtcctccggtctgtactcactgtccagtgtcgtaaccgtcccttctagcagcttgggaa cccagacctacatctgtaacgtcaaccataaaccatccaacacaaaggtggataagaaggttgaaccaaagagctgtga taagacacatacatgcccctccttgtcctgcaccagagctcctcggaggtccatctgtgttcctgtttccccccaaacccaag gacactcttatgatctctcgtactccagaggtcacctgtgttgttgtcgacgtgagccatgaagatcccgaggttaaattcaa ctggtacgtggatggagtcgaggttcacaatgccaagaccaagcccagggaggagcaatataattctacatatcgggta gtgagcgttctgaccgtgctccaccaagattggctcaatggaaaagagtacaagtgcaaggtgtccaacaaggctcttcc cgctcccattgagaaaactatctccaaagccaagggcagccacgggaaccccagtgtatacattgcccccatctaga gacgagctgaccaagaaccaggtgagtctcacttgtctggtcaaggggttttaccttctgacattgctgtagagtgggag tctaacggacagccagaaaacaactacaagacaactcccccagtgctggacagcgacgggagcttcttcctctactcca agttgactgtagacaagtctagatggcagcaaggaaacgttttctcctgctcagtaatgcatgaggctctgcacaatcacta tacccagaaatcactgtcccttagcccagggtgactcgag (SEQ ID NO: 154) |
| chCD37-12 | aagcttgccaccatggggttggtcatgcataatcctctttctggtcgctactgctaccggtgtgcactcacagattcagctgg ttcaaagtggcccagagctgaaaaagccaggggaaacagtgaaaataagttgcaaggcatccgttacactttcacaaa gtacggcatgaactgggtcaagcaggcccagggcaagggggctcaaatggatgggttggatcaataccaacactggcg agtctaggaatgctgaggagtttaagggccggtttgccttcagcctggagacaagtgccagcacagcttacctgcaaatc aacaatctgaagtatgaggatacagcaaccctatttctgcggccgcggcactgtcgttgcagactggggacaaggtacca ccttgactgtatccagtgccagcactaagggcccatcagttttccccttggctccaagttctaaatccacaagcggtggaa cagctgcactgggatgcctcgttaaagattatttccctgagcctgtgacagtgagctggaatagcggagcattgacttcag gtgtgcacacttttcccgctgtgttgcagtcctccggtctgtactcactgtccagtgtcgtaaccgtcccttctagcagcttgg gaacccagacctacatctgtaacgtcaaccataaaccatccaacacaaaggtggataagaaggttgaaccaaagagctg tgataagacacatacatgcccctccttgtcctgcaccagagctcctcggaggtccatctgtgttcctgtttccccccaaaccc aaggacactcttatgatctctcgtactccagaggtcacctgtgttgttgtcgacgtgagccatgaagatcccgaggttaaatt caactggtacgtggatggagtcgaggttcacaatgccaagaccaagcccagggaggagcaatataattctacatatcgg gtagtgagcgttctgaccgtgctccaccaagattggctcaatggaaaagagtacaagtgcaaggtgtccaacaaggctct tcccgctcccattgagaaaactatctccaaagccaagggcagccacgggaaccccagtgtatacattgcccccatct agagacgagctgaccaagaaccaggtgagtctcacttgtctggtcaaggggttttaccttctgacattgctgtagagtgg gagtctaacggacagccagaaaacaactacaagacaactcccccagtgctggacagcgacgggagcttcttcctctact ccaagttgactgtagacaagtctagatggcagcaaggaaacgttttctcctgctcagtaatgcatgaggctctgcacaatc actatacccagaaatcactgtcccttagcccagggtgactcgag (SEQ ID NO: 155) |

TABLE 9-continued

Full-length heavy chain polynucleotide sequences

| Antibody | Full-Length Heavy Chain Polynucleotide Sequence (SEQ ID NO) |
|---|---|
| chCD37-38 | aagcttgccaccatgggctggagttgtatcattctgttttggtggccaccgccactggagtccattcccaagtgcaactcc aggaatctggccctgacctggttaagccatctcagagcctctccctgacctgcactgttacaggatactcaatcacatcag gctttggctggcactggatcagacaatttcccgggaacaagttggaatggatgcttacattctgtatagcggggtaccg attacaatccttccctcaagagccgaatctctatcaccagggatacaagcaagaaccaattttttctccgcctcagctctgtg actaccgaagataccgctacttactattgtgccaggggctactatggatatggtgcatggttcgtctattggggccaggga accctggtgactgtgagcgctgcctctaccaagggcccatcagttttccccttggctccaagttctaaatccacaagcggt ggaacagctgcactgggatgcctcgttaaagattatttccctgagcctgtgacagtgagctggaatagcggagcattgact tcaggtgtgcacacttttcccgctgtgttgcagtcctccggtctgtactcactgtccagtgtcgtaaccgtcccttctagcag cttgggaacccagacctacatctgtaacgtcaaccataaaccatccaacacaaaggtggataagaaggttgaaccaaag agctgtgataagacacatacatgcccctccttgtctgcaccagagctcctcggaggtccatctgtgttcctgtttccccca aacccaaggacactcttatgatctctcgtactccagaggtcacctgtgttgttgtcgacgtgagccatgaagatcccgagg ttaaattcaactggtacgtggatggagtcgaggttcacaatgccaagaccaagcccagggaggagcaatataattctaca tatcgggtagtgagcgttctgaccgtgctccaccaagattggctcaatggaaaagagtacaagtgcaaggtgtccaacaa ggctcttcccgctcccattgagaaaactatctccaaagccaaggggcagccacgggaacccaggtgtatacattgccc ccatctagagacgagctgaccaagaaccaggtgagtctcacttgtctggtcaaggggttttacccttctgacattgctgtag agtgggagtctaacggacagccagaaaacaactacaagacaactcccccagtgctggacagcgacgggagcttcttcc tctactccaagttgactgtagacaagtctagatggcagcaaggaaacgttttctcctgctcagtaatgcatgaggctctgca caatcactatacccagaaatcactgtcccttagcccagggtgactcgag (SEQ ID NO: 156) |
| huCD37-38 | aagcttgccaccatgggttggagctgcatcattctttcctggtcgctactgcaactggagtccactcacaggtccagctgc aagagtccggtcctggccttgtgaaacccagccagtccctcagtctcacctgtactgtctctggctactcattaccagtgg gttcggctggcattggattaggcagtttcccggtaagggctggagtggatggcatatatctgtacagccggaggaacc gattacaaccccaagtctgaagagcaggatcagcattacccggacacaagcaaaaaccagttttttcttcggctgtctagt gttacagctgcagacaccgctacttactattgtgctcggggttactatggctatggggcttggtttgtgtattggggacaag gcactcttgtgaccgtgagcagcgcctcaacaaagggcccatcagttttcccttggctccaagttctaaatccacaagcg gtggaacagctgcactgggatgcctcgttaaagattatttccctgagcctgtgacagtgagctggaatagcggagcattg acttcaggtgtgcacacttttcccgctgtgttgcagtcctccggtctgtactcactgtccagtgtcgtaaccgtcccttctagc agcttgggaacccagacctacatctgtaacgtcaaccataaaccataaaccatccaacacaaaggtggataagaaggttgaaccaa agagctgtgataagacacatacatgcccctccttgtcctgcaccagagctcctcggaggtccatctgtgttcctgtttccccc caaacccaaggacactcttatgatctctcgtactccagaggtcacctgtgttgttgtcgacgtgagccatgaagatcccga ggttaaattcaactggtacgtggatggagtcgaggttcacaatgccaagaccaagcccagggaggagcaatataattcta catatcgggtagtgagcgttctgaccgtgctccaccaagattggctcaatggaaaagagtacaagtgcaaggtgtccaac aaggctcttcccgctcccattgagaaaactatctccaaagccaaggggcagccacgggaacccaggtgtatacattgc cccatctagagacgagctgaccaagaaccaggtgagtctcacttgtctggtcaaggggttttacccttctgacattgctgt agagtgggagtctaacggacagccagaaaacaactacaagacaactcccccagtgctggacagcgacgggagcttctt cctctactccaagttgactgtagacaagtctagatggcagcaaggaaacgttttctcctgctcagtaatgcatgaggctctg cacaatcactatacccagaaatcactgtcccttagcccagggtgactcgag (SEQ ID NO: 157) |
| huCD37-50 | aagcttgccaccatggggtggtcctgcataatccttttcctggttgctactgctaccggagtccattcacaggtgcagctgc aggagtccggccccggcctgctcaagccttctcagagtctgagtctgacttgtactgtttctggctacagcataaccagcg gtttcgcttggcactggatcagacagcatcccggcaacaaactggagtggatgggatacatactgtactcaggctcaact gtctattcccctccctgaaatcccggatcagtattacccgtgacacttctaagaaccattttttctgcagctgaacagcgtt accgcagctgacactgcaacctactactgtgcccggggatattatggatacggagcttggttcgcttactggggccaagg caccctcgtaactgtgagtgctgcttccaccaagggcccatcagttttccccttggctccaagttctaaatccacaagcggt ggaacagctgcactgggatgcctcgttaaagattatttccctgagcctgtgacagtgagctggaatagcggagcattgact tcaggtgtgcacacttttcccgctgtgttgcagtcctccggtctgtactcactgtccagtgtcgtaaccgtcccttctagcag cttgggaacccagacctacatctgtaacgtcaaccataaaccatccaacacaaaggtggataagaaggttgaaccaaag agctgtgataagacacatacatgcccctccttgtcctgcaccagagctcctcggaggtccatctgtgttcctgtttccccca aacccaaggacactcttatgatctctcgtactccagaggtcacctgtgttgttgtcgacgtgagccatgaagatcccgagg ttaaattcaactggtacgtggatggagtcgaggttcacaatgccaagaccaagcccagggaggagcaatataattctaca tatcgggtagtgagcgttctgaccgtgctccaccaagattggctcaatggaaaagagtacaagtgcaaggtgtccaacaa ggctcttcccgctcccattgagaaaactatctccaaagccaaggggcagccacgggaacccaggtgtatacattgccc ccatctagagacgagctgaccaagaaccaggtgagtctcacttgtctggtcaaggggttttacccttctgacattgctgtag agtgggagtctaacggacagccagaaaacaactacaagacaactcccccagtgctggacagcgacgggagcttcttcc tctactccaagttgactgtagacaagtctagatggcagcaaggaaacgttttctcctgctcagtaatgcatgaggctcgca caatcactatacccagaaatcactgtcccttagcccagggtgactcgag (SEQ ID NO: 158) |
| huCD37-51 | aagcttgccaccatggggttggtcttgcatcatcctgttcctggtggccactgccactggcgtgcattcagaagttcagttggt ggagtccggccccgaaagtgctgaaacccggcgaatcactgtccctgacttgtaccgtgtcaggttatgcatcagcagc ggctttgcttggcactggattcggcagtttccaggcaagggactggaatggatgggctacatccattacagtggctcaac caattacagccctagcctgcagggccgaatctctataccagggatagttctattaaccagttttcctgcagcttaattccgt gactgcctctgacacagcaacttactattgcgcccgtggctactacgggttcggagcctggtttgtatactggggtcaggg caccctggtcactgtctcagccgcctctaccaagggcccatcagttttcccttggctccaagttctaaatccacaagcggt ggaacagctgcactgggatgcctcgttaaagattatttccctgagcctgtgacagtgagctggaatagcggagcattgact tcaggtgtgcacacttttcccgctgtgttgcagtcctccggtctgtactcactgtccagtgtcgtaaccgtcccttctagcag cttgggaacccagacctacatctgtaacgtcaaccataaaccatccaacacaaaggtggataagaaggttgaaccaaag agctgtgataagacacatacatgcccctccttgtcctgcaccagagctcctcggaggtccatctgtgttcctgtttccccca aacccaaggacactcttatgatctctcgtactccagaggtcacctgtgttgttgtcgacgtgagccatgaagatcccgagg ttaaattcaactggtacgtggatggagtcgaggttcacaatgccaagaccaagcccagggaggagcaatataattctaca tatcgggtagtgagcgttctgaccgtgctccaccaagattggctcaatggaaaagagtacaagtgcaaggtgtccaacaa ggctcttcccgctcccattgagaaaactatctccaaagccaaggggcagccacgggaacccaggtgtatacattgccc ccatctagagacgagctgaccaagaaccaggtgagtctcacttgtctggtcaaggggttttacccttctgacattgctgtag agtgggagtctaacggacagccagaaaacaactacaagacaactcccccagtgctggacagcgacgggagcttcttcc tctactccaagttgactgtagacaagtctagatggcagcaaggaaacgttttctcctgctcagtaatgcatgaggctctgca caatcactatacccagaaatcactgtcccttagcccagggtgactcgag (SEQ ID NO: 159) |

TABLE 9-continued

Full-length heavy chain polynucleotide sequences

| Antibody | Full-Length Heavy Chain Polynucleotide Sequence (SEQ ID NO) |
|---|---|
| huCD37-56 | aagcttgccaccatggggtggagctgcattatcctgttcctcgtcgccaccgcaaccggcgtccactcccaggtgcagct gcaagaaagcgggccaggattggtaaaaccttcccagtctctgagtcttacttgtaccgtatctggatacagtatcacatct ggcttcgcctggcattggattcgccagtttcccggcaaggggcttgagtggatggggtatattcattattctggaggtacca actacaaccttccctgaagagtcgagtctcaattaccagggacacttccaagaaccaattcttttgcagcttaattcagtg accgctgccgacaccgctacttactactgcgcccggggctactatgggttttggtgcctggttcgcctactggggccaggg gaccctggtgcccgtgtctgctgcctccacaaaggggcccatcagttttcccctggctccaagtctaaatccacaagcgg tggaacagctgcactgggatgcctcgttaaagattatttccctgagcctgtgacagtgagctggaatagcggagcattgac ttcaggtgtgcacacttttcccgctgtgttgcagtcctccggtctgtactcactgtccagtgtcgtaaccgtcccttctagcag cttgggaaacccagacctacatctgtaacgtcaaccataaaccatccaacacaaaggtggataagaaggttgaaccaaag agctgtgataagacacatacatgccctcttgtcctgcaccagagctcctcggaggtccatctgtgttcctgtttccccca aacccaaggacactcttatgatctctcgtactccagaggtcacctgtgttgttgtcgacgtgagccatgaagatcccgag ttaaattcaactggtacgtggatggagtcgaggttcacaatgccaagaccaagcccaggggaggagcaatataattctaca tatcgggtagtgagcgttctgaccgtgctccaccaagattggctcaatggaaaagagtacaagtgcaaggtgtccaacaa ggctcttcccgctcccattgagaaaactatctccaaagccaaggggcagccacgggaacccccaggtgtatacattgccc ccatctagagacgagctgaccaagaaccaggtgagtctcacttgtctggtcaagggggttttacccttctgacattgctgtag agtgggagtctaacggacagccagaaaacaactacaagacaactcccccagtgctggacagcgacgggagcttcttcc tctactccaagttgactgtagacaagtctagatggcagcaaggaaacgttttctcctgctcagtaatgcatgaggctctgca caatcactatacccagaaatcactgtcccttagcccagggtgactcgag (SEQ ID NO: 160) |
| huCD37-57 | aagcttgccaccatgggctggagctgcatcattctgtttctggtggccacagcaactggcgttcacgtcaagtccaactg caggagagcggcccggactcctgaaaccatctcagtcactcagtctgacatgtactgtgagcggctacagcattacctc aggcttgcttggcattggatcaggcagttcccggaaaaggtctggagtggatggggtacattctgtacagcggcagta cagtgtattcaccctcctggaaatctaggatatcaatcacacgtgatacaagcaaaaatcagttcttcctccagctgaactcc gtcaccgccgcagacacagcaacctattattgtgctcgcggatactacggatatggcgcatggttcgcctattggggcca ggggacactcgtgaccgtttccgccgcctccacaaagggcccatcagttttcccctggctccaagtctaaatccacaag cggtggaacagctgcactgggatgcctcgttaaagattatttccctgagcctgtgacagtgagctggaatagcggagcat tgacttcaggtgtgcacactttccccgctgtgttgcagtcctccggtctgtactcactgtccagtgtcgtaaccgtcccttcta gcagcttgggaacccagacctacatctgtaacgtcaaccataaaccatccaacacaaaggtggataagaaggttgaacc aaagagctgtgataagacacatacatgccctcttgtcctgcaccagagctcctcggaggtccatctgtgttcctgtttccc cccaaacccaaggacactcttatgatctctcgtactccagaggtcacctgtgttgttgtcgacgtgagccatgaagatccc gaggttaaattcaactggtacgtggatggagtcgaggttcacaatgccaagaccaagcccaggggaggagcaatataatt ctacatatcgggtagtgagcgttctgaccgtgctccaccaagattggctcaatggaaaagagtacaagtgcaaggtgtcc aacaaggctcttcccgctcccattgagaaaactatctccaaagccaaggggcagccacgggaacccccaggtgtatacat tgcccccatctagagacgagctgaccaagaaccaggtgagtctcacttgtctggtcaagggggttttacccttctgacattg ctgtagagtgggagtctaacggacagccagaaaacaactacaagacaactcccccagtgctggacagcgacggagc ttcttcctctactccaagttgactgtagacaagtctagatggcagcaaggaaacgttttctcctgctcagtaatgcatgaggc tctgcacaatcactatacccagaaatcactgtcccttagcccagggtgactcgag (SEQ ID NO: 161) |

TABLE 10

Full-length light chain polynucleotide sequences

| Antibody | Full-length Light Chain Polynucleotide Sequence (SEQ ID NO) |
|---|---|
| cgCD37-3 | gaattcgccaccatgagtgtgcccactcaggtcctggggttgctgctgctgtggcttacagatgccagatgtgacatccag atgactcagtctccagcctcccttcctgtatctgtgggagaaactgtcaccatcacatgtcgagcaagtgagaatattcgca gtaatttagcatggtatcagcagaaacagggaaaatctcctcagctcctggtcaatgttgcaacaaacttagcagatggtgt gccatcaaggttcagtggcagtggatcaggcacacagtattccctcaagatcaacagcctgcagtctgaagattttggga cttattactgtcaacattattgggtactacgtggacgttcggtggaggcaccaagctggaaatcaaacgtacggtggctg caccatctgtcttcatcttcccgccatctgatgagcagttgaaatctggaactgcctctgttgtgtgcctgctgaataacttcta tcccagagaggccaaagtacagtggaaggtggataacgccctccaatcgggtaactcccaggagagtgtcacagagc aggacagcaaggacagcacctacagcctcagcagcaccctgacgctgagcaaagcagactacgagaaacacaaagt ctacgcctgcgaagtcacccatcagggcctgagctcgcccgtcacaaagagcttcaacaggggagagtgttag (SEQ ID NO: 162) |
| huCD37-3 (1.0 and 1.1) | gaattcgccaccatgggttggtcctgcatcatcttgtttctcgtggccacagccaccggtgttcactctgatatacaaatgac tcaaagccctccagtttgagcgtaagtgtgggtgaacgcgtaacaatcacctgtagagctagtgaaaacatccgcagta atctcgcatggtaccaacaaaagccaggtaagtcacctaagctcctcgtgaatgttgctaccaacctcgctgatggtgtgc cttcacgattctctgttcaggttccggtaccgattattccttaagatcaactcactccaaccagaagattcggtacatatta ctgtcaacactatggggtacgactggacattcggtcaaggtactaagctggaaatcaagcgtacggtggctgccaccat ctgtcttcatcttcccgccatctgatgagcagttgaaatctggaactgcctctgttgtgtgcctgctgaataacttctatccca gagaggccaaagtacagtggaaggtggataacgccctccaatcgggtaactcccaggagagtgtcacagagcaggac agcaaggacagcacctacagcctcagcagcaccctgacgctgagcaaagcagactacgagaaacacaaagtctacgc ctgcgaagtcacccatcagggcctgagctcgcccgtcacaaagagcttcaacaggggagagtgttag (SEQ ID NO: 163) |
| chCD37-12 | gaattcgccaccatgggttggtcctgtataatcctgttcttggtggccaccgctactggcgttcatagtgatattgtactcact cagtcaccagccagtctggcagtgtccctgggcagcgtgccaccatctcctgccgggcctcacagtccgtgagcacta gctcttattcctatctctcactggtttcaacagaagccaggacagcccccttaagctgctgatcaagtacgcctccaacctcgc cagcggcgtcccgctagattctctggttccggtagcggaactgatttcactttgaacatccacccgttgaggaagagga taccgccacttactattgtcaacactcttgggagattccttacacctttggaggaggaacaaagctcgaaattaagcgtacg gtggctgcaccatctgtcttcatcttcccgccatctgatgagcagttgaaatctggaactgcctctgttgtgtgcctgctgaat aacttctatcccagagaggccaaagtacagtggaaggtggataacgccctccaatcgggtaactcccaggagagtgtca |

TABLE 10-continued

Full-length light chain polynucleotide sequences

| Antibody | Full-length Light Chain Polynucleotide Sequence (SEQ ID NO) |
|---|---|
| | cagagcaggacagcaaggacagcacctacagcctcagcagcaccctgacgctgagcaaagcagactacgagaaaca<br>caaagtctacgcctgcgaagtcacccatcagggcctgagctcgccgtcacaaagagcttcaacaggggagagtgtta<br>g (SEQ ID NO: 164) |
| chCD37-38 | gaattcgccaccatgggctggtcctgtatcatcctgtttctcgtggccacagctacaggtgttcattctcagattgtgctgac<br>ccaatcaccagctattatgtccgctagcccggcgagaaagtgacaatgacatgtagcgctagctcttctgtgacttacat<br>gcattggtatcaacagaagtcaggtaccagtcccaagcgttggatctacgacacatccaaactggcctccggagtccctg<br>ccaggttcagcggaggtgggtccggcaccagttattcactgaccatatcctctatggaagctgaagatgctgctacttatta<br>ttgtcaacaatggatttctaaccccccccacctttggtggcggacaaaagctggagatcaagcgtacggtggctgcaccat<br>ctgtcttcatcttcccgccatctgatgagcagttgaaatctggaactgcctctgttgtgtgcctgctgaataacttctatccca<br>gagaggccaaagtacagtggaaggtggataacgccctccaatcgggtaactcccaggagagtgtcacagagcaggac<br>agcaaggacagcacctacagcctcagcagcaccctgacgctgagcaaagcagactacgagaaacacaaagtctacgc<br>ctgcgaagtcacccatcagggcctgagctcgccgtcacaaagagcttcaacaggggagagtgttag (SEQ ID NO: 165) |
| huCD37-38 | gaattcgccaccatgggatggtcctgcattattctgttcttggtcgccactgctactggcgttcactctgacattgtgctcaca<br>cagtctccagcctcaatgtctgcttccccggtgagcgggtgaccatgacatgctctgccagttcctccgtgacatatatgc<br>attggtatcagcaaaaaccggtacctctcaaaaagatgtactacacttcaaagcttgcatcaggcgttcctgcca<br>gattttccgggtctgggtctggcacttcatacagtctgaccattagttccatggaagctgaagatgcagccacctattactgt<br>cagcagtggatttcaaatcctcctaccttcggcggcggaaccaaactggagataaagcgtacggtggctgcaccatctgt<br>cttcatcttcccgccatctgatgagcagttgaaatctggaactgcctctgttgtgtgcctgctgaataacttctatcccagaga<br>ggccaaagtacagtggaaggtggataacgccctccaatcgggtaactcccaggagagtgtcacagagcaggacagca<br>aggacagcacctacagcctcagcagcaccctgacgctgagcaaagcagactacgagaaacacaaagtctacgcctgc<br>gaagtcacccatcagggcctgagctcgccgtcacaaagagcttcaacaggggagagtgttag (SEQ ID NO: 166) |
| huCD37-50 | gaattcgccaccatgggttggtcatgcattattctgttcctggttgctaccgcaacaggagtacatagtgagatagtcctcac<br>ccaaagtcctgctactatgtctgccagcccaggagagcgtgtgaccatgacttgctctgcaacctcaagtgtgacatacat<br>gcattggtatcagcaaaagcctggccaatcccctaaaaggtggatctacgatacttctaatctgccatacggtgtgcccgc<br>aaggttctccgggagtggcagtggcaccagttatagtctgaccatcagttcaatggaagcagaggatgcagcaacctatt<br>attgtcagcagtggtccgataatccccctacttttggtcagggtacaaagctggagattaagcgtacggtggctgcaccat<br>ctgtcttcatcttcccgccatctgatgagcagttgaaatctggaactgcctctgttgtgtgcctgctgaataacttctatccca<br>gagaggccaaagtacagtggaaggtggataacgccctccaatcgggtaactcccaggagagtgtcacagagcaggac<br>agcaaggacagcacctacagcctcagcagcaccctgacgctgagcaaagcagactacgagaaacacaaagtctacgc<br>ctgcgaagtcacccatcagggcctgagctcgccgtcacaaagagcttcaacaggggagagtgttag (SEQ ID NO: 167) |
| huCD37-51 | gaattcgccaccatgggatggagctgtattattctgttcctggttgctactgctactggcgtccattccgagatagtcctcac<br>ccagagccccgcaaccatgagtgcctccctggggagcgagtgactatgacttgttccgccacttcttcagttacctatat<br>gcattggtatcagcagaaacctggacagtctccaaagcgttggatttacgacacctccaacctggcttcaggagttcctgc<br>taggttcagcggatctgggtctggcacaagttattcactcaccattagttccatggaggccgaagatgccgctactttactac<br>tgtcagcagtggagcagcaaccccctacattcgggcagggaactaagctggagatcaaacgtacggtggctgcacca<br>tctgtcttcatcttcccgccatctgatgagcagttgaaatctggaactgcctctgttgtgtgcctgctgaataacttctatcca<br>gagaggccaaagtacagtggaaggtggataacgccctccaatcgggtaactcccaggagagtgtcacagagcaggac<br>agcaaggacagcacctacagcctcagcagcaccctgacgctgagcaaagcagactacgagaaacacaaagtctacgc<br>ctgcgaagtcacccatcagggcctgagctcgccgtcacaaagagcttcaacaggggagagtgttag (SEQ ID NO: 168) |
| huCD37-56 | gaattcgccaccatgggctggtcctgtatcatcctgtttctggtggcaaccgctactggggttcactctgatattgtcctgac<br>acagagtccagccttcatgagtgcttctctcccggagaaaagtcaaatgacttgttcagcttcctcctccgtcacatacatg<br>cattggtaccagcagaagcctgaccagagtcctaagaggtggatctatgataccaagcaatctggcttccggtgtccctc<br>ccgcttttcaggcggcggaagcggaactgactatagccttaccatctcctcaatggaagccgaggacgctgctacatatt<br>actgccagcaatggatcagcgacccctacttcggacagggaacaaaattggaaattaagcgtacggtggctgcacc<br>atctgtcttcatcttcccgccatctgatgagcagttgaaatctggaactgcctctgttgtgtgcctgctgaataacttctatccc<br>agagaggccaaagtacagtggaaggtggataacgccctccaatcgggtaactcccaggagagtgtcacagagcagga<br>cagcaaggacagcacctacagcctcagcagcaccctgacgctgagcaaagcagactacgagaaacacaaagtctacg<br>cctgcgaagtcacccatcagggcctgagctcgccgtcacaaagagcttcaacaggggagagtgttag (SEQ ID NO: 169) |
| huCD37-57 | gaattcgccaccatggggtggtcctgtattatcctgttcctggtcgcaaccgccacaggcgttcactccgagatcgtgttga<br>ctcagagcccagccaccatgtccgcttccccggggagagagtgacaatgacttgttccgccacaagttctgtaacctac<br>atgcattggtaccagcaaaaaccaggacagagtccccgtcgttggatttatgatacctctaacctggcttcaggcgttcctg<br>cccgcttttctggtagtggatctgggacttcctatagccttaccataagctctatggaagccgaggacgccgctacatacta<br>ctgccagcagtggtgataacccccccacctcgggcagggaaccaaattggagatcaaacgtacggtggctgcacc<br>atctgtcttcatcttcccgccatctgatgagcagttgaaatctggaactgcctctgttgtgtgcctgctgaataacttctatccc<br>agagaggccaaagtacagtggaaggtggataacgccctccaatcgggtaactcccaggagagtgtcacagagcagga<br>cagcaaggacagcacctacagcctcagcagcaccctgacgctgagcaaagcagactacgagaaacacaaagtctacg<br>cctgcgaagtcacccatcagggcctgagctcgccgtcacaaagagcttcaacaggggagagtgttag (SEQ ID NO: 170) |

Also provided is a polynucleotide having at least about 95%, at least about 96%, at least about 97%, at least about 98%, or at least about 99% sequence identity to SEQ ID NOs:121-170, 182, or 183. Thus, in certain embodiments, the polynucleotide comprises (a) a polynucleotide having at least about 95% sequence identity to SEQ ID NOs:121-135, 152-161, or 182, and/or (b) a polynucleotide having at least about 95% sequence identity to SEQ ID NOs:136-151, 162-170, or 183. In certain embodiments, the polynucleotide comprises (a) a polynucleotide having the nucleic acid sequence of SEQ ID NOs: 121-135, 152-161 or 182; and/or (b) a polynucleotide having the nucleic acid sequence of SEQ ID NOs: 136-151, 162-170, or 183.

In some embodiments, the polynucleotide encodes the light chain encoded by the recombinant plasmid DNA phuCD37-3LC (ATCC Deposit Designation PTA-10722, deposited with the ATCC on Mar. 18, 2010) or a light chain that is at least about 85%, at least about 90%, at least about 95%, or at least about 99% to the light chain encoded by phuCD37-3LC (PTA-10722). In some embodiments, the polynucleotide encodes the heavy chain encoded by the recombinant plasmid DNA phuCD37-3HCv.1.0 (ATCC Deposit Designation PTA-10723, deposited with the ATCC on Mar. 18, 2010) or a heavy chain that is at least about 85%, at least about 90%, at least about 95%, or at least about 99% identical to the heavy chain encoded by phuCD37-3HCv.1.0 (PTA-10723). In certain embodiments the polynucleotide is the recombinant plasmid DNA phuCD37-3LC (PTA-10722) or the recombinant plasmid phuCD37-3HCv.1.0 (PTA-10723).

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons. e.g., to optimize codon expression for a particular host (change codons in the human mRNA to those preferred by a bacterial host such as *E. coli*).

Vectors and cells comprising the polynucleotides described herein are also provided.

IV. METHODS OF USE AND PHARMACEUTICAL COMPOSITIONS

The CD37-binding agents (including antibodies, immunoconjugates, and polypeptides) of the invention are useful in a variety of applications including, but not limited to, therapeutic treatment methods, such as the treatment of cancer, such as B-cell malignancies, autoimmune diseases, and inflammatory diseases. In certain embodiments, the agents are useful for depleting B-cells. In certain embodiments, the agents are useful for depleting autoreactive B-cells. In certain embodiments, the agents are useful for depleting peripheral B-cells. In certain embodiments, the agents are useful for preventing inappropriate T-cell stimulation. The T-cell stimulation can be in connection with a B-cell pathway. The methods of use can be in vitro, ex vivo, or in viva methods. In certain embodiments, the CD37-binding agent or antibody or immunoconjugate, or polypeptide is an antagonist of the human CD37 to which it binds.

In one aspect, anti-CD37 antibodies and immunoconjugates of the invention are useful for detecting the presence of CD37 in a biological sample. The term "detecting" as used herein encompasses quantitative or qualitative detection. In certain embodiments, a biological sample comprises a cell or tissue. In certain embodiments, such issues include tissues that express CD37 at higher levels relative to other tissues, for example, B-cells and/or B-cell associated tissues.

In one aspect, the invention provides a method of detecting the presence of CD37 in a biological sample. In certain embodiments, the method comprises contacting the biological sample with an anti-CD37 antibody under conditions permissive for binding of the anti-CD37 antibody to CD37, and detecting whether a complex is formed between the anti-CD37 antibody and CD37.

In one aspect, the invention provides a method of diagnosing a disorder associated with increased expression of CD37. In certain embodiments, the method comprises contacting a test cell with an anti-CD37 antibody; determining the level of expression (either quantitatively or qualitatively) of CD37 by the test cell by detecting binding of the anti-CD37 antibody to CD37; and comparing the level of expression of CD37 by the test cell with the level of expression of CD37 by a control cell (e.g., a normal cell of the same tissue origin as the test cell or a cell that expresses CD37 at levels comparable to such a normal cell), wherein a higher level of expression of CD37 by the test cell as compared to the control cell indicates the presence of a disorder associated with increased expression of CD37. In certain embodiments, the test cell is obtained from an individual suspected of having an autoimmune disorder or inflammatory disorder. In some embodiments, the disorder is associated with increased expression of CD37. In some embodiments, the disorder is associated with increased number of B-cells. In some embodiments, the disorder is associated with increased activity of B-cells.

In certain embodiments, a method of diagnosis or detection, such as those described above, comprises detecting binding of an anti-CD37 antibody to CD37 expressed on the surface of a cell or in a membrane preparation obtained from a cell expressing CD37 on its surface. In certain embodiments, the method comprises contacting a cell with an anti-CD37 antibody under conditions permissive for binding of the anti-CD37 antibody to CD37, and detecting whether a complex is formed between the anti-CD37 antibody and CD37 on the cell surface. An exemplary assay for detecting binding of an anti-CD37 antibody to CD37 expressed on the surface of a cell is a "FACS" assay.

Certain other methods can be used to detect binding of anti-CD37 antibodies to CD37. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-CD37 antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-CD37 antibodies are immobilized on an insoluble matrix. Immobilization entails separating the anti-CD37 antibody from any CD37 that remains free in solution. This conventionally is accomplished by either insolubilizing the anti-CD37 antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-CD37 antibody after formation of a complex between the anti-CD37 antibody and CD37, e.g., by immunoprecipitation.

Any of the above embodiments of diagnosis or detection can be carried out using an immunoconjugate of the invention in place of or in addition to an anti-CD37 antibody.

In certain embodiments, the disease treated with the CD37-binding agent is an autoimmune or inflammatory disease. In certain embodiments, the autoimmune or inflammatory disease is selected from the group consisting of psoriasis, dermatitis, systemic scleroderma and sclerosis, responses associated with inflammatory bowel disease, Crohn's disease, ulcerative colitis, respiratory distress syndrome, adult respiratory distress syndrome (ARDS), dermatitis, meningitis, encephalitis, uveitis, colitis, glomerulonephritis, allergic conditions, eczema, asthma, conditions involving infiltration of T cells and chronic inflammatory responses, atherosclerosis, leukocyte adhesion deficiency, rheumatoid arthritis, systemic lupus crythematosus (SLE), diabetes mellitus, multiple sclerosis, Reynaud's syndrome, autoimmune thyroiditis, allergic encephalomyclitis, Sjorgen's syndrome, juvenile onset diabetes, immune responses associated with acute and delayed hypersensitivity mediated by cytokines and T-lymphocytes, tuberculosis, sarcoidosis, polymyositis, granulomatosis, vasculitis, pernicious anemia (Addison's disease), diseases involving leukocyte diapedesis, central nervous system (CNS) inflammatory disorder, multiple organ injury syndrome, hemolytic anemia, myasthenia gravis, antigen-antibody complex mediated diseases, anti-glomerular basement membrane disease, antiphospholipid syndrome, allergic neuritis, Graves' disease, Lambert-Eaton myasthenic syndrome, pemphigoid bullous, pemphigus, autoimmune polyendocrinopathies, Reiter's disease, stiff-man syndrome, Beheet disease, giant cell arteritis, immune complex nephritis, IgA nephropathy, IgM polyneuropathies, idiopathic thrombocytopenic purpura (ITP) and autoimmune thrombocytopenia.

In some embodiments, the autoimmune or inflammatory disease is selected from the group consisting of: RA, lupus, immune thrombocytopenic purpura, pure red cell aplasia, autoimmune anemia, cold agglutinin disease, type B syndrome of severe insulin resistance, mixed cryoglobulinermia, myasthenia gravis, Wegener's granulomatosis, microscopic polyangiitis (MPA), refractory pemphigus vulgaris, dermatomyositis, Sjogren's syndrome, active type-II mixed cryoglobulinemia, pemphigus vulgaris, autoimmune neuropathy, paraneoplastic opsoclonus-myoclonus syndrome, and relapsing-remitting multiple sclerosis (RRMS).

In certain embodiments, the autoimmune disease or inflammatory disease is characterized by CD37 expressing cells to which the CD37-binding agent (e.g., antibody) binds.

The present invention provides for methods of treating autoimmune and inflammatory diseases comprising administering a therapeutically effective amount of a CD37-binding agent to a subject (e.g., a subject in need of treatment). In certain embodiments, the subject is a human.

The present invention further provides methods for depleting B-cells, e.g., autoreactive B-cells, using the antibodies or other agents described herein. In certain embodiments, the method of depleting B-cells comprises contacting a B-cell with a CD37-binding agent (e.g., antibody) in vitro. For example, a cell line that expresses CD37 is cultured in medium to which is added the antibody or other agent to deplete the cells. In some embodiments, the cells are isolated from a patient sample such as, for example, a tissue biopsy, pleural effusion, or blood sample and cultured in medium to which is added an CD37-binding agent to deplete the cells.

In some embodiments, the method of depleting B-cells, e.g. autoreactive B-cells, comprises contacting the cells with the CD37-binding agent (e.g., antibody) in vivo. In certain embodiments, contacting a cell with a CD37-binding agent is undertaken in an animal model. For example, CD37-binding agents can be administered to xenografts expressing one or more CD37s that have been grown in immunocompromised mice (e.g. NOD/SCID mice). In some embodiments, cells are isolated from a patient sample such as, for example, a tissue biopsy, pleural effusion, or blood sample and injected into immunocompromised mice that are then administered a CD37-binding agent to deplete B-cells. In some embodiments, the CD37-binding agent is administered at the same time or shortly after introduction of cells into the animal. In further examples, CD37 binding agents can be administered in vivo to mice expressing one or more CD37 antigens. In some embodiments, these mice can be engineered to express human CD37 in addition to, or instead of, murine CD37. In some embodiments, these mice are disease models, e.g. models for autoimmune disease. In some embodiments, administering a CD37 binding agent depletes B-cells in vivo. In some embodiments, a CD37 binding agent prevents T-cell stimulation. In some embodiments, administering a CD37 binding agent prevents or alleviates an autoimmune disease.

In certain embodiments, the B-cells overexpress CD37. In other embodiments, the B-cells do not overexpress CD37. In some embodiments, the B-cells are not cancer cells. In some embodiments, the B-cells are not tumor cells. In some embodiments, the B-cells are not cancerous cells.

The present invention further provides pharmaceutical compositions comprising one or more of the CD37-binding agents described herein. In certain embodiments, the pharmaceutical compositions further comprise a pharmaceutically acceptable vehicle. These pharmaceutical compositions find use in treating autoimmune and inflammatory disease in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride: antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-autoimmune or inflammatory properties. The second compound of the pharmaceutical combination formulation or dosing regimen can have complementary activities to CD37-binding agent of the combination such that they do not adversely affect each other. Pharmaceutical compositions comprising the CD37-binding agent and the second agent are also provided. For example, CD37-binding agents can be administered in combination with CD20-binding agents, such as Rituximab. In other embodiments, CD37-binding agents can be administered in combination with salicylate; nonsteroidal anti-inflammatory drugs such as indomethacin, phenylbutazone, phenylacetic acid derivatives (e.g., ibuprofen and fenoprofen), naphthalene acetic acids (naproxen), pyrrolealkanoic acid (tometin), indoleacetic acids (sulindac), halogenated anthranilic acid (meclofenamate sodium), piroxicam, zomepirac and diflunisal; antimalarials such as chloroquine; gold salts; penicillamine; or immunosuppressive agents such as methotrexate or corticosteroids. In some embodiments, the CD37-binding agent is administered in combination with a second therapeutic selected from the group consisting of methotrexate, an anti-CD20 therapeutic, an anti-IL-6 receptor therapeutic, an anti-IL-12/23p40 therapeutic, a chemotherapeutic, an immunosuppressant, an anti-interferon beta-1a therapeutic, glatiramer acetate, an anti-α4-integrin therapeutic, fingolimod, an anti-BLys therapeutic, CTLA-Fc, or an anti-TNF therapeutic. In some embodiments, the CD37-binding agent is administered in combination with a second therapeutic that is an antibody directed against an antigen selected from a group consisting of CD3, CD14, CD19, CD20, CD22, CD25, CD28, CD30, CD33, CD36, CD33, CD40, CD44, CD52, CD55, CD59, CD56, CD70, CD79, CD80, CD103, CD134, CD137, CD138, and CD152. In some embodiments, the CD37-binding agent is administered in combination with a second thereapeutic that is an antibody directed against a target selected from the group consisting of IL-2, IL-6, IL-12, IL-23, IL-12/23 p40, IL-17, IFNγ, TNFα, IFNα, IL-15, IL-21, IL-1a, IL-1b, IL-18, IL-8, IL-4, GM-CSF, IL-3, and IL-5. In some embodiments, the CD37-binding agents are administered in combination with methotrexate.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is affected or a diminution of the disease state is achieved. Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 µg to 100 mg per kg of body weight, and can be given once or more daily, weekly, monthly or yearly. In certain embodiments, the antibody or other CD37-binding agent is given once every two weeks or once every three weeks. In certain embodiments, the dosage of the antibody or other CD37-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation: (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. KITS COMPRISING CD37-BINDING AGENTS

The present invention provides kits that comprise the antibodies, immunoconjugates or other agents described herein and that can be used to perform the methods described herein. In certain embodiments, a kit comprises at least one purified antibody against CD37 in one or more containers. In some embodiments, the kits contain all of the components necessary and/or sufficient to perform a detection assay, including all controls, directions for performing assays, and any necessary software for analysis and presentation of results. A label or indicator describing, or a set of instructions for use of, kit components in a ligand detection method of the present invention, can also be included. The instructions may be associated with a package insert and/or the packaging of the kit or the components thereof. One skilled in the art will readily recognize that the disclosed antibodies, immunoconjugates or other agents of the present invention can be readily incorporated into one of the established kit formats which are well known in the art. Such kits can also include, for example, other compounds and/or compositions, a device(s) for administering the compounds and/or compositions, and written instructions in a form prescribed by a governmental agency regulating the manufacture, use or sale of pharmaceuticals or biological products.

Further provided are kits comprising a CD37-binding agent (e.g., a CD37-binding antibody), as well as a second agent. In certain embodiments, the second agent is rituximab. In certain embodiments, the second agent is methotrexate.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

It is understood that the examples and embodiments described herein are for illustrative purposes only and that various modifications or changes in light thereof will be suggested to persons skilled in the art and are to be included within the spirit and purview of this application.

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

Example 1

CD37 Expression in Normal Human PBMCs

The CD37 antigen was reported to be expressed on B-cells from the pre-B stage to the peripheral mature B-cell stage, while being absent on B-cell progenitors and terminally differentiated plasma cells. (Link et al., 1987, J Pathol. 152:12-21). In addition, the CD37 antigen is only weakly expressed on T-cells, myeloid cells and granulocytes (Schwartz-Albiez et al. 1988, J. Immunol., 140(3)905-914).

The ability of antibodies (including certain CD37 antibodies and immunoconjugates previously described in U.S. Published Application No. 2011/0256153, which is herein incorporated by reference in its entirety) to bind to normal human B-cells was measured using flow cytometry assays with fluorescently labeled antibodies. In addition, the commercially available QuantiBRITE system from BD Biosciences was used to estimate antigen density based on the number of antibodies bound to the cells (ABC). The QuantiBRITE system from BD Biosciences utilizes the following reagents: anti-CD20-PE supplied at 100 μg/mL and QuantiBRITE PE supplied as lyophilized PE-labeled beads. In addition, the huCD37-3 antibody was labeled with PE to obtain an antibody-PE conjugate with an Ab:PE ratio of approximately 1:1.

Fresh buffy coats from healthy donors were obtained from Research Blood Components (Brighton, Mass., US) as a source of normal blood cells. Buffy coats were prepared by centrifugation of a unit of whole blood and collecting the interface between the plasma and the red blood cells. This unpurified buffy coat contains PBMCs, neutrophils, platelets, red blood cells, and plasma and was used for experiments on the same day it was drawn. Peripheral blood mononuclear cells (PBMCs) were prepared from buffy coats by standard density gradient centrifugation using Ficoll-Paque as follows. Blood was diluted 1:3 with 1×HBSS containing 5 mM EDTA and up to 30 mL were added to a 50 mL conical tube. Ten mL of Ficoll-Paque (GE Healthcare) were slowly added to the bottom of each tube. Samples were centrifuged at 500×g with no brake at RT for 30 minutes to obtain a layer of PBMCs below the plasma and to remove red blood cells and most granulocytes. The PBMCs were transferred to new tubes and washed twice with 1×HBSS containing 5 mM EDTA by centrifugation at 400×g for 10 minutes at RT. Staining buffer (1×HBSS, 1% BSA, 0.1% sodium azide) was then used to resuspend the PBMC pellets at $6.25 \times 10^6$ cells/mL. Eighty μL of cells were transferred to a round-bottom 96-well plate to achieve $5 \times 10^5$ cells/assay and 20 μL of human serum (Sigma H4522) were added to block Fc receptor-mediated binding and incubated with cells on ice for 20 min in the dark. Fluorescently labeled antibodies obtained from Miltenyi were used to identify PBMC populations: anti-CD3-allophycocyanin (APC) was used to identify T-cells, anti-CD19-APC for B-cells, anti-CD56-APC for natural killer (NK) cells and anti-CD14-APC for monocytes.

Cells were co-stained for CD37 expression using 20 μL of huCD37-3-PE for a final concentration of approximately 10 μg/mL. Likewise, cells were co-stained for CD20 expression using 20 μL of anti-CD20-PE. As a control a non-binding PE-labeled huIgG1 isotype control antibody was used at 10 μg/mL. Staining was carried out for 1 hour on ice in the dark. Samples were washed twice with staining buffer and fixed in 200 μL of 1% formaldehyde in 1×PBS. Samples were stored at 4° C. in the dark until acquisition, which was performed within 4 days of sample preparation.

A fresh tube of QuantiBRITE beads was reconstituted in the supplied tube with 0.5 mL of staining buffer just prior to sample acquisition. Samples were acquired on a FACSCalibur flow cytometer (BD Biosciences). Compensation controls were run with each assay to select appropriate instrument settings and at least 10,000 events were collected for each sample. Instrument settings for fluorescence and compensation were kept the same for both cell sample and bead sample acquisition to allow for an accurate comparison. CellQuest (version 5.2.1, BD Biosciences) was used for acquisition control and analysis.

The QuantiBRITE analysis utilizes on a bead standard with 4 bead populations conjugated with a known number of PE molecules. For data analysis, a G1 gate was drawn around the bead singlets on an FSC-H/SSC-H scatter plot: This gated bead population was subsequently analyzed using a histogram plot of FL2-H to evaluate the level of PE staining. Separate markers were drawn around the peaks of the four bead populations (M1-M4) and the geometric mean for FL2 of each bead population was determined. The FL2 geometric mean of each bead was plotted against the lot specific PE/bead values in a log-log plot. Linear regression was performed to obtain a standard curve using the following equation: y=mx+c, with "m" equal to the slope and "c" equal to the y-intercept.

For PBMC sample analysis, a G1 gate was drawn around the positive fluorescent cell population of interest on an SSC-H/FL4-H dot plot. This gated cell population was subsequently analyzed using a histogram plot of FL2-H to evaluate the level of PE-labeled antibody staining. The FL2 geometric mean was determined for each blood cell sample stained with anti-CD37-PE or anti-CD20-PE, as well as unstained control samples. All geometric mean values for FL2 were plotted against the bead standard curve and values for PE per cell were extrapolated. Since both antibody-PE conjugates were at a PE:Ab ratio of approximately 1:1, the values for PE per cell correspond to the number of antibodies bound per cell (ABC) value. Experiments were performed with duplicate samples for each assay. The mean and standard deviation was determined from several assays for each blood cell population.

Figure 1:
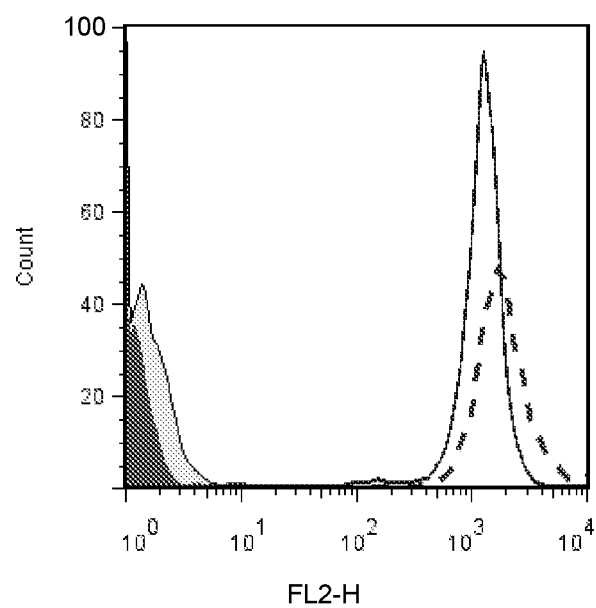
FIG. 1 depicts an FL2-H (PE) histogram overlay for a flow cytometry experiment with human B-cells. The following conditions are shown: antibody control (dark filled), isotype control stain (light filled), anti-CD37 stain (thick black line), and anti-CD20 stain (dashed line) for CD19+ B-cells.

CD37 expression was evaluated in normal blood cells from 4 independent donors. Results were compared to CD20 staining, unstained cells and a non-binding huIgG-PE conjugate as controls. An example of a typical staining profile of normal B-cells is given in a histograms in FIG. 1. The average ABC values of 4 different experiments for CD37 and CD20 were calculated and listed in Table 1.

TABLE 1

ABC values for CD37 and CD20 expression on human PBMC samples

|  | CD37 ABC | CD20 ABC | No Ab control | huIgG-PE control |
| --- | --- | --- | --- | --- |
| CD19+ B-cells | 77,440 | 94,598 | 80 | 76 |
| CD3+ T cells | 2,016 | 336 | 74 | 68 |
| CD56+ NK cells | 3,090 | 264 | 85 | 88 |
| CD14+ monocytes | 5,244 | 794 | 180 | 215 |

The highest overall CD37 staining level was found in CD19+ B-cells at approximately 77,000 ABC. In addition, CD37 staining was seen at low levels in other PBMC populations examined, with CD14+ monocytes showing CD37 staining at approximately 5,000 ABC, CD56+ NK cells at 3,000 ABC, and CD3+ T cells at 2,000 ABC. Staining with the non-binding huIgG-PE control resulted in ABC values of approximately 70-90 for B, T and NK cells and approximately 200 for monocytes. In the same 4 donors CD20 expression was evaluated in comparison to CD37. In accordance with published findings, the CD20 staining was restricted mainly to CD19+ B-cells with an ABC value of approximately 95,000 ABC. The CD20 expression level was just slightly higher than the CD37 expression level. Only minimal CD20 staining was observed in other PBMC populations examined, with CD14+ monocytes showing CD20 staining at 794 ABC, CD56+ NK cells at 264 ABC and CD3+ T cells at 336 ABC.

This result demonstrates that high CD37 expression is mainly restricted to B-cells in peripheral blood samples with only minor expression on peripheral T cells, NK cells and monocytes. This is consistent with published findings ((Moore et al. 1986, J Immunol. 137(9):3013-8; Schwartz-Albiez et al. 1988, J. Immunol., 140(3)905-914). In addition, we found that the CD37 expression levels on peripheral B-cells is similar to the level of CD20 expression. This expression pattern strongly suggest that CD37 directed therapies may be a suitable for targeting B-cells in diseases such as B-cell malignancies, autoimmune diseases, inflammatory diseases or other disorders of the immune system analogous to the use of CD20 directed therapies.

Example 2A

In Vitro B-Cell Depletion Using Purified PBMCs

The ability of humanized antibodies to deplete B-cells was measured using: in vitro assays with human PBMCs according to published studies performed with rituximab (Vugmeyster et al. Cytometry A. 2003; 52(2):101-9 and Vugmeyster et al. Int Immunopharmacol. 2004; 4(8):1117-24). Alemtuzumab (Campath) was used as appositive control, since it has been reported to efficiently deplete lymphocytes in vivo and in vitro (Hale, Blood. 1983 October; 62(4):873-82 and Waldmann, Philos Trans R Soc Lond B Biol Sci. 2005 Sep. 29; 360(1461):1707-11).

Fresh buffy coats from healthy donors were obtained from Research Blood Components (Brighton, Mass., US) as a source of normal blood cells for all experiments within this study. Buffy coats were prepared by centrifugation of a unit of whole blood and collecting the interface between the plasma and the red blood cells. This unpurified buffy coat contains PBMCs, neutrophils, platelets, red blood cells, and plasma and was used for experiments on the same day it was drawn. Peripheral blood mononuclear cells (PBMCs) were prepared from buffy coats by standard density gradient centrifugation using Ficoll-Paque as follows. Blood was diluted 1:3 with 1×HBSS containing 5 mM EDTA and up to mL were added to a 50 mL conical tube. Ten mL of Ficoll-Paque (GE Healthcare) were slowly added to the bottom of each tube. Samples were centrifuged at 500×g with no brake at RT for 30 minutes to obtain a layer of PBMCs below the plasma and to remove red blood cells and most granulocytes. The PBMCs were transferred to new tubes and washed twice with 1×HBSS containing 5 mM EDTA by centrifugation at 400×g for 10 minutes at RT. Staining buffer (1×HBSS, 1% BSA, 0.1% sodium azide) was then used to resuspend the PBMC pellets in the initial blood volume to achieve the original cell density.

To assess the effect of huCD37-3, huCD37-3-SMCC-DM1, huCD37-50, huCD37-50-SMCC-DM1, rituximab, alemtuzumab (Campath), and TRU-016 on PBMC depletion, 90 µL of purified cells were added to 12×75 mm polystyrene tubes and incubated with 10 µL of a 100 µg/mL solution of each sample or a huIgG isotype control antibody for 1 hr at 37° C. in a humidified 5% $CO_2$ incubator. The final antibody (Ab) concentration was 10 µg/mL in a final volume of 100 µL in staining buffer. Three independent samples were prepared for each treatment.

To identify populations of PBMCs, all samples were co-stained immediately after Ab incubation with 10-20 µL of fluorescently labeled Abs obtained from, for example, BD Biosciences or Miltenyi. Anti-CD3-PerCP-Cy5.5 was used to identify T cells, anti-CD19-APC for B-cells, and anti-CD14-FITC for monocytes. Staining was carried out in a total of 150 µL for 30 min in the dark at RT. CountBright Absolute Counting Beads (Invitrogen) were vortexed and added to each sample at 50 µL per tube. For PBMC prep samples, cells were washed once with 1 mL staining buffer and centrifuged at 400×g for 3-5 min. Supernatant was removed with a 1 mL pipette and cells were resuspended in 500 µL of 1% formaldehyde in 1×PBS. Samples were stored at 4° C. in the dark until acquisition, which was performed within 4 days of sample preparation.

TreeStar FlowJo software (version PC 7.5) was used for data analysis. A gate was drawn around the CountBright bead population on an FSC-H vs SSC-H dot plot to determine a total bead count for the sample. To determine the total count for each PBMC population of interest, a separate gate was drawn around the positive fluorescent population on an SSC-H vs FL(x)-H dot plot, where x is the channel of interest. Specifically, a total count for T cells in a sample was found by gating the positive population on an SSC-H vs FL3-H dot plot; for B-cells, the positive population was found on an SSC-H vs FL4-H dot plot; for NK cells, an SSC-H vs FL2-H dot plot was used; for monocytes, an SSC-H vs FL4-H dot plot was used. The ratio of CD19+ cells for B-cells (CD3+ cells for T cells, CD56+ cells for NK cells, or CD14+ cells for monocytes) relative to beads was determined and multiplied by 100. Percent depletion was then calculated by taking the ratio of the cell to bead ratio in treated samples relative to the cell to bead ratio in isotype control treated samples, subtracting this from 1 and multiplying by 100. This corresponds to the following formula: Percent Depletion=100×(1−cell to bead ratio of treated sample/cell to bead ratio of control sample). Data for all cell types was analyzed in the same manner.

Figure 2:
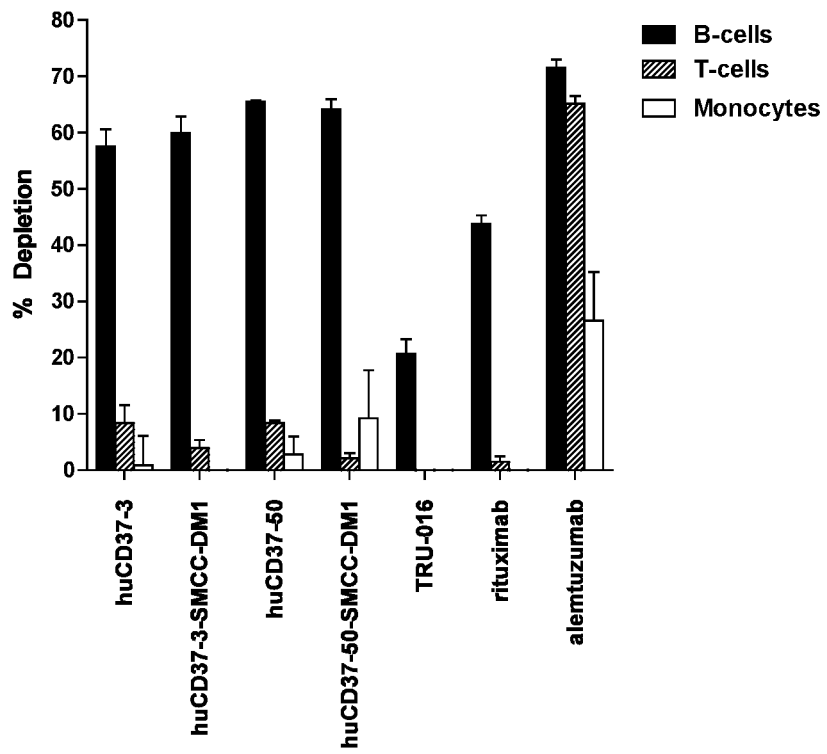
FIG. 2 depicts the results of in vitro depletion experiments using purified human PBMC samples treated with 10 μg/mL of huCD37-3, huCD37-3-SMCC-DM1, huCD37-50, huCD37-50-SMCC-DM1, rituximab, TRU-016, or alemtuzumab. Results from two different donors are shown in panel A and B.
Figure 2:
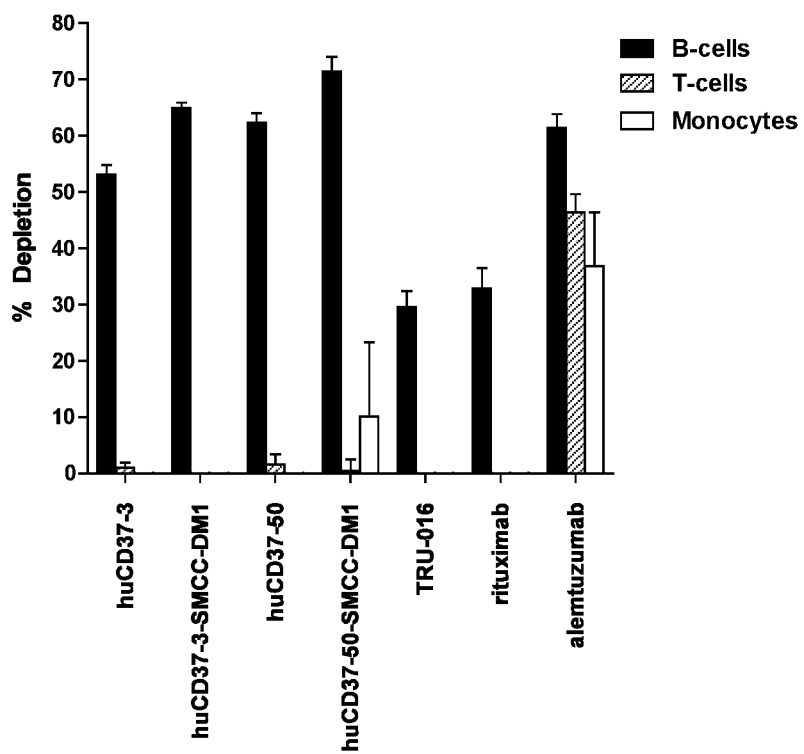

For two donors tested, treatment of purified PBMC samples with huCD37-3, huCD37-3-SMCC-DM1, huCD37-50 or huCD37-50-SMCC-DM1 resulted in approximately 55-70% depletion of B-cells (see FIG. 2). There was less than 10% depletion of T cells or monocytes. The B-cell restricted depletion effect indicates that this activity is linked to the high CD37 expression on B-cells. In comparison, treatment with the anti-CD20 antibody rituximab resulted in approximately 30-40% depletion of B-cells. Treatment with the anti-CD37 SMIP™ TRU-016 resulted in only 20-30% depletion of B-cells. Alemtuzumab treatment resulted in depletion of 60-70% of B-cells, 55-65% of T cells and 40-65% of monocytes.

Example 2B

Dose Response for In Vitro B-Cell Depletion Using Purified PBMCs

To evaluate the dose-response of the antibodies and conjugates, purified PBMCs from 2 donors were incubated with a 5-fold sample dilution series. Each sample dilution was added at 10 µL per tube to 90 µL of purified cells in triplicate and incubated for 1 hour at 37° C. in a humidified 5% $CO_2$ incubator. The final concentration ranged from 10 µg/mL to 0.13 ng/mL. The same amount of a non-binding huIgG Ab was used as an isotype control.

For two donors tested, treatment of purified PBMC samples with huCD37-3-SMCC-DM1 resulted in a clear dose-response for the B-cell depletion activity (see FIGS. 3A and B). Incubation with huCD37-3-SMCC-DM1 caused in vitro depletion of approximately 60% of B-cells with an EC50 of 40-75 ng/mL. For an additional donor tested, treatment of purified PBMC samples with huCD37-3, huCD37-38, huCD37-50, and huCD37-56 antibodies also resulted in a clear dose-response for the B-cell depletion activity (see FIG. 3C). Incubation with these antibodies caused in vitro depletion of approximately 60-70% of B-cells with an EC50 of 20-30 ng/mL.

Example 2C

In Vitro B-Cell Depletion Using Whole Blood

The ability of humanized antibodies to deplete B-cells was measured using in vitro assays with whole blood according to published studies performed with rituximab (Vugmeyster et al. Cytometry A. 2003; 52(2): 101-9 and Vugmeyster et al. Int Immunopharmacol. 2004; 4(8): 1117-24).

Fresh buffy coats from healthy donors were obtained from Research Blood Components (Brighton, Mass., US) as a source of normal blood cells for all experiments within this study. To assess the effect of huCD37-3, huCD37-3-SMCC-DM1, rituximab, alemtuzumab (Campath), and TRU-016 on peripheral blood cells (PBCs) in a whole blood matrix, 90 µL of whole blood from a buffy coat were incubated with Abs or isotype control as detailed above in a total volume of 100 µL. Three independent samples were prepared for each Ab treatment.

To identify populations of blood cells, all samples were co-stained immediately after Ab incubation with 10-20 µL of fluorescently labeled Abs obtained from, for example, BD Biosciences or Miltenyi. Anti-CD3-PerCP-Cy5.5 was used to identify T cells, anti-CD19-APC for B-cells, anti-CD56-PE for NK cells, and anti-CD14-FITC for monocytes. Staining was carried out in a total of 150 µL for 30 min in the dark at RT. CountBright Absolute Counting Beads (Invitrogen #C36950) were vortexed and added to each sample at 50 µL per tube to allow standardization of cell counts.

Following cell staining, 2 mL of BD FACS Lysing Solution (BD Biosciences, diluted 1:10 in $dH_2O$ according to the manufacturer's instructions) were added to each sample in order to lyse the RBCs present. Samples were incubated at RT for 15-20 min in the dark, centrifuged at 400×g for 3-5 min, and resuspended in 500 µL of 1% formaldehyde in 1×PBS. Samples were stored at 4° C. in the dark until acquisition, which was performed within 4 days of sample preparation. Samples were acquired on a BD FACSCalibur. Compensation controls were run with each assay to confirm instrument settings. A total of 160,000 ungated events were acquired for each sample using BD CellQuest software (version 5.2). TreeStar FlowJo software (version PC 7.5) was used for data analysis as described above.

For one donors tested, treatment of purified PBMC samples with huCD37-3, huCD37-3-SMCC-DM1, huCD37-50 or huCD37-50-SMCC-DM1 resulted in approximately 40% depletion of B-cells (see FIG. 4). There was less than 10% depletion of T cells, NK cells or monocytes. As seen for purified PBMCs, the in vitro depletion is restricted to B-cells indicating that the activity is linked to the high CD37 expression on B-cells. In comparison, treatment with the anti-CD20 antibody rituximab or the anti-CD37 SMIP™ TRU-016 resulted in a less than 10% depletion of B-cells. Alemtuzumab treatment resulted in depletion of 40% of B-cells, 80% of T cells, 15% of NK cells and 20% of monocytes.

Example 2D

Dose Response for In Vitro B-Cell Depletion Using Whole Blood

To evaluate the dose-response of the antibodies and conjugates, whole blood from 2 donors was incubated with a 10-fold sample dilution series. Each sample dilution was added at 10 µL per tube to 90 µL of purified cells in triplicate and incubated for 1 hr at 37° C. in a humidified 5% $CO_2$ incubator. The final concentration ranged from 10 µg/mL to 0.1 ng/mL. The same amount of a non-binding huIgG Ab was used as an isotype control.

For two donors tested, treatment of whole blood samples with huCD37-3 or huCD37-3-SMCC-DM1 resulted in a clear dose response for the B-cell depletion activity (see FIGS. 5A and B). In addition, huCD37-50 was tested for one donor and also showed a similar dose response for the B-cell depletion activity (see FIG. 5B). Incubation with huCD37-3, huCD37-3-SMCC-DM1 or huCD37-50 caused a maximum response of in vitro depletion of approximately 30-45% of B-cells with an EC50 of 40-120 ng/mL.

In addition to the in vitro experiment described above, the capacity of CD37 antibodies to deplete B cells in vivo can be tested in huCD37 expressing mice (described in Example 3) and, for antibodies that crossreact with macaque CD37, in monkey.

Example 2E

In Vitro Cytokine Release Studies Using Human PBMCs

In vitro cytokine release was measured by ELISpot for IFN-γ (Interferon), TNF-α (Tumor Necrosis Factor) and IL-6 (Interleukin-6) using peripheral blood mononuclear cells (PBMCs) from healthy human donors incubated for 18-20 hours with compounds at a concentration of 2.5 ng/mL to 250 μg/mL. The ELISpot method is designed to measure the number of cells secreting cytokine by capturing the cytokine onto the assay plate during the entire length of the incubation. In all assays the positive control anti-CD3 antibody CD3-2, as well as a negative non-binding isotype huIgG control antibody was included. Alemtuzumab (Campath®) and rituximab (Rituxan®) were used in comparison, since both have been reported to induce cytokine release in patients (Wing, *J Clin Invest.* 98:2819-26 (1996) and Winkler, *Blood* 94:2217-2224 (1999)). The assay conditions were chosen to reflect conditions that are relevant for antibody therapeutics. The highest concentration of 250 μg/mL tested corresponds to the maximum serum concentration of an antibody, such as for example the CD20-directed rituximab, in patient plasma after an infusion of 10 mg/kg of antibody.

As can be seen in FIGS. 6 and 7, the positive control anti-CD3 antibody induced release of very high levels of IFN-γ, TNF-α and IL-6 with PBMCs from two different donors. In the same assays, alemtuzumab caused intermediate cytokine release, while rituximab caused moderate cytokine release with PBMCs from two different donors. In contrast, huCD37-3, huCD37-50, huCD37-3-SMCC-DM1 or huCD37-50-SMCC-DM1 did not cause significant cytokine release in our assays.

This underscores the utility off the described CD37-targeting antibodies or conjugates as therapeutics as they combine potent activity, such as B-cell depletion, with a favorable safety profile with respect to cytokine release.

Example 3

In Vivo Models to Evaluate the Activity of CD37 Directed Antibodies or Conjugates B-cell depletion is known to ameliorate autoimmune diseases. In fact, rituximab has been approved for rheumatoid arthritis treatment (Edwards J C et al. Nat Rev Immunol. 6: 119 (2006)). In animal models, B-cell depletion using antibodies against B-cell antigens such as CD20, CD19 and CD79 has been shown to inhibit or ameliorate several autoimmune diseases including systemic lupus erythematosus (SLE), experimental autoimmune encephalomyelitis (EAE; mouse model of multiple sclerosis), type-1 diabetes (T1D) and rheumatoid arthritis (RA). The CD37 antigen is expressed at high levels in human B-cells. Therefore, antibodies or immunoconjugates directed against the CD37 antigen could potentially deplete B-cells and be therefore useful to treat multiple autoimmune diseases.

To test the utility of CD37 targeting antibodies and immunoconjugates to treat human autoimmune diseases, the activity of such CD37 targeting antibodies and immunoconjugates can be studied in mice using several murine autoimmune disease models.

For example, anti-murine CD37 antibodies can be generated using CD37-knock-out mice or other species such as rat and hamster, and antibodies that deplete B-cell in vivo effectively can be selected. The therapeutic potential of anti-CD37 antibodies can be tested in mouse models representing human autoimmune diseases, for example, a spontaneous T1D model in NOD mice, a myelin oligodendrocyte glycoprotein (MOG) peptide induced EAE model in wild type C57/Bl6 mice, a collagen induced rheumatoid arthritis model in DBA/1 mice or a spontaneous systemic lupus erythematosus (SLE) model in MRL/lpr mice. Examples of murine CD37 antibodies and their therapeutic efficacy in various animal models of autoimmune disease are provided below.

Alternatively, the therapeutic potential of anti-human CD37 antibodies and immunoconjugates can also be tested in murine autoimmune disease models that have been engineered to express the human CD37 antigen. Such human CD37 (huCD37) expressing mice can be generated using standard knock in (KI) or transgenic (Tg) approaches. For example, to generate huCD37 KI mice, human CD37 cDNA can be inserted into the murine CD37 locus in the C57/Bl6 embryonic stem (ES) cells. The homozygous huCD37 KI mice will express human CD37 cDNA under the regulation of the endogenous murine CD37 promoter, thus the expression pattern of the huCD37 would mimic that of the endogenous muCD37. The different approach utilizes bacterial artificial chromosome (BAC) containing the human CD37 gene that can be randomly inserted into the mouse genome. This transgenic approach has been used successfully to generate huCD20 Tg mice resulting in B-cell specific high level expression of the antigen.

The resulting huCD37 expressing mice based on the C57/Bl6 background can be used to further develop several autoimmune disease model. For examples, MOG peptide immunization in the C57/Bl6 strain background can induces severe EAE in two weeks. In addition, introducing a FcγRIIB knock out phenotype by breeding huCD37 expressing mice with C57/Bl6 FcγRIIB knock out mice should yield a mouse model that spontaneously develop SLE and develop RA upon immunization with collagen II antigen. Alternatively, backcrossing of the huCD37 expressing, C57/Bl6 mice into the NOD or MRU/lpr background for 10 generations can provide spontaneous T1D and SLE models, respectively.

Example 4A

Generation of Anti-muCD37 Monoclonal Antibody Clone 252-3

To develop proof of concept that CD37 targeting antibody and immunoconjugate can inhibit autoimmune disease, anti-murine CD37 (muCD37) monoclonal antibodies were generated by immunizing CD37-knock-out C57Bl/6 mice with 300-19, a murine pre-B cell line that endogenously expresses the muCD37 antigen. The immunogen was injected subcutaneously at the dose of $5 \times 10^6$ cells per mouse every 2 weeks for 5 times. Three days before being sacrificed for hybridoma generation, the immunized mice received intraperitoneal injection of another dose of antigen. The spleen cells were fused with murine myeloma P3X63Ag8.653 cells (P3 cells) (J. F. Kearney et al. 1979, *J Immunol,* 123:1548-1550) at ratio of 1 P3 cells:3 spleen cells according to standard procedure. The fused cells were cultured in RPMI-1640 selection medium containing hypoxanthine-aminopterin-thymidine (HAT) (Sigma Aldrich) in 5% $CO_2$ incubator at 37° C. until hybridoma clones were ready for antibody screening.

Screening was done using flow cytometric binding assay with spleen cells from wild type mice and CD37-knock-out mice. The spleen cells were counterstained with anti-CD45R (B220) antibody to identify B cells that constitutively express CD37 antigen. The hybridomas producing antibody that bound the wild type, but not CD37-knock-out, B cells were subcloned by limiting dilution. One stable subclone (clone 252-3) was obtained. The 252-3 hybridoma was expanded in low IgG serum containing media and the antibody was purified using standard methods with protein A/G chromatography.

Example 4B

Characterization of Anti-muCD37 Monoclonal Antibody Clone 252-3

The purified 252-3 monoclonal antibody was identified as a mouse IgG2a with IsoStrip mouse monoclonal antibody isotyping kit (Roche Diagnostics Corporation, Indianapolis, Ind.). To determine the binding affinity to the muCD37 antigen, various concentrations of 252-3 antibody were incubated with 300-19 cells, a murine pre-B cell line that expresses the muCD37 antigen, for 30 minutes at 4° C. Cells were then washed and counterstained with anti muIgG-PE conjugate (Jackson Immunoresearch, West Grove, Pa.) for 30 minutes at 4° C. The cells were finally washed, fixed in formalin and analyzed by flow cytometry using a FACSarray (BD Bioscience, San Jose, Calif.). The flow cytometry data were analyzed using FlowJo (Tree Star Inc., Ashland, Oreg.) and the geometric mean fluorescence intensity was plotted against the antibody concentration in a semi-log plot (FIG. 8). A dose-response curve was generated by non-linear regression and the EC50 value of the curve, which corresponds to the apparent dissociation constant (Kd) of the antibody, was calculated using GraphPad Prism (GraphPad Software Inc., La Jolla, Calif.). It was found that the Kd of the 252-3 antibody was 14 nM. In contrast, the 252-3 antibody did not bind to human tumor cells expressing the human CD37 antigen. The 252-3 antibody was then used as a surrogate antibody in murine autoimmune disease models to demonstrate the therapeutic potential of a CD37-targeting antibody for the treatment of autoimmune diseases (Examples 5-7).

Example 5

Anti-muCD37 Monoclonal Antibody Inhibits Experimental Autoimmune Encephalomyelitis Experimental autoimmune encephalomyelitis (EAE) is an animal model of inflammatory demyelinating disease of the central nervous system (CNS), including multiple sclerosis in human. Murine EAE is commonly induced by immunization of spinal cord homogenates, brain extracts, or CNS protein such as myelin protein or peptide, followed by injection of pertussis toxin to break down the blood-brain barrier and allow immune cells access to the CNS tissue. This immunization leads to multiple small disseminated lesions of demyelination in the brain and spinal cord, causing tail paralysis followed by limb paralysis.

To test the activity of anti-muCD37 antibody in the EAE model, we first studied the capacity of the 252-3 antibody to deplete B cells in vivo. C57Bl/6 mice were injected intraperitoneally with 25 mg/kg of 252-3 antibody or polyclonal murine IgG (Jackson Immunoresearch, West Grove, Pa.) as a control. Peripheral blood was collected at different time points and analyzed for B and T cell levels by flow cytometry. Allophycocyanin (APC)-conjugated anti-mouse CD45R (B220) antibody (ebioscience, San Diego, Calif.) and fluorescein isothiocyanate (FITC)-conjugated anti CD3ε antibody (ebioscience, San Diego, Calif.) were used to stain B and T cell populations, respectively. B cell depletion was assessed by calculating the ratio of B to T cells for each sample and the B/T ratio was normalized by setting the average B/T ratio of murine IgG-treated samples to 100%. The normalized B/T cell ratio was plotted for muIgG control mice and 252-3 antibody treated mice (FIG. 9A). The result show that the B cell level of the mice treated with 252-3 antibody was rapidly reduced within a few hours after the antibody injection. The B cell depletion reached ~70% at 3 h and peaked at day 3 (>95%). After day 3, the B cell level slowly increased and reached ~60% of the normal level at day 14. This data suggests that the 252-3 antibody can rapidly and efficiently deplete peripheral blood B cells, and this effect was sustained for at least 7 days after the antibody injection.

The second study tested the capacity of 252-3 antibody to inhibit EAE. In this study, EAE was induced in C57Bl/6 mice by subcutaneous immunization of $MOG_{35-55}$ peptide emulsified in complete Freund's adjuvant (EAE kit from Hooke Laboratories, Lawrence, Mass.) into the upper and lower back at day 0 and two intraperitoneal injections of pertussis toxin at 2 h and 24 h after antigen immunization. Mice were checked for EAE signs daily starting on day 7 after immunization. The disease severity was scored on a scale of 0 to 5 using the following criteria:

| Score | Clinical Observations |
|---|---|
| 0 | No obvious changes in motor functions of the mouse in comparison to non-immunized mice. When picked up by the tail, the tail has tension and is erect. Hind legs are usually spread apart. When the mouse is walking, there is no gait or head tilting. |
| 1 | Limp tail. When the mouse is picked up by tail, instead of being erect, the whole tail drapes over your finger. |
| 2 | Limp tail and weakness of hind legs. When the mouse is picked up by tail, legs are not spread apart, but held closer together. When the mouse is observed when walking, it has clearly apparent wobbly walk. |
| 3 | Limp tail and complete paralysis of hind legs (most common) OR, Limb tail with paralysis of one front and one hind leg. OR, ALL of: Severe head tilting Walking only along the edges of the cage Pushing against the cage wall Spinning when picked up by the tail |
| 4 | Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, a score of 5 is entered for that mouse for the rest of the experiment. |
| 5 | Complete hind and front leg paralysis, no movement around the cage. OR, Mouse is spontaneously rolling in the cage. OR, Mouse is found dead due to paralysis. If mouse is alive, euthanize the mouse immediately if it scores 5. Once mouse scored 5, the same score is entered for all the days for the rest of the experiment. |

All mice started to show signs of EAE between 12 to 18 days after antigen immunization. At the disease onset, mice were randomized and the 252-3 antibody or polyclonal muIgG was injected once intraperitoneally at a 25 mg/kg dose. A total of 10 mice were enrolled for each group. At the end of the study (18 days after the disease onset), the data were synchronized based on the day of disease onset for each mouse. The disease progression plot (FIG. 9B) shows that mice from both groups had relapsing-remitting form of EAE. During the first wave of clinical symptoms, the control mice reached the mean of 3 while the mice treated with 252-3 antibody had a mean of 2. The difference in disease severity between these two groups was sustained for more than 2 weeks after the disease onset. Taken together, this data suggests that the 252-2 antibody treatment rapidly depletes the B cell population and alleviates EAE.

Example 6

Anti-muCD37 Monoclonal Antibody Inhibits Type-1 Diabetes in NOD Mice

Type-1 diabetes (T1D) or juvenile diabetes or insulin-dependent diabetes millitus (IDDM) is caused by auto-immune reaction against insulin-producing pancreatic beta cells. Destruction of beta cells reduces insulin production and increases glucose level that produces various clinical symptoms. T1D incidence in Northern Europe and the US is between 8 and 17/100,000. Insulin supplement is the most common treatment of the disease.

Non-obese diabetic (NOD) mice spontaneously develop T1D and have been widely used to model the human disease. In NOD mice, the disease starts with leukocytic infiltration of the pancreatic islets (called insulitis) as early as 4 weeks of age. The insulitis progresses rapidly, leading to destruction of pancreatic islets and diabetes starting at 12-15 weeks of age. B cell depletion using anti-CD20 antibody in the early stage of insulitis has been reported to delay the disease onset (Hu et al., J Clin Inves. 117, 3857 (2007)), suggesting that B cells play a critical role in the disease pathogenesis in NOD mice.

To test the activity of anti-muCD37 antibody, the 252-3 antibody was injected into six female NOD mice intraperitoneally at 25 mg/kg every 10 days for a total of 4 injections starting at 5 weeks of age (n=6). The control mice (n=6) were injected with polyclonal murine IgG (Jackson Immunoresearch, West Grove, Pa.). Three days after the last injection, the B and T cell levels in peripheral blood were examined by flow cytometry. Allophycocyanin (APC)-conjugated anti-mouse CD45R (B220) antibody (ebioscience, San Diego, Calif.) and fluorescein isothiocyanate (FITC)-conjugated anti CD3ε antibody (ebioscience, San Diego, Calif.) were used to stain B and T cell populations, respectively. The B/T cell ratio was normalized to murine IgG control treated samples as described above and the normalized B/T cell ratio was plotted for muIgG control mice and 252-3 antibody treated mice (FIG. 10A). The results show that the B cell level of the mice treated with 252-3 antibody was significantly reduced as compared to the control mice, suggesting that the 252-3 antibody efficiently depletes peripheral blood B cells in NOD mice. To examine the effect of B cell depletion by anti-muCD37 antibody, blood glucose level was measured weekly starting at 12 weeks of age. Mice with blood glucose level ≥250 mg/dL in two consecutive weeks are considered diabetic. The data in FIG. 10B shows that the control mice started to develop diabetes on week 15 and 83% of the mice had diabetes on week 22. In contrast, the mice treated with 252-3 antibody started to develop diabetes on week 17 and only 50% of the mice were diabetic on week 27. This data shows that treatment of 252-3 antibody efficiently depletes B cells in NOD mice, delays the onset of diabetes and significantly reduces the disease incidence.

Example 7

Anti-muCD37 Monoclonal Antibody Inhibits Collagen-Induced Arthritis

Collagen-induced arthritis (CIA) is an animal model of rheumatoid arthritis (RA) that is widely used to investigate disease pathogenesis and to validate therapeutic targets. Arthritis is normally induced in mice or rats by immunization with autologous or heterologous type II collagen in adjuvant. This immunization elicits a robust T- and B-cell response to the antigen leading to proliferative synovitis with infiltration of polymorphonuclear and mononuclear cells, pannus formation, cartilage degradation, bone erosion and fibrosis.

Since different mouse strains have different susceptibility to antibody-mediated B cell depletion (Ahuja et al., *J. Immunol.*, 179: 3351-3361 (2007)), to test the activity of anti-muCD37 antibody in CIA model, we first studied the capacity of the 252-3 antibody to deplete B cells in DBA/1 mice. Mice were injected intraperitoneally with 25 mg/kg of 252-3 antibody or polyclonal murine IgG (Jackson Immunoresearch, West Grove, Pa.) as control. Peripheral blood was collected at different time points and analyzed for B and T cell levels by flow cytometry. Allophycocyanin (APC)-conjugated anti-mouse CD45R (B220) antibody (ebioscience, San Diego, Calif.) and fluorescein isothiocyanate (FITC)-conjugated anti CD3ε antibody (ebioscience, San Diego, Calif.) were used to stain B and T cell populations, respectively. The normalized B/T cell ratio was calculated as described above and compared between the muIgG control mice and 252-3 antibody treated mice (FIG. 11A). The result show that the 252-3 antibody significantly reduced the peripheral blood B cell level to ~20% and ~8% in 1 and 3 days after the antibody injection, and this low B cell level was maintained at 7 days after the antibody injection. This data suggests that the 252-3 antibody can rapidly and efficiently deplete peripheral blood B cells, and this effect was sustained for at least 7 days after the antibody injection.

The second study tests the capacity of 252-3 antibody to inhibit CIA. In this study, CIA was induced in DBA/l mice by subcutaneous immunization of chicken collagen/CFA (complete Freund's adjuvant) on day 0 and chicken collagen/IFA (incomplete Freund's adjuvant) on day 21 (Hooke Laboratories, Lawrence, Mass.). Mice were checked for CIA signs daily starting on day 21 after immunization. The CIA severity was scored on a scale of 0 to 16 (based on a score of 0 to 4 for each paw) using the following criteria:

| Paw Score | Clinical Observations |
|---|---|
| 0 | Normal paw. |
| 1 | One toe inflamed and swollen. |
| 2 | More than one toe, but not entire paw, inflamed and swollen, OR Mild swelling of entire paw. |
| 3 | Entire paw inflamed and swollen. |
| 4 | Very inflamed and swollen paw or ankylosed paw. If the paw is ankylosed, the mouse cannot grip the wire top of the cage. |

At the onset of arthritis symptoms, mice were randomized into two groups and injected with the 252-3 antibody or polyclonal muIgG intraperitoneally at 10 mg/kg dose at three consecutive days. A total of 12 mice were enrolled for each group. At the end of the study (21 days after the disease onset), the data were synchronized based on the day of disease onset for each mouse. The disease progression plot (FIG. 11B) shows that the disease severity in control mice increased rapidly from mean score of 2 at day 1 to 9.5 at day 7. In contrast, the disease in mice treated with the 252-3 antibody progressed significantly slower with mean score of 4.4 at day 7. Altogether, this data suggests that the 252-2 antibody treatment significantly depletes the B cell population and alleviates CIA.

In conclusion, the above experiments using a surrogate anti-muCD37 antibody provide evidence that a CD37-targeting antibody, or an immunoconjugate that includes a CD37 antibody, can inhibit autoimmune diseases in animal models.

It is to be appreciated that the Detailed Description section, and not the Abstract section, is intended to be used to interpret the claims. The Abstract Abstract may set forth one or more but not all exemplary embodiments of the present invention as contemplated by the inventors, and thus, is not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patents, and patent applications mentioned in this specification are herein incorporated by reference to the same extent as if each independent publication, patent, or patent application was specifically and individually indicated to be incorporated by reference.

What is claimed is:

1. A method for treating a patient having an autoimmune or inflammatory disease comprising administering to said patient a therapeutically effective amount of an antibody that specifically binds to CD37 or antigen-binding fragment thereof, wherein said antibody or antigen-binding fragment comprises a heavy chain variable region and a light chain variable region, wherein the CDR1, CDR2, and CDR3 of said heavy chain variable region and the CDR1, CDR2, and CDR3 of said light chain variable region comprise the polypeptide sequences of:
   (a) SEQ ID NOs: 4, 5, and 6 and SEQ ID NOs: 28, 29, and 30, respectively;
   (b) SEQ ID NOs: 7, 8, and 9 and SEQ ID NOs: 31, 32, and 33, respectively;
   (c) SEQ ID NOs: 10, 11, and 12 and SEQ ID NOs: 34, 35, and 36, respectively;
   (d) SEQ ID NOs: 13, 14, and 15 and SEQ ID NOs: 37, 38, and 39, respectively;
   (e) SEQ ID NOs: 13, 14, and 15 and SEQ ID NOs: 37, 40, and 39, respectively;
   (f) SEQ ID NOs: 16, 17, and 18 and SEQ ID NOs: 41, 42, and 43, respectively;
   (g) SEQ ID NOs: 19, 20, and 21 and SEQ ID NOs: 44, 45, and 46, respectively;
   (h) SEQ ID NOs: 19, 20, and 21 and SEQ ID NOs: 44, 47, and 46, respectively;
   (i) SEQ ID NOs: 22, 23, and 24 and SEQ ID NOs: 48, 49, and 50, respectively;
   (j) SEQ ID NOs: 22, 23, and 24 and SEQ ID NOs: 48, 51, and 50, respectively; or
   (k) SEQ ID NOs: 25, 26, and 27 and SEQ ID NOs: 52, 53, and 54, respectively.

2. The method of claim 1, wherein the heavy chain variable region and the light chain variable region of the antibody or antigen-binding fragment thereof comprise the polypeptide sequences of:
   (a) SEQ ID NO:56 and SEQ ID NO:73 respectively;
   (b) SEQ ID NO:57 and SEQ ID NO:74 respectively;
   (c) SEQ ID NO:58 and SEQ ID NO:74 respectively;
   (d) SEQ ID NO:60 and SEQ ID NO:76 respectively;
   (e) SEQ ID NO:62 and SEQ ID NO:78 respectively;
   (f) SEQ ID NO:63 and SEQ ID NO:79 respectively;
   (g) SEQ ID NO:65 and SEQ ID NO:81 respectively;
   (h) SEQ ID NO:67 and SEQ ID NO:83 respectively;
   (i) SEQ ID NO:69 and SEQ ID NO:85 respectively; or
   (j) SEQ ID NO:71 and SEQ ID NO:87 respectively.

3. The method of claim 1, wherein the antibody or antigen-binding fragment thereof is linked via a linker (L) to a cytotoxic agent (C) to form an immunoconjugate.

4. The method of claim 3, wherein the immunoconjugate comprises 2-6 (C).

5. The method of claim 3, wherein said linker is selected from the group consisting of a cleavable linker, a non-cleavable linker, a hydrophilic linker, and a dicarboxylic acid based linker.

6. The method of claim 3, wherein said linker is selected from the group consisting of: N-succinimidyl 4-(2-pyridyldithio)pentanoate (SPP); N-succinimidyl 4-(2-pyridyldithio) butanoate (SPDB) or N-succinimidyl 4-(2-pyridyldithio)-2-sulfobutanoate (sulfo-SPDB); N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide).

7. The method of claim 3, wherein said cytotoxic agent is selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent.

8. The method of claim 7, wherein said maytansinoid is N(2')-deacetyl-N(2')-(3-mercapto-1-oxopropyl)-maytansine (DM1) or N(2')-deacetyl-N(2')-(4-mercapto-4-methyl-1-oxopentyl)-maytansine (DM4).

9. A method for treating a patient having an autoimmune or inflammatory disease comprising administering to said patient a composition comprising immunoconjugates, wherein the immunoconjugates comprise an antibody that specifically binds to CD37 or an antigen-binding fragment thereof (A) linked via a linker (L) to a cytotoxic agent (C),
   wherein the composition comprises an average of 3 to 4 (C) per antibody or antigen binding fragment thereof (A), and
   wherein said antibody or antigen-binding fragment comprises a heavy chain variable region and a light chain variable region, wherein the CDR1, CDR2, and CDR3 of said heavy chain variable region and the CDR1, CDR2, and CDR3 of said light chain variable region comprise the polypeptide sequences of:
   (a) SEQ ID NOs: 4, 5, and 6 and SEQ ID NOs: 28, 29, and 30, respectively;
   (b) SEQ ID NOs: 7, 8, and 9 and SEQ ID NOs: 31, 32, and 33, respectively;
   (c) SEQ ID NOs: 10, 11, and 12 and SEQ ID NOs: 34, 35, and 36, respectively;
   (d) SEQ ID NOs: 13, 14, and 15 and SEQ ID NOs: 37, 38, and 39, respectively;
   (e) SEQ ID NOs: 13, 14, and 15 and SEQ ID NOs: 37, 40, and 39, respectively;
   (f) SEQ ID NOs: 16, 17, and 18 and SEQ ID NOs: 41, 42, and 43, respectively;
   (g) SEQ ID NOs: 19, 20, and 21 and SEQ ID NOs: 44, 45, and 46, respectively;
   (h) SEQ ID NOs: 19, 20, and 21 and SEQ ID NOs: 44, 47, and 46, respectively;
   (i) SEQ ID NOs: 22, 23, and 24 and SEQ ID NOs: 48, 49, and 50, respectively;
   (j) SEQ ID NOs: 22, 23, and 24 and SEQ ID NOs: 48, 51, and 50, respectively; or
   (k) SEQ ID NOs: 25, 26, and 27 and SEQ ID NOs: 52, 53, and 54, respectively.

10. The method of claim 1, further comprising administering a second therapeutic agent.

11. The method of claim 10, wherein the second therapeutic is selected from the group consisting of methotrexate, an anti-CD20 therapeutic, an anti-IL-6 receptor therapeutic, an anti-IL-12/23p40 therapeutic, a chemotherapeutic, an immunosuppressant, an anti-Interferon beta-1a therapeutic, glatiramer acetate, an anti-α4-integrin therapeutic, fingolimod, an anti-BLyS therapeutic, CTLA-Fc, or an anti-TNF therapeutic.

12. The method of claim 1, wherein said autoimmune or inflammatory disease is selected from the group consisting of rheumatoid arthritis, multiple sclerosis, type I diabetes mellitus, idiopathic inflammatory myopathy, systemic lupus erythematosus (SLE), myasthenia gravis, Grave's disease, dermatomyositis, polymyositis, Crohn's disease, ulcerative colitis, gastritis, Hashimoto's thyroiditis, asthma, psoriasis, psoriatic arthritis, dermatitis, systemic scleroderma and sclerosis, inflammatory bowel disease (IBD), respiratory distress syndrome, meningitis, encephalitis, uveitis, glomerulonephritis, eczema, atherosclerosis, leukocyte adhesion deficiency, Raynaud's syndrome, Sjörgen's syndrome, Reiter's disease, Beheet's disease, immune complex nephritis, IgA nephropathy, IgM polyneuropathies, immune-mediated thrombocytopenias, acute idiopathic thrombocytopenic purpura, chronic idiopathic thembocytopenic purpura, hemolytic anemia, myasthenia gravis, lupus nephritis, atopic dermatitis, pemphigus vulgaris, opsoclonus-myoclonus syndrome, pure red cell aplasia, mixed cryoglobulinemia, ankylosing spondylitis, hepatitis C-associated cryoglobulinemic vasculitis, chronic focal encephalitis, bullous pemphigoid, hemophilia A, membranoproliferative glomerulonephritis, adult and juvenile dermatomyositis, adult polymyositis, chronic urticaria, primary biliary cirrhosis, neuromyelitis optica, Graves' dysthyroid disease, bullous pemphigoid, membranoproliferative glomerulonephritis, Churg-Strauss syndrome, juvenile onset diabetes, hemolytic anemia, atopic dermatitis, systemic sclerosis, Sjörgen's syndrome and glomerulonephritis, dermatomyositis, ANCA, aplastic anemia, autoimmune hemolytic anemia (AIHA), factor VIII deficiency, hemophilia A, autoimmune neutropenia, Castleman's syndrome, Goodpasture's syndrome, solid organ transplant rejection, graft versus host disease (GVHD), autoimmune hepatitis, lymphoid interstitial pneumonitis, HIV, bronchiolitis obliterans (non-transplant), Guillain-Barre Syndrome, large vessel vasculitis, giant cell (Takayasu's) arteritis, medium vessel vasculitis, Kawasaki's Disease, polyarteritis nodosa, Wegener's granulomatosis, microscopic polyangiitis (MPA), Omenn's syndrome, chronic renal failure, acute infectious mononucleosis, HIV and herpes virus associated diseases.

13. The method of claim 1, wherein the CDR1, CDR2, and CDR3 of said heavy chain variable region and the CDR1, CDR2, and CDR3 of said light chain variable region comprise the polypeptide sequences of SEQ ID NOs: 4, 5, and 6 and SEQ ID NOs: 28, 29, and 30, respectively.

14. The method of claim 2, wherein the heavy chain variable region and the light chain variable region of the antibody or antigen-binding fragment thereof comprise the polypeptide sequences of SEQ ID NO:57 and SEQ ID NO:74, respectively.

15. The method of claim 1, wherein the CDR1, CDR2, and CDR3 of said heavy chain variable region and the CDR1, CDR2, and CDR3 of said light chain variable region comprise the polypeptide sequences of SEQ ID NOs: 13, 14, and 15 and SEQ ID NOs: 37, 40, and 39, respectively.

16. The method of claim 2, wherein the heavy chain variable region and the light chain variable region of the antibody or antigen-binding fragment thereof comprise the polypeptide sequences of SEQ ID NO:65 and SEQ ID NO:81, respectively.

17. The method of claim 15, wherein the antibody or antigen-binding fragment thereof is linked via a linker (L) to a cytotoxic agent (C) to form an immunoconjugate.

18. The method of claim 16, wherein the antibody or antigen-binding fragment thereof is linked via a linker (L) to a cytotoxic agent (C) to form an immunoconjugate.

19. The method of claim 17, wherein said linker is N-succinimidyl 4-(maleimidomethyl) cyclohexanecarboxylate (SMCC).

20. The method of claim 18, wherein said linker is N-succinimidyl 4-(maleimidomethyl) cyclohexanecarboxylate (SMCC).

21. The method of claim 17, wherein said cytotoxic agent is a maytansinoid.

22. The method of claim 18, wherein said cytotoxic agent is a maytansinoid.

23. The method of claim 21, wherein said maytansinoid is N(2')-deacetyl-N(2')-(3-mercapto-1-oxopropyl)-maytansine (DM1) or N(2')-deacetyl-N(2')-(4-mercapto-4-methyl-1-oxopentyl)-maytansine (DM4).

24. The method of claim 22, wherein said maytansinoid is N(2')-deacetyl-N(2')-(3-mercapto-1-oxopropyl)-maytansine (DM1) or N(2')-deacetyl-N(2')-(4-mercapto-4-methyl-1-oxopentyl)-maytansine (DM4).

25. The method of claim 1, wherein said autoimmune or inflammatory disease is rheumatoid arthritis.

26. The method of claim 2, wherein the heavy chain variable region and the light chain variable region of the antibody or antigen-binding fragment thereof comprises the polypeptide sequences of:
    (a) SEQ ID NO:57 and SEQ ID NO:74, respectively;
    (b) SEQ ID NO:58 and SEQ ID NO:74, respectively; or
    (c) SEQ ID NO:65 and SEQ ID NO:81, respectively.

27. The method of claim 15, wherein said autoimmune or inflammatory disease is rheumatoid arthritis.

* * * * *